United States Patent
Marfat et al.

(10) Patent No.: US 6,380,218 B1
(45) Date of Patent: Apr. 30, 2002

(54) NICOTINAMIDE DERIVATIVES

(75) Inventors: Anthony Marfat; Robert J. Chambers, both of Mystic; John W. Watson, Ledyard; John B. Cheng, Waterford; Allen J. Duplantier, Ledyard; Edward F. Kleinman, Pawcatuck, all of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/308,956

(22) PCT Filed: Mar. 10, 1998

(86) PCT No.: PCT/IB98/00315

§ 371 Date: May 27, 1999

§ 102(e) Date: May 27, 1999

(87) PCT Pub. No.: WO98/45268

PCT Pub. Date: Oct. 15, 1998

Related U.S. Application Data

(60) Provisional application No. 60/043,403, filed on Apr. 4, 1997, now abandoned.

(51) Int. Cl.$^7$ .................. A61K 31/4436; C07D 409/12
(52) U.S. Cl. ................. 514/326; 546/280.4; 546/379.7; 546/317
(58) Field of Search .............................. 546/317, 279.7, 546/280.4; 514/350, 351, 354, 326

(56) References Cited

U.S. PATENT DOCUMENTS

| | | | | |
|---|---|---|---|---|
| 4,861,891 A | * | 8/1989 | Saccomano et al. | 546/194 |
| 6,022,884 A | * | 2/2000 | Mantlo et al. | 514/352 |

* cited by examiner

*Primary Examiner*—Alan L. Rotman
*Assistant Examiner*—Rita Desai
(74) *Attorney, Agent, or Firm*—Peter C. Richardson; Paul H. Ginsburg; Raymond M. Speer

(57) ABSTRACT

A compound of formula (I) wherein m, n, o, p, q, r, A, B, D, E, $R^1$, $R^2$, $R^3$, $R^4$, $R^5$, $R^6$, $R^7$ and $R^8$ are as defined in the description, useful in the treatment of respiratory, allergic, rheumatoid, body weight regulation, inflammatory and central nervous system disorders such as asthma, chronic obstructive pulmonary disease, adult respiratory diseases syndrome, shock, fibrosis, pulmonary hypersensitivity, allergic rhinitis, atopic dermatitis, psoriasis, weight control, rheumatoid arthritis, cachexia, crohn's disease, ulcerative colitis, arthritic conditions and other inflammatory diseases, depression, multi-infarct dementia and AIDS.

8 Claims, No Drawings

NICOTINAMIDE DERIVATIVES

REFERENCE TO RELATED OR COPENDING APPLICATIONS

This application is a Continued Prosecution Application under 37 CFR §1.53(d) based on U. S. application Serial No. 09/308,956 filed May 27, 1999; which is a §371 application based on International application Serial No. PCT/IB98/00315 filed Mar. 10, 1998; which is a continuation of U. S. Provisional application Serial No. 60/043,403 filed Apr. 4, 1997, now abandoned, benefit of the priority of which is claimed and which is incorporated herein by reference in its entirety.

BACKGROUND OF THE INVENTION

This invention relates to nicotinamide derivatives that are selective inhibitors of phosphodiesterase type 4 (PDE4) and the production of tumor necrosins factor (TNF), and as such are useful in the treatment of respiratory, allergic, rheumatoid, body weight regulation, inflammatory and central nervous system disorders such as asthma, chronic obstructive pulmonary disease, adult respiratory diseases syndrome, shock, fibrosis, pulmonary hypersensitivity, allergic rhinitis, atopic dermatitis, psoriasis, weight control, rheumatoid arthritis, cachexia, crohn's disease, ulcerative colitis, arthritic conditions and other inflammatory diseases, depression, multi-infarct dementia, and AIDS.

This invention also relates to a method of using such compounds in the treatment of the foregoing diseases in mammals, especially humans, and to pharmaceutical compositions containing such compounds.

Since the recognition that cyclic adenosine tri-phosphate (cAMP) is an intracellular second messenger, inhibition of the phosphodiesterases has been a target for modulation and, accordingly, therapeutic intervention in a range of disease processes. More recently, distinct classes of PDE have been recognized and their selective inhibition has led to improved drug therapy. More particularly, it has been recognized that inhibition of PDE4 can lead to inhibition of inflammatory mediator release and airway smooth muscle relaxation. Thus, compounds that inhibit PDE4, but which have poor activity against other PDE types, would inhibit the release of inflammatory mediators and relax airway smooth muscle without causing cardiovascular effects or antiplatelet effects.

Recent molecular cloning has revealed a complexity and diversity of PDE4 enzymes. It is now known that there are four distinct PDE4 isozymes (A, B, C and D), each encoded for by a separate gene. Kinetic studies of human recombinant materials suggest that these four isozymes may differ in their Km's and Vmax's for hydrolysis of cAMP. Analysis of tissue distribution of PDE4 mRNAs suggests that each isozyme may be localized in a cell-specific pattern. For example, unlike human skeletal muscle human peripheral blood leukocytes do not express PDE4C message, and guinea pig eosinophils express predominantly PDE4D message. The structural and distribution diversity of PDE4 isozymes offers an opportunity to discover an isozyme selective inhibitor that blocks the function of inflammatory cells only. Using PDE4D isozyme selective inhibitors, we have demonstrated that the PDE4D isozyme plays a key role in regulating the activation and degranulation of human eosinophils. In a primate model of asthma, PDE4D isozyme selective compounds inhibit antigen-induced pulmonary eosinophilia. Therefore, by selectively blocking the D isozyme, PDE4D inhibitors exhibit reduced side effects and retain anti-asthmatic (anti-inflammatory) efficacy.

SUMMARY OF THE INVENTION

The present invention relates to a compound of the formula

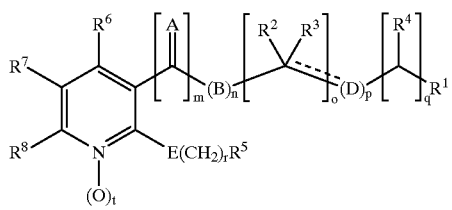

I or the pharmaceutically acceptable salt thereof, wherein the broken line represents an optional double bond;

m is 0 or 1;

n is 0 or 1;

o is 0, 1, 2, 3 or 4;

p is 0 or 1;

q is 0, 1, 2 or 3;

r is 0, 1, 2, 3, or 4;

t is 0 or 1;

A is oxygen, >NH or sulfur;

B is oxygen or NH;

D is oxygen or $NR^9$, wherein $R^9$ is hydrogen or $(C_1-C_6)$alkyl;

E is $CH_2$, O, NH or $S(O)_a$ wherein a is 0, 1 or 2;

$R^1$ is hydrogen, $(C_1-C_6)$alkyl, $(C_3-C_7)$cycloalkyl, $(C_3-C_7)$cycloalkenyl, $(C_6-C_{10})$aryl, bridged$(C_7-C_9)$ bicycloalkyl or a saturated or unsaturated cyclic or bicyclic $(C_3-C_7)$heterocyclic group;

wherein said saturated or unsaturated cyclic or bicyclic $(C_3-C_7)$heterocyclic group contains from one to four heteroatoms independently selected from the group consisting of oxygen, sulfur, nitrogen and $NR^9$, wherein $R^9$ is as defined above;

wherein said $R^1$ cycloalkyl, cycloalkenyl, cycloalkanone, aryl, bicycloalkyl and heterocyclic groups are optionally substituted by one to three substituents independently selected from the substituents consisting of halo, cyano, carboxy, amino, nitro, hydroxy, $(C_1-C_6)$alkyl, $(C_1-C_6)$alkoxy, $(C_3-C_7)$cycloalkyl, hydroxy$(C_1-C_6)$alkyl, hydroxy$(C_1-C_6)$alkylamino, $(C_1-C_6)$alkoxy, difluoromethyl, trifluoromethyl, difluoromethoxy, trifluoromethoxy, $(C_1-C_6)$acyl, $(C_1-C_6)$acylamino, $(C_1-C_6)$acyloxy, $(C_1-C_6)$alkylamino, $((C_1-C_6)$alkyl$)_2$amino, $(C_1-C_6)$alkyl-NH—(C=O)—, $((C_1-C_6)$alkyl$_2$-N—(C=O)—, aminosulfonyl, $(C_1-C_6)$alkylaminosulfonyl, or a saturated or unsaturated cyclic or bicyclic $(C_3-C_7)$ heterocycle;

wherein said saturated or unsaturated cyclic or bicyclic $(C_3-C_7)$heterocycle substituents on said $R^1$ cycloalkyl, cycloalkenyl, aryl, bicycloalkyl and heterocyclic groups contain from one to four heteroatoms independently selected from the group consisting of oxygen, sulfur, nitrogen and $NR^9$, wherein $R^9$ is as defined above, and wherein the heterocycles are optionally substituted by one to three substituents independently selected from halo, cyano, carboxy, amino, nitro, hydroxy, $(C_1-C_6)$alkyl, hydroxy$(C_1-C_6)$alkyl, $(C_1-C_6)$ alkoxy, $(C_1-C_6)$alkylthio, difluoromethyl, trifluoromethyl, difluoromethoxy, trifluoromethoxy, $(C_1-C_6)$acyl, $(C_6-C_{10})$aryl, $(C_1-C_6)$acylamino, $(C_1-C_6)$acyloxy, $(C_1-C_6)$alkylamino, $((C_1-C_6)$alkyl$)_2$amino, $(C_1-C_6)$alkylsulfonyl, aminosulfonyl, $(C_1-C_6)$alkylaminosulfonyl, $((C_1-C_6)$alkyl$)_2$aminosulfonyl or $(C_2-C_9)$heteroaryl;

wherein said alkyl, alkoxy or cycloalkyl substituents on said $R^1$ cycloalkyl, cycloalkenyl, aryl, bicycloalkyl and heterocyclic groups are optionally further independently substituted by one to three sub-substituents independently selected from halo, cyano, carboxy, amino, nitro, hydroxy, $(C_1-C_6)$alkyl, hydroxy$(C_1-C_6)$alkyl, $(C_1-C_6)$alkoxy, $(C_1-C_6)$alkylthio, difluoromethyl, trifluoromethyl, difluoromethoxy, trifluoromethoxy, $(C_1-C_6)$acyl, $(C_6-C_{10})$aryl, $(C_1-C_6)$acylamino, $(C_1-C_6)$acyloxy, $(C_1-C_6)$alkylamino, $((C_1-C_6)$alkyl$)_2$amino, $(C_1-C_6)$alkylsulfonyl, aminosulfonyl, $(C_1-C_6)$alkylaminosulfonyl, $((C_1-C_6)$alkyl$)_2$aminosulfonyl or $(C_2-C_9)$heteroaryl;

or said $R^1$ cycloalkyl, cycloalkenyl, aryl, bicycloalkyl and heterocyclic groups are additionally optionally independently substituted with from one to three substituents of the formula

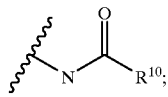

wherein $R^{10}$ is hydrogen, $(C_1-C_6)$alkyl, $(C_1-C_6)$alkoxy, $(C_3-C_7)$cycloalkyl, $(C_3-C_7)$cycloalkenyl, $(C_6-C_{10})$arylamino, $(C_6-C_{10})$aryl, bridged$(C_7-C_9)$ bicycloalkyl or a saturated or unsaturated cyclic or bicyclic $(C_3-C_7)$heterocycle;

wherein said $R^{10}$ saturated or unsaturated cyclic or bicyclic $(C_3-C_7)$heterocycle contains from one to four heteroatoms independently selected from the group consisting of oxygen, sulfur, nitrogen and $NR^9$, wherein $R^9$ is as defined above;

wherein said $R^{10}$ alkyl, alkoxy, cycloalkyl, cycloalkenyl, aryl, bicycloalkyl and heterocycle groups are optionally substituted by one to three substituents independently selected from halo, cyano, carboxy, amino, nitro, hydroxy, $(C_1-C_6)$alkyl $(C_1-C_6)$alkoxy, $(C_3-C_7)$cycloalkyl, hydroxy $(C_1-C_6)$alkyl, hydroxy$(C_1-C_6)$alkylamino, $(C_1-C_6)$alkoxy, difluoromethyl, trifluoromethyl, difluoromethoxy, trifluoromethoxy, $(C_1-C_6)$acyl, $(C_1-C_6)$acylamino, $(C_1-C_6)$acyloxy, $(C_1-C_6)$alkylamino, $((C_1-C_6)$alkyl$)_2$amino, aminosulfonyl, $(C_1-C_6)$alkylaminosulfonyl, or a saturated or unsaturated cyclic or bicyclic $(C_3-C_7)$ heterocycle;

wherein said saturated or unsaturated cyclic or bicyclic $(C_3-C_7)$ heterocycle contains from one to four heteroatoms independently selected from oxygen, sulfur, nitrogen and $NR^9$, wherein $R^9$ is as defined above; wherein the heterocycle is optionally substituted by from one to three substituents independently selected from halo, cyano, carboxy, amino, nitro, hydroxy, $(C_1-C_6)$alkyl, hydroxy$(C_1-C_6)$ alkyl, $(C_1-C_6)$alkoxy, $(C_1-C_6)$alkylthio, difluoromethyl, trifluoromethyl, difluoromethoxy, trifluoromethoxy, $(C_1-C_6)$ acyl, $(C_6-C_{10})$aryl, $(C_1-C_6)$acylamino, $(C_1-C_6)$acyloxy, $(C_1-C_6)$alkylamino, $((C_1-C_6)$alkyl$)_2$amino, $(C_1-C_6)$alkylsulfonyl, aminosulfonyl, $(C_1-C_6)$alkylaminosulfonyl, $((C_1-C_6)$alkyl$)_2$aminosulfonyl or $(C_2-C_9)$ heteroaryl;

wherein the alkyl, alkoxy or cycloalkyl substituents on said $R^{10}$ alkyl, alkoxy, cycloalkyl, cycloalkenyl, aryl, bicycloalkyl and heterocyclic groups are optionally substituted by one to three substituents independently selected from halo, cyano, carboxy, amino, nitro, hydroxy, $(C_1-C_6)$alkyl, hydroxy$(C_1-C_6)$alkyl, $(C_1-C_6)$alkoxy, $(C_1-C_6)$alkylthio, difluoromethyl, trifluoromethyl, difluoromethoxy, trifluoromethoxy, $(C_1-C_6)$acyl, $(C_6-C_{10})$aryl, $(C_1-C_6)$acylamino, $(C_1-C_6)$acyloxy, $(C_1-C_6)$alkylamino, $((C_1-C_6)$alkyl$)_2$amino, $(C_1-C_6)$alkylsulfonyl, aminosulfonyl, $(C_1-C_6)$alkylaminosulfonyl, $((C_1-C_6)$alkyl$)_2$aminosulfonyl or $(C_2-C_9)$heteroaryl;

or $R^1$ is a group of the formula

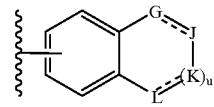

wherein $u$ is 0 or 1; and

G, J, K and L are each independently oxygen, sulfur, nitrogen, $NR^9$, wherein $R^9$ is as defined above, carbonyl or $CHR^{16}$; wherein the dashed lines represent optional double bonds and where it is understood that when a double bond exists between G and J, J and K or K and L that $R^9$ is absent, $>CHR^{16}$ is $>CR^{16}$ and G, J, K or L cannot be carbonyl; wherein $R^{16}$ is hydrogen, halo, cyano, carboxy, amino, nitro, hydroxy, $(C_1-C_6)$ alkyl $(C_1-C_6)$alkoxy, $(C_3-C_7)$cycloalkyl, hydroxy $(C_1-C_6)$alkyl, hydroxy$(C_1-C_6)$alkylamino, $(C_1-C_6)$ alkoxy, difluoromethyl, trifluoromethyl, difluoromethoxy, trifluoromethoxy, $(C_1-C_6)$acyl, $(C_1-C_6)$acylamino, $(C_1-C_6)$acyloxy, $(C_1-C_6)$ alkylamino, $((C_1-C_6)$alkyl$)_2$amino, aminosulfonyl, $(C_1-C_6)$alkylaminosulfonyl, or a saturated or unsaturated cyclic or bicyclic $(C_3-C_7)$ heterocycle containing one to four heteroatoms independently selected from the group consisting of oxygen, sulfur, nitrogen and $NR^9$, wherein $R^9$ is as defined above, wherein said heterocycle is optionally substituted by one to three substituents independently selected from halo, cyano, carboxy, amino, nitro, hydroxy, $(C_1-C_6)$alkyl, hydroxy $(C_1-C_6)$alkyl, $(C_1-C_6)$alkoxy, $(C_1-C_6)$alkylthio, difluoromethyl, trifluoromethyl, difluoromethoxy, trifluoromethoxy, $(C_1-C_6)$acyl, $(C_6-C_{10})$aryl, $(C_1-C_6)$ acylamino, $(C_1-C_6)$acyloxy, $(C_1-C_6)$alkylamino, $((C_1-C_6)$alkyl$)_2$amino, $(C_1-C_6)$alkylsulfonyl, aminosulfonyl, $(C_1-C_6)$alkylaminosulfonyl, $((C_1-C_6)$alkyl$)_2$aminosulfonyl or $(C_2-C_9)$heteroaryl;

wherein said $R^{16}$ alkyl, alkoxy or cycloalkyl substituents are optionally substituted by one to three substituents independently selected from halo, cyano, carboxy, amino, nitro, hydroxy, $(C_1-C_6)$ alkyl, hydroxy$(C_1-C_6)$alkyl, $(C_1-C_6)$alkoxy, $(C_1-C_6)$alkylthio, difluoromethyl, trifluoromethyl, difluoromethoxy, trifluoromethoxy, $(C_1-C_6)$acyl, ($C_6$–$C_{10}$)aryl, ($C_1$–$C_6$)acylamino, ($C_1$–$C_6$)acyloxy, ($C_1$–$C_6$)alkylamino, (($C_1$–$C_6$)alkyl)$_2$amino, ($C_1$–$C_6$)alkylsulfonyl, aminosulfonyl, ($C_1$–$C_6$)alkylaminosulfonyl, (($C_1$–$C_6$) alkyl)$_2$aminosulfonyl or ($C_2$–$C_9$)heteroaryl;

wherein each $R^2$, $R^3$ and $R^4$ is independently hydrogen, hydroxy, halo, cyano, carboxy, nitro, amino, ($C_1$–$C_6$)alkylamino, (($C_1$–$C_6$)alkyl)$_2$amino, hydroxyamino, ($C_1$–$C_6$)alkyl, hydroxy($C_1$–$C_6$)alkyl, or a group of the formula

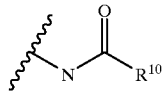

wherein $R^{10}$ is as defined above;

or $R^2$ and $R^3$ can be taken together with the carbon to which they are attached to form a carbonyl group or $R^2$ and $R^3$ taken together with the carbon to which they are attached form a ($C_3$–$C_7$)cycloalkyl ring;

or when m is 1, n is 1, o is 1 and p is 0, A and $R^2$ can be taken together to form a group of the formula

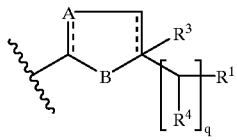

wherein the broken lines represent optional double bonds and q, A, B, $R^1$, $R^3$ and $R^4$ are as defined above and when a double bond contains the carbon atom to which $R^3$ is attached then $R^3$ is absent;

or when m is 1, n is 1, o is 1 and p is 0, A and $R^2$ are taken together and $R^3$ and —[$R^4$]$_q$—$R^1$ are taken together to form a group of the formula

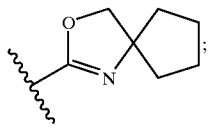

$R^5$ is a saturated or unsaturated cyclic or bicyclic ($C_3$–$C_7$) heterocyclic group containing one to four heteroatoms independently selected from oxygen, sulfur, nitrogen and $NR^9$, wherein $R^9$ is as defined above; wherein the heterocyclic group is optionally substituted by one to three substituents independently selected from halo, cyano, carboxy, amino, nitro, hydroxy, ($C_1$–$C_6$)alkyl ($C_1$–$C_6$)alkoxy, ($C_3$–$C_7$)cycloalkyl, hydroxy($C_1$–$C_6$)alkyl, ($C_1$–$C_6$)alkoxy, difluoro trifluoromethyl, difluoromethoxy, trifluoromethoxy, ($C_1$–$C_6$)acyl, ($C_1$–$C_6$)acylamino, ($C_1$–$C_6$)acyloxy, ($C_1$–$C_6$)alkylamino, (($C_1$–$C_6$)alkyl)$_2$amino, ($C_1$–$C_6$)alkyl-NH—(C=O)—, (($C_1$–$C_6$)alkyl)$_2$-N—(C=O)—, aminosulfonyl, ($C_1$–$C_6$)alkylaminosulfonyl, or a saturated or unsaturated cyclic or bicyclic ($C_3$–$C_7$) heterocycle containing one to four heteroatoms independently selected from the group consisting of oxygen, sulfur, nitrogen and $NR^9$, wherein $R^9$ is as defined above;

wherein the heterocycle substituent on said $R^5$ saturated or unsaturated cyclic or bicyclic ($C_3$–$C_7$) heterocyclic group is optionally substituted by one to three substituents independently selected from halo, cyano, carboxy, amino, nitro, hydroxy, ($C_1$–$C_6$)alkyl, hydroxy($C_1$–$C_6$)alkyl, ($C_1$–$C_6$)alkoxy, ($C_1$–$C_6$) alkylthio, difluoromethyl, trifluoromethyl, difluoromethoxy, trifluoromethoxy, ($C_1$–$C_6$)acyl, ($C_6$–$C_{10}$)aryl, ($C_1$–$C_6$)acylamino, ($C_1$–$C_6$)acyloxy, ($C_1$–$C_6$)alkylamino, (($C_1$–$C_6$)alkyl)$_2$amino, ($C_1$–$C_6$) alkylsulfonyl, aminosulfonyl, ($C_1$–$C_6$) alkylaminosulfonyl, (($C_1$–$C_6$)alkyl)$_2$aminosulfonyl or ($C_2$–$C_9$)heteroaryl;

wherein the alkyl, alkoxy or cycloalkyl substituents on said $R^5$ saturated or unsaturated cyclic or bicyclic ($C_3$–$C_7$)heterocyclic group, are optionally substituted by one to three sub-substituents independently selected from halo, cyano, carboxy, amino, nitro, hydroxy, ($C_1$–$C_6$)alkyl, hydroxy($C_1$–$C_6$)alkyl, ($C_1$–$C_6$)alkoxy, ($C_1$–$C_6$)alkylthio, difluoromethyl, trifluoromethoxy, difluoromethoxy, trifluoromethoxy, ($C_1$–$C_6$)acyl, ($C_6$–$C_{10}$)aryl, ($C_1$–$C_6$)acylamino, ($C_1$–$C_6$)acyloxy, ($C_1$–$C_6$)alkylamino, (($C_1$–$C_6$) alkyl)$_2$ amino, ($C_1$–$C_6$)alkylsulfonyl, aminosulfonyl, ($C_1$–$C_6$)alkylaminosulfonyl, (($C_1$–$C_6$)alkyl)$_2$ aminosulfonyl or ($C_2$–$C_9$)heteroaryl;

or said $R^5$ saturated or unsaturated cyclic or bicyclic ($C_3$–$C_7$)heterocyclic group is additionally optionally substituted by a group of the formula

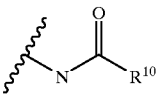

wherein $R^{10}$ is as defined above;
or $R^5$ is a group of the formula

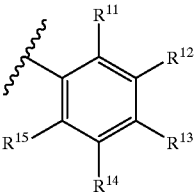

wherein $R^{11}$, $R^{12}$, $R^{13}$, $R^{14}$ and $R^{15}$ are each substituents independently selected from the group consisting of hydrogen, halo, cyano, carboxy, amino, nitro, hydroxy, ($C_1$–$C_6$)alkyl ($C_1$–$C_6$)alkoxy, ($C_3$–$C_7$)cycloalkyl, hydroxy, ($C_1$–$C_6$)alkyl, ($C_1$–$C_6$)alkoxy, difluoromethyl, trifluoromethyl, difluoromethoxy, trifluoromethoxy, ($C_1$–$C_6$)acyl, ($C_1$–$C_6$)acylamino, ($C_6$–$C_{10}$)alkyl-(C=O)—NH—(C=O), ($C_6$–$C_{10}$)aryl-(C=O)—NH—(C=O)—, ($C_1$–$C_6$)acyloxy, ($C_1$–$C_6$alkylamino, (($C_1$–$C_6$)alkyl)$_2$amino, ($C_1$–$C_6$)alkyl-NH—(C=O—, (($C_1$–$C_6$)alkyl)$_2$-N—(C=O)—, aminosulfonyl, ($C_1$–$C_6$)alkylaminosulfonyl, (($C_1$–$C_6$)alkyl)$_2$aminosulfonyl or a saturated or unsaturated cyclic or bicyclic ($C_3$–$C_7$)heterocycle containing one to four heteroatoms independently selected from oxygen, sulfur, nitrogen and $NR^9$, wherein $R^9$ is as defined above, and wherein said heterocycle is optionally substituted by one to three substituents independently selected from the group consisting of halo, cyano, carboxy, amino, nitro, hydroxy, ($C_1$–$C_6$)alkyl, hydroxy ($C_1$–$C_6$)alkyl, ($C_1$–$C_6$)alkoxy, ($C_1$–$C_6$)alkylthio, difluoromethyl, trifluoromethyl, difluoromethoxy, trifluoromethoxy, $(C_1-C_6)$acyl, $(C_6-C_{10})$aryl, $(C_1-C_6)$acylamino, $(C_1-C_6)$acyloxy, $(C_1-C_6)$alkylamino, $((C_1-C_6)alkyl)_2$amino, $(C_1-C_6)$alkylsulfonyl, aminosulfonyl, $(C_1-C_6)$alkylaminosulfonyl, $((C_1-C_6)alkyl)_2$aminosulfonyl or $(C_2-C_9)$heteroaryl;

or, $R^{11}$, $R^{12}$, $R^{13}$, $R^{14}$ and $R^{15}$ are optionally independently a group of the formula

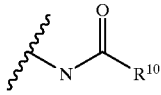

wherein $R^{10}$ is as defined above;

wherein the alkyl, alkoxy or cycloalkyl groups of said $R^{11}$, $R^{12}$, $R^{13}$, $R^{14}$ and $R^{15}$ groups are optionally substituted by one to three substituents independently selected from halo, cyano, carboxy, amino, nitro, hydroxy, $(C_1-C_6)$alkyl, hydroxy($C_1-C_6$)alkyl, $(C_1-C_6)$alkoxy, $(C_1-C_6)$alkylthio, difluoromethyl, trifluoromethyl, difluoromethoxy, trifluoromethoxy, $(C_1-C_6)$acyl, $(C_6-C_{10})$aryl, $(C_1-C_6)$acylamino, $(C_1-C_6)$acyloxy, $(C_1-C_6)$alkylamino $((C_1-C_6)alkyl)_2$amino, $(C_1-C_6)$alkylsulfonyl, aminosulfonyl, $(C_1-C_6)$alkylamino, $((C_1-C_6)alkyl)_2$aminosulfonyl or $(C_2-C_9)$heteroaryl;

or $R^{12}$ and $R^{13}$ can be taken together with the carbons to which they are attached to form a group of the formula

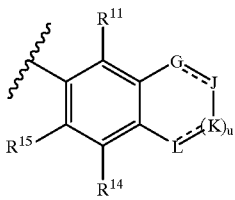

wherein u, G, J, K and L are as defined above;

$R^6$, $R^7$, and $R^8$ are each independently hydrogen, halo, cyano, carboxy, amino, nitro, hydroxy, $(C_1-C_6)$alkyl, hydroxy$(C_1-C_6)$alkyl, $(C_1-C_6)$alkoxy, $(C_1-C_6)$alkylthio, difluoromethyl, trifluoromethyl, difluoromethoxy, trifluoromethoxy, $(C_1-C_6)$acyl, $(C_6-C_{10})$aryl, $(C_1-C_6)$acylamino, $(C_1-C_6)$acyloxy, $(C_1-C_6)$alkylamino, $((C_1-C_6)alkyl)_2$amino, $(C_1-C_6)$alkylsulfonyl, aminosulfonyl, $(C_1-C_6)$alkylaminosulfonyl, $((C_1-C_9)alkyl)_2$aminosulfonyl or $(C_2-C_9)$heteroaryl;

or $R^7$ and $R^8$ may be taken together with the carbons to which they are attached to form a fused bicyclic ring of the formula

II

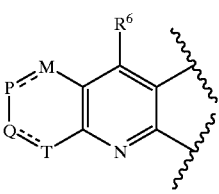

wherein the dashed lines represent optional double bonds; and M, P, Q and T are each independently oxygen, nitrogen or $CR^{17}$ wherein $R^{17}$ is hydrogen or $(C_1-C_6)$alkyl;

with the proviso that when m is 1; n is 1; o is 1; p is 0; q is 0; r is 0; A is oxygen, B is NH; $R^2$ and $R^3$ are hydrogen; $R^1$ is phenyl substituted by methyl, methoxy, chloro or fluoro; E is oxygen and $R^5$ is phenyl optionally substituted by one or two fluoro or chloro; then $R^1$ must be at least di-substituted by substituents other than methyl, methoxy or halo;

with the proviso that when t is one that the compound of formula I is a zwiterionic N-oxide, with the proviso that adjacent positions defined by G, J, K and L cannot both be defined by oxygen; and with the proviso that when the broken line of formula I represents a double bond, p is 0 and $R^3$ is absent.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl.

The term "a saturated or unsaturated, cyclic or bicyclic $(C_3-C_7)$ heterocyclic group containing as the heteroatom one to four of the group consisting of oxygen, sulfur, nitrogen and $NR^9$ wherein $R^9$ is as defined above", as used herein, unless otherwise indicated, includes but is not limited to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, , 3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5, 6, 7, 8-tetrahydro-quinolin-3-yl, benzoxazolyl, benzothiazolyl, benzothiadiazole, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl. Preferably, heterocyclic refers to furyl, thienyl, thiazolyl, oxazolyl, isoxazolyl, 1,2,3-thiadiazolyl, pyridyl, benzoxazolyl or indolyl.

The term "acyl", as used herein, unless otherwise indicated, includes a radical of the general formula RCO wherein R is alkyl, alkoxy, aryl, arylalkyl or arylalkyloxy and the terms "alkyl" or "aryl" are as defined above.

The term "acyloxy", as used herein, includes O-acyl groups wherein "acyl" is defined above.

The compound of formula I may have chiral centers and therefore exist in different enantiomeric forms. This invention relates to all optical isomers and stereoisomers of the compounds of formula I and mixtures thereof.

Preferred compounds of formula I include those wherein m is 1; n is 1; o is 1; p is 0; q is 0; r is 0; A is oxygen or nitrogen; B is NH; $R^2$ is hydrogen or $(C_1-C_6)$alkyl; $R^3$ is hydrogen; $R^1$ is $(C_6-C_{10})$aryl, $(C_3-C_7)$cycloalkyl or a saturated or unsaturated, cyclic or bicyclic $(C_3-C_7)$ heterocyclic group containing as the heteroatom one to four of the group consisting of oxygen, sulfur, nitrogen and $NR^9$ wherein $R^9$ is hydrogen or $(C_1-C_6)$alkyl wherein the aryl, cycloalkyl and heterocyclic groups are optionally substituted by halo, $(C_1-C_6)$alkyl, $(C_1-C_6)$alkoxy, hydroxy$(C_1-C_6)$alkyl, amino, $(C_1-C_6)$alkylamino, $((C_1-C_6)$alkyl$)_2$amino or hydroxy$(C_1-C_6)$alkylamino; E is oxygen and $R^5$ is a group of the formula

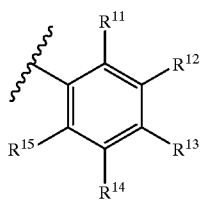

or $R^5$ is a saturated or unsaturated, cyclic or bicyclic $(C_3-C_7)$ heterocyclic group containing as the heteroatom one to four of the group consisting of oxygen, sulfur, nitrogen and $NR^9$ wherein $R^9$ is hydrogen or $(C_1-C_6)$alkyl.

More preferred compounds of formula I are those wherein $R^1$ is optionally substituted $(C_6-C_{10})$aryl wherein said substituents are hydroxy$(C_1-C_6)$alkyl or wherein at least one of $R^{11}$, $R^{12}$, $R^{13}$, $R^{14}$ or $R^{15}$ is halo or wherein $R^{12}$ and $R^{13}$ are taken together to form a fused bicyclic ring wherein u is zero, G and L are oxygen and J is $CH_2$.

Other preferred compounds of formula I include those wherein m is 0; n is 0; o is 3; p is 0; q is 0; r is 0; $R^2$ and $R^3$ are hydrogen; $R^1$ is $(C_6-C_{10})$aryl optionally substituted by halo, $(C_1-C_6)$alkyl, $(C_1-C_6)$alkoxy, hydroxy$(C_1-C_6)$alkyl, amino, $(C_1-C_6)$alkylamino, $((C_1-C_6)$alkyl$)_2$amino or hydroxy$(C_1-C_6)$alkylamino; E is oxygen and $R^5$ is a group of the formula

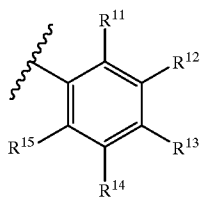

or $R^5$ is a saturated or unsaturated, cyclic or bicyclic $(C_3-C_7)$ heterocyclic group containing as the heteroatom one to four of the group consisting of oxygen, sulfur, nitrogen and $NR^9$ wherein $R^9$ is hydrogen or $(C_1-C_6)$alkyl.

Other preferred compounds of formula I include those wherein m is 1; n is 0; o is 2; p is 0; q is 0; r is 0; A is oxygen; $R^2$ and $R^3$ are hydrogen; $R^1$ is $(C_6-C_{10})$aryl optionally substituted by halo, $(C_1-C_6)$alkyl, $(C_1-C_6)$alkoxy, hydroxy$(C_1-C_6)$alkyl, amino, $(C_1-C_6)$alkylamino, $((C_1-C_6)$alkyl$)_2$amino or hydroxy$(C_1-C_6)$alkylamino; E is oxygen and $R^5$ is a group of the formula

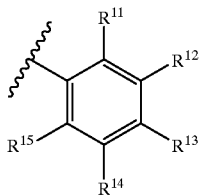

or $R^5$ is a saturated or unsaturated, cyclic or bicyclic $(C_3-C_7)$ heterocyclic group containing as the heteroatom one to four of the group consisting of oxygen, sulfur, nitrogen and $NR^9$ wherein $R^9$ is hydrogen or $(C_1-C_6)$alkyl.

Other preferred compounds of formula I include those wherein m is 0; n is 0; o is 1; p is 1; q is 1; r is 0; $R^2$ and $R^3$ are hydrogen; D is oxygen; $R^4$ is hydrogen; $R^1$ is $(C_6-C_{10})$aryl optionally substituted by halo, $(C_1-C_6)$alkyl, $(C_1-C_6)$alkoxy, hydroxy$(C_1-C_6)$alkyl, amino, $(C_1-C_6)$alkylamino, $((C_1-C_6)$alkyl$)_2$amino or hydroxy$(C_1-C_6)$alkylamino; E is oxygen and $R^5$ is a group of the formula

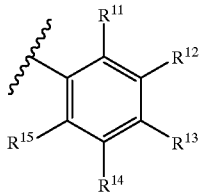

or $R^5$ is a saturated or unsaturated, cyclic or bicyclic $(C_3-C_7)$ heterocyclic group containing as the heteroatom one to four of the group consisting of oxygen, sulfur, nitrogen and $NR^9$ wherein $R^9$ is hydrogen or $(C_1-C_6)$alkyl.

Other preferred compounds of formula I include those wherein m is 0; n is 0, o is 3; p is 0; q is 0; r is 0; $R^2$ is hydrogen or hydroxy, $R^3$ is hydrogen; $R^1$ is $(C_6-C_{10})$aryl optionally substituted by halo, $(C_1-C_6)$alkyl, $(C_1-C_6)$alkoxy, hydroxy$(C_1-C_6)$alkyl, amino, $(C_1-C_6)$alkylamino, $((C_1-C_6)$alkyl$)_2$amino or hydroxy$(C_1-C_6)$alkylamino; E is oxygen and $R^5$ is a group of the formula

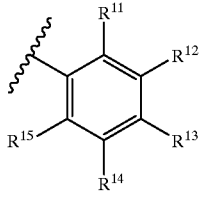

or $R^5$ is a saturated or unsaturated, cyclic or bicyclic $(C_3-C_7)$ heterocyclic group containing as the heteroatom one to four of the group consisting of oxygen, sulfur, nitrogen and $NR^9$ wherein $R^9$ is hydrogen or $(C_1-C_6)$alkyl.

Other preferred compounds of formula I include those wherein m is 1; n is 0; o is 1; p is q is 0; r is 0; A is oxygen; $R^2$ and $R^3$ are hydrogen; D is oxygen; $R^1$ is $(C_6-C_{10})$aryl optionally substituted by halo, $(C_1-C_6)$alkyl, $(C_1-C_6)$alkoxy, hydroxy$(C_1-C_6)$alkyl, amino, $(C_1-C_6)$alkylamino, $((C_1-C_6)$alkyl$)_2$amino or hydroxy$(C_1-C_6)$alkylamino; E is oxygen and $R^5$ is a group of the formula

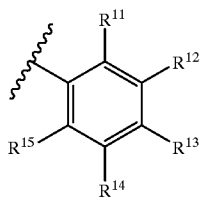

or $R^5$ is a saturated or unsaturated, cyclic or bicyclic ($C_3$–$C_7$) heterocyclic group containing as the heteroatom one to four of the group consisting of oxygen, sulfur, nitrogen and $NR^9$ wherein $R^9$ is hydrogen or ($C_1$–$C_6$)alkyl, Other preferred compounds of formula I include those wherein m is 1; n is 1; o is 1; p is 0; q is 0; r is 0; A is oxygen; B is oxygen; $R^2$ and $R^3$ are hydrogen; $R^1$ is ($C_6$–$C_{10}$)aryl optionally substituted by halo, ($C_1$–$C_6$)alkyl, ($C_1$–$C_6$)alkoxy, hydroxy($C_1$–$C_6$)alkyl, amino, ($C_1$–$C_6$)alkylamino, (($C_1$–$C_6$)alkyl)$_2$amino or hydroxy($C_1$–$C_6$)alkylamino; E is oxygen and $R^5$ is a group of the formula

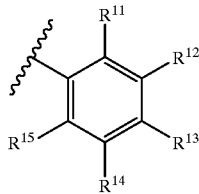

or $R^5$ is a saturated or unsaturated, cyclic or bicyclic ($C_3$–$C_7$) heterocyclic group containing as the heteroatom one to four of the group consisting of oxygen, sulfur, nitrogen and $NR^9$ wherein $R^9$ is hydrogen or ($C_1$–$C_6$)alkyl.

Other preferred compounds of formula I include those wherein m is 1; n is 1; o is 0; p is 1; q is 0; r is 0; A is oxygen; B is NH; D is $NR^8$ wherein $R^8$ is hydrogen or ($C_1$–$C_6$)alkyl; $R^1$ is ($C_6$–$C_{10}$)aryl optionally substituted by halo, ($C_1$–$C_6$)alkyl, ($C_1$–$C_6$)alkoxy, hydroxy($C_1$–$C_6$)alkyl, amino, ($C_1$–$C_6$)alkylamino, (($C_1$–$C_6$)alkyl)$_2$amino or hydroxy($C_1$–$C_6$)alkylamino; E is oxygen and $R^5$ is a group of the formula

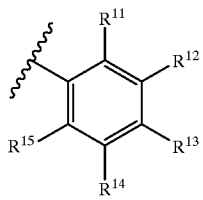

or $R^5$ is a saturated or unsaturated, cyclic or bicyclic ($C_3$–$C_7$) heterocyclic group containing as the heteroatom one to four of the group consisting of oxygen, sulfur, nitrogen and $NR^9$ wherein $R^9$ is hydrogen or ($C_1$–$C_6$)alkyl.

Other preferred compounds of formula I include those wherein m is 0; n is 1; o is 1; p is 0; q is 1; r is 0; B is NH; $R^2$ and $R^3$ are taken together to form a carbonyl group; $R^4$ is hydrogen; $R^1$ is ($C_6$–$C_{10}$)aryl optionally substituted by halo, ($C_1$–$C_6$)alkyl, ($C_1$–$C_6$)alkoxy, hydroxy($C_1$–$C_6$)alkyl, amino, ($C_1$–$C_6$)alkylamino, (($C_1$–$C_6$)alkyl)$_2$amino or hydroxy($C_1$–$C_6$)alkylamino; E is oxygen and $R^5$ is a group of the formula

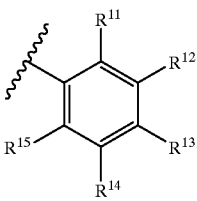

or $R^5$ is a saturated or unsaturated, cyclic or bicyclic ($C_3$–$C_7$) heterocyclic group containing as the heteroatom one to four of the group consisting of oxygen, sulfur, nitrogen and $NR^9$ wherein $R^9$ is hydrogen or ($C_1$–$C_6$)alkyl.

Other preferred compounds of formula I include those wherein m is 1; n is 1; o is 1; p is 0; q is 0; r is 0; A and $R^2$ are taken together to form a group of the formula

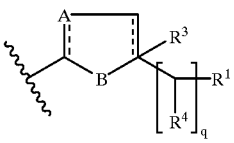

wherein A is nitrogen; B is NH; R is ($C_1$–$C_6$)alkyl or ($C_1$–$C_{10}$)aryl wherein the aryl group is optionally substituted by halo, ($C_1$–$C_6$)alkyl, ($C_1$–$C_6$)alkoxy, hydroxy ($C_1$–$C_6$)alkyl, amino, ($C_1$–$C_6$)alkylamino, (($C_1$–$C_6$)alkyl)$_2$amino or hydroxy($C_1$–$C_6$)alkylamino; E is oxygen and $R^5$ is a group of the formula

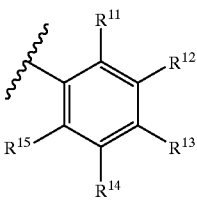

or $R^5$ is a saturated or unsaturated, cyclic or bicyclic ($C_3$–$C_7$) heterocyclic group containing as the heteroatom one to four of the group consisting of oxygen, sulfur, nitrogen and $NR^9$ wherein $R^9$ is hydrogen or ($C_1$–$C_6$)alkyl.

Other preferred compounds of formula I include those wherein m is 0; n is 0; o is 1; p is 0; q is 2; r is 0; $R^2$ is hydrogen or hydroxy; $R^3$ is hydrogen; $R^4$ is independently hydrogen or hydroxy; $R^1$ is ($C_6$–$C_{10}$)aryl optionally substituted by halo, ($C_1$–$C_6$)alkyl, ($C_1$–$C_6$)alkoxy, hydroxy ($C_1$–$C_6$)alkyl, amino, ($C_1$–$C_6$)alkylamino, (($C_1$–$C_6$)alkyl)$_2$ amino or hydroxy($C_1$–$C_6$)alkylamino; E is oxygen and $R^5$ is a group of the formula

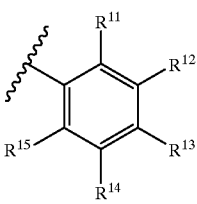

or $R^5$ is a saturated or unsaturated, cyclic or bicyclic ($C_3$–$C_7$) heterocyclic group containing as the heteroatom one to four of the group consisting of oxygen sulfur, nitrogen and NR$^9$ wherein R$^9$ is hydrogen or (C$_1$–C$_6$)alkyl.

Other preferred compounds of formula I include those wherein m is 1; n is 1; o is 1, 2, 3 or 4; p is 0; q is 1, 2 or 3; r is 0; A is oxygen; B is oxygen; R$^2$, R$^3$, R$^4$ and R$^1$ are hydrogen; E is oxygen and R$^5$ is a group of the formula

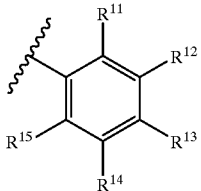

or R$^5$ is a saturated or unsaturated, cyclic or bicyclic (C$_3$–C$_7$) heterocyclic group containing as the heteroatom one to four of the group consisting of oxygen, sulfur, nitrogen and NR$^9$ wherein R$^9$ is hydrogen or (C$_1$–C$_6$)alkyl.

Other preferred compounds of formula I include those wherein m is 1; n is 1; o is 1; p is 0; q is 0; r is 0; A and R$^2$ are taken together to form a group of the formula

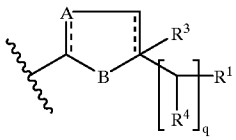

wherein A is nitrogen; B is oxygen; R$^1$ is (C$_1$–C$_6$)alkyl or (C$_6$–C$_{10}$)aryl wherein the aryl group is optionally substituted by halo, (C$_1$–C$_6$)alkyl, (C$_1$–C$_6$)alkoxy, hydroxy (C$_1$–C$_6$)alkyl, amino, (C$_1$–C$_6$)alkylamino, ((C$_1$–$_6$)alkyl)$_2$amino or hydroxy(C$_1$–C$_6$)alkylamino; E is oxygen and R$^5$ is a group of the formula

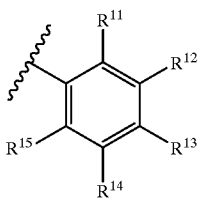

or R$^5$ is a saturated or unsaturated, cyclic or bicyclic (C$_3$–C$_7$) heterocyclic group containing as the heteroatom one to four of the group consisting of oxygen, sulfur, nitrogen and NR$^9$ wherein R$^9$ is hydrogen or (C$_1$–C$_6$)alkyl.

Other preferred compounds of formula I include those wherein m is 1; n is 1; o is 1; p is 0; q is 0; r is 0; A and R$^2$ are taken together to form a group of the formula

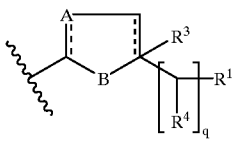

wherein A is oxygen; B is oxygen; R$^1$ is (C$_1$–C$_6$)alkyl or (C$_6$–C$_{10}$)aryl wherein the aryl group is optionally substituted by halo, (C$_1$–C$_6$)alkyl, (C$_1$–C$_6$)alkoxy, hydroxy (C$_1$–C$_6$)alkyl, amino, (C$_1$–C$_6$)alkylamino, ((C$_1$–C$_6$) lkyl)$_2$amino or hydroxy(C$_1$–C$_6$)alkylamino; E is oxygen and R$^5$ is a group of the formula

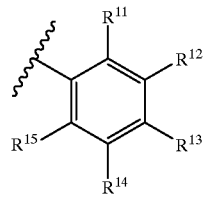

or R$^5$ is a saturated or unsaturated, cyclic or bicyclic (C$_3$–C$_7$) heterocyclic group containing as the heteroatom one to four of the group consisting of oxygen, sulfur, nitrogen and NR$^9$ wherein R$^9$ is hydrogen or (C$_1$–C$_6$)alkyl.

Other preferred compounds of formula I include those wherein m is 1; n is 0; o is 0; p is 0; q is 0; r is 0; A is oxygen; R$^1$ is (C$_6$–C$_{10}$)aryl or a saturated or unsaturated, cyclic or bicyclic (C$_3$–C$_7$) heterocyclic group containing as the heteroatom one to four of the group consisting of oxygen, sulfur, nitrogen and NR$^9$ wherein R$^9$ is a hydrogen or (C$_1$–C$_6$)alkyl wherein the aryl or heterocyclic groups are optionally substituted by halo, (C$_1$–C$_6$)alkyl, (C$_1$–C$_6$) alkoxy, hydroxy(C$_1$–C$_6$)alkyl, amino, (C$_1$–C$_6$)alkylamino, ((C$_1$–C$_6$)alkyl)$_2$amino or hydroxy(C$_1$–C$_6$)alkylamino; E is oxygen and R$^5$ is a group of the formula

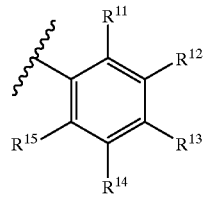

or R$^5$ is a saturated or unsaturated, cyclic or bicyclic (C$_3$–C$_7$) heterocyclic group containing as the heteroatom one to four of the group consisting of oxygen, sulfur, nitrogen and NR$^9$ wherein R$^9$ is hydrogen or (C$_1$–C$_6$)alkyl.

Other preferred compounds of formula I include those wherein m is 1; n is 1; o is 0; p is 0; q is 1; r is 0; A is oxygen; B is NH; R$^4$ is hydroxy (C$_1$–C$_6$)alkyl; R$^1$ is (C$_1$–C$_6$)alkyl; E is oxygen and R$^5$ is a group of the formula

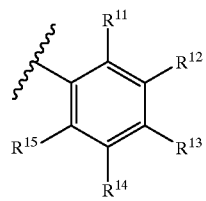

or R$^5$ is a saturated or unsaturated, cyclic or bicyclic (C$_3$–C$_7$) heterocyclic group containing as the heteroatom one to four of the group consisting of oxygen, sulfur, nitrogen and NR$^9$ wherein R$^9$ is hydrogen or (C$_1$–C$_6$)alkyl.

Specific preferred compounds of formula I include the following:

N-(4-(1-Hydroxy-1-methyl-ethyl)-benzyl)-2-(3-methyl-benzo(d)isoxazol-7-yloxy)-nicotinamide;
N-(4-(1-Hydroxy-1-methyl-ethyl)-benzyl)-2-(3-oxo-indan-5-yloxy)-nicotinamide;
2-(3-(1-Hydroxyimino-ethyl)-phenoxy)-N-(4-(1-Hydroxy-1-methyl-ethyl)-benzyl)-nicotinamide;
N-(4-(1-Hydroxy-1-methyl-ethyl)-benzyl)-2-(4-oxo-chroman-6-yloxy)-nicotinamide;
(±) 2-(3-Acetyl-phenoxy)-N-(1-hydroxy-indan-5-ylmethyl)-nicotinamide;
2-(2,3-Dihydro-benzo(1,4)dioxin-6-yloxy)-N-(4-(1-Hydroxy-1-methyl-ethyl)-benzyl)-nicotinamide;
N-(4-(1-Hydroxy-1-methyl-ethyl)-benzyl)-2-(3-(1-methoxyimino-ethyl)-phenoxy)-nicotinamide;
N-(2-Chloro-benzyl)-2-(4-fluoro-phenoxy)-nicotinamide;
N-(5-Chloro-thiophen-2-ylmethyl)-2-(pyridin-3-yloxy)-nicotinamide;
2-(4-Fluoro-phenoxy)-N-[4-(3-hydroxy-azetidin-1-yl)-benzyl]-nicotinamide;
N-[4-(1-Hydroxy-1-methyl-ethyl)-benzyl]-2-(3-nitro-phenoxy)-nicotinamide;
2-(4-Fluoro-phenoxy)-N-(2-oxo-2,3-dihydro-1H-indol-5-ylmethyl)-nicotinamide;
N-[2-(3-Acetyl-phenoxy)-pyridin-3-yl]-2-[4-(1-hydroxy-1-methyl-ethyl)-phenyl]-acetamide;
3-{3-[4-(1-Hydroxy-1-methyl-ethyl)-benzylcarbamoyl]-pyridin-2-yloxy}-benzoic acid methyl ester;
2-(4-Fluoro-phenoxy)-N-[4-(1-hydroxy-1-methyl-ethyl)-benzyl]-nicotinamide;
2-(4-Fluoro-phenoxy)-N-(1-thiophen-2-yl-ethyl)-nicotinamide;
N-[2-Chloro-4-(1-hydroxy-1-methyl-ethyl)-benzyl]-2-(3-cyano-phenoxy)-nicotinamide;
2-(3-Cyano-4-fluoro-phenoxy)-N-[4-(1-hydroxy-1-methyl-ethyl)-benzyl]-nicotinamide;
N-[2-Chloro-4-(1-hydroxy-1-methyl-ethyl)-benzyl]-2-(3,4-difluoro-phenoxy)-nicotinamide;
(+)-2-(Benzo[1,3]dioxol-5-yloxy)-N-[4-(1-hydroxy-ethyl)-cyclohexylmethyl]-nicotinamide;
(−)-2-(3-Cyano-4-fluoro-phenoxy)-N-[4-(1-hydroxy-ethyl)-cyclohexylmethyl]-nicotinamide;
(+)-2-(3-Cyano-4-fluoro-phenoxy)-N-[4-(1-hydroxy-ethyl)-cyclohexylmethyl]-nicotinamide;
(+)-2-(2,3-Dihydro-benzo[1,4]dioxin-6-yloxy)-N-[4-(1-hydroxy-ethyl)-cyclohexylmethyl]-nicotinamide;
(−)-2-(2,3-Dihydro-benzo[1,4]dioxin-6-yloxy)-N-[4-(1-hydroxy-ethyl)-cyclohexylmethyl]-nicotinamide;
2-(Benzo[1,3]dioxol-5-yloxy)-N-[4-(1-hydroxy-1-methyl-ethyl)-benzyl]-nicotinamide,
2-(Benzo[1,3]dioxol-5-yloxy)-N-[4-(1-hydroxy-1-methyl-ethyl)-cyclohexylmethyl]-nicotinamide;
2-(3-Acetyl-phenoxy)-N-[4-(1-hydroxy-ethyl)-cyclohexylmethyl]-nicotinamide; and
2-(3-Cyano-4-fluoro-phenoxy)-N-[2-fluoro-4-(1-hydroxy-1-methyl-ethyl)-benzyl]-nicotinamide;
N-[2-Chloro-4-(1-hydroxy-1-methyl-ethyl)-benzyl]-2-(3-cyano-4-fluoro-phenoxy)-nicotinamide;
2-(3-Acetyl-phenoxy)-N-[2-chloro-4-(1-hydroxy-1-methyl-ethyl)-benzyl]-nicotinamide;
2-(3-Acetyl-phenoxy)-N-[4-(1-hydroxy-1-methyl-ethyl)-cyclohexylmethyl]-nicotinamide;
2-(3-Acetyl-phenoxy)-N-[4-(1-hydroxy-1-methyl-ethyl)-benzyl]-nicotinamide;
2-(3,4-Difluoro-phenoxy)-N-[4-(1-hydroxy-1-methyl-ethyl)-benzyl]-nicotinamide;
2-(4-Fluoro-phenoxy)-N-[4-(1-hydroxy-1-methyl-ethyl)-cyclohexylmethyl]-nicotinamide;
2-(3-Cyano-phenoxy)-N-[4-(1-hydroxy-1-methyl-ethyl)-cyclohexylmethyl]-nicotinamide;
N-[4-(1-Hydroxy-1-methyl-ethyl)-benzyl]-2-(3-methoxy-phenoxy)-nicotinamide;
2-(3-Cyano-phenoxy)-N-[4-(1-hydroxy1-methyl-ethyl)-benzyl]-nicotinamide;
N-[4-(1-Hydroxy-1-methyl-ethyl)-benzyl]-2-(pyridin-3-yloxy)-nicotinamide; and
2-(3-Acetyl-phenoxy)-N-[4-(1-hydroxy-1-methyl-ethyl)-benzyl]-nicotinamide.

The present invention also relates to a pharmaceutical composition for the treatment of respiratory, allergic, rheumatoid, body weight regulation, inflammatory and central nervous system disorders such as asthma, chronic obstructive pulmonary disease, adult respiratory diseases syndrome, shock, fibrosis, pulmonary hypersensitivity, allergic rhinitis, atopic dermatitis, psoriasis, weight control, rheumatoid arthritis, cachexia, crohn's disease, ulcerative colitis, arthritic conditions and other inflammatory diseases, depression, multi-infarct dementia and AIDS in a mammal, including a human, comprising an amount of a compound of claim 1 or a pharmaceutically acceptable salt thereof, effective in such preventions or treatment and a pharmaceutically acceptable carrier.

The present invention also relates to a method for the treatment of respiratory, allergic, rheumatoid, body weight regulation, inflammatory and central nervous system disorders such as asthma, chronic obstructive pulmonary disease, adult respiratory diseases syndrome, shock, fibrosis, pulmonary hypersensitivity, allergic rhinitis, atopic dermatitis, psoriasis, weight control, rheumatoid arthritis, cachexia, crohn's disease, ulcerative colitis, arthritic conditions and other inflammatory diseases, depression, multi-infarct dementia and AIDS in a mammal, including a human, comprising administering to said mammal an amount of a compound of claim 1 or a pharmaceutically acceptable salt thereof, effective in such treatment The present invention also relates to a pharmaceutical composition for selective inhibition of PDE4 D isozymes which regulate the activation and degranulation of human eosinophils useful in the treatment of respiratory, allergic, rheumatoid, body weight regulation, inflammatory and central nervous system disorders such as asthma, chronic obstructive pulmonary disease, adult respiratory diseases syndrome, shock, fibrosis, pulmonary hypersensitivity, allergic rhinitis, atopic dermatitis, psoriasis, weight control, rheumatoid arthritis, cachexia, crohn's disease, ulcerative colitis, arthritic conditions and other inflammatory diseases, depression, multi-infarct dementia and AIDS in a mammal, including a human, comprising administering to said mammal a PDE4 D isozyme inhibiting effective amount of a PDE4 D isozyme inhibiting compound or a pharmaceutically acceptable salt thereof, effective in such treatment and a pharmaceutically acceptable carrier.

The present invention also relates to a method for selective inhibition of PDE4 D isozymes which regulate the activation and degranulation of human eosinophils useful in the treatment of respiratory, allergic, rheumatoid, body weight regulation, inflammatory and central nervous system disorders such as asthma, chronic obstructive pulmonary disease, adult respiratory diseases syndrome, shock, fibrosis, pulmonary hypersensitivity, allergic rhinitis, atopic dermatitis, psoriasis, weight control, rheumatoid arthritis, cachexia, crohn's disease, ulcerative colitis, arthritic conditions and other inflammatory diseases, depression, multi-infarct dementia and AIDS in a mammal, including a human, comprising administering to said mammal a PDE4 D isozyme inhibiting effective amount of a PDE4 D isozyme inhibiting compound or a pharmaceutically acceptable salt thereof, effective in such treatment.

DETAILED DESCRIPTION OF THE INVENTION

The following reaction Schemes illustrate the preparation of compounds of the present invention.

SCHEME 1
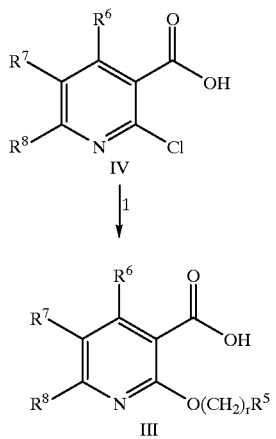
SCHEME 2
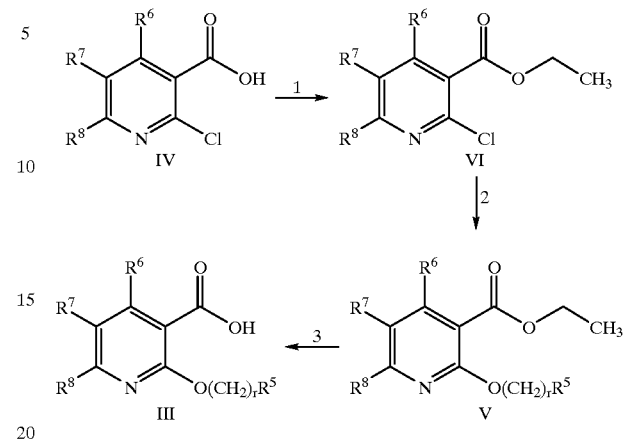
SCHEME 3
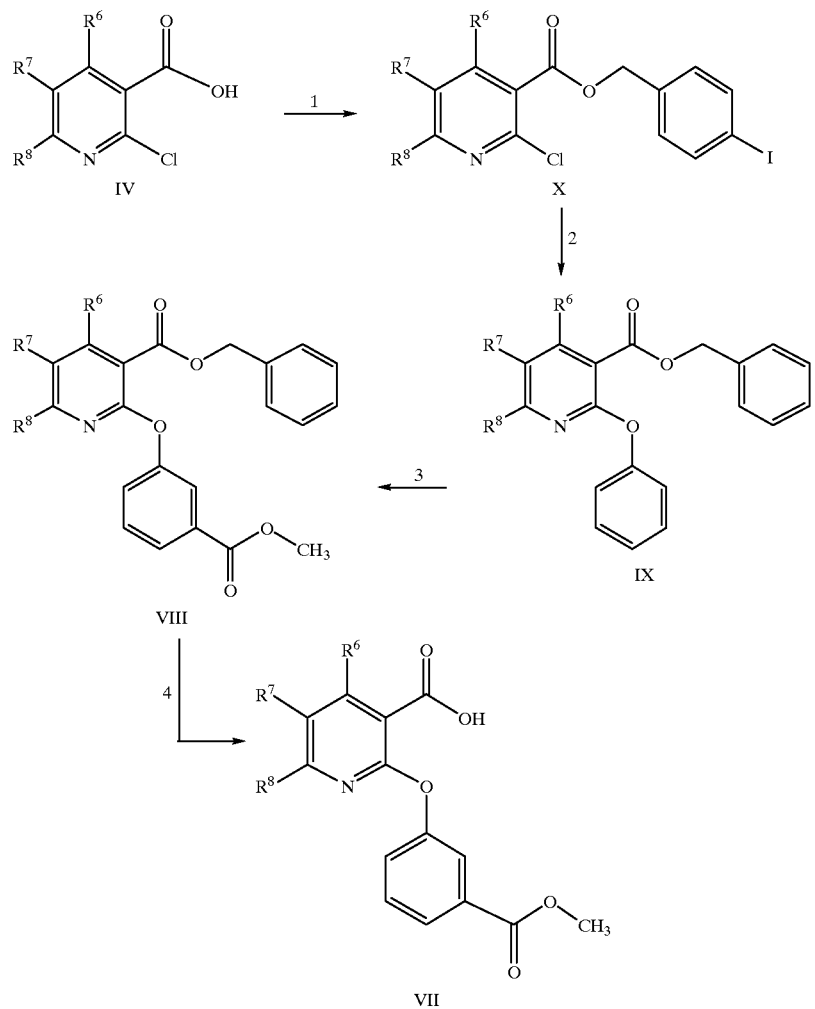

SCHEME 4
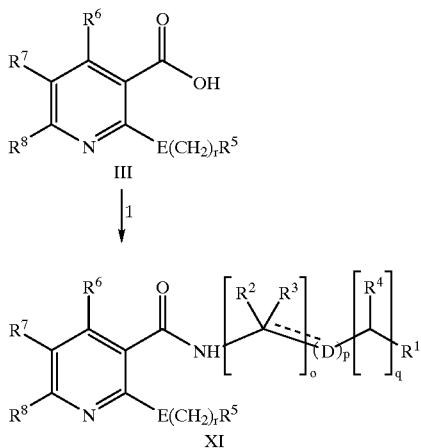
SCHEME 5
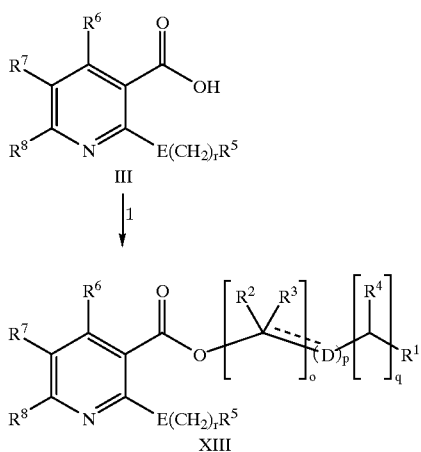
SCHEME 6
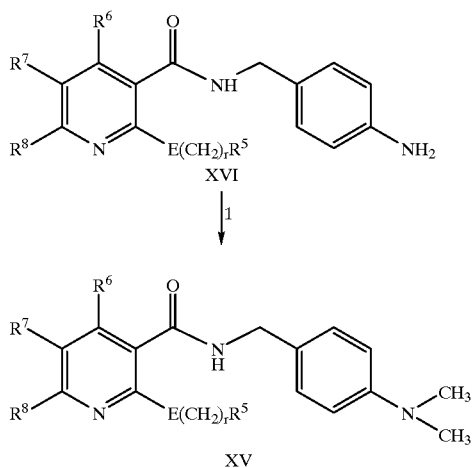
SCHEME 7
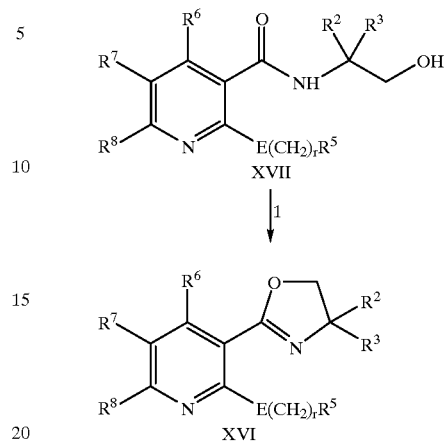
SCHEME 8
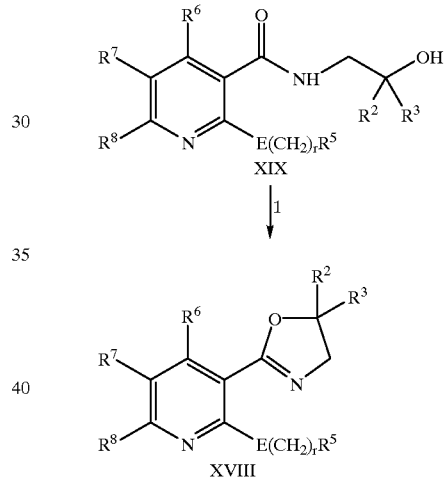
SCHEME 9
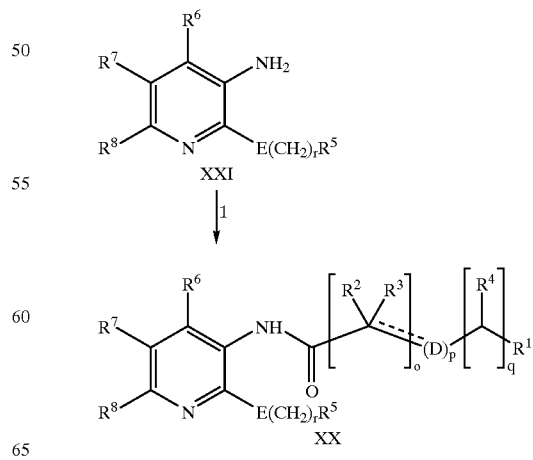

SCHEME 10
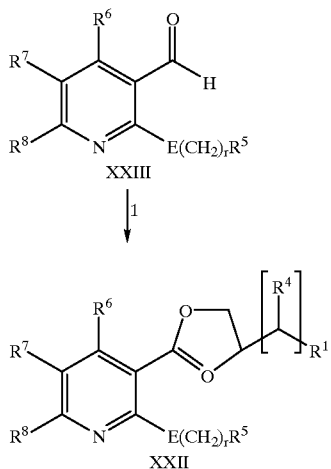
SCHEME 11
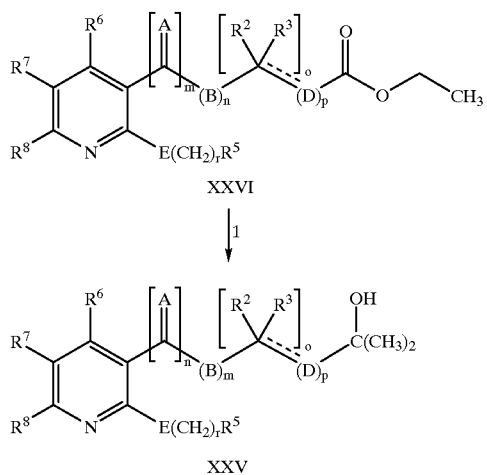
SCHEME 12
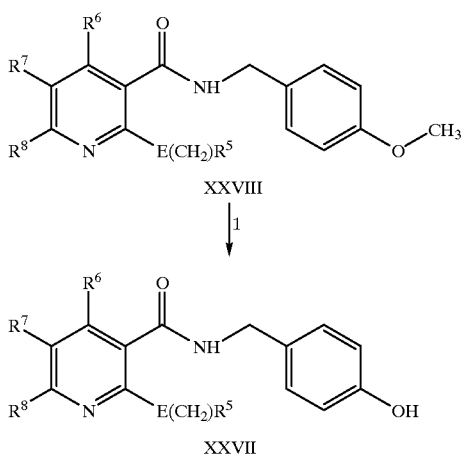
SCHEME 13
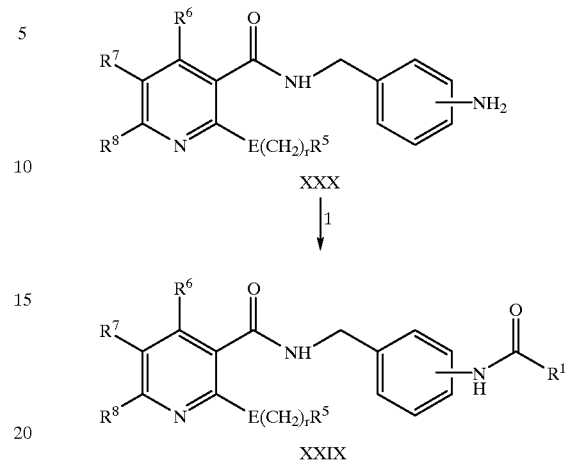
SCHEME 14
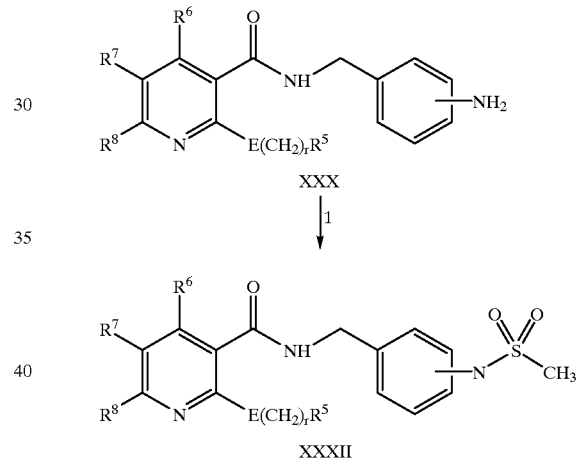
SCHEME 15
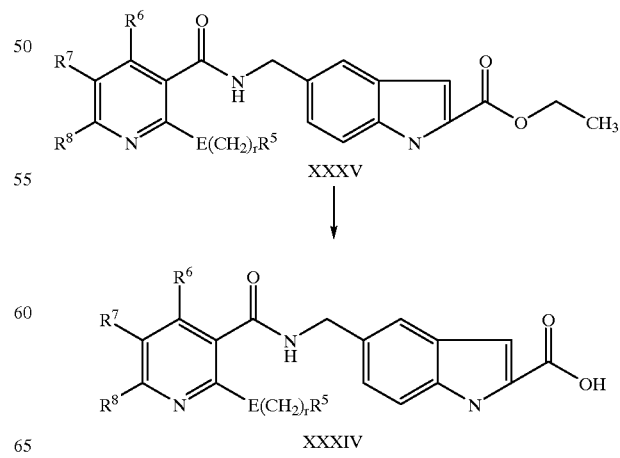

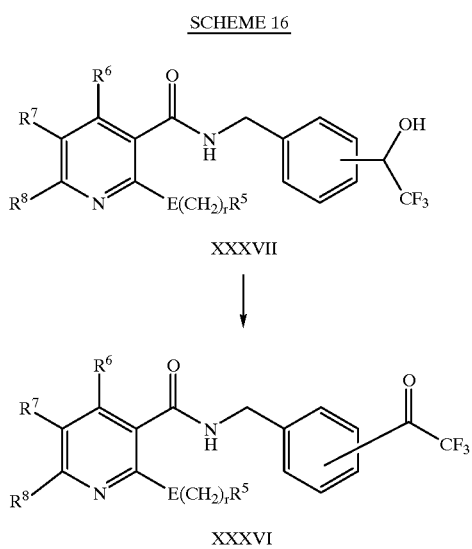

SCHEME 20
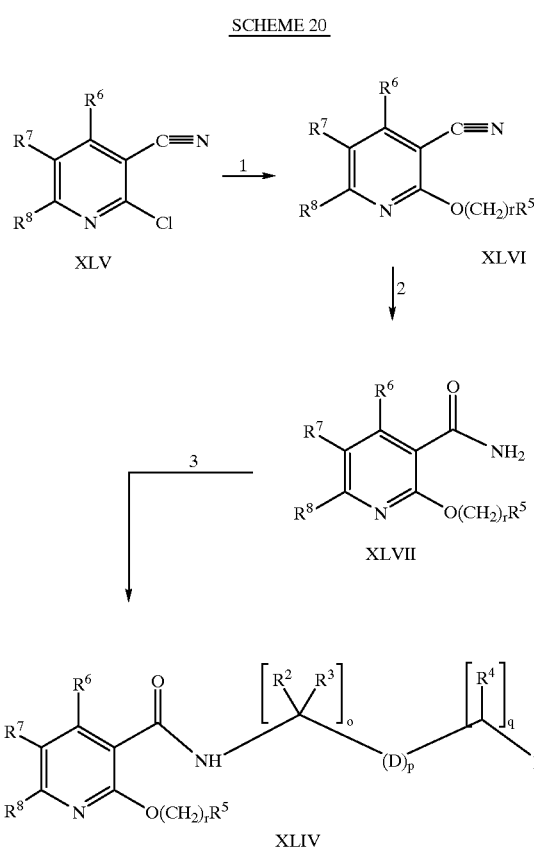
SCHEME 21
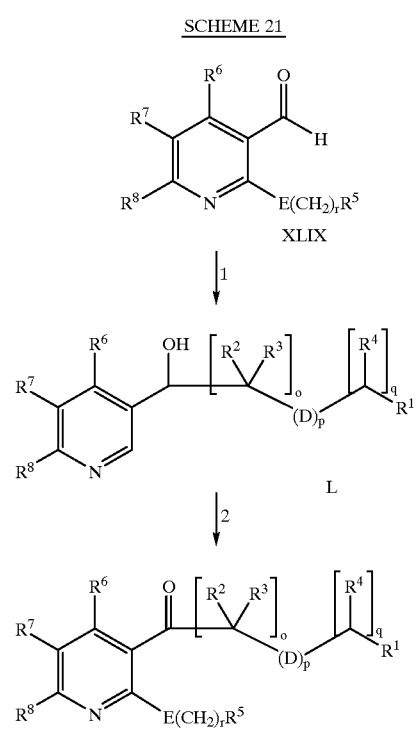
SCHEME 22
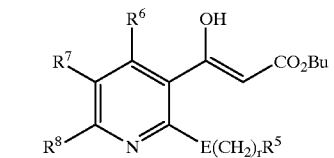
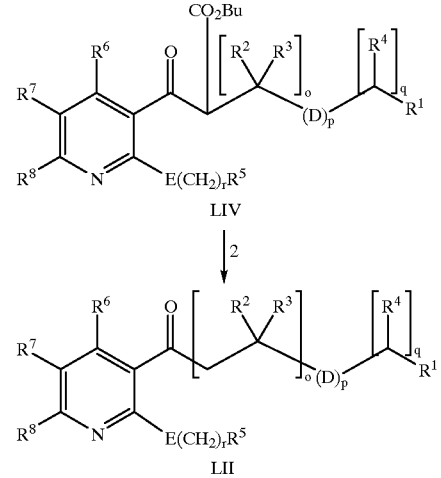
SCHEME 23
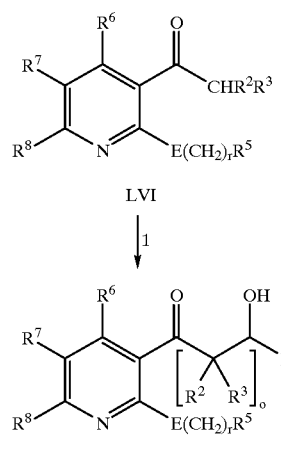
SCHEME 24
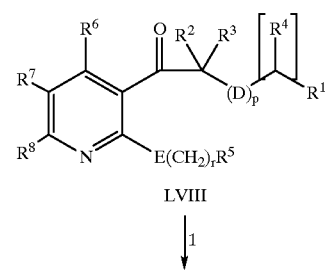

-continued

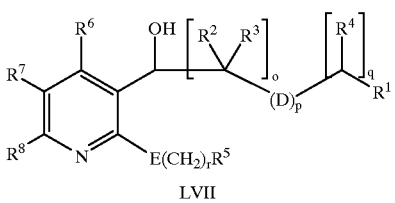
LVII

SCHEME 25

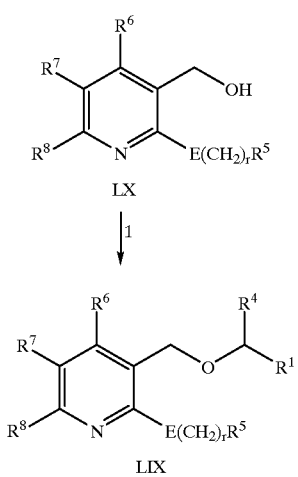

SCHEME 26

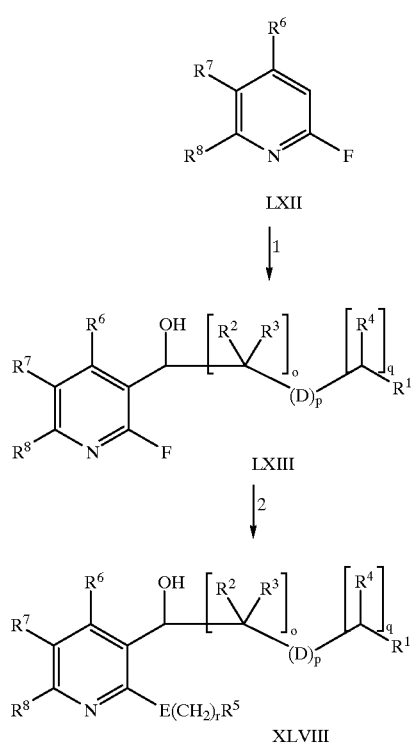

SCHEME 27

LXVI

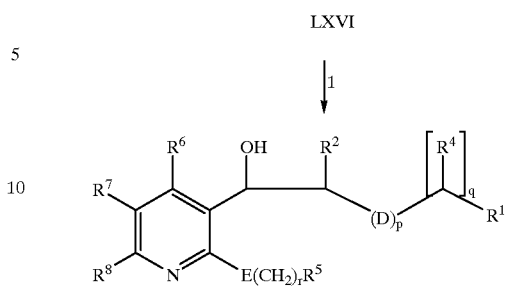

LXVII

SCHEME 28

LXVI

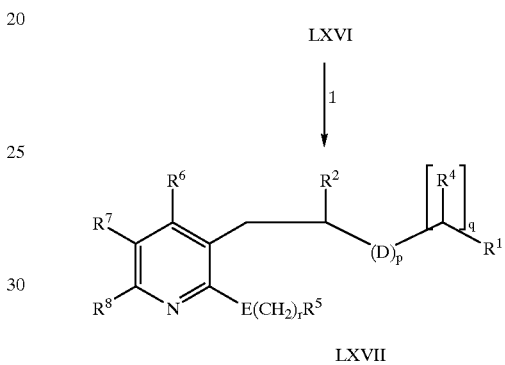

LXVII

In reaction 1 of Scheme 1, the 2-chloropyridine compound of formula IV is converted to the corresponding compound of formula III by reacting IV with a compound of the formula, $R^5(CH_2)_r$—OH, in the presence of sodium hydride and a polar aprotic solvent, such as dimethylformamide. The reaction is carried out at room temperature for a time period between about 3 hours to about 20 hours, preferably about 4 hours.

In reaction 1 of Scheme 2, the 3-carboxylic acid compound of formula IV is converted to the corresponding ethyl ester pyridine compound of formula VI by reacting IV with ethanol in the presence of thienyl chloride. The reaction mixture is heated to reflux for a time period between about 1 hour to about 3 hours, preferably about 1.5 hours.

In reaction 2 of Scheme 2, the 2-chloropyridine compound of formula VI is converted to the corresponding compound of formula V by reacting IV with a compound of the formula, $R^5(CH_2)_r$—OH, in the presence of cesium carbonate and a polar aprotic solvent, such as; dimethylformamide. The reaction is carried out at a temperature between about 65° C. to about 90° C., preferably about 65° C., for a time period between about 10 hours to about 18 hours, preferably about 10 hours.

In reaction 3 of Scheme 2, the ethyl ester pyridine compound of formula V is converted to the corresponding 3-carboxylic acid compound of formula III by reacting V with ethanol in the presence of sodium hydroxide. The reaction mixture is heated to reflux for a time period between about 3 hours to about 5 hours, preferably about 4 hours.

In reaction 1 of Scheme 3, the 3-carboxylic acid compound of formula IV is converted to the corresponding benzyl ester pyridine compound of formula X by reacting IV with benzyl bromide in the presence of potassium carbonate and a polar aprotic solvent, such as dimethylformamide. The reaction is carried out at room temperature for a time period between about 1 hour to about 24 hours, preferably about 10 hours.

In reaction 2 of Scheme 3, the 2-chloropyridine compound of formula X is converted to the corresponding compound of formula IX by reacting X with 3-iodophenol in the presence of cesium carbonate and a polar aprotic solvent, such as dimethylformamide. The reaction is carried out at a temperature between about 70° C. to about 80° C., preferably about 75° C., for a time period between about 1 hours to about 6 hours, preferably about 2 hours.

In reaction 3 of Scheme 3, the (3-iodo-phenoxy) pyridine compound of formula IX is converted to the corresponding compound of formula VIII by reacting IX with carbon monoxide and methanol in the presence of palladium acetate, 1,1-bix(diphenylphosphino)-ferrocene, triethylamide and a polar aprotic solvent, such as dimethylformamide. The reaction mixture is heated to a temperature between about 50° to about 70° C., preferably about 60° C., for a time period between about 2 hours to about 4 hours, preferably about 4 hours.

In reaction 4 or Scheme 3, the benzyl ester pyridine compound of formula VIII is converted to the corresponding compound of VIII by hydrogenating VIII in the presence of palladium on carbon, methanol and ethyl acetate. The reaction is carried out at room temperature for a time period between about 1 hour to about 2 hours, preferably about 2 hours.

In reaction 1 of Scheme 4, the carboxylic acid pyridine compound of formula III is converted to the corresponding compound of formula XI by reacting III with a compound of the formula

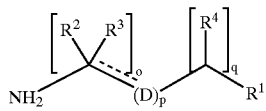

XII by one of four different synthetic methods.

In the first method, the compound of formula III is reacted with XII in the presence of 1-ethyl-3-(3-dimethylaminopropyl)carbodiimide, 1-hydroxybenzotriazole hydrate and a polar aprotic solvent, such as dimethylformamide. The reaction is carried out at room temperature for a time period between about 1 hour to about 24 hours, preferably about 10 hours. In the second method, III is reacted a chloroformate such as isobutylchloroformate, in the presence of N-methylmorpoline and a polar aprotic solvent, such as methylene chloride, at a temperature between about 0° C. to about −20° C., preferably about −10° C., for a time period between about 15 minutes to about 1 hour, preferably about 30 minutes. The reaction mixture is warmed to room temperature and the compound of formula XII is added. The resulting reaction mixture is stirred for a time period between about 1 hour to about 24 hours, preferably about 10 hours.

In the third method, the compound of formula III is heated to reflux in the presence of thionyl chloride for a time period between about 1 hour to about 24 hours, preferably about 1 hours. The resulting acid chloride is then reacted with the compound of formula XII in the presence of pyridine and a polar aprotic solvent, such as tetrahydrofuran. The reaction is carried out at a temperature between about 0° C. to about room temperature, preferably about 0° C.

In the fourth method, the compound of formula II is reacted with XII in the presence of BOP, diisopropyl ethyl amine and a polar aprotic solvent,such as dimethylformamide. The reaction is carried out at room temperature for a time period between about 3 hours to about 4 hours, preferably about 4 hours.

In reaction 1 of Scheme 5the 3-carboxylic acid pyridine compound of formula III is converted to the corresponding compound of formula XIII by reacting III with a compound of the formula

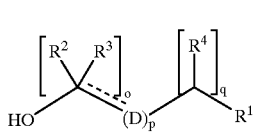

XIV in the presence of 4-dimethylaminopyridine, 1-(3-dimethylaminopropyl)-3-ethylcarbodiimide hydrochloride, pyridine and diethyl ether. The reaction is carried out at room temperature for a time period between about 1 hour to about 3 hours, preferably about 1 hours.

In reaction 1 of Scheme 6, the compound of formula XVI is converted to the corresponding compound of formula XV by reacting XVI with acetonitrile in the presence of formaldehyde and sodium cyanoborohydride. The reaction is carried out at room temperature for a time period between about 14 hours to about 16 hours, preferably about 16 hours.

In reaction 1 of Scheme 7, the compound of formula XVII is converted to the corresponding compound of formula XVI by first reacting XVII with phosphorus oxychloride in an aprotic solvent, such as toluene, then treating the compound so formed with sodium hydroxide in a polar protic solvent, such as methanol. The reaction is carried out at a temperature between about 0° C. to room temperature, preferably about 22° C., for a time period between about 1 hour to about 24 hours, preferably about 12 hours.

In reaction 1 of Scheme 8, the compound of formula XIX is converted to the corresponding compound of formula XVIII by a method to that described in reaction 1 of Scheme 7.

In reaction 1 of Scheme 9, the 3-aminopyridine compound of formula XXI is converted to the corresponding compound of formula XX by reacting XXI with a compound of the formula

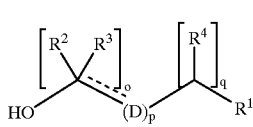

XIV in the presence of 1-hydroxybenzotriazole hydrate and a polar aprotic solvent, such as dimethylformamide. The reaction is carried out at room temperature for a time period between about 1 hour to about 24 hours, preferably about 16 hours.

In reaction 1 of Scheme 10, the compound of formula XXIII is converted to the corresponding compound of formula XXII by reacting XXIII with a compound of the formula

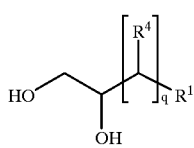

XXIV in the presence of p-toluenesulfonic acid and an aprotic solvent, such as toluene. The reaction is mixture heated to reflux for a time period between about 1 hour to about 48 hours, prefereably about 24 hours.

In reaction 1 of Scheme 11, the compound of formula XXVI is converted to the corresponding compound of formula XXV by reacting XXVI with methyl lithium in an aprotic solvent, such as tetrahydrofuran. The reaction is carried out at a temperature between about 75° C. to about −85° C., preferably about −78° C., for a time period between about 1 hour to about 6 hours, preferably about 2 hours.

In reaction 1 of Scheme 12, the compound of formula XXVII by reacting XXVIII with boron tribromide in a polar aprotic solvent, such as methylene chloride. The reaction is carried out at a temperature between about −78° C. to room temperature, preferably about 0° C., for a time period between about 1 hour to about 24 hours, preferably about 16 hours.

In reaction 1 of Scheme 13, the compound of formula XXX is converted to the corresponding compound of formula XXIX by reacting XXX with a compound of the formula

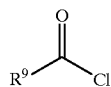

XXXI in the presence of triethylamine and a polar aprotic solvent, such as methylene chloride. The reaction is carried out at a temperature between about 0° C. to room temperature, preferably about 0° C., for a time period between about 30 minutes to about 2 hours, prefereably about 1 hours.

In reaction 1 of Scheme 14, the compound of formula XXX is converted to tie corresponding compound of formula XXXII by reacting XXX with methanesulfonic anhydride in the presence of triethylamine. The reaction is carried out at room temperature for a time period between about 30 minutes to about 24 hours, preferably about 12 hours.

In reaction 1 of Scheme 15, the compound of formula XXXV is converted to the corresponding compound of formula XXXIV by reacting XXXV with sodium hydroxide in a polar aprotic solvent, such as ethanol. The reaction is heated to reflux for a time period between about 1 hour to about 24 hours, preferably about 9 hours.

In reaction 1 of Scheme 16, the compound of formula XXXVII is converted to the corresponding compound of formula XXXVI by oxidizing XXXVII with tetrapropylammonium perruthenate and 4-methylmorpholine N-oxide in a polar aprotic solvent, such as methylene chloride. The reaction is carried out at room temperature for a time period between about 2 hours to about 6 hours, perferably about 4 hours.

In reaction 1 of Scheme 17, the 2-aminopyridine compound of formula XXXIX is converted to the corresponding compound of formula XXXVIII by reacting XXXIX with a compound of the formula, $R^5$—N=C=O. The reaction is heated to reflux for a time period between about 1 hour to about 24 hours, preferably about 16 hours.

In reaction 1 of Scheme 18, the 2-nitropyridine compound of formula XLI is converted to the correspond 2-aminopyridine compound of formula XL by reducing XLI with 10% platinum oxide on carbon, methanol and tetrahydrofuran. The reaction is carried out at room temperature for a time period between about 1 hour to about 3 hours, preferably about 2 hours.

In reaction 1 of Scheme 19, the compound of formula XLIII is converted to the corresponding compound of formula XLII by reacting XLIII with MCPBA in a polar aprotic solvent, such as methylene chloride. The reaction is carried out at room temperature for a time period between about 1 hour to about 4 hours, prefereably about 1 hours.

In reaction 1 of Scheme 20, the 2-chloropyridine compound of formula XLV is converted to the corresponding compound of formula XLVI by reacting XLV with a compound of the formula, $R^5(CH_2)_rOH$, in the presence of cesium carbonate and a polar aprotic solvent, such as dimethylformamide. The reaction is carried out at a temperature between about 65° C. to about 90° C., preferably about 80° C., for a time period between about 10 hours to about 18 hours, preferably about 16 hours.

In reaction 2 of Scheme 20, the 3-cyanopyridine compound of formula XLVI is converted to the corresponding compound of formula XLVII by reacting XLVI with hydrogen peroxide in the presence of potassium hydroxide and a polar protic solvent, such as ethanol. The reaction is carried out at room temperature for a time period between about 1 hour to about 24 hours, preferably about 12 hours.

In reaction 3 of Scheme 20, the compound of formula XLVII is converted to the corresponding compound of formula XLIV by reacting XLVII with a compound of the formula

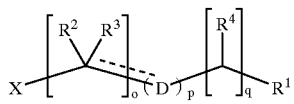

XLVIII wherein X is chloro, bromo or iodo, in the presence of potassium hydroxide and a polar aprotic solvent, such as dimethyl sulfoxide. The reaction is carried at room temperature for a time period between about 1 hour to about 24 hours, preferably about 1 hours.

In reaction 1 of Scheme 21, the compound of formula XLIX is converted to the corresponding compound of formula L by reacting XLIX with a compound of the formula

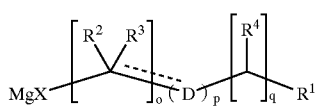

in a polar aprotic solvent, such a tetrahydrofuran. The reaction is carried out at a temperature between about −85° C. to about −75° C., preferably about 78° C., for a time period between about 0.5 hours to about 16 hours, preferably about 2 hours.

In reaction 2 of Scheme 21, the compound of formula L is converted to the corresponding compound of formula XLVIII by reacting L with chromic acid, sulfuric acid and water in a polar aprotic solvent, such as acetone. The reaction is carried out at a temperature between about 0° C. to about 25° C., preferably about 0° C., for a time period between about 0.5 hours to about 16 hours, preferably 2 hours.

In reaction 1 of Scheme 22, the compound of formula LIII is converted to the corresponding compound of formula LIV by reacting LIII with a compound of the formula

XLVIII

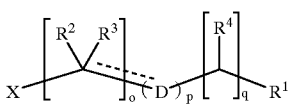

in the presence of sodium hydride and a polar aprotic solvent, such as tetrahydrofuran. The reaction is carried out at a temperature between about 0° C. to about 60° C., preferably about 0° C., for a time period between about 1 hours to about 16 hours, preferably about 4 hours.

In reaction 2 of Scheme 22, the compound of formula LIV is converted to the corresponding compound of formula LII by reacting LIV with trifluoroacetic acid neat for a time period between about 1 hours to about 16 hours, preferably about 4 hours.

In reaction 1 of Scheme 23, the compound of formula LVI is converted to the corresponding compound of formula LV by reacting LVI with a compound of the formula, $R^1CHO$, in the presence of lithium diisopropylamide and a polar aprotic solvent, such as tetrahydrofuran. The reaction is carried out at a temperature between about −75° C. to about −85° C., preferably about −78° C., for a time period between about 1 hour to about 6 hours, preferably about 1 hours.

In reaction 1 of Scheme 24, the compound of formula LVIII is converted to the corresponding compound of formula LVII by reacting LVIII with sodium borohydride in the presence of a polar protic solvent, such as methanol. The reaction is carried out at a temperature between about −10° C. to about 10° C., preferably about 0° C., for a time period between about 0.5 hours to about 16 hours, preferably about 1 hours.

In reaction 1 of Scheme 25, the compound of formula LX is converted to the corresponding compound of formula LIX by reacting LX with a compound of the formula

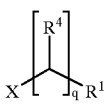

wherein X is chloro, bromo or iodo, in the presence of sodium hydride and a polar aprotic solvent, such as dimethylformamide.

In reaction 1 of Scheme 26, the 2-fluoropyridine compound of formula LXII is converted to the corresponding compound of formula LXIII, by reacting LXII, with a compound of the formula

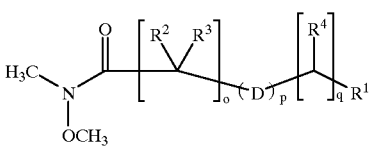

in the presence of lithium diisopropylamide and a polar aprotic solvent, such as tetrahydrofuran.

In reaction 2 of Scheme 26, the compound of formula LXIII is converted to the corresponding compound of formula XLVIII, by reacting LXIII with a compound of the formula, $HE—(CH_2)_r—R^5$, in the presence of sodium hydride and a polar aprotic solvent, such as dimethylformamide.

In reaction 1 of Scheme 27, the compound of formula LXV is converted to the corresponding compound of formula LXVI, by reacting LXV with the Burgess reagent, $CH_3OOCNSO_2NCH_2CH_3$, in the presence of benzene.

In reaction 2 of Scheme 27, the compound of formula LXVI is converted to the corresponding compound of formula LXIV, by reacting LXVI with osminum tetroxide in the presence of tert-butanol, NMO and actone.

In reaction 1 of Scheme 28, the compound of formula LXVI is converted tot he corresponding compound of formula LXVII by hydrogenating LXVI in the presence of pallidium on carbon and ethanol.

The compounds of formula I that are basic in nature are capable of forming a wide variety of different salts with various inorganic and organic acids. Although such salts must be pharmaceutically acceptable for administration to humans or animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Pharmaceutically acceptable salts of amino groups include hydrochloride (preferred), hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. Cationic salts of the compounds of formula I are similarly prepared except through reaction of a carboxy group, such as where $R^6$ is carboxy, with an appropriate cationic salt reagent such as sodium, potassium, calcium, magnesium, ammonium, N,N'-dibenzylethylenediamine, N-methylglucamine (meglumine), ethanolamine, tromethamine, or diethanolamine.

For administration to humans in the curative or prophylactic treatment of inflammatory diseases, oral dosages of a compound of formula I or a pharmaceutically acceptable salt thereof (the active compounds) are generally in the range of 0.1 to 1000 mg daily, in single or divided doses, for an average adult patient (70 kg). The active compounds can be administered in single or divided doses. Individual tablets or capsules should generally contain from 0.1 to 100 mg of active compound, in a suitable pharmaceutically acceptable vehicle or carrier. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For human use, the active compounds of the present invention can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substance; for example, enough salts or glucose to make the solution isotonic.

Additionally, the active compounds may be administered topically when treating inflammatory conditions of the skin and this may be done by way of creams, jellies, gels, pastes, and ointments, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The ability of the compounds of formula I or the pharmaceutically acceptable salts thereof to inhibit $PDE_4$ may be determined by the following assay.

Inhibition of Eosinophil Degranulation and Activation in Human Whole Blood

Human Blood Eosinophil Degranulation and Activation Measurement

Blood Collection and Compound Incubation

One hundred ml blood is obtained from normal volunteers in Vacutainer tube #6480 (14.3 USP units sodium heparin/ml blood). Heparinized blood is pooled in 50 ml conical centrifuge tubes at 22° C. On ml blood is placed in a 12×75 mm siliconized glass tube containing 1 ul DMSO or 1 ul test compound in triplicate. After mixing, tubes are placed in a shaking water bath at 37° C. for 15 minutes. One ul PGE1 in DMSO is added to all tubes to give a final concentration of 1 uM. After mixing, 100 ul PBS (negative control) or Sephadex G-15 beads in PBS (8.25–16.5 mg/ml final concentration) is added to tubes. After mixing, all tubes are incubated in a shaking water bath at 37° C. for 1–2 hours.

Preparation of Plasma Samples

At the end of incubation, 20 ul of 15% EDTA in PBS is added to each assay tube. After mixing, the samples are centrifuged at 2,000 rpm (Sorvall 6000B centrifuge) at 22° C. for 5 minutes.

EDN (or EPX) and LTE4 Measurements and the Effect of Compounds

All plasma samples are tested for EDN (eosinophil derived neurotoxin) and LTE4 (leukotriene E4) levels. Extensive studies suggest that Sephadex beads trigger eosinophil-mediated EDN and LTE4 release in human whole blood. The levels of EDN and LTE4 are determined by a RIA (Kabi Pharmacia Diagnostics) and EIA (Cayman Chemical), respectively. EDN and LTE4 levels are calculated by comparison to a standard curve using Microsoft Excel or other appropriate software. Percent of control EDN or LTE4 release is calculated by:

% Control EDN=[EDN(compound)−EDN(blank)]/[EDN(total)−EDN(blank)]

% Control LTE4=[LTE4(compound)−LTE4(blank)]/[LTE4(total)−LTE4(blank)]

where the blank is the level of EDN or LTE4 in the absence of Sephadex beads and the total is the level of EDN or LTE4 in the presence of Sephadex beads. An $IC_{30}$ or $IC_{50}$ value is defined as the concentration of a compound that inhibits specific EDN or LTE 4 release by 30 or 50%, respectively.

Inhibition of PDE4 Isozyme and Eosinophil Activation by (+) and (−) Enantiomers

To assess pharmacologically which PDE4 isozyme(s) is responsible for eosinophil activation, we have prepared enantiomers of PDE4 inhibitors and compare the inhibitory effect of these enantiomers on PDE activity and eosinophil activation. PDE4 activity is assessed by measuring hydrolysis of 1 uM cAMP by individual human recombinant PDE4 isozymes (PDE4A, 4B, 4C or 4D). Eosinophil activation is estimated by measuring Sephadex beads-induced release of eosinophil derived neurotoxin (EDN) and leukotriene E4 in human whole blood. Table 1 illustrates comparison of one example of (−) and (+) enantiomers on the activity of individual PDE4 isozymes and on the release of END and LTE4. (+) Enantiomer ((S)-(−)2(4-Fluoro-phenoxy)-N-[1-(4-methoxy-phenyl)-ethyl]nictinamide) is 22 times more potent in inhibiting PDE4D than (−) enantiomer ((R)2-(4-Fluoro-phenoxy)-N-[1-(4-metoxy-phenyl)-ethyl]-nicotinamide); however, they are approximately equipotent in inhibiting the other 3 isozymes, i.e., PDE4A, 4B and 4C. Importantly, the (+) enantiomer is 20–37 fold more effective against the EDN and LTE4 response. These results indicate that the differential effect of (+) and (−) enantiomers on PDE4D isozyme inhibition is identical to their effects on eosinophil EDN/LTE4 release, demonstrating that the PDE4D isozyme plays a key role in regulating eosinophil.

TABLE 1

(+) vs. (−) enantiomers on PDE4 Isozymes and Eosinophil Responses

| | Isozyme - $IC_{50}$, uM | | | | HWB Eosinophil $IC_{30}$ or $IC_{50}$, uM | |
|---|---|---|---|---|---|---|
| | A | B | C | 4D | EDN | LTE4 |
| (+) Enantiomer | .6(3) | .6(3) | .8(1) | 0.009(3) | 0.05(2) | 0.008(2) |
| (−) Enantiomer | .6(3) | .3(3) | .4(4) | 0.2(3) | 1.0(1) | 0.3(2) |
| Enantiomer | | | | | | |
| (+) vs. (−) | .s. | .5X | 0.5X | 22X | 20X | 37X |

Including the aforementioned enantiomer, a total of 8 pairs of (+) and (−) enantiomers has been prepared. As illustrated in Table 2, the enantioselective effect of these compounds on PDE4D isozyme inhibition correlates significantly with those on the EDN and LTE4 response.

TABLE 2

Correlation of enantioselective effects on the PDE activity and EDN/LTE4 response by 8 compounds, each having (+) and (−) enantiomers.
Correlation of differential effects of (+) and (−) enantiomers on:

|  | vs. END response | vs. LTE4 response |
|---|---|---|
| PDE4A | No correlation | No correlation |
| PDE4B | No correlation | No correlation |
| PDE4C | No correlation | No correlation |
| PDE4D | Positive correlation ($p < 0.02$) | Positive correlation ($p < 0.005$) |

Inhibition of Pulmonary Eosinophilia

To evaluate these compounds for pulmonary efficacy, we have used a well-characterized monkey model of asthma (Turner et al., *Am. J. Respir. Crit. Care Med.* 149, 1153–1159, 1994). Exposure of atopic *Macaca fascicularis* monkeys to antigen causes a significant influx of inflammatory cells observed in the bronchoalveolar (BAL) fluid of these monkeys at 4–24 hours post antigen challenge. In this model, PDE4D isozyme selective compounds given subcutaneously significantly inhibit pulmonary eosinophil infiltration by 59–76% at 24 h post antigen challenge. These compounds, however, do not affect neutrophil or lymphocyte infiltration, demonstrating selective inhibition of the eosinophil response by these compounds.

Inhibition of TNF Production in Isolated Human-Monocytes

The ability of the compounds I or the pharmaceutically acceptable salts thereof to inhibit the production TNF and, consequently, demonstrate their effectiveness for treating disease involving the production of TNF is shown by the following In vitro assay:

Peripheral blood (100 mls) from human volunteers is collected in ethylenediaminetetraacetic acid (EDTA). Mononuclear cells are isolated by FICOLL/Hypaque and washed three times in incomplete HBSS. Cells are resuspended in a final concentration of $1 \times 10^6$ cells per ml in pre-warmed RPMI (containing 5% FCS, glutamine, pen/step and nystatin). Monocytes are plated as $1 \times 10^6$ cells in 1.0 ml in 24-well plates. The cells are incubated at 37° C. (5% carbon dioxide) and allowed to adhere to the plates for 2 hours, after which time non-adherent cells are removed by gentle washing. Test compounds (10ml) are then added to the cells at 3–4 concentrations each and incubated for 1 hour. LPS (10ml) is added to appropriate wells. Plates are incubated overnight (18 hrs) at 37° C. At the end of the incubation period TNF was analyzed by a sandwich ELISA (R&D Quantikine Kit). $IC_{50}$ determinations are made for each compound based on linear regression analysis.

Mass spectra were determined by the GC-MS, AMPI, APCI or thermospray method.

All $^1$H NMR were taken on a 400 MHz instrument.

Preparation 1

2-(4-Fluoro-phenoxy)-nicotinic acid

To a stirred solution of 4-fluorophenol (5.0 grams, 44.6 mmole) in dimethylformamide (40 ml) at room temperature was added 60% sodium hydride (3.6 grams, 89.0 mmole) portionwise and stirred for 30 minutes. 2-Chloronicotinic acid (7.1 grams, 45.0 mmole) was added portionwise and the mixture was refluxed for 3 hours. The solution was poured into 300 ml water and washed with diethyl ether. The aqueous was poured into 400 ml ice/water and acidified to pH 3 with acetic acid. The resulting precipitate was isolated by filtration to give an off-white solid (5.2 g). M.P. 180–182° C.; MW 233.21; MS (m/e) 234 (M$^+$+1).

The compounds of Preparation 2–5 were prepared according to the procedure of Preparation 1 substituting the corresponding alcohol for 4-fluorophenol. The duration of reaction was between 1 and 24 hours.

Preparation 2

2-(3-Fluoro-phenoxy)-nicotinic acid

MW 233.21; MS (m/e) 233 (M$^+$).

Preparation 3

2-(2,4-difluoro-phenoxy)-nicotinic acid

MW 251.19; MS (m/e) 252 (M$^+$+1).

Preparation 4

2-(3-chloro-phenoxy)-nicotinic acid

MW 249.65; MS (m/e) 250 (M$^+$+1).

Preparation 5

2-(3-Methoxy-phenoxy)-nicotinic acid

MW 245.23; MS (m/e) 261 (M$^+$+18).

Preparation 6

2-(pyridin-3-yloxy)-nicotinic acid

A solution of 2-(Pyridin-3-yloxy)-nicotinic acid ethyl ester (0.419 grams, 1.71 mmole) in ethanol (10 ml) and 1 N sodium hydroxide (4 ml) was refluxed for 4 hours. The mixture was poured into 100 ml water, acidified to pH 4 with 1 N hydrochloric acid and concentrated to dryness to give a solid (0.643 g). MW 216.21; MS (m/e) 217 (M$^+$+1).

The compounds of Preparations 7–22 were prepared according to the procedure of Preparation 6 substituting the corresponding ester for 2-(Pyridin-3-yloxy)-nicotinic acid ethyl ester. The duration of reaction was between 1 and 24 hours.

Preparation 7

2-(5-Chloro-pyridin-3-yloxy)-nicotinic acid

MW 250.65; MS (m/e) 251 (M$^+$+1).

Preparation 8

2-(3-Nitro-phenoxy)-nicotinic acid

M.P. 172–174° C.; MW 260; MS (m/e) 261 (M$^+$+1) Anal. calcd. for $C_{12}H_8N_2O_5$; C, 55.39; H, 3.10; N, 10.77. Found: C, 54.71; H, 3.15; N, 10.65.

Preparation 9

2-(3-Cyano-phenoxy)-nicotinic acid

M.P. 220–222° C.; MW 240.22; MS (m/e) 240 (M$^+$).

Preparation 10

2-(3-Dimethylamino-phenoxy)-nicotinic acid

MW 258.27; MS (m/e) 259 (M$^+$+1).

Preparation 11

2-(3-Acetylamino-phenoxy)-nicotinic acid

M.P. 273–275° C.; MW 272.26; MS (m/e) 273 (M$^+$+1).

Preparation 12

2-(1H-indol-4-yloxy)-nicotinic acid

MW 254; MS (m/e) 255 (M$^+$+1).

Preparation 13

2-(3-Trifluoromethyl-phenoxy)-nicotinic acid

M.P. 148–150° C.; MW 283.05; Anal. calcd. for $C_{13}H_8NO_3F_3$: C, 55.10; H, 2.85; N, 4.95. Found: C, 54.71; H, 2.51; N, 4.83.

Preparation 14

2-(3-Tetrazol-1-yl-phenoxy)-nicotinic acid

M.P. 185–188° C.; MW 283.2; MS (m/e) 282 (M$^+$−1).

Preparation 15

2-(3-Methylsulfanyl-phenoxy)-nicotinic acid

MW 261.302; MS (m/e) 262 (M$^+$+1).

Preparation 16

2-(3-Acetyl-phenoxy)-nicotinic acid

MW 257.248; MS (m/e) 256 (M$^+$−1).

Preparation 17

2-(3-Trifluoromethoxy-phenoxy)-nicotinic acid

MW 299.208; MS (m/e) 300 (M$^+$+1).

Preparation 18

2-(3,4-difluoro-phenoxy)-nicotinic acid

MW 251.20; MS (m/e) 251 (M$^+$).

Preparation 19

2-(3,5-difluoro-phenoxy)-nicotinic acid

MW 251.20; MS (m/e) 252 (M$^+$+1).

Preparation 20

2-(3-Fluoro-phenoxy)-nicotinic acid

M.P. 135–137° C.; Anal. calcd. for $C_{12}H_8NO_3F$: C, 61.79; H, 3.46; N, 6.01. Found: C, 61.51; H, 3.69; N, 5.78.

Preparation 21

2-(Benzo[1,3]dioxol-5-yloxy)-nicotinic acid

M.P. 162–164° C.; $^1$H NMR (DMSO-d$^6$) d 6.0 (2H, s), 6.5–8.3 (6H, m).

Preparation 22

2-(3-Dimethylcarbamoyl-phenoxy)-N-[4-(1-hydroxy-1-methyl-ethyl)-benzyl]-nicotinic acid $^1$H NMR (DMSO-d$^6$) d 2.88 (3H, s), 2.93 (3H, s), 7.08 (4H, m), 7.42 (1H, m), 8.22 (2H, m).

Preparation 23

2-(pyridin-3-yloxy)-nicotinic acid ethyl ester

A solution 2-Chloro-nicotinic acid ethyl ester (0.53 grams, 2.85 mmole), cesium carbonate (2.326 grams, 6.73 mmole) and Pyridin-3-ol (0.271 grams, 2.85 mmole) in dimethylformamide (20 ml) was heated to 65° C. for 10 hours. The mixture was diluted with 300 ml water and extracted with ethyl acetate. The combined extracts were washed with water and brine, dried over $Na_2SO_4$, filtered, and concentrated to an oil (0.55 g). MW 244.25; MS (m/e) 244 (M$^+$).

The compounds of Preparations 24–43 were prepared according to the procedure of Preparation 23 substituting the corresponding alcohol for Pyridin-3-ol. The duration of reaction was between 1 and 24 hours.

Preparation 24

2-(5-Chloro-pyridin-3-yloxy)-nicotinic acid ethyl ester

A solution of 2-Chloro-nicotinic acid ethyl ester (2.07 grams, 11.2 mmole), Cesium carbonate (7.27 grams, 22.3 mmole) and 5-chloro-3-pyridinol (1.45 grams, 11.2 mmole) in dry dimethylformamide (40 ml) was stirred at 90° C. overnight. The suspension was cooled to room temperature, poured into water and extracted with diethyl ether. The combined organics were washed with water and brine, dried over $MgSO_4$, and concentrated to a tan solid. Recrystalization from hexane gave a yellow solid (1.0 g). M.P. 65–69° C.; Anal. calcd. for $C_{13}H_{11}ClN_2O_3$: C, 56.03; H, 3.98; N, 10.05. Found: C, 56.14; H, 4.04; N, 10.16.

MW 278.72; MS (m/e) 279 (M$^+$+1).

Preparation 25

2-(3-Nitro-phenoxy)-nicotinic acid ethyl ester

M.P. 70–72° C.; MW 288.26; MS (m/e) 289 (M$^+$+1).

Preparation 26

2-(3-Cyano-phenoxy)-nicotinic acid ethyl ester

MW 268; $^1$H NMR (CDCl$_3$) d 1.4 (3H, t), 4.39 (2H, q), 7.12–8.4 (7H, m).

Preparation 27

2-(3-Dimethylamino-phenoxy)-nicotinic acid ethyl ester

MW 286.33; MS (m/e) 287 (M$^+$+1).

Preparation 28

2-(4-Cyano-phenoxy)-nicotinic acid ethyl ester

MW 268; MS (m/e) 268 (M$^+$).

Preparation 29

2-(3-Acetylamino-phenoxy)-nicotinic acid ethyl ester

MW 300.32; MS (m/e) 301 (M$^+$+1).

Preparation 30

2-(3-chloro-phenoxy)-nicotinic acid ethyl ester

MW 277.71; MS (m/e) 278 (M$^+$+1).

Preparation 31

2-(1H-Indol-4-yloxy)-nicotinic acid ethyl ester

MW 282; $^1$H NMR (DMSO-d$^6$) d 5.9 (1H, s), 6.4–8.4 (7H, m), 11.20 (1H, bs).

Preparation 32

2-(3-Trifluoromethyl-phenoxy)-nicotinic acid ethyl ester

M.P. 46–48° C.; MW 311; MS (m/e) 312 (M$^+$+1).

Preparation 33

2-(3-Tetrazol-1-yl-phenoxy)-nicotinic acid ethyl ester

M.P. 100–102° C.; MW 311.27; MS (m/e) 312 (M$^+$+1).

Preparation 34

2-(3-Methylsulfanyl-phenoxy)-nicotinic acid ethyl ester

MW 289.356; MS (m/e) 290 (M$^+$+1).

Preparation 35

2-(3-Acetyl-phenoxy)-nicotinic acid ethyl ester

MW 285.302; MS (m/e) 286 (M$^+$+1).

Preparation 36

2-(3-Trifluoromethoxy-phenoxy)-nicotinic acid ethyl ester

MW 327.262; MS (m/e) 328 (M$^+$+1).

Preparation 37

2-(3,4-difluoro-phenoxy)-nicotinic acid ethyl ester

MW 279.26; MS (m/e) 279 (M$^+$).

Preparation 38

2-(3,5-difluoro-phenoxy)-nicotinic acid ethyl ester

MW 279.26; MS (m/e) 279 (M$^+$).

Preparation 39

2-(3-Fluoro-phenoxy)-nicotinic acid ethyl ester

MW 261.26 MS (m/e) 262 (M$^+$).

Preparation 40

2-(3-Cyano-4-fluoro-phenoxy)-nicotinic acid ethyl ester

MW 286.28 MS (m/e) 286 (M$^+$).

Preparation 41

2-(Benzo[1,3]dioxol-5-yloxy)-nicotinic acid ethyl ester

MW 287, $^1$H NMR (DMSO-d$^6$) d 1.2 (3H, t), 4.30 (2H, q), 6.0 (2H, s), 6.5–8.4 (6H, m).

Preparation 42

2-(3-Dimethylcarbamoyl-phenoxy)-nicotinic acid ethyl ester $^1$H NMR (CDCL$_3$) d 1.36 (3H, t), 3.00 (3H, s), 3.07 (3H, s), 4.38 (2H, q), 7.06 (1H, m), 7.19 (1H, m), 7.24 (2H, m), 7.42 (1H, m), 8.24 (2H, dd).

Preparation 43

2-(3-Formyl-phenoxy)-nicotinic acid ethyl ester

MW 271.29 MS (m/e) 271 (M$^+$).

Preparation 44

2-Chloro-nicotinic acid ethyl ester

To a solution 2-Chloro-nicotinic acid (12.5 g) in Ethanol (250 ml) was added thionyl chloride (5.77 ml) dropwise and refluxed for 1.5 hours. The mixture was concentrated to remove ethanol and diluted with 300 ml water. Solid sodium bicarbonate was added to adjust the solution to pH 8.0. This was extracted with ethyl acetate, washed with water, saturated bicarbonate solution, water and brine, dried over Na$_2$SO$_4$, filtered and concentrated to a yellow liquid (10.0 g). MW 185.61; MS (m/e) 185 (M$^+$).

Preparation 45

2-(4-Cyano-phenoxy)-nicotinic acid

A solution of 2-(4-Cyano-phenoxy)-nicotinic acid methyl ester (0.200 grams, 0.787 mmole) in tetrahydrofuran (3 ml) and 1 M LiOH.H$_2$O (1.97 ml) was stirred over night. The mixture was diluted with 25 ml water, acidified to pH 1 with 2 N hydrochloric acid and filtered to give a white solid (0.144 g). MW 240; $^1$H NMR (DMSO-d$^6$) d 7.2 (3H, m), 7.90 (2H, m), 8.35 (2H, m), 13.5 (1H, bs).

The compounds of Preparations 46 was prepared according to the procedure of Preparation 45 substituting the corresponding ester for 2-(4-Cyano-phenoxy)-nicotinic acid methyl ester. The duration of reaction was between 1 and 24 hours.

Preparation 46

2-(3-Cyano-4-fluoro-phenoxy)-nicotinic acid

MW 258.22 MS (m/e) 258, 257 (M$^+$).

Preparation 47

2-(4-aminomethyl-phenyl)-propan-2-ol

To a stirred solution of 4-(1-hydroxy-1-methyl-ethyl)-benzonitrile (20.9 g, 0.13 mol.) in dry tetrahydrofuran (300 mL) at 0° C. was added slowly dropwise 1.0M lithium aluminium hydride in tetrahydrofuran (388 mL, 0.39 mol.). The mixture was refluxed for 30 min. then cooled to 0° C. and quenched with methanol (50 mL) added slowly dropwise. The mixture was concentrated in vacuo to half volume and diluted with chloroform (1200 mL) then washed with water (300 mL). The resulting suspension was filtered through Celite and the filtrate layers seperated. The organic extract was dried (MgSO$_4$) and concentrated to give 16.2 g as a light yellow solid mp 64–6° C. NMR (CDCl$_3$): 7.45 (d, 2H), 7.26 (d, 2H), 3.83 (s, 2H), 1.57 (s, 6H). GC-MS (m/e, %): 164 (M$^+$, 15), 150 (80), 132 (75), 106 (100).

Preparation 48

2-(4-Cyano-phenoxy)-nicotinic acid methyl ester

A solution of 2-(4-Cyano-phenoxy)-nicotinic acid ethyl ester (0.90 grams, 2.44 mmole) in methanol (10 ml) and potassium carbonate (1.01 grams, 7.33 mmole) was refluxed for 20 minutes. The mixture was diluted with 100 ml water, acidified to pH 1 and filtered to give a solid (0.200 g). MW 254; MS (m/e) 254 (M$^+$).

Preparation 49

2-(3-Chloro-phenoxy)-nicotinamide

A solution of 2-(3-Chloro-phenoxy)-nicotinonitrile (7.81 grams, 33.9 mmole), 3% hydrogen peroxide (190 ml, 169 mmole) and 50% potassium hydroxide (380 ml, 3.39 mmole) in ethanol (100 ml) was stirred at 70° C. over night. The mixture was concentrated to 250 ml and cooled to 0° C. A solid was isolated by filtration, dissolved in ethyl acetate, dired over magnesium sulfate and concentrated to a white solid (6.51 g). M.P. 225–228° C.; MW 248.67; MS (m/e) 250 (M$^+$+1).

Preparation 50

2-(3-Chloro-phenoxy)-nicotinonitrile

A solution 2-Chloro-nicotinonitrile (5.0 grams, 36.1 mmole), cesium carbonate (23.5 grams, 72.2 mmole) and 3-chlorophenol (4.65 grams, 36.1 mmole) in dimethylformamide (100 ml) was heated to 80° C. over night. The mixture was cooled and poured into 500 ml water and extracted with diethyl ether. The combined extracts were washed with water and brine, dried over MgSO$_4$, filtered, and concentrated to a white solid (8.21 g). M.P. 88–90° C.; Anal. calcd. for $C_{12}H_7N_2OCl$: C, 62.49; H, 3.06; N, 12.15. Found: C, 62.43; H, 3.00; N, 12.13.

Preparation 51

2-(4-Fluoro-phenoxy)-pyridin-3-ylamine

To a solution 2-(4-Fluoro-phenoxy)-3-nitro-pyridine (3.00 grams, 12.81 mmole) in ethyl acetate (100 ml) was added 10% palladium on carbon (0.600 g). This was shaken under 50 psi hydrogen for 1 hour. The catalyst was removed by filtration, and the solution was concentrated to give a white solid (2.49 g). M.P. 92–94° C.; MW 204.20; MS (m/e) 204 (M$^+$).

The compound of Preparation 10a was prepared according to the procedure of Preparation 10 substituting the corresponding nitro for 2-(4-Fluoro-phenoxy)-3-nitro-pyridine. The duration of reaction was between 1 and 24 hours.

Preparation 52

2-(Pyridin-3-yloxy)-pyridin-3-ylamine

MW 187; MS (m/e) 188 (M$^+$+1).

Preparation 53

2-(4-Fluoro-phenoxy)-3-nitro-pyridine

A solution 2-Chloro-3-nitro-pyridine (5.0 grams, 31.54 mmole), cesium carbonate (25.7 grams, 78.85 mmole) and 4-fluorophenol (3.6 grams, 34.69 mmole) in dimethylformamide (85 ml) was stirred for 2 hours at room temperature. The mixture was diluted with 250 ml water and extracted with ethyl acetate. The combined extracts were washed with 1 N NaOH, water and brine, dried over Na$_2$SO$_4$, filtered, and concentrated to a yellow solid (7.16 g). M.P. 87–89° C.; MW 234.1; MS (m/e) 234 (M$^+$).

The compound of Preparation 54 was prepared according to the procedure of Preparation 53 substituting the corresponding alcohol for 4-fluorophenol. The duration of reaction was between 1 and 24 hours.

Preparation 54

2-(Pyridin-3-yloxy)-3-nitro-pyridine

MW 217.186; MS (m/e) 218 (M$^+$+1).

Preparation 55

2-(3-Chloro-phenoxy)-pyridine-3-carbaldehyde

To a solution of methyl sulfoxide (0.23 ml, 3.3 mmole) and methylene chloride (10 ml) at –70° C. was added oxalyl chloride (0.20 ml, 2.3 mmole) dropwise over 5 minutes and stirred for 1 hour. A solution of [2-(3-Chloro-phenoxy)-pyridin-3-yl]-methanol (0.39 grams, 1.7 mmole) in methylene chloride (10 ml) was added to the stirring mixture dropwise and stirred at –70° C. for 1 hour. It was warmed to –35° C. for 15 minutes and cooled down to –70° C. at which time triethylamine (1.15 ml, 8.3 mmole) was added and the mixture was warmed to 0° C. The mixture was diluted with 20 ml methylene chloride and washed with saturated sodium hydrogencarbonate and brine, dried over Na$_2$SO$_4$, filtered, and concentrated to an orange oil which was which was purified by chromatography on silica gel eluting with 1/3 ethyl acetate/hexane to give a yellow oil (0.180 g). MW 233.65; MS (m/e) 234 (M$^+$+1).

The compound of Preparation 56 was prepared according to the procedure of Preparation 55 substituting the corresponding alcohol for [2-(3-Chloro-phenoxy)-pyridin-3-yl]-methanol. The duration of reaction was between 1 and 24 hours.

Preparation 56

2-(Pyridin-3-yloxy)-pyridine-3-carbaldehyde

MW 200.20; MS (m/e) 201 (M$^+$+1).

Preparation 57

[2-(3-Chloro-phenoxy)-pyridin-3-yl]-methanol

To a solution of 2-(3-Chloro-phenoxy)-nicotinic acid ethyl ester (0.5 g) and tetrahydrofuran (10 ml) at 0° C. was added lithium aluminum hydride (0.4 g) in two portions and stirred for 30 minutes. The solution was allowed to warm to room temperature and stirred over night. The mixture was quenched with 1 N sodium hydroxide (0.5 ml) and diluted with water. The mixture was filtered through celite which was washed with ethyl acetate to extract the product. The combined extracts were washed with water and brine, dried over MgSO$_4$, filtered, and concentrated to an oil (0.39 g). MW 235.67; MS (m/e) 236 (M$^+$+1).

The compound of Preparation 58 was prepared according to the procedure of Preparation 57 substituting the corresponding ester for 2-(3-Chloro-phenoxy)-nicotinic acid ethyl ester. The duration of reaction was between 1 and 24 hours.

Preparation 58

[2-(Pyridin-3-yloxy)-pyridin-3-yl]-methanol

MW 202.21; MS (m/e) 203 (M$^+$+1).

Preparation 59

3-Tetrazol-1-yl-phenol

To a solution 1-(3-Benzyloxy-phenyl)-1H-tetrazole (0.640 grams, 2.54 mmole) in ethanol (15 ml) was added 10% palladium on carbon (~0.100 g). This was stirred under hydrogen balloon over night. The catalyst was removed by filtration, and the solution was concentrated to give a white solid (0.364 g). M.P. 171–172° C.; MW 162.12; MS (m/e) 163 (M$^+$+1).

Preparation 60

1-(3-Benzyloxy-phenyl)-1H-tetrazole

To a solution of 3-Benzyloxy-phenylamine (1.50 grams, 7.53 mmole) and acetic acid (15 ml) at 70° C. was added a solution of ethyl orthoformate (1.116 g, 7.53 mmole) in acetic acid (4 ml) and stirred for 4 hours. To the solution was added sodium azide (1.468 g, 22.6 mmole) in two portions and stirred for 20 hours at 70° C. The mixture was extracted with ethyl acetate. The combined extracts were washed with saturated sodium hydrogencarbonate and brine, dried over $Na_2SO_4$, filtered, and concentrated. The product was purified via flash chromatography on silica using 3/1 hexane/ethyl acetate as eluent to give white crystals (0.650 g). M.P. 85–86° C.; MW 252.25; MS (m/e) 252.8 ($M^+$).

Preparation 61

3-Methylsulfanyl-phenol

To a solution of acetic acid (200 ml) was cooled to −50° C. was bubbled in HBr gas (20 g). m-Methoxyphenylmethylsulfide (20 grams, 130 mmole) and 48% aqueous HBr (10 ml) was added and the mixture was refluxed for 3 hours. The acetic acid was removed, and the oil was poured into 150 ml ice water. It was extracted with diethyl ether. The combined extracts were washed with 15% KOH, and the aqueous was acidified with concentrated hydrochloric acid and extracted with diethyl ether. The combined extracts were dried over $Na_2SO_4$, filtered, and concentrated to an oil (11.5 g). MW 140.205; MS (m/e) 141 ($M^+$+1).

Preparation 62

1-Methoxy-3-methylsulfanyl-benzene

To a suspension of magnesium (7.2 grams, 296 mmole) and iodine (100 ml) in diethyl ether (250 ml) m-Bromoanisole (47.0 grams, 250 mmole) was added slowly with spontaneous refluxing. Methyl disulfide (16.0 grams, 160 mmole) was added and stirred for 1 hour. A solution of water (100 ml) and concentrated hydrochloric acid (30 ml) was added as the mixture was being cooled. The layers were separated and the aqueous was extracted with diethyl ether. The combined extracts were dried over $MgSO_4$, filtered and concentrated to an oil which was purified by distilation (20 mm Hg) at 130–135° C. (23.5 g).

Preparation 63

2-(Pyridin-3-ylmethoxy)-nicotinic acid ethyl ester

To a solution of Pyridin-3-yl-methanol (0.59 grams, 5.4 mmole) in dimethylformamide (20 ml) sodium hydride (0.259 grams, 6.5 mmole) was added and stirred for 30 minutes. 2-Chloro-nicotinic acid ethyl ester (1.0 grams, 5.4 mmole) was added via syringe and stirred at room temperature over night. The mixture was diluted with water (150 ml) and extracted by diethyl ether and ethyl acetate. The combined extracts were washed with 1$\underline{N}$ NaOH, water and brine, dried over $Na_2SO_4$, filtered, and concentrated to an oil (1.3 g). MW 258.28; MS (m/e) 259 ($M^+$+1).

Preparation 64

2-(3-Methoxycarbonyl-phenoxy)-nicotinic acid

To a solution 2-(3-Methoxycarbonyl-phenoxy)-nicotinic acid benzyl ester (1.1 g) in methanol (15 ml) and ethyl acetate (15 ml) was added 10% palladium on carbon (0.2 g). This was shaken under 30 psi hydrogen for 2 hours. The catalyst was removed by filtration, and the solution was concentrated to give a solid which was triturated in methylene chloride/hexane to give a white solid (0.630 g). MW 273.26; MS (m/e) 274 ($M^+$+1).

Preparation 65

2-(3-Methoxycarbonyl-phenoxy)-nicotinic acid benzyl ester

Into a solution of 2-(3-Iodo-phenoxy)-nicotinic acid benzyl ester (1.7 grams, 3.94 mmole), dppf (0.131 grams, 0.24 mmole), $Pd(OAc)_2$ (0.027 grams, 0.12 mmole) and triethylamine (0.797 grams, 7.9 mmole) in methanol (10 ml) was bubbled in carbon monoxide gas for 5 minutes. The mixture was heated to 60° C. for 4 hours, poured into 200 ml water, and extracted with diethyl ether. The combined extracts were washed with water and brine, dried over $MgSO_4$, filtered, and concentrated to an oil which was purified via flash chromatography on silica using 25% ethyl acetate/hexane as eluent (1.2 g). MW 363.39; MS (m/e) 364 ($M^+$+1).

Preparation 66

2-(3-Iodo-phenoxy)-nicotinic acid benzyl ester

A solution 2-Chloro-nicotinic acid benzyl ester (1.7 grams, 6.86 mmole), cesium carbonate (4.5 grams, 13.7 mmole) and 3-iodophenol (1.7 grams, 7.54 mmole) in dimethylformamide (20 ml) was stirred for 2 hours at 70–80° C. The mixture was poured into 150 ml water and extracted with diethyl ether. The combined extracts were washed with water and brine, dried over $MgSO_4$, filtered, and concentrated to an oil which was purified via flash chromatography on silica using 30% ethyl acetate/hexane as eluent (2.32 g). MW 431.24; MS (m/e) 432 ($M^+$+1).

Preparation 67

2-Chloro-nicotinic acid benzyl ester

A solution 2-Chloro-nicotinic acid (3.0 grams, 19.0 mmole), potassium carbonate (6.5 grams, 48.0 mmole) and benzyl bromide (2.8 ml, 24.0 mmole) in dimethylformamide (20 ml) was stirred at room temperature over night. The mixture was poured into 200 ml water and extracted with diethyl ether. The combined extracts were washed with water and brine, dried over $MgSO_4$, filtered, and concentrated to an oil which was purified via flash chromatography on silica using 10% ethyl acetate/hexane as eluent (2.8 g). MW 247.69; MS (m/e) 247 ($M^+$).

Preparation 68

C-(5-Chloro-furan-2-yl)-methylamine

To a solution of 5-Chloro-furan-2-carbaldehyde oxime (1.38 grams, 9.5 mmole) in tetrahydrofuran (30 ml) was added dropwise 1.0 $\underline{M}$ lithium aluminum hydride (21 ml, 21 mmole) and refluxed for 30 minutes. The mixture was cooled to 0° C. and quenched with 5 ml methanol and 5 ml saturated $NH_4Cl$. The mixture was poured into 150 ml water and extracted with diethyl ether. The combined extracts were washed with water and brine, dried over $MgSO_4$, filtered, and concentrated to an oil (0.403 g). MW 131.57; MS (m/e) 130/131 ($M^+$).

The compounds of Preparations 69–71 were prepared according to the procedure of Preparation 68 substituting the corresponding oxime for 5-Chloro-furan-2-carbaldehyde oxime. The duration of reaction was between 30 minutes and 24 hours.

Preparation 69

C-(5-Methyl-furan-2-yl)-methylamine

MW 111.16; MS (m/e) 111 (M$^+$).

Preparation 70

C-(4-Chloro-thiophen-2-yl)-methylamine

MW 147.64.

Preparation 71

C-Thiazol-2-yl-methylamine

MW 114.19.

Preparation 72

5-Chloro-furan-2-carbaldehyde oxime

To a solution 5-Chloro-furan-2-carbaldehyde (1.3 grams, 9.96 mmole) and NaOAc (1.8 grams, 21.9 mmole) in methylene chloride (30 ml) and water (30 ml) was added NH$_2$OH.HCl (0.761 grams, 10.96 mmole) and stirred at room temperature over night. The mixture was poured into 150 ml water and extracted with diethyl ether. The combined extracts were washed with water and brine, dried over MgSO$_4$, filtered, and concentrated to a solid (1.38 g). MW 145.55; MS (m/e) 145/147 (M$^+$).

The compounds of Preparations 73–75 were prepared according to the procedure of Preparation 72 substituting the corresponding aldehyde for 5-Chloro-furan-2-carbaldehyde. The duration of reaction was between 1 and 24 hours.

Preparation 73

5-Methyl-furan-2-carbaldehyde oxime

Mixture of E/Z isomers; MW 125.11; $^1$H NMR (CDCl$_3$) d 2.32 (3H, s), 6.03 (1H, d), 6.12 (1H, d), 6.0 (2H, s), 6.48 (1H, d), 7.22 (1H, d), 7.42 (1H, s), 7.91 (1H, s).

Preparation 74

4-Chloro-thiophene-2-carbaldehyde oxime

MW 161.62.

Preparation 75

Thiazole-2-carbaldehyde oxime

MW 128.17.

Preparation 76

5-Chloro-furan-2-carbaldehyde

A solution of 5-Nitro-furan-2-carbaldehyde (14.1 g) in concentrated hydrochloric acid (60 ml) was steam distilled until ~150 ml liquid was collected. The mixture was poured into 150 ml water and extracted with diethyl ether. The combined extracts were washed with saturated NaHCO$_3$, water and brine, dried over MgSO$_4$, filtered, and concentrated to an oil which was purified via flash chromatography on silica using 20% ethyl acetate/hexane as eluent to give a white solid (1.3 g). MW 130.53; MS (m/e) 129/131 (M$^+$+1).

Preparation 77

2,4,6-Trifluoro-benzylamine

A solution of 2-Bromomethyl-1,3,5-trifluoro-benzene (2.0 g, 8.9 mmole) and HMTA (3.1 grams, 22.2 mmole) in chloroform (35 ml) was refluxed for 18 hours. A resulting precipitate was isolated by filtration and taken up into methanol (10 ml), water (5 ml) and concentrated hydrochloric acid (5 ml) and refluxed for 4 hours. The mixture was poured into 200 ml water and washed with diethyl ether. The aqueous was basified with 5 $\underline{N}$ sodium hydroxide and extracted with diethyl ether. The combined extracts were washed with water and brine, dried over MgSO$_4$, filtered, and concentrated to an oil which solidified on standing (1.32 g). MW 161.14; MS (m/e) 145 (M$^+$–NH$_2$).

The compounds of Preparation 78–79 were prepared according to the procedure of Preparation 77 substituting the corresponding halide for 2-Bromomethyl-1,3,5-trifluoro-benzene. The duration of reaction was between 1 and 24 hours.

Preparation 78

C-(5-Chloro-thiophen-2-yl)-methylamine

MW 147.64; MS (m/e) 147 (M$^+$).

Preparation 79

C-(3,5-Dichloro-thiophen-2-yl)-methylamine

MW 182.08; MS (m/e) 181–186 (M$^+$).

Preparation 80

C-(3,4-Dichloro-thiophen-2-yl)-methylamine

To a solution 3,4-Dichloro-thiophene-2-carboxylic acid amide (0.640 grams, 3.3 mmole) in tetrahydrofuran (20 ml) was added dropwise 1.0 $\underline{M}$ lithium aluminum hydride (7 ml, 7 mmole) and stirred at room temperature for 30 minutes. The mixture was cooled to 0° C. and quenched with 3 ml methanol and 5 ml saturated NH$_4$Cl added dropwise. The mixture was poured into 100 ml water and extracted with diethyl ether. This was then filtered through celite. The combined extracts were washed with water and brine, dried over MgSO$_4$, filtered, and concentrated to an oil which was purified via flash chromatography on silica using 5% methanol/methylene chloride as eluent to give an oil (0.335 g). MW 182.08; $^1$H NMR (CDCl$_3$) d 4.01 (2H, s), 7.09 (1H, s).

The compounds of Preparations 81–88 were prepared according to the procedure of Preparation 80 substituting the corresponding amide for 3,4-Dichloro-thiophene-2-carboxylic acid amide. The duration of reaction was between 30 minutes and 24 hours.

Preparation 81

C-(3-Chloro-thiophen-2-yl)-methylamine

MW 147.64; $^1$H NMR (CDCl$_3$) d 3.99 (2H, s), 6.86 (1H, d), 7.16 (1H, d).

Preparation 82

C-Benzo[b]thiophen-2-yl-methylamine

MW 163.26; MS (m/e) 163 (M$^+$).

Preparation 83

C-(5-Trifluoromethyl-thiophen-2-yl)-methylamine

MW 181.20; MS (m/e) 181 (M$^+$).

Preparation 84

2-(5-Aminomethyl-thiophen-2-yl)-propan-2-ol

MW 171.29.

Preparation 85

2-(5-Aminomethyl-3-chloro-thiophen-2-yl)-propan-2-ol

MW 205.73; $^1$H NMR (CDCl$_3$) d 1.69 (6H, s), 3.92 (2H, s), 6.69 (1H, s).

Preparation 86

2-(5-Aminomethyl-furan-2-yl)-propan-2-ol

MW 155.22; $^1$H NMR (CDCl$_3$) d 1.56 (6H, s), 3.77 (2H, s), 6.02 (1H, d), 6.06 (1H, d).

Preparation 87

3-(5-Aminomethyl-thiophen-2-yl)-pentan-3-ol

MW 199.35; $^1$H NMR (CDCl$_3$) d 0.85 (6H, t), 1.82 (4H, q), 3.97 (2H, s), 6.67 (1H, d), 6.73 (1H, d).

Preparation 88

2-(5-Aminomethyl-4-chloro-thiophen-2-yl)-propan-2-ol

MW 205.73; $^1$H NMR (CDCl$_3$) d 1.60 (6H, s), 3.92 (2H, s), 6.71 (1H, s).

Preparation 89

3,4Dichloro-thiophene-2-carboxylic acid amide

To a stirred suspension of 3,4-Dichloro-thiophene-2-carboxylic acid (1.0 grams, 5.08 mmole) in methylene chloride (20 ml) and dimethylformamide (0.2 ml) was added thionyl chloride (1.9 ml, 25.3 mmole) and refluxed for 3 hours. The mixture was concentrated to give an oil. The oil was taken up in methylene chloride (15 ml), cooled to 0° C. and NH$_3$ gas was bubbled in for 5 minutes and stirred for 20 minutes. The mixture was diluted with methylene chloride (150 ml) washed with water and brine, dried over MgSO$_4$, filtered, and concentrated to a solid which was purified via flash chromatography on silica using 2.5% methanol/methylene chloride as eluent to give a solid which was triturated in methylene chloride to give a white solid (0.475 g). MW 196.06; MS (m/e) 195/197 (M$^+$).

The compounds of Preparations 90–92 were prepared according to the procedure of Preparation 89 substituting the corresponding acid for 3,4-Dichloro-thiophene-2-carboxylic acid. The duration of reaction was between 1 and 24 hours.

Preparation 90

3-Chloro-thiophene-2-carboxylic acid amide

MW 161; MS (m/e) 161/163 (M$^+$).

Preparation 91

5-Trifluoromethyl-thiophene-2-carboxylic acid amide

MW 195.18; MS (m/e) 196 (M$^+$+1).

Preparation 92

5-(1-Hydroxy-1-methylethyl)-furan-2-carboxylic acid amide

MW 169.18; $^1$H NMR (DMSO-d$^6$) d 1.40 (6H, s), 5.20 (1H, d), 6.26 (1H, d), 6.93 (1H, d), 7.24 (1H, bs), 7.58 (1H, bs).

Preparation 93

4-(2,2,2-Trifluoro-ethoxy)-benzylamine

To a solution 4-(2,2,2-Trifluoro-ethoxy)-benzonitrile (0.5 grams, 2.48 mmole) in tetrahydrofuran (10 ml) was added 1.0 M lithium aluminum hydride (6.2 ml, 6.2 mmole) and refluxed for 40 minutes. The mixture was cooled to 0° C. and quenched with 5 ml methanol added dropwise and diluted with saturated NH$_4$Cl (50 ml). The mixture was extracted with diethyl ether. The combined extracts were washed with brine, dried over Na$_2$SO$_4$, filtered, and concentrated to an oil which was purified via flash chromatography on silica using 5% methanol/methylene chloride as eluent to give an oil (0.230 g ). MW 205.18; MS (m/e) 206(M$^+$+1).

The compounds of Preparations 94–106 were prepared according to the procedure of Preparation 93 substituting the corresponding nitrile for 4-(2,2,2-Trifluoro-ethoxy)-benzonitrile. The duration of reaction was between 30 minutes and 24 hours.

Preparation 94

4-Difluoromethoxy-benzylamine

MW 173.18; $^1$H NMR (CDCl$_3$) d 3.85 (2H, s), 6.48 (1H, t), 7.09 (2H, m), 7.30 (2H, m).

Preparation 95

C-(1H-Indol-5-yl)-methylamine

MW 146.21; MS (m/e) 146 (M$^+$).

Preparation 96

5-Fluoro-thiophene-2-(2-methylamine)

$^1$H-NMR (CDCl$_3$): d 6.47 (m, 1H), 6.26 (m, 1H), 3.91 (m, 2H). GC-MS (m/e, %) 131 (M$^+$, 100).

Preparation 97

4-Aminomethyl-2,6-di-tert-butyl-phenol

MW 235; MS (m/e) 235 (M$^+$).

Preparation 98

2,3-Difluoro-benzylamine

MW 143.14.

Preparation 99

2-(4-Aminomethyl-2-chloro-phenyl)-propan-2-ol

MW 199.70; MS (m/e) 199/201 (M$^+$).

Preparation 100

2-(4-Aminomethyl-3-chloro-phenyl)-propan-2-ol

MW 199.70; MS (m/e) 198/200 (M$^+$+1).

$^1$H NMR (CDCl$_3$) d 1.54 (6H, s), 3.89 (2H, s), 7.31 (2H, m), 7.48 (1H, d).

Preparation 101

1-(4-Aminomethyl-phenyl)-cyclobutanol

MW 177.27; MS (m/e, %) 177 (M$^+$, 3), 160 (45),148 (100).

Preparation 102

1-(4-Aminomethyl-phenyl)-prop-2-yn-1-ol

MW 161.22; MS (m/e, %) 160(M$^+$, 15), 115 (20), 106 (100).

Preparation 103

4-(2-Methyl-[1,3]dioxolan-2-yl)-benzylamine

MW 193.248; MS (m/e) 178 (M$^+$–NH$_3$).

Preparation 104

C-(1,4-Dioxa-spiro[4,5]dec-8-yl)-methylamine

MW 171.241; MS (m/e) 172 (M$^+$+1).

Preparation 105

1-(4-Aminomethyl-phenyl)-ethanol

MW 151.21; MS (m/e) 152 (M$^+$+1).

Preparation 106

2-(4-Aminomethyl-3-fluoro-phenyl)-propan-2-ol $^1$H NMR (CDCl$_3$) d 1.54 (6H, s), 3.89 (2H, s), 7.30 (2H, m), 7.48 (1H, s).

Preparation 107

4-(1-hydroxy-1-methyl-ethyl)-benzonitrile

To a stirred solution of 4-cyanoacetophenone (49.5 g, 0.34 mol.) in dry tetrahydrofuran (400 mL) at −78° C. was added dropwise 3.0 M methylmagnesium chloride (150 mL, 0.45 mol.). The mixture was allowed to slowly warm to 0° C. over 3.5 h then quenched with methanol (80 mL) added dropwise. The mixture was poured into water (1000 mL) and acidified to pH~3 with oxalic acid then extracted with ethyl acetate (2×500 mL). The organic extracts were combined and washed with water (2×100 mL), brine (100 mL), dried (MgSO$_4$) then concentrated to give a white residue. Flash Chromatography on Silica Gel eluting with 20% ethyl acetate/hexanes yielded 13.5 g clear oil which solidified upon standing mp 45–7° C.

Preparation 108

4-(2,2,2-Trifluoro-ethoxy)-benzonitrile

To a solution 4-cyanophenol (5.0 grams, 42.0 mmole) in HMPT (40 ml) was added sodium hydride (1.68 grams, 42.0 mmole) and stirred for 15 minutes at room temperature. Via syringe 2,2,2-trifluoroethyl methane sulphonate (8.98 grams, 50.4 mmole) was added and the mixture was stirred at 140° C. over night. The mixture was cooled to room temperature, diluted with 300 ml ice water and 50 ml 2 N hydrochloric acid and extracted with diethyl ether. The combined extracts were washed with water, 1N sodium hydroxide and brine, dried over Na$_2$SO$_4$, filtered, and concentrated to an oil which was purified via flash chromatography on silica using 25% diethyl ether/hexane as eluent to give an oil (2.68 g). Synthesis 727 (1980).

Preparation 109

1-(5-Chloro-thiophen-2-yl)-ethylamine

A solution of 1-(5-Chloro-thiophen-2-yl)-ethanone (5.0 grams, 31.0 mmole) in formamide (6 ml, 150.0 mmole) was stirred at 160° C. for 18 hours. The mixture was poured into 200 ml and extracted with diethyl ether. The combined extracts were washed with water and brine, dried over MgSO$_4$, filtered, and concentrated to an oil which was purified via flash chromatography on silica using 20% ethyl acetate/hexane as eluent to give an oil. The oil was taken up in 26 ml 6 N NaOH, 20 ml methanol and 5 ml tetrahydrofuran and refluxed for three hours. The mixture was poured into 200 ml and extracted with diethyl ether. The combined extracts were concentrated to give a dark oil (2.3 g). MW 161.67; MS (m/e) 161 (M$^+$).

The compounds of Preparation 110–111 were prepared according to the procedure of Preparation 109 substituting the corresponding aldehyde or ketone for 1-(5-Chloro-thiophen-2-yl)-ethanone. The duration of reaction was between 30 minutes and 24 hours.

Preparation 110

C-(5-Methyl-thiophen-2-yl)-methylamine

MW 127.23; MS (m/e) 127 (M$^+$).

Preparation 111

C-(3-Methyl-thiophen-2-yl)-methylamine

MW 127.23; MS (m/e) 127 (M$^+$).

Preparation 112

5-Aminomethyl-1,3-dihydro-indol-2-one

To a solution of 2-Oxo-2,3-dihydro-1H-indole-5-carbonitrile (1.3 g) in methanol (30 ml) was added 10% PtO$_2$ (0.200 g). This was shaken under 44 psi hydrogen over night. The catalyst was removed by filtration, and the mixture was dried over Na$_2$SO$_4$. The solution was concentrated to give a yellow solid, (1.1 g). MW 162; MS (m/e) 162 (M$^+$).

Preparation 113

2-Oxo-2,3-dihydro-1H-indole-5-carbonitrile

A solution of 3,3-Dibromo-2-oxo-2,3-dihydro-1H-indole-5-carbonitrile (10.5 grams, 33.3 mmole) and Zn dust (22.0 grams, 338.5 mmole) in acetic acid (250 ml) was stirred at room temperature for 45 minutes. The mixture was filtered through celite and concentrated to dryness. The resulting oil was diluted with 300 ml water and extracted with ethyl acetate. The combined extracts were washed with 1 N sodium hydroxide and brine, dried over MgSO$_4$, filtered, and concentrated to give a white solid (1.9 g). MW 158.

Preparation 114

3,3-Dibromo-2oxo-2,3-dihydro-1H-indole-5-carbonitrile

To a solution of 1H-Indole-5-carbonitrile (5.0 grams, 35.2 mmole) in t-Butanol (300 ml) was added pyridinium bromide perbromide (37.5 grams, 105.6 mmole) over 10 minutes and stirred at room temperature for 2 hours. The mixture was concentrated to an orange oil. The resulting oil was diluted with 500 ml water and extracted with ethyl acetate. The combined extracts were washed with water and brine, dried over Na$_2$SO$_4$, filtered, and concentrated to give a yellow solid (10.37 g). MW 315.95; MS (m/e) 316 (M$^+$+1).

Preparation 115

6-Amino-3H-benzooxazol-2-one

A solution of 6-Nitro-3H-benzooxazol-2-one (8.4 grams, 46.0 mmole) and Tin (16.0 g) in concentrated hydrochloric acid (100 ml) was stirred at 60° C. for 2 hours. The mixture was diluted with water, basified to pH 12 and extracted with ethyl acetate. The combined extracts were dried over $Na_2SO_4$, filtered, and concentrated to give an orange solid (2.45 g). MW 150; MS (m/e) 151 ($M^+$+1).

Preparation 116

6-Nitro-3H-benzooxazol-2-one

A solution of 3H-Benzooxazol-2-one (10.0 g) in concentrated $HNO_3$ (100 ml) was stirred at 40° C. A precipitate formed and the reaction temperature rose. It was cooled below 50 ° C. in an ice bath. The mixture was diluted with ice water, and the precipitate was isolated by filtration. The product was washed with water to give a white solid. (8.4 g). M.P. 239–241.

Preparation 117

5-Aminomethyl-1H-indole-2-carboxylic acid ethyl ester

A solution of 5-Cyano-1H-indole-2carboxylic acid ethyl ester (1.8 grams, 8.4 mmole) and $Bu_4N^+BH_3^-$ in methylene chloride (80 ml) was refluxed for 4 hours. The mixture was concentrated to a brown oil which was dissolved in 10% hydrochloric acid (50 ml) and refluxed for 1 hour. The mixture was extracted with ethyl acetate (discarded) and the pH was neutralized. The aqueous was extracted with ethyl acetate. The combined extracts were dried over $Na_2SO_4$, filtered, and concentrated to give a solid. (0.920 g). MW 218.258; MS (m/e) 218 ($M^+$).

Preparation 118

3,5-Di-tert-butyl-4-hydroxy-benzonitrile

A solution of 3,5-Di-tert-butyl-4-hydroxy-benzaldehyde oxime (3.0 grams, 8.4 mmole) in acetic anhydride (6 ml) was was refluxed for 2 hours. The mixture was cooled to 0° C. and saturated sodium hydrogencarbonate was added. The mixture was extracted with methylene chloride. The combined extracts were washed with saturated $NaHCO_3$, dried over $Na_2SO_4$, filtered, and concentrated to give a solid. This was dissolved in diethyl ether and extracted with 1 $\underline{N}$ sodium hydroxide which was then acidified to pH 1 and extracted with ethyl acetate. The extract was dried and concentrated to a yellow solid which was recrystalized from ethyl acetate/hexane to give white crystals (1.05 g). MW 231; MS (m/e) 249 ($M^+$+$NH4^+$).

Preparation 119

3,5-Di-tert-butyl-4-hydroxy-benzaldehyde oxime

A solution of 3,5-Di-tert-butyl-4-hydroxy-benzaldehyde (10.0 grams, 42.67 mmole), $NH_2OH\cdot HCl$ (14.83 grams, 213.3 mmole) and 40% KOH (80 ml) in methanol (100 ml) was stirred at room temperature over the weekend. The mixture was concentrated to remove methanol. The aqueous phase was acidified and extracted with ethyl acetate. The combined extracts were washed with water and brine, dried over $Na_2SO_4$, filtered, and concentrated to give a yellow solid. (8.9 g). M.P. 122–124° C.; MW 249; MS (m/e) 249 ($M^+$).

The compound of Preparation 120 was prepared according to the procedure of Preparation 119 substituting the corresponding aldehyde for 3,5-Di-tert-butyl-4-hydroxy-benzaldehyde. The duration of reaction was between 1 and 48 hours.

Preparation 120

4-Hydroxy-3,5-dimethyl-benzaldehyde oxime

MW 165; MS (m/e) 166 ($M^+$+1).

Preparation 121

4-Aminomethyl-2,6-dimethyl-phenol

A solution of 4-Hydroxy-3,5-dimethyl-benzaldehyde oxime (1.0 grams, 6.06 mmole) in acetic acid (30 ml) and Zn dust (4.0 grams, 61.2 mmole) was stirred at ~60° C. for 2 hours. The mixture was filtered through celite, basified by aqueous ammonium hydroxide and extracted with chloroform. The combined extracts were dried over $MgSO_4$, filtered, and concentrated to give a foam (0.90 g). MW 151; MS (m/e) 151 ($M^+$).

Preparation 122

1-(2-Chloro-phenyl)-ethane-1,2-diol

To a vigrouosly stirred mixture of AD-mix (1.4 g) in water (5 ml) and t-butanol (5 ml) at 0° C. was added 1-Chloro-2-vinyl-benzene (0.140 grams, 1.0 mmole) and stirred at 0° C. for 2 hours. To the mixture sodium sulfite (1.5 g) was added and allowed to warm to room temperature for 1 hour. The mixture was extracted with methylene chloride. The combined extracts were washed with brine, dried over $Na_2SO_4$, filtered, and concentrated to give a colorless oil (0.190 g). MW 172.61; MS (m/e) 190 ($M^+$+18).

Preparation 123

4-Chloro-5-(1-hydroxy-1-methyl-ethyl)-thiophene-2-carboxylic acid amide

A solution of 4-Chloro-5-(1-hydroxy-1-methyl-ethyl)-thiophene-2-carboxylic acid methyl ester (2.4 g) in condensed $NH_3$ (20 ml) and methanol (10 ml) was stirred at room temperature in a sealed tube for 3 days. The solvent was evaporated to give a solid which was purified via flash chromatography on silica using 5% methanol/methylene chloride as eluent to give a tan solid. This was triturated in diethyl ether to give a white solid (1.6 g). MW 219.71; MS (m/e) 237 ($M^+$+18) 220 ($M^+$+1) .

The compounds of Preparations 124–125 were prepared according to the procedure of Preparation 123 substituting the corresponding ester for 4-Chloro-5-(1-hydroxy-1-methyl-ethyl)-thiophene-2-carboxylic acid methyl ester. The duration of reaction was between 1 and 72 hours.

Preparation 124

5-(1-Ethyl-1-hydroxy-propyl)-thiophene-2-carboxylic acid amide

MW 213.33; MS (m/e) 213 ($M^+$).

Preparation 125

3-Chloro-5-(1-hydroxy-1-methyl-ethyl)-thiophene-2-carboxylic acid amide

MW 186.63; $^1$H NMR ($CDCl_3$) d 1.63 (6H, s), 6.85 (1H, s).

Preparation 126

4-Chloro-5-(1-hydroxy-1-methyl-ethyl)-thiophene-2-carboxylic acid methyl ester

To a solution of diisopropyl amine (6 ml, 38.9 mmole) in tetrahydrofuran (15 ml) at 0° C. was added dropwise 2.5 $\underline{M}$ nBuLi (16 ml) and stirred at 0° C. for 10 minutes. The mixture was cooled to −78° C. and 4-Chloro-thiophene-2-carboxylic acid (3.0 grams, 18.5 mmole) in tetrahydrofuran (15 ml) was added dropwise and stirred for 20 minutes then acetone (1.6 mL, 22.2 mmol.) was added and the mixture was allowed to warm to room temperature over 1 hour. The mixture was poured into 200 ml water and extracted with diethyl ether. The aqueous was acidified to pH 4 with oxalic acid and extracted with methylene chloride. The combined extracts were washed with water dried over MgSO$_4$, filtered, and concentrated to a solid. This was taken up in diethyl ether (100 ml) and treated with CH$_2$N$_2$ at 0° C. The reaction was quenched with acetic acid, diluted with diethyl ether (300 ml) and washed with saturated NaHCO$_3$, water, and brine, dried over MgSO$_4$, filtered, and concentrated to give an oil which was purified via flash chromatography on silica using 20% ethyl acetate/hexane as eluent to give a solid (2.42 g). MW 234.72; MS (m/e) 234/236 (M$^+$+1).

The compounds of Preparations 127–129 were prepared according to the procedure of Preparation 126 substituting the corresponding acid for 4-Chloro-thiophene-2-carboxylic acid. The duration of reaction was between 1 and 24 hours.

Preparation 127

5-(1-Hydroxy-1-methyl-ethyl)-furan-2-carboxylic acid amide

MW 184.21; MS (m/e) 184 (M$^+$).

Preparation 128

5-(1-Ethyl-1-hydroxy-propyl)-thiophene-2-carboxylic acid methyl ester

MW 228.34; MS (m/e) 228 (M$^+$).

Preparation 129

3-Chloro-5-(1-hydroxy-1-methyl-ethyl)-thiophene-2-carboxylic acid methyl ester

MW 234.70; $^1$H NMR (CDCl$_3$) d 1.62 (6H, s), 3.85 (3H, s), 6.84 (1H, s).

Preparation 130

5-Amino-pentanoic acid ethyl ester

A solution of 5-Amino-pentanoic acid (1.06 grams, 9.0 mmole) and thionyl chloride (20.0 ml) was stirred at room temperature for 2 hours. The solvent was evaporated and ethanol (26.5 ml) was added and gently warmed. After 2 hours the solution was concentrated to give a yellow solid (0.580 g). MW 145.22; MS (m/e) 146 (M$^+$+1).

The compound of Preparations 131 was prepared according to the procedure of Preparation 130 substituting the corresponding acid for 5-Amino-pentanoic acid. The duration of reaction was between 1 and 24 hours.

Preparation 131 trans-4-Aminomethyl-cyclohexanecarboxylic acid ethyl ester

MW 185.28; MS (m/e) 186 (M$^+$+1).

Preparation 132

5-(1-Hydroxy-1-methyl-ethyl)-furan-2-carboxylic acid methyl ester

To a solution of diisopropylamine (7.6 ml, 54.0 mmole) in tetrahydrofuran (20 ml) at 0° C. was added 2.5 $\underline{M}$ nButyl lithium (22 ml, 54.0 mmole). The mixture was cooled to −78° C. and a solution of Furan-2-carboxylic acid (3.0 grams, 27.0 mmole) in tetrahydrofuran (20 ml) was added dropwise and stirred for 20 minutes and acetone (2.4 ml, 32.0 mmole) was added. The mixture was stirred at −78° C. for 10 minutes and allowed to warm to room temperature over 1 hour. The mixture was poured into 200 ml water, acidified with oxalic acid to pH 2 and extracted with diethyl ether. The combined extracts were washed with water and brine, dried over MgSO$_4$, filtered, and concentrated to give a solid. (0.580 g). MW 145.22; MS (m/e) 146 (M$^+$+1).

Preparation 133

3-Chloro-4-(1-hydroxy-1-methyl-ethyl)-benzonitrile

To a solution of 3-Chloro-4-cyano-benzoic acid methyl ester (2.0 grams, 10.0 mmole) in tetrahydrofuran (30 ml) at −40° C. was added 3.0 $\underline{M}$ CH$_3$MgCl (8 ml, 22.0 mmole) dropwise. The mixture was allowed to warm to room temperature over one hour. The reaction was quenched with 10 ml methanol added dropwise, poured into 200 ml water, acidified with oxalic acid and extracted with ethyl acetate. The combined extracts were washed with water and brine, dried over MgSO$_4$, filtered, and concentrated to give an oil. (2.1 g). MW 195.60; MS (m/e) 195/197 (M$^{30}$).

The compound of Preparation 134 was prepared according to the procedure of Preparation 133 substituting the corresponding ester for 3-Chloro-4-cyano-benzoic acid methyl ester. The duration of reaction was between 1 and 24 hours.

Preparation 134

2-Chloro-4-(1-hydroxy-1-methyl-ethyl)-benzonitrile

MW 195.60; MS (m/e) 195/197 (M$^+$).

Preparation 135

2-Chloro-4-cyano-benzoic acid methyl ester

A solution of 4-Bromo-2-chloro-benzoic acid methyl ester (3.1 grams, 12.0 mmole), Zn(CN)$_2$ 0.875 grams, 7.0 mmole) and PH(PPh$_3$)$_4$ (0.555 grams, 48.0 mmole) in dimethylformamide (30 ml) was heated to 90° C. over night. The reaction was poured into 200 ml saturated sodium hydrogencarbonate and extracted with diethyl ether. The combined extracts were washed with water and brine, dried over MgSO$_4$, filtered, and concentrated to give an oil which was purified via flash chromatography on silica using 20% ethyl acetate/hexane as eluent to give a white solid. (2.1 g). MW 195.61; MS (m/e) 195/197 (M$^+$).

The compounds of Preparation 136 was prepared according to the procedure of Preparation 135 substituting 3-chloro-4trifluoromethane sulfonyloxy-benzoic acid methyl ester for 4-Bromo-2-chloro-benzoic acid methyl ester. The duration of reaction was between 1 and 24 hours.

Preparation 136

4-Trifluoroacetyl-benzonitrile

MW 199.13; MS (m/e) 199 (M$^+$).

Preparation 137

(S)-(+)-trans-1-(4-Aminomethyl-cyclohexyl)-ethanol.

Prepared in an analogous manner to that of Preparation 253 from (S)-(+)-(trans-4-(1-Hydroxy-ethyl)- cyclohexylmethyl)carbamic acid benzyl ester which was obtained from (trans-4-Acetyl-cyclohexylmethyl)-carbamic acid benzyl ester using (R)-2-Methyl-CBS-oxazaborolidine monohydrate in an analogous fashion as that of Preparation 254.

Preparation 138

1-(4-Aminomethyl-phenyl)-2,2,2-trifluoro-ethanol

To a solution of 4Trifluoroacetyl-benzonitrile (0.840 grams, 4.49 mmole) in tetrahydrofuran (20 ml) was added 1.0 M lithium aluminum hydride (15 ml, 14.8 mmole) dropwise, stirred at 0° C. for 10 minutes and refluxed for 30 minutes. The mixture was cooled to 0° C., quenched with 10 ml methanol added dropwise and diluted with chloroform (300 ml). The mixture was washed with water, dried over $MgSO_4$, filtered, and concentrated to an oil which was purified via flash chromatography on silica using 5% methanol/methylene chloride as eluent to give a solid (0.350 g). MW 205.20; MS (m/e) 205($M^+$).

The compound of Preparation 139 was prepared according to the procedure of preparation 138 substituting the corresponding nitrile for 4-Trifluoroacetyl-benzonitrile. The duration of reaction was between 30 minutes and 24 hours.

Preparation 139

7-Aminomethyl-chroman-4-ol

MW 179.24; MS (m/e) 179 ($M^+$).

Preparation 140

4-Oxo-chroman-7-carbonitrile

A solution of Trifluoro-methanesulfonic acid 4-oxo-chroman-7-yl ester (2.0 grams, 6.80 mmole), $Zn(CN)_2$ (0.476 grams, 4.1 mmole) and $Pd(PPh_3)_4$ (0.314 grams, 0.27 mmole) in dimethylformamide (20 ml) was heated to 80° C. over night. The reaction was poured into 200 ml 1/1 saturated $NaHCO_3$/water and extracted with diethyl ether. The combined extracts were washed with water and brine, dried over $MgSO_4$, filtered, and concentrated to give an oil which was purified via flash chromatography on silica using 30% ethyl acetate/hexane as eluent to give a solid. (1.02 g). MW 173.20; MS (m/e) 173 ($M^+$).

The compound of Preparation 141 was prepared according to the procedure of Preparation 140 substituting the corresponding triflate for Trifluoro-methanesulfonic acid 4-oxo-chroman-7-yl ester. The duration of reaction was between 30 minutes and 24 hours.

Preparation 141

3-Chloro-4-cyano-benzoic acid methyl ester

MW 195.61 MS (m/e, %) 195($M^+$, 25), 164 (100).

Preparation 142

4-(1-Hydroxy-cyclobutyl)-benzonitrile

To a solution of 4-Bromo-benzonitrile (2.0 grams, 10.99 mmole) in tetrahydrofuran (30 ml) at −100° C. was added dropwise 2.5 M nBuLi (4.8 ml) and stirred at −100° C. for 15 minutes. Cyclobutanone (0.965 grams, 13.19 mmole) was added dropwise and stirred for 10 minutes and allowed to warm to room temperature over 1 hour. The mixture was poured into 200 ml water and extracted with diethyl ether. The combined extracts were washed with water and brine, dried over $MgSO_4$, filtered, and concentrated to an oil which was purified via flash chromatography on silica using 40% ethyl acetate/hexane as eluent to give a clear oil (1.5 g). MW 173.23; MS (m/e) 173 ($M^+$).

Preparation 143

4-(1-Hydroxy-prop-2-ynyl)-benzonitrile

To a solution of 4-Formyl-benzonitrile (1.5 grams, 10.0 mmole) in tetrahydrofuran (20 ml) at −78° C. was added 0.5 M ethynyl magnesium bromide (26 ml, 13.0 mmole) dropwise. The mixture was stirred at −78° C. for 30 minutes and allowed to warm to room temperature over one hour. The reaction was cooled to 0° C., quenched with 10 ml methanol, poured into 200 ml water, acidified with oxalic acid and extracted with diethyl ether. The combined extracts were washed with water and brine, dried over $MgSO_4$, filtered, and concentrated to give an oil which was purified via flash chromatography on silica using 30% ethyl acetate/hexane as eluent to give a solid. (1.6 g). MW 157.18; MS (m/e) 157 ($M^+$).

Preparation 144

3-Chloro-4-trifluoromethanesulfonyloxy-benzoic acid methyl ester

To a solution of 3-Chloro-4-hydroxy-benzoic acid methyl ester (15.0 grams, 80.0 mmole), triethylamine (20.2 grams, 200 mmole) and DMAP (1.0 grams, 8.0 mmole) in methylene chloride (200 ml) at 0° C. was added triflic anhydride (17 ml, 100.0 mmole) dropwise. The mixture was allowed to warm to room temperature and stirred for four hours. It was diluted with methylene chloride (600 ml), washed with water, dried over $MgSO_4$, filtered, and concentrated to give an oil which was purified via flash chromatography on silica using 20% ethyl acetate/hexane as eluent to give an oil. (20.9 g). MW 322.05; MS (m/e) 322 ($M^+$).

Preparation 145

4-(1-Azetedinyl)-benzonitrile

A mixture of 6.34 9 (52.5 mmol) of 4-fluorobenzonitrile, 3.00 g (52.5 mmol) of azetidine, 7.26 g (52.5 mmol) of $K_2CO_3$, and 50 mL of methyl sulfoxide was heated to 60° C. for 16 h. The cooled mixture was diluted with 200 mL of water and extracted with EtOAc (2×150 mL). The combined organic extracts were washed with water (1×150 mL), brine (1×150 mL), dried ($Na_2SO_4$), and evaporated to 5.65 g of a white solid. Trituration in hexane gave 3.85 g (56% yield) of the title compound as a white solid, mp 98–99° C. $^1$H NMR ($CDCl_3$) d 2.39–2.45 (2H, m), 3.96 (4H, t, J=7 Hz), 6.32 (2H, d, J=9 Hz), 7.41 (2H, d, J=9 Hz); AMPI MS (m/e) 159 ($M^+$+1).

The compounds of Preparations 146–151 were prepared according to the procedure of Preparation 145 substituting the corresponding amine for azetidine. Temperatures ranged from 90–115° C. For preparations of the amines used in Preparations 54a and 54f, see: Rosenberg, S. H. et al. *J. Med. Chem.*, 1993, 36, 460 and Goldberg, S. D.; *J. Am. Chem. Soc.*, 1939, 61, 3526, respectively. Temperatures ranged from 90–115° C. Mass spectra were determined by the AMPI method.

Preparation 146

4-(3-Hydroxy-azetidin-1-yl)-benzonitrile

M.P. 75–78° C.; $^1$H NMR ($CDCl_3$) d 2.37 (1H, d, J=7 Hz), 4.04 (4H, ABX pattern, $J_{AB}$=8 Hz, $J_{AX}$=7 Hz, $J_{BX}$=4 Hz), 4.77–4.88 (1H, m), 6.36 (2H, d, J=8 Hz), 7.41 (2H, d, J=8 Hz); MS (m/e) 175 (M$^+$+1).

Preparation 147

4-Pyrrolidin-1-yl-benzonitrile

M.P. 75–76° C.; $^1$H NMR (CDCl$_3$) d 2.01–2.04 (4H, m), 3.29–3.33 (4H, m), 6.49 (2H, d, J=8 Hz), 7.43 (2H, d, J=8 Hz); MS (m/e) 173 (M$^+$+1).

Preparation 148

4-Piperidin-1-yl-benzonitrile $^1$H NMR (CDCl$_3$) d 1.63–1.69 (6H, m), 3.29–3.33 (4H, m), 6.83 (2H, d, J=9 Hz), 7.44 (2H, d, J=9 Hz).

Preparation 149

4-Morpholin-4-yl-benzonitrile

M.P. 81–82° C.; $^1$H NMR (CDCl$_3$) d 3.25–3.27 (4H, m), 3.82–3.85 (4H, m), 6.85 (2H, d, J=9 Hz), 7.49 (2H, d, J=9 Hz); MS (m/e) 189 (M$^+$+1).

Preparation 150

4-(1,4-Dioxa-8-aza-spiro[4,5]dec-8-yl)-benzonitrile

M.P. 133–134° C.; Anal. Calcd for C$_{14}$H$_{16}$N$_2$O$_2$: C, 68.83; H, 6.60; N, 11.47. Found: C, 69.21; H, 6.64; N, 11.61.

Preparation 151

4-[(2-Hydroxy-2-methyl-propyl)-methyl-amino]-benzonitrile $^1$H NMR (CDCl$_3$) d 1.27 (6H, s), 1.56 (1H, s), 3.09 (3H, s), 3.39 (2H, s), 6.79 (2H, d, J=9 Hz), 7.44 (2H, d, J=9 Hz); MS (m/e) 205 (M$^+$+1).

Preparation 152

1-[4-(Aminomethyl)phenyl]-azetidine

To a solution of 2.00 g (12.6 mmol) of the compond of Preparation 145 in 50 mL of tetrahydrofuran was added portionwise 479 mg (12.6 mmol) of lithium aluminum hydride. When the addition was complete, the mixture was stirred for 4 h at rt. The mixture was quenched by the sequential addition of 2 mL of water, 2 mL of aqueous 15% sodium hydroxide solution, and 6 mL of water. The precipitate was removed by filtration washing well with THF. The filtrate was dried (Na$_2$SO$_4$) and evaporated to a yellow solid, which was purified by flash chromatography using EtOAc followed by 76:20:4 CHCl$_3$:MeOH: conc. NH$_3$ (aq.) as eluants to give 1.22 g of a semisolid. Trituration in hexane afforded 815 mg (40% yield) of the title compound as a yellow solid, mp 58–60° C. $^1$H NMR (CDCl$_3$) d 1.60 (2H, s), 2.29–2.37 (2H, m), 3.73 (2H, s), 3.83 (4H, t, J=7 Hz), 6.42 (2H, d, J=8 Hz), 7.13 (2H, d, J=8 Hz).

The compounds of Preparations 153–158 were prepared according to the procedure of Preparation 55 substituting the appropriate substrate for the compound of Preparation 145. Mass spectra were determined by the AMPI method.

Preparation 153

1-(4-Aminomethyl-phenyl)-azetidin-3-ol $^1$H NMR (CDCl$_3$) d 2.65 (3H, br s), 3.54–3.61 (2H, m), 3.70 (2H, s), 4.08–4.12 (2H, m), 4.68–4.79 (1H, m), 6.40 (2H, d, J=8 Hz), 7.09 (2H, d, J=8 Hz); MS (m/e) 162 (M$^+$+2–18 (H$_2$O)).

Preparation 154

1-(4-Aminomethyl-phenyl)-azetidin-3-ol

M.P.108–110° C.; $^1$H NMR (CDCl$_3$) d 1.87 (2H, s), 1.96–1.99 (4H, m), 3.25 (4H, t, J=7 Hz), 3.73 (2H, s), 6.52 (2H, d, J=8 Hz), 7.15 (2H, d, J=8 Hz); MS (m/e) 160 (M$^+$+2–18)).

Preparation 155

4-Piperidin-1-yl-benzylamine

M.P.108–110° C.; $^1$H NMR (CDCl$_3$) d 1.52–1.58 (2H, m), 1.68–1.72 (4H, m), 1.80 (2H, s), 3.08–3.12(4H, m), 3.76 (2H, s), 6.89(2H, d, J=9 Hz), 7.17 (2H, d, J=9 Hz).

Preparation 156

4-Morpholin-4-yl-benzylamine

M.P.53–54° C; $^1$H NMR (CDCl$_3$) d 1.51 (2H, s), 3.11–3.14 (4H, m), 3.78 (2H, s), 3.83–3.86(4H, m), 6.88(2H, d, J=8 Hz), 7.22(2H, d, J=8 Hz).

Preparation 157

4-(1,4-Dioxa-8-aza-spiro[4,5]dec-8-yl)-benzylamine

M.P.107–110° C.; $^1$H NMR (CDCl$_3$) d 1.81 (4H, t, J=6 Hz), 3.07 (2H, br s), 3.29 (4H, t, J=6 Hz), 3.80 (2H, s), 3.98 (4H, s), 6.89 (2H, d, J=8 Hz), 7.22 (2H, d, J=8 Hz).

Preparation 158

1-[(4-Aminomethyl-phenyl)-methyl-amino]-2-methyl-propan-2-ol $^1$H NMR (CDCl$_3$) d 1.26 (6H, s), 1.97 (3H, br s), 2.97 (3H, s), 3.25 (2H, s), 3.78 (2 H, s),6.80 (2H, d, J=9 Hz), 7.20(2H, d, J=9 Hz).

Preparation 159

2-(4-Fluorophenoxy)-3-pyridinecarboxylic Acid Methyl Ester

A mixture of 20.0 g (89.6 mmol) of 2-(4-fluorophenoxy)-3-pyridinecarboxylic acid (for preparation, see: Villani, F. J. et al. *J. Med. Chem.*, 1975, 18,3), 300 mL of methanol, and 5.5 mL of concentrated sulfuric acid was heated to reflux for 2 h. The cooled mixture was poured onto 500 mL of ice cold saturated aqueous sodium hydrogencarbonate solution, and the resulting precipitate was filtered, washed with water, and dreid under vacuum to give 12.9 g (64% yield) of the title compound as a white solid, mp 97–99° C. Anal. Calcd for C$_{13}$H$_{10}$NO$_3$F: C, 63.16; H, 4.08; N, 5.67. Found: C, 62.80; H, 4.08; N, 5.50.

Preparation 160

2-(4-Fluorophenoxy)-3-pyridinemethanol

A solution of 10.00 g (40.45 mmol) of the compound of Preparation 56 in 200 mL of anhydrous toluene was cooled to −78° C. and treated dropwise with 84.95 mL (84.95 mmol) of a 1 M solution of diisobutylaluminum hydride in CH$_2$Cl$_2$. When the addition was complete, 200 mL of water was added followed by 200 mL of EtOAc, and the mixture was allowed to warm to rt. Following adjustment of the aqueous layer to pH 4 with aqueous 1N hydrochloric acid solution, the organic layer was separated and combined with a 200 mL backwash of the aqueous layer. The organic extracts were washed with saturated aqueous sodium hydrogencarbonate solution, brine, dried ($Na_2SO_4$), and evaporated to give 9.00 g (90% yield) of the title compound as an off-white solid, mp 70–72° C. $^1$H NMR ($CDCl_3$) d 1.59 (1H, s), 4.84 (2H, d, J=6 Hz), 6.99–7.13 (5H, m), 7.76–7.80 (1H, m), 8.07 (1H, dd, J=2.5 Hz).

Preparation 161

2-(4Fluorophenoxy)-3-pyridinecarboxaldehyde

A mixture of 932 mg (4.25 mmol) of the compound of Preparation 57, 2.00 g (23.0 mmol) of manganese dioxide, and 30 mL of benzene was heated to reflux for 3 h with water separation. The cooled mixture was filtered, evaporated to a white solid, and purified by flash chromatography using 15% EtOAc-hexane as eluant to provide 735 mg (80% yield) of the title compound as a white solid, mp 61–62 ° C. $^1$H NMR ($CDCl_3$) d 7.08–7.21 (5H, m), 8.19–8.32 (2 H, m), 10.55 (1H, s).

Preparation 162

3-[2-(4-Fluorophenoxy)-3-pyridinyl]-3-hydroxypropenoic Acid t-Butyl Ester

At −78 ° C., 115.3 mL (115.3 mmol) of a solution of 1 M lithium bis(trimethylsilyl)amide, in tetrahydrofuran was treated dropwise with 15.43 mL (13.39 grams, 115.3 mmol) of t-butyl acetate. When the addition was complete, the mixture was stirred for 15 min and then treated with a solution of 9.500 g (38.43 mmol) of the compound of Preparation 56 in 50 mL of THF. When the addition was complete, the mixture was stirred for 15 min and then quenched by the addition of 230 mL of aqueous 1N hydrochloric acid solution. After warming to rt, the organic layer was extracted with ether (2×500 mL) and the combined organic layers were washed with saturated aqueous sodium hydrogencarbonate solution (1×100 mL), brine (1×200 mL.), dried ($Na_2SO_4$), and evaporated to 13.8 g of a pale yellow oil. Purification by flash chromatography using 15 to 85% ether-hexane as eluant gave 11.7 g of a semi-solid, which was triurated with hexane to give 6.124 g (48% yield) of the title compound as a white solid, mp 87–89° C. $^1$H NMR ($CDCl_3$) d 1.54 (9H, s), 6.12 (1H, s), 7.01–7.16 (5H, m), 8.14 (1H, dd, J=2.5 Hz), 8.30 (1H, dd, J=2.8 Hz), 12.99 (1H, s). The NMR also showed the presence of <10% of the keto tautomer. After standing for 12 days, the concentrated mother liquor crystallized and was triurated in hexane to give an additional 2.21 g (17% yield) of the title compound.

Preparation 163 a-[(2-Chlorophenyl)methyl]-2-(4-fluorophenoxy)-β-oxo-3-pyridinepropanoic Acid t-Butyl Ester The sodium hydride obtained after washing 28.9 mg (0.604 mmol) of 50% sodium hydride dispersion in mineral oil with pentane (3×5 mL) was suspended in 5 mL of THF, cooled to 0° C., and treated dropwise with a solution of 200 mg (0.604 mmol) of the compound of preparation 59 in 5 mL of THF. After stirring for 15 min, 0.078 mL (124 mg, 0.604 mmol) of 2-chlorobenzyl bromide was added, and the mixture was allowed to warm to rt, stirred for 4 h, and then heated to reflux for 16 h. The cooled mixture was partitioned between 100 mL of saturated aqueous $NH_4Cl$ solution and 200 mL of EtOAc. The separated organic layer was washed with saturated aqueous sodium hydrogencarbonate solution (100 mL), brine (100 mL), dried ($Na_2SO_4$), and evaporated to an oil. Purification by flash chromatography using 60% $CH_2Cl_2$-hexane as eluant gave 226 mg (82% yield) of the title compound as an oil. $^1$H NMR ($CDCl_3$) d 1.54 (9H, s), 3.32–3.52 (2H, m), 5.09 (1H, dd, J=7.8 Hz), 7.02–7.30 (9H, m), 8.05 (1H, dd, J=2.8 Hz), 8.22 (1H, dd, J=2.5 Hz). The NMR also showed the presence of <10% of the enol tautomer.

The compounds of Preparations 164–168 were prepared according to the procedure of Preparation 163 substituting the indicated benzyl halide for 2-chlorobenzyl bromide. In the cases of Preparations 165–168 one equivalent of KI was added immediately after the addition of the benzyl halide. All compounds were oils. Mass spectra were determined by the thermospray method.

Preparation 164

2-(4-Fluoro-benzyl)-3-[2-(4-fluoro-phenoxy)-pyridin-3-yl]-3-oxo-propionic acid tert-butyl ester MS (m/e) 440 ($M^+$+1); $^1$H NMR ($CDCl_3$) d 1.27 (9H, s), 3.17–3.44 (2H, m), 4.80 (1H, dd, J=7.8 Hz), 6.85–7.30 (9H, m), 8.08 (1H, dd, J=2.8 Hz), 8.23–8.25 (1H, m).

Preparation 165

3-[2-(4-Fluoro-phenoxy)-pyridin-3-yl]-3-oxo-2-(47-trifluoromethyl-benzyl)-propionic acid tert butyl ester MS (m/e) 490 ($M^+$+1); $^1$H NMR ($CDCl_3$) d 1.24 (9H, s), 3.36 (2H, ABX pattern, $J_{AB}$=14 Hz, $J_{AX}$=7 Hz, $J_{BX}$ =8 Hz), 4.83 (1H, dd, J=7.8 Hz), 6.99–7.50 (9H, m), 8.02–8.22 (2H, m).

Preparation 166

3-[2-(4-Fluoro-phenoxy)-pyridin-3-yl]-3-oxo-2-(4-trifluoromethoxy-benzyl)-propionic acid tert-butyl ester MS (m/e) 506 ($M^+$+1); $^1$H NMR ($CDCl_3$) d 1.25 (9H, s), 3.32–3.46 (2H, m), 4.82 (1H, t, J=7), 7.03–7.28 (9H, m), 8.09 (1H, dd, J=2,8 Hz), 8.24 (1H, dd, J=2.5 Hz).

Preparation 167

2-(3,5-Difluoro-benzyl)-3-[2-(4-fluoro-phenoxyl-pyridin-3yl]-3-oxo-propionic acid tert-butyl ester MS (m/e) 458($M^+$+1); $^1$H NMR ($CDCl_3$) d 1.25 (9H, s), 3.28 (2H, ABX pattern, $J_{AB}$=14 Hz, $J_{AX}$=7 Hz, $J_{BX}$=8 Hz), 4.79(1H, dd, J=7,8 Hz), 6.55–7.18 (8H, m), 8.09 (1H, dd, J=2,8 Hz), 8.23(1H, dd, J=2,4 Hz).

Preparation 168

3-[2-(4-Fluoro-phenoxy)-pyridin-3-yl]-3-oxo-2-(2,4, 6-trifluoro-benzyl)-propionic acid tert-butyl ester MS (m/e) 476($M^+$+1); $^1$H NMR ($CDCl_3$) d 1.22 (9H, s), 3.22–3.35 (2H, m), 4.82 (1H, J=8 Hz), 6.56 (2H, t, J=8 Hz), 7.02–7.12 (5H, m), 8.11 (1H, dd, J=2.8 Hz), 8.22 (1H, dd, J=2.5 Hz).

Preparation 169

4-(1-Hydroxy-1-methylethyl)-benzeneproanoic Acid

A mixture of 12.61 g (224.7 mmol) of KOH, 73 mL of water, and 425 mL of ethanol was combined with 15.00 g (68.10 mmol) of 3-[4-(1-oxyethyl)phenyl]propionic acid ethyl ester (for preparation, see: Marechal, E.; Quere, J.-P. *Bull. Chem. Soc. Fr.,* 1971, 2227), and the resulting mixture was stirred at rt for 2 h. The mixture was concentrated, and the residue was dissolved in 100 mL of water, cooled to 0° C., and acidified with concentrated aqueous hydrochloric acid solution. The precipitate was filtered and recrystallized from methanol-water to give 10.11 g (77% yield) of 3-[4-(1-oxoethyl)phenyl]propionic acid as a white solid, mp 118–119° C. Anal. Calcd for $C_{11}H_{12}O_3$: C, 68.52; H, 6.06. Found: C, 68.74; H, 6.29.

A solution of 5.000 g (26.01 mmol) of the above acid in 500 mL of tetrahydrofuran was cooled to −17° C. and treated dropwise with 21.67 mL (65.03 mmol) of a 3 M solution of methylmagnesium iodide in ether. Additional Griganrd reagent solution was added in three portions, 5, 5, and 10 mL, respectively, over several hours, as the course of the reaction was monitored by NMR. The mixture was cooled to −30° C., quenched by the addition of 200 mL of saturated aqueous $NH_4Cl$ solution, and allowed to warm to rt. The aqueous layer was adjusted to pH 1 with aqueous 1 N hydrochloric acid solution, and the organic layer was extracted with EtOAc (2×200 mL). The combined organic layers were washed with brine (3×500 mL), dried ($Na_2SO_4$), and evaporated to 5.62 g of a yellow solid. Recrystallization from hexane-EtOAc gave 2.20 g (40% yield) of the title compound as a pale yellow solid, mp 92–94° C. $^1$H NMR (DMSO-d$^6$) d 1.36 (6H, s), 2.47 (2H, t, J=7 Hz), 2.74 (2H, t, J=7 Hz), 4.90 (1H, s), 7.21 (4H, AB quartet, J=7 Hz), 12.09 (1H, s).

Preparation 170

N-Methoxy-N-methyl-4-fluoro-benzenepropanamide

A suspension of 10.00 g (59.46 mmol) of 3-(4-fluorophenyl)propionic acid, 12.54 g (65.41 mmol) of 1-ethyl-3-(3-dimethylaminopropyl)carbodiimide hydrochloride, 6.381 g (65.41 mmol) of N,O-dimethylhydroxylamine hydrochloride in 300 mL of $CH_2Cl_2$ was cooled to 0° C. and treated with 18.23 mL (13.23 grams, 130.8 mmol) of triethylamine. The mixture was stirred for 16 h with slow warming to rt. The mixture was concentrated, and the residue was partitioned between 300 mL of EtOAc and 200 mL of aqueous 1 N hydrochloric acid solution. The separated organic layer was washed with aqueous 1 N hydrochloric acid solution (1×100 mL), saturated aqueous sodium hydrogencarbonate solution (2×200 mL), brine (1×100 mL), dried ($Na_2SO_4$), and evaporated to give 9.56 g (76% yield) of the title compound as an oil. $^1$H NMR (CDCl$_3$) d 2.70(2H, t, J=8 Hz), 2.91 (2H, t, J=8 Hz), 3.15 (3H, s), 3.59 (3H, s), 6.92–6.97 (2H, m), 7.15–7.19 (2H, m). APCI MS (m/e) 212 (M$^+$+1).

The compounds of Preparations 171–180 were prepared according to the procedure of Preparation 170 substituting the corresponding carboxylic acid for 3-(4-fluorophenyl) propionic acid. The carboxylic acid used in Preparation 174 was the compound of Preparation 163, whereas all other carboxylic acids were commercially available. Mass spectra were determined by the APCI method.

Preparation 171

N-Methoxy-N-methyl-3-phenyl-propionamide

Anal. Calcd for $C_{11}H_{15}NO_2$: C, 68.37,H, 7.82; N, 7.25. Found: C, 68.65; H, 8.11; N, Preparation 172

N-Methoxy-2,N-dimethyl-3-phenyl-propionamide $^1$H NMR (CDCl$_3$) d 1.16 (3H, d, J=7 Hz), 2.83–3.28 (2H, ABX pattern, $J_{AB}$=13 Hz, $J_{AX}$=7 Hz, $J_{BX}$=8 Hz), 3.08–3.18 (1H, m), 3.14 (3H, s), 3.48 (3H, s), 7.15–7.32 (5H, m); MS (m/e) 208 (M$^+$+1).

Preparation 173

N-Methoxy-N-methyl-3-phenyl-butyramide $^1$H NMR (CDCl$_3$) d 1.31 (3H, d, J=7 Hz), 2.59–2.78 (2H, m), 3.14 (3H, s), 3.32–3.44 (1H, m), 3.58 (3H, s), 7.14–7.32 (5H, m); MS (m/e) 208 (M$^+$+1).

Preparation 174

3-[4-(1-Hydroxy-1-methyl-ethyl)-phenyl]-N-methoxy-N-methyl-propionamide $^1$H NMR (CDCl$_3$) d 1.56 (6H, s), 1.71 (1H, s), 2.72 (2H, t, J=8 Hz), 2.93 (2H, t, J=8 Hz), 3.17 (3H, s), 3.60 (3H, s), 7.30 (4H, AB quartet, J=8 Hz); MS (m/e) 234(M$^+$+1−18 (H$_2$O)).

Preparation 175

N-Methoxy-N-methyl-2-phenyl-acetamide $^1$H NMR (CDCl$_3$) d 3.18 (3H, s), 3.54 (3H, s), 3.78 (2H, s), 7.20–7.34 (5 H, m); MS (m/e) 180 (M$^+$+1).

Preparation 176

N-Methoxy-N-methyl-2-phenoxy-acetamide $^1$H NMR (CDCl$_3$) d 3.22 (3H, s), 3.74 (3H, s), 4.79 (2H, s), 6.92–6.97 (3 H, m), 7.24–7.29 (2H, m); MS (m/e) 196 (M$^+$+1).

Preparation 177

N-Methoxy-N-methyl-3-phenyl-acrylamide

M.P. 40–42° C.; $^1$H NMR (CDCl$_3$) d 3.30 (3H, s), 3.76 (3H, s), 7.02 (1H, d, J=16 Hz), 7.34–7.39 (3H, m), 7.55–7.57 (2H, m), 7.72 (1H, d, J=16 Hz); MS (m/e) 192 (M$^+$+1).

Preparation 178

Benzofuran-3-carboxylic acid methoxy-methyl-amide $^1$H NMR (CDCl$_3$) d 3.41 (3H, s), 3.82 (3H, s), 7.24–7.43 (2H, m), 7.50 (1 H, s), 7.59 (1H, dd, J=1.8 Hz), 7.66 (1H, dd, J=1.8 Hz); MS (m/e) 206 (M$^+$+1).

Preparation 179

1H-Indole-3-carboxylic acid methoxy-methyl-amide

M.P. 136–137° C.; Anal. Calcd for $C_{11}H_{12}N_2O_2$: C, 64.69; H, 5.94; N, 13.72. Found: C, 64.97; H, 5.81; N, 13.65.

Preparation 180

2-(2-Chloro-phenoxy)-N-methoxy-N-methyl-acetamide $^1$H NMR (CDCl$_3$) d 3.21 (3H, s), 3.74 (3H, s), 4.88 (2H, s), 6.89–6.93 (2 H, m), 7.15–7.19 (1H, m), 7.34–7.36 (1H, m).

Preparation 181

1-[2-Fluoro-3-pyridinyl]-3-(4-fluorophenyl)-1-propanone

A solution of 5.90 mL (4.56 grams, 45.0 mmol) of diisopropylamine in 20 mL of tetrahydrofuran was cooled to −78° C. and treated dropwise with 18.0 mL (45.0 mmol) of a solution of 2.5 M n-butyllithium in hexane. When the addition was complete, the mixture was stirred for 0.5 h at −78° C. and treated dropwise with 3.88 mL (4.37 grams, 45.0 mmol) of freshly distilled 2-fluoropyridine. After the addition was complete, the resulting yellow suspension was stirred for 0.5 h at −78° C. To the suspension was added dropwise a solution of 9.51 g (45.0 mmol) of the compound of Preparation 62 in 200 mL of tetrahydrofuran dropwise. The mixture was stirred for 16 h with slowing warming to rt as the dry ice/acetone bath melted. The mixture was quenched by the addition of 50 mL of aqueous 1 N hydrochloric acid solution, and the THF was removed by partial evaporation. The residue was partitioned between EtOAc (300 mL) and aqueous 1 N hydrochloric acid solution (100 mL). The separated organic layer was washed with aqueous 1 N hydrochloric acid solution (100 mL), saturated aqueous sodium hydrogencarbonate solution (100 mL), brine (100 mL), dried ($Na_2SO_4$), and evaporated to 12.6 g of a yellow oil. Purification by flash chromatography using 25% EtOAc-hexane as eluant gave 7.11 g of a yellow which solidified on standing. Trituration in hexane gave 6.87 g (62% yield) of the title compound as a light yellow solid, mp 73–74° C. $^1$H NMR ($CDCl_3$) d 3.02 (2H, t, J=7 Hz), 3.29–3.36 (2H, m), 6.91–6.99 (2H, m), 7.17–7.33 (3 H, m), 8.29–8.38 (2H, m); APCI MS (m/e) 248 ($M^+$+1).

The compounds of Preparations 182–190 were prepared according to the procedure of Preparation 191 substituting the corresponding N-methoxy-N-methylamide or ester substrate for the compound of Preparation 170 In the case of Preparations 185 and 191, an additional equivalent of in situ-prepared 2-fluoro-3-lithiopyridine was utilized. Products were purified by direct trituration and/or flash chromatography. Mass spectra were determined by the APCI method.

Preparation 182

1-(2-Fluoro-pyridin-3-yl)-3-phenyl-propan-1-one $^1$H NMR ($CDCl_3$) d 3.05 (2H, t, J=7 Hz), 3.32–3.64 (2H, m), 7.17–7.33 (6 H, m), 8.29–8.38 (2H, m).

Preparation 183

1-(2-Fluoro-pyridin-3-yl)-2-methyl-3-phenyl-propan-1-one $^1$H NMR ($CDCl_3$) d 1.18 (3H, d, J=7 Hz), 2.88 (2H, ABX pattern, $J_{AB}$=14 Hz, $J_{AX}$=6 Hz, $J_{BX}$=8 Hz), 3.63–3.72 (1H, m), 7.14–7.29 (6H, m), 8.14–8.19 (1H, m), 8.33–8.35 (1H, m); MS (m/e) 244 ($M^+$+1).

Preparation 184

1-(2-Fluoro-pyridin-3-yl)-3-phenyl-butan-1-one

M.P. 51–53° C.; Anal. Calcd for $C_{15}H_{14}FNO$: C, 74.06; H, 6.00; N, 5.76. Found: C, 73.82; H, 5.83; N, 5.90.

Preparation 185

1-(2-Fluoro-pyridin-3-yl)-3-[4-(1-hydroxy-1-methyl-ethyl)-phenyl]-propan-1-one $^1$H NMR ($CDCl_3$) d 1.56 (6H, s), 3.03 (2H, t, J=7 Hz), 3.31–3.36 (2H, m), 7.20–7.25 (2H, m), 7.30–7.34 (1H, m), 7.40–7.42 (2H, m), 8.30–8.38 (2H, m); MS (m/e) 270 ($M^+$+1−18 ($H_2O$)).

Preparation 186

1-(2-Fluoro-pyridin-3-yl)-2-phenyl-ethanone $^1$H NMR ($CDCl_3$) d 4.31 (2H, s), 7.19–7.34 (6H, m), 8.27–8.37 (2H, m); MS (m/e) 216 ($M^+$+1).

Preparation 187

1-(2-Fluoro-pyridin-3-yl)-2-phenoxy-ethanone

M.P. 82–83° C.; $^1$H NMR ($CDCl_3$) d 5.21 (2H, d, J=3 Hz), 6.91–7.01 (3H, m), 7.27–7.31 (2H, m), 7.37–7.40 (1H, m), 8.41–8.45 (2H, m); MS (m/e) 232 ($M^+$+1).

Preparation 188

2-(2-Chloro-phenoxy)-1-(2-fluoro-pyridin-3-yl)-ethanone

M.P. 84–86° C.; $^1$H NMR ($CDCl_3$) d 5.34 (2H, d, J=3 Hz), 6.85–7.45 (5H, m), 8.42–8.50 (2H, m); MS (m/e) 266, 268 ($M^+$+1).

Preparation 189

1-(2-Fluoro-pyridin-3-yl)-3-phenyl-propenone

M.P. 83–84° C.; $^1$H NMR ($CDCl_3$) d 7.34–7.37 (1H, m), 7.41–7.47 (4H, m), 7.62–7.65 (2H, m), 7.90 (1H, d, J=15 Hz), 8.29–8.31 (1H, m), 8.38–8.41 (1H, m).

Preparation 190

Benzofuran-3-yl-(2-fluoro-pyridin-3-yl)-methanone

M.P. 110–111° C.; Anal. Calcd for $C_{14}H_8FNO_2$: C, 69.71; H, 3.34; N, 5.81. Found: C, 69.64; H, 3.36; N, 6.12.

Preparation 191

(2-Fluoro-pyridin-3-yl)-(1H-indol-3-yl)-methanone

M.P. 195–198° C.; Anal. Calcd for $C_{14}H_9FN_2O_2$: C, 70.00; H, 3.78; N, 11.66. Found: C, 69.69; H, 3.60; N, 11.59.

Preparation 192

1-(2-Fluoro-pyridin-3-yl)-ethanone $^1$H NMR ($CDCl_3$) d 2.67 (3H, d, J=0.5 Hz),), 7.30–7.33 (1H, m), 8.30–8.38 (2H, m).

Preparation 193

1-(2-Fluoro-pyridin-3-yl)-2-(methyl-phenyl-amino)-ethanone $^1$H NMR ($CDCl_3$) d 3.10 (3H, s), 4.72 (2H, d, J=3 Hz), 6.63–6.74 (3H, m), 7.18–7.24 (2H, m), 7.32–7.36 (1H, m), 8.30–8.42 (2H, m); MS (m/e) 245 ($M^+$+1).

Preparation 194

1-[2-(4-Fluorophenoxy)-3-pyridinyl]-ethanone $^1$H NMR ($CDCl_3$) d 2.75 (3H, s), 7.07–7.12 (5H, m), 8.20 (1H, dd, J 2, 7 Hz), 8.24 (1H, dd, J=2.5 Hz).

Preparation 195

1-[2-(3-Pyridinyloxyl-3-pyridinyl]-ethanone $^1$H NMR ($CDCl_3$) d 2.76 (3H, s), 7.13–7.15 (1H, m), 7.39 (1H, dd, J=5.9 Hz), 7.53–7.56 (1H, m), 8.22–8.24 (2H, m), 8.50–8.53 (2H, m).

Preparation 196

2-Fluoro-a-phenyl-3-pyridinemethanol $^1$H NMR ($CDCl_3$) d 2.61 (1H, br s), 6.03 (1H, s), 7.14–7.38 (6H, m), 7.97–8.08 (2H, m).

Preparation 197

(2-Fluoro-3-pyridinyl)phenyl-methanone $^1$H NMR (CDCl$_3$) d 7.32–7.38 (1H, m), 7.47–7.50 (2H, m), 7.61–7.67 (1H, m), 7.78–7.82 (2H, m), 7.98–8.07 (1H, m), 8.38–8.42 (1H, m).

Preparation 198

4-(1-hydroxy-1-methyl-ethyl)-benzonitrile

To a stirred suspension of anhydrous cerium (III) chloride (3.8 g, 16 mmol) in 20 mL dry tetrahydrofuran at 0° C. was added slowly dropwise a solution of 3.0M methyl magnesium chloride in tetrahydrofuran (10 mL, 31 mmol). The mixture was stirred at 0° C. for 30 min. then a solution of Methyl 4-cyanobenzoate (2.0 g, 12.4 mmol) in 20 mL dry tetrahydrofuran slowly dropwise. The mixture was stirred for an additional 30 min. at 0° C. then quenched with 2.0 M acetic acid (~10 mL) added slowly dropwise. The mixture was poured into 200 mL water and extracted with ethyl acetate (2×200 mL). The organic extracts were combined, washed with sodium bicarbonate solution (1×40 mL), water (2×40 mL), brine (1×40 mL), dried (MgSO$_4$) and concentrated in vacuo to give an oil. The oil was absorbed onto Silica Gel (10 g) and washed with ethyl acetate/hexane (1:2, 1500 mL). Concentration of the washings in vacuo afforded 1.75 g (88%) 4-(1-hydroxy-1-methyl-ethyl)-benzonitrile as a clear oil. $^1$H-NMR (CDCl$_3$): δ7.60 (m, 4H), 1.58 (m, 6H). GC-MS (m/e, %): 161 (M$^+$, 2), 146 (100).

Preparation 199

2-Fluoro-5-hydroxy-benzonitrile

To a solution of 2-Fluoro-5-methoxy-benzonitrile (4.0 grams, 26.5 mmole) in CH$_2$Cl$_2$ (100 ml) at 0° C. was added 1.0 M BBr$_3$ (29 ml, 29 mmole) dropwise, warmed to room temperature and stirred over night. The mixture was poured into 300 ml ice water and stirred for 10 minutes. This was poured into 100 ml methylene chloride, and the layers were separated. The mixture was washed with water, dried over MgSO$_4$, filtered, and concentrated to a solid (2.8 g). MW 137.12; MS (m/e) 137(M$^+$).

The compound of Preparation 200 was prepared according to the procedure of Preparation 199 substituting the corresponding ether for 2-Fluoro-5-methoxy-benzonitrile. The duration of reaction was between 1 and 24 hours.

Preparation 200

3-Hydroxy-N,N-dimethyl-benzamide

MW 165.21 MS (m/e, %) 165(M$^+$, 30), 121 (100).

Preparation 201

2-Fluoro-5-methoxy-benzonitrile

A solution of 2-Chloro-1-fluoro-4-methoxy-benzene (10.4 grams, 65.0 mmole), CuCN (6.4 grams, 71.0 mmole) and N-methylpyrrolidinone (100 ml) was refluxed for 18 hours. An additional 2.3 g CuCN was added, and the mixture was refluxed for 40 hours. The mixture was poured into 300 ml ice water and stirred for 10 minutes. This was poured into 100 ml methylene chloride and the layers were separated. The mixture was washed with water, dried over MgSO$_4$, filtered, and concentrated to a solid (2.8 g). MW 137.12; MS (m/e) 137(M$^+$).

Preparation 202

1,4-Dioxa-spiro[4,5]decane-8-carbonitrile

To a solution of 1,4-Dioxa-spiro[4,5]decan-8-one (2.0 grams, 12.8 mmole) and tosyl-methyl isocyanate (5.0 grams, 25.6 mmole) in dimethylformamide (25 ml) at 0° C. was added 1.0 M tBuOK in tButanol (25.6 ml) and stirred at 0° C. for 1 hour and room temperature over night. The mixture was diluted with water and extracted with diethyl ether. The combined extracts were washed with water and brine, dried over MgSO$_4$, filtered, and concentrated to a solid which was purified via flash chromatography on silica using 30% ethyl acetate/hexane as eluent to give a solid (1.45 g). MW 167.209; MS (m/e) 168 (M$^+$+1).

Preparation 203

C-(4,5-Dichloro-thiophen-2-yl)-methylamine

To a stirred suspension of 2-(4,5-Dichloro-thiophen-2-ylmethyl)-isoindole-1,3-dione (0.770 grams, 2.47 mmole) in methanol (30 ml) and tetrahydrofuran (10 ml) at room temperature was added hydrazine hydrate (0.395 grams, 12.3 mmole) and stirred at room temperature over night. A precipitate formed, and the mixture was concentrated to about 15 ml and filtered. The filtrate was poured into 100 ml water and extracted with diethyl ether. The combined extracts were washed with water and brine, dried over MgSO$_4$, filtered, and concentrated to an oil which was purified via flash chromatography on silica using 5% methanol/methylene chloride as eluent to give an oil (0.341 g). MW 182.08; MS (m/e) 183 (M$^+$+1).

Preparation 204

2-(4,5-Dichloro-thiophen-2-ylmethyl)-isoindole-1,3-dione

To a stirred solution of (4,5-Dichloro-thiophen-2-yl)-methanol (0.660 grams, 3.60 mmole), Phthalimide (0.636 grams, 4.32 mmole), and triphenyl phosphene (1.1 grams, 4.32 mmole) in tetrahydrofuran (20 ml) at room temperature was added diethyl azodicarboxylate (0.395 grams, 12.3 mmole) and stirred at room temperature over night. The mixture was poured into 100 ml water and extracted with diethyl ether. The combined extracts were washed with 1 N NaOH, water and brine, dried over MgSO$_4$, filtered, and concentrated to an oil from which triphenylphosphine was crystalized out using diethyl ether/hexane. The mother liquor was concentrated to give a solid which was purified via flash chromatography on silica using 30% ethyl acetate/hexane as eluent to give a yellow solid. This was triturated in hexane to give a white solid (0.772 g). MW 312.18; MS (m/e) 313 (M$^+$+1).

Preparation 205

(4,5-Dichloro-thiophen-2-yl)-methanol

To a solution of 4,5-Dichloro-thiophene-2-carboxylic acid (0.500 grams, 2.53 mmole) and thionyl chloride (1.0 ml) in methylene chloride (10 ml) was refluxed for 3 hours. The mixture was concentrated to remove solvent and diluted with 15 ml dioxane and sodium borohydride (0.143 grams, 3.8 mmole) and refluxed for 3 hours. The mixture was cooled to 0° C. and 3 ml water was added dropwise. The mixture was poured into 100 ml water. This was extracted with diethyl ether, washed with 1N NaOH, water, and brine, dried over MgSO$_4$, filtered and concentrated to an oil which was purified via flash chromatography on silica using 30% ethyl acetate/hexane as eluent to give an oil (0.671 g). MW 183.06; MS (m/e) 184 (M$^+$+1).

Preparation 206

4,5-Dichloro-thiophene-2-carboxylic acid

Into a solution of sodium hydroxide (19.2 grams, 48.0 mmole) in water (30 ml) and ice (120 g) at −10° C. was bubbled Cl$_2$ gas until 14.4 g was obtained. The solution was warmed to 50° C. and 1-(4,5-Dichloro-thiophen-2-yl)-ethanone (8.5 0 grams, 40.0 mmole) in dioxane (40 ml) was added dropwise as the temperature rose to 80–90° C. This temperature was maintained for 30 minutes. The mixture was poured into 500 ml water. This was extracted with diethyl ether, and the aqueous was treated with NaHSO$_3$, then acidified to pH 1 with concentrated HCl. The resultant precipitate was filtered, and dried to give a white solid. (5.7 g). MW 197.04; $^1$H NMR (DMSO-d$^6$) d 7.731 (1H, s).

Preparation 207

1-(4,5-Dichloro-thiophen-2-yl)-ethanone

To a solution of 1-Thiophen-2-yl-ethanone (5.0 grams, 40.0 mmole) in chloroform (50 ml) at 20° C. was added portionwise aluminum chloride (15.9 grams, 119.0 mmole). The mixture was stirred at 20° C. for 10 minutes and 1 $\underline{M}$ Cl$_2$ in carbon tetrachloride (120 ml) was added dropwise. The mixture was stirred at room temperature for 30 minutes and diluted with methylene chloride (300 ml) and washed with 1 $\underline{N}$ sodium hydroxide and water and dried over magnesium sulfate and concentrated to give a solid (8.5 g). MW 195.07; MS (m/e) 196 (M$^+$+1).

Preparation 208

2-Bromomethyl-3,5-dichloro-thiophene

A solution of 3,5-Dichloro-2-methyl-thiophene (1.3 grams, 7.8 mmole), NBS (1.4 grams, 7.8 mmole) and benzoyl peroxide (0.065 g) in carbon tetrachloride (40 ml) was refluxed for 18 hours. The mixture was cooled to 0° C., diluted with 40 ml hexane and filtered. The filtrate was concentrated to an oil which was purified via flash chromatography on silica using hexane as eluent to give an oil (1.06 g). MW 245.95; MS (m/e) 246 (M$^+$+1).

Preparation 209

3,5-Dichloro-2-methyl-thiophene

To a solution of 2-methylthiophene (7.0 grams, 70.0 mmole), in methylene chloride (50 ml) at room temperature was added SO$_2$Cl$_2$ dropwise. The mixture was stirred at room temperature over night, diluted with hexane (300 ml), washed with 1$\underline{N}$ NaOH, water and brine, dried over MgSO$_4$, filtered and concentrated to an oil which was purified via vacuum distillation to give an oil. This was further purified via chromatography on silica using hexane as eluent to give an oil (1.32 g). MW 167.06; MS (m/e) 166 (M$^+$−1).

Preparation 210

2-(3-Carbamoyl-phenoxy)-N-(2-chloro-benzyl)-nicotinic acid

A solution of 2-(3-Carbamoyl-phenoxy)-N-(2-chloro-benzyl)-nicotinic acid ethyl ester (4.31 grams, 16.08 mmole) in ethanol (100 ml) and 1 $\underline{N}$ sodium hydroxide (40.21 ml) was refluxed for 4 hours. The mixture was concentrated to 1/3 volume, diluted to 300 ml with water, acidified to pH 3 with 1 $\underline{N}$ hydrochloric acid and filtered to isolate a white solid which was recrystalized from ethyl acetate/hexane (3.8 g). M.P. 220–224° C.; Anal. calcd. for $C_{13}H_{10}N_2O_4$: C, 60.45; H, 3.91; N, 10.85. Found: C, 61.70; H, 3.61; N, 10.69.

Preparation 211

3-Methoxy-N,N-dimethyl-benzamide

Into a solution of 3-Methoxy-benzoyl chloride (5.0 g) in methylene chloride (50 ml) at 0° C. was bubbled in dimethylamine gas for 5 minutes. The mixture was stirred at 0° C. for 30 minutes, diluted with 300 ml methylene chloride, washed with water, dried over MgSO$_4$, filtered and concentrated to give an oil (4.8 g). MW 179.24; MS (m/e) 179 (M$^+$).

Preparation 212

2-[3-(2,2,2-Trifluoro-1-hydroxy-ethyl)-phenoxyl-nicotinic acid ethyl ester

To a solution of 2-(3-Formyl-phenoxy)-nicotinic acid ethyl ester (2.0 grams, 7.4 mmole) in 0.5 $\underline{M}$ trimethyl (trifluoromethyl)silane (18 ml) in tetrahydrofuran (20 ml) at 0° C. was added tetrabutyl ammonium fluoride (0.050 g). The mixture was stirred at 0° C. for 1 hour. To the mixture was added 1.0 $\underline{N}$ hydrochloric acid (10 ml) and stirred at room temperature for 30 minutes. The mixture was poured into 200 ml water and extracted with diethyl ether. The combined extracts were washed with saturated NaHCO$_3$, and water, dried over magnesium sulfate and concentrated to give an oil which was purified via flash chromatography on silica using 60% ethyl acetate/hexane as eluent to give an oil (1.97 g). MW 341.31; MS (m/e) 341 (M$^+$).

Preparation 213

2-Fluoro-4-(1-hydroxy-1-methyl-ethyl)-benzonitrile

To a stirred suspension of CeCl$_3$ (4.7 grams, 19.0 mmole) in tetrahydrofuran (30 ml) at 0° C. was added dropwise 3.0 $\underline{M}$ methyl magnesium chloride (6.0 ml, 19.0 mmole). The mixture was stirred at 0° C. for 45 minutes and 4-Acetyl-2-fluoro-benzonitrile (2.5 grams, 15.0 mmole) in tetrahydrofuran (20 ml) was added dropwise. The mixture was stirred at 0° C. for 1 hour and quenched with 5 ml 2 $\underline{N}$ acetic acid added dropwise. The mixture was poured into 200 ml water, acidified to pH 2 with 2 $\underline{N}$ acetic acid and extracted with ethyl acetate. The combined extracts were washed with water and brine, dried over magnesium sulfate and concentrated to give an oil which was purified via flash chromatography on silica using 50% ethyl acetate/hexane as eluent to give an oil (1.95 g). MW 179.21; MS (m/e) 179 (M$^+$).

Preparation 214

4-Acetyl-2-fluoro-benzonitrile

A mixture of 4-Bromo-2-fluoro-benzonitrile (5.0 grams, 20.0 mmole), butyl vinyl ether (12.5 grams, 124.0 mmole), triethylamine (4.0 grams, 40.0 mmole), dppp (0.453 grams, 1.1 mmole), Thallium acetate (5.8 grams, 22.0 mmole) and Pd(OAc)$_2$ (0.224 grams, 1.0 mmole) in dimethylformamide (50 ml) under N2 was heated to 90° C. for 3 hours. An additional 0.453 g dpp and 0.244 g Pd(OAc)$_2$ was added and the mixture was heated to 90° C. for 4 hours. The mixture was cooled to room temperature, 25 ml 2 N hydrochloric acid was added and the mixture was stirred at room temperature for 30 hours. The mixture was poured into 300 ml water and extracted with diethyl ether. The combined extracts were washed with water and brine, dried over magnesium sulfate and concentrated to give an oil which was purified via flash chromatography on silica using 30% ethyl acetate/hexane as eluent to give an oil (2.5 g). $^1$H-NMR (CDCl$_3$): δ2.63 (s, 3H), 7.73 (m, 2H), 7.81 (m, 1H).

Preparation 215

4-Oxo-cyclohexanecarbonitrile

A solution of 1,4-Dioxa-spiro[4.5]decane-8-carbonitrile (2.0 grams, 12.8 mmole) and 2 N hydrochloric acid (21.0 grams, 42.0 mmole) in tetrahydrofuran (30 ml) at room temperature was stirred over night. The mixture was diluted with ethyl acetate, washed with water and brine, dried over MgSO$_4$, filtered, and concentrated to an oil which was purified via flash chromatography on silica using 10% ethyl acetate/hexane as eluent to give an oil (0.800 g). MW 123.15.

Preparation 216

2-[4-(1-Hydroxy-1-methyl-ethyl)-cyclohex-1-enylmethyl]-isoindole-1,3-dione

To a stirred solution of 2-(4-Hydroxymethyl-cyclohex-3-enyl)-propan-2-ol (5.765 grams, 34.270 mmole), Phthalimide (6.50 grams, 44.208 mmole), and triphenyl phosphene (11.60 grams, 44.208 mmole) in tetrahydrofuran (200 ml) at room temperature was added DIAD (9.010 grams, 44.552 mmole) dropwise, and the peach mixture was stirred at room temperature over night. The mixture was quenched with 150 ml water and extracted with 2×100 ml ethyl acetate. It was then concentrated to a yellow residue. This was taken up in diethyl ether, diluted with hexane, chilled and filtered. The crude product was purified via flash chromatography on silica using 50% ethyl acetate/hexane as eluent to give a yellow gum (5.73 g). MW 299.373; MS (m/e) 279 (M$^+$–18).

Preparation 217

2-(Benzo[1,3]dioxol-5-yloxy)-nicotinic acid ethyl ester

A solution 2-Chloro-nicotinic acid ethyl ester (5.0 grams, 27.0 mmole), cesium carbonate (2.96 grams, 67.5 mmole) and Benzo[1,3]dioxol-5-ol (4.19 grams, 29.7 mmole) in dimethylformamide (80 ml) was heated to 65° C. for 10 hours. The mixture was diluted with water and extracted with ethyl acetate. The combined extracts were washed with water and brine, dried over MgSO$_4$, filtered, and concentrated to a solid (7.0 g). MW 287.275.

Preparation 218

2-[4-(1-Hydroxy-1-methyl-ethyl)-cyclohex-1-enylmethyl]-isoindole-1,3-dione

To a stirred solution of 2-(4-Hydroxymethyl-cyclohex-3-enyl)-propan-2-ol (5.765 grams, 34.270 mmole), Phthalimide (6.50 grams, 44.208 mmole), and triphenyl phosphene (11.60 grams, 44.208 mmole) in tetrahydrofuran (200 ml) at room temperature was added DIAD (9.010 grams, 44.552 mmole) dropwise, and the peach mixture was stirred at room temperature over night. The mixture was quenched with 150 ml water and extracted with 2×100 ml ethyl acetate. It was then concentrated to a yellow residue. This was taken up in diethyl ether, diluted with hexane, chilled and filtered. The crude product was purified via flash chromatography on silica using 50% ethyl acetate/hexane as eluent to give a yellow gum (5.73 g). MW 299.373; MS (m/e) 279 (M$^+$–18).

Preparation 219

2-(4-Aminomethyl-cyclohex-3-enyl)-propan-2-ol

A solution of 0.3 M methanolic hydrazine hydrate was prepared by adding hydrazine hydrate (1.96 g) to 204 ml methanol. This was added to 2-[4-(1-Hydroxy-1-methyl-ethyl)-cyclohex-1-enylmethyl]-isoindole-1,3-dione (5.73 g, 19.140 mmole) and stirred at room temperature over night. 5% hydrochloric acid was added and a precipitate was formed over two hours, which was filtered through celite and washed with water. The filtrate was poured into water and extracted with diethyl ether. The aqueous layer was basified to pH=9 with sodium hydroxide and extracted with diethyl ether. The combined extracts were washed with water and brine, dried over MgSO$_4$, filtered, and concentrated to an oil which solidified on. standing (0.188 g ). M.P. 95–97° C.; MW 169.269.

The compounds in Preparations 220–228 were synthesized in a manner analogous to that of Preparation 23 substituting the indicated phenol.

Preparation 220

2-(3-Oxo-indan-5-yloxy)-nicotinic acid ethyl ester

Prepared using 6-hydroxy-indan-1-one ( Phialas et. al. J. Chem. Soc. Perkin Trans. 1, 4,1984, 687–695). MS (m/e): 297 (M$^+$).

Preparation 221

2-(2-Methyl-benzothiazol-5-yloxy)-nicotinic acid ethyl ester

Prepared using 2-methyl-5-benzothiazolol. MS (m/e): 314 (M$^+$)

Preparation 222

2-(2-Methyl-benzothiazol-6-yloxy)-nicotinic acid ethyl ester

Prepared using 2-methyl-6-benzothiazolol (Tardieu et. al. Helv. Chim. Acta, 75, 4, 992, 1185–1197). MS (m/e): 314 (M$^+$).

Preparation 223

2-(Benzothiazol-6-yloxy)-nicotinic acid ethyl ester

Prepared using benzothiazol-6-ol (El'tsov et. al. J. Gen. Chem. USSR 51, 1981, 1822–831). MS (m/e): 301 (M$^+$+1, 100).

Preparation 224

2-(Benzooxazol-6-yloxy)-nicotinic acid ethyl ester

Prepared using benzoxazol-6-ol (Cole et. al. Aust. J. Chem. 39, 2, 1986, 295–301). MS (m/e): 284 (M$^+$)

Preparation 225

2-(3-Acetyl-4-chloro-phenoxy)-nicotinic acid ethyl ester

Prepared using 3-acetyl-4-chlorophenol. MS (m/e): 319 (M$^+$)

Preparation 226

2-(3-Acetyl-5-chloro-phenoxy)-nicotinic acid ethyl ester

Prepared using 1-(3-chloro-5-hydroxy-phenyl)-ethanone. MS (m/e): 319 (M+)

Preparation 227

2-(3-Methyl-benzo-(d)isoxazol-5-yloxy)-nicotinic acid ethyl ester

Prepared from 5-hydroxy-3-methyl-benzo(d)isoxazole. MS (m/e): 299 (M++1, 100).

Preparation 228

2-(3-Methyl-benzo-(d)isoxazol-7-yloxy)-nicotinic acid ethyl ester

Prepared from 7-hydroxy-3-methyl-benz(d)isoxazole. MS (m/e): 298 (M+)

Preparation 229

2-(2,3-Dihydro-benzo[1,4]dioxin-6-yloxy)-nicotinic acid ethyl ester

Prepared from 2,3-Dihydro-benzo[1,4]dioxin-6-ol (Biosci. Biotech. Biochem., 56(4), 1992, 630–635)
MS: m/e 302 (M++1)

Preparation 230

3-acetyl-4-chlorophenol

A mixture of 3-acetyl-4-chloroanisole (6.3 g, 0.03 mol.), (Atkinson et. al. J. Med. Chem. 26, 10, 1983, 1353–1360) and pyridine hydrochloride (19.4 g, 0.17 mol.) was heated at 220° C. for 2 hrs. The mixture was poured into water (200 mL) and extracted with ethyl acetate (2×200 mL). The organic extracts were combined, washed with water (40 mL), brine (40 mL), dried (MgSO$_4$) and concentrated to give an oil. Chromatography on Silica Gel eluting with ethyl acetate/hexanes (1:1) gave 5.1 g oil. MS (m/e): 172/170 (M+, 100).

Preparation 231

7-hydroxy-3-methyl-benz(d)isoxazole

A mixture of 7-methoxy-3-methyl-benz(d)isoxazole (2.9 g, 0.017 mmol.) (Borsche et. al. Justus Liebigs Ann. Chem. 570, 1950, 155, 163) in glacial acetic acid (15 mL) and 48% hydrobromic acid (15 mL) was refluxed for 6 hrs. The mixture was concentrated to give 4.0 g solid. MS (m/e): 227/229 (M++HBr), 149(M+).

Preparation 232

1-(3-chloro-5-hydroxy-phenyl)-ethanone

A mixture of 1-(3-chloro-5-methoxy-phenyl)-ethanone (14.3 g, 0.08 mol.) and pyridine hydrochloride (44.8 g, 0.39 mol.) was heated at 220° C. for 2 hrs. The mixture was poured into water (200 mL) and extracted with ethyl acetate (2×200 mL). The organic extracts were combined, washed with water (40 mL), brine (40 mL) and concentrated to give an oil. Flash Chromatography on Silica Get eluting with ethyl acetate/hexanes (1:1) gave 6.6 g solid. MS (m/e): 170/172 (M+).

Preparation 233

1-(3-chloro-5-methoxy-phenyl)-ethanone

A mixture of trifluoromethanesulfonic acid 3-chloro-5-methoxy-phenyl ester (26.5 g, 0.091 mol.), butyl vinyl ether (59 mL, 0.46 mol.), 1,3-Bis(diphenyl-phosphinopropane) (1.1 g, 0.003 mol.), palladium acetate (0.51 g, 0.002 mol.) and triethylamine (28 mL, 0.20 mol.) in dimethylforamide (90 mL) was heated at 80° C. for 4 hrs. The mixture was poured into water (400 mL) and extracted with diethyl ether (2×400 mL). The organic extracts were combined, washed with 1N hydrochloric acid (80 mL), 1N sodium hydroxide (80 mL), water (80 mL), brine (80 mL), dried (MgSO$_4$) and concentrated to give an oil. Flash Chromatography on Silica Gel eluting with ethyl acetate/hexanes (1:9) gave 14.3 g solid. MS (m/e): 184/186 (M+).

Preparation 234

Trifluoromethanesulfonic acid 3-chloro-5-methoxy-phenyl ester

To a stirred solution of 3-chloro-5-methoxyphenol (15 g, 0.09 mol.), triethylamine (31 mL, 0.23 mol.) and 4-dimethylaminipyridine (1.1 g, 0.009 mol.) in methylene chloride (200 mL) at −78° C. was added dropwise, trifluoromethanesulfonic anhydride (20 mL, 0.118 mol.). The mixture was allowed to slowly warm to room temperature over 2 hrs., then diluted with methylene chloride (400 mL) and washed with water (100 mL), dried (MgSO$_4$) and concentrated to give an oil. Flash Chromatography on Silica Gel eluting with ethyl acetate/hexanes (1:9) gave 26.6 g oil. MS (m/e): 290 (M+).

Preparation 235

5-hydroxy-3-methyl-benzo(d)isoxazole

A mixture of 5-Methoxy-3-methyl-benzo(d)isoxazole (4.9 g, 0.03 mol.) in 48% hydrobromic acid (20 mL) and acetic acid (20 mL) was refluxed for 4 hrs. The mixture was concentrated to give 6.2 g solid. MS (m/e): 149 (M+).

Preparation 236

5-Methoxy-3-methyl-benzo(d)isoxazole

A mixture of 1-(2-Hydroxy-5-methoxy-phenyl)-ethanone-O-acetyl oxime (15.3 g, 0.069 mol.) in pyridine (50 mL) was refluxed for 4 hrs. The mixture was poured into water (800 mL), acidified with concentrated hydrochloric acid to pH 1, then extracted with ethyl acetate (2×800 mL). The organic extracts were combined, washed with 1 N hydrochloric acid (100 mL), 1N sodium hydroxide (100 mL), water (100 mL), brine (100 mL), dried (MgSO$_4$) and concentrated to give an oil. Flash Chromatography on Silica Gel eluting with ethyl acetate/hexanes (1:2) gave 5.9 g solid. MS (m/e): 163 (M+).

Preparation 237

1-(2-Hydroxy-5-methoxy-phenyl)-ethanone-O-acetyl oxime

A mixture of 1-(2-Hydroxy-5-methoxy-phenyl)-ethanone oxime (13.7 g, 0.076 mol.) and acetic anhydride (50 mL) was heated at 50° C. for 10 min. The mixture was cooled to 0° C., filtered, and the filtrant washed with water (50 mL) and dried to give 15.5 g solid. MS (m/e): 224 (M++1), 164 (100).

Preparation 238

1-(2-Hydroxy-5-methoxy-phenyl)-ethanone oxime

A mixture of 2-Hydroxy-5-methoxyacetophenone (15.0 g, 0.09 mol.), potassium hydroxide (23.6 g, 0.36 mol.) and hydroxylamine hydrochloride (9.4 g, 0.14 mol.) in water (300 mL) was refluxed for 2 hrs. The mixture was poured into ice and acidified with 1N hydrochloric acid to pH 1. The resulting precipitate was filtered and dried to give 13.7 g solid. MS (m/e): 182 ($M^+$+1, 100).

The compounds in Preparations 238–247 were synthesized in a manner analogous to that of Preparation 45.

Preparation 239

2-(3-Oxo-indan-5-yloxy)-nicotinic acid

MS (m/e): 269 ($M^+$)

Preparation 240

2-(2-Methyl-benzothiazol-5-yloxy)-nicotinic acid

MS (m/e): 287 ($M^+$+1, 100)

Preparation 241

2-(2-Methyl-benzothiazol-6-yloxy)-nicotinic acid

MS (m/e): 287 ($M^+$+1, 100)

Preparation 242

2-(Benzothiazol-6-yloxy)-nicotinic acid

MS (m/e): 273 ($M^+$+1)

Preparation 243

2-(Benzooxazol-6-yloxy)-nicotinic acid

MS (m/e): 256 ($M^+$), 211 (100)

Preparation 244

2-(3-Acetyl-4-chloro-phenoxy)-nicotinic acid

MS (m/e): 292/290 ($M^+$, 100)

Preparation 245

2-(3-Acetyl-5-chloro-phenoxy)-nicotinic acid

MS (m/e): 292/290 ($M^+$, 100)

Preparation 246

2-(3-Methyl-benzo-(d)isoxazol-5-yloxy)-nicotinic acid

MS (m/e): 270 ($M^+$+1, 100)

Preparation 247

2-(3-Methyl-benzo-(d)isoxazol-7-yloxy)-nicotinic acid

MS (m/e): 270 ($M^+$+1, 100)

Preparation 248

2-(2,3-Dihydro-benzo[1,4]dioxin-6-yloxy)-nicotinic acid

MS: m/e274 ($M^+$+1)

Preparation 249

(S)-(−)-1-(4-Aminomethyl-phenyl)-ethanol

To a stirred solution of (S)-(−)-4-(1-Hydroxy-ethyl)-benzonitrile (2.2 g, 0.015 mol.) in tetrahydrofuran (20 mL) at 0° C. was added dropwise a 1.0M solution of lithium aluminium hydride in tetrahydrofuran (45 mL, 0.045 mol.). The mixture was refluxed for 30 min. then cooled to 0° C. then quenched with methanol (5 mL) added dropwise. The mixture was diluted with chloroform (300 mL) and washed with water (40 mL). The resulting suspension was filtered through Celite and the organic extract of the filtrate separated, dried ($MgSO_4$) and concentrated to give 2.0 g solid. $\alpha_D$ ($CHCl_3$) −40.3°.

Preparation 250

(S)-(−)4-(1-Hydroxy-ethyl)-benzonitrile

To a stirred solution of 4-acetylbenzonitrile (3.0 g, 0.021 mol.) and a solution of 1.0 M (R)-2-Methyl-CBS-oxazaborolidine in toluene (1.0 mL, 0.001 mol.) in tetrahydrofuran (50 mL) at room temperature was added dropwise a solution of 2.0M Borane-Dimethylsulfide complex in tetrahydrofuran (9.0 mL, 0.017 mol.) over 30 min, The mixture was stirred at room temperature for 1 hr., cooled to 0° C., then quenched with methanol (10 mL) added dropwise. The volume was reduced by half, diluted with diethyl ether (300 mL) and washed with pH 4 buffer (40 mL), water (40 mL), brine (40 mL), dried ($MgSO_4$) then concentrated to give an oil. Flash Chromatography on Silica Gel eluting with ethyl acetate/hexane (2:3) to give 2.2 g clear oil. $\alpha_D$ ($CHCl_3$) −40.0°.

Preparation 251

(R)-(+)-1-(4-Aminomethyl-phenyl)-ethanol

Prepared in an analogous manner to that of Preparation 247 starting with (R)-(+)-4-(1-Hydroxy-ethyl)-benzonitrile which is obtained from 4-acetylbenzonitrile using 1.0 M (S)-2-Methyl-CBS-oxazaborolidine in toluene in an analogous fashion as in Preparation 248.

Preparation 252 trans-2-(Aminomethyl-cyclohexyl)-propan-2-ol

A mixture of trans-(4-(1-Hydroxy-1-methyl-ethyl)-cyclohexylmethyl)-carbamic acid benzyl ester (8.3 g, 0.027 mole) and Pearlman's catalyst (400 mg) in ethyl acetate (100 mL) and methanol (25 mL) was shaken in a Parr Apparatus under 40 psi hydrogen at room temperature for 1 hr. The mixture was filtered through Celite and the filtrate concentrated to give 5.1 g white solid. MS (m/e): 171 ($M^+$, 100).

Preparation 253 trans-(4-(1-Hydroxy-1-methyl-ethyl)-cyclohexylmethyl)-carbamic acid benzyl ester A mechanically stirred suspension of anhydrous cerium (III) chloride (29.8 g, 0.12 mol.) in tetrahydrofuran was refluxed for 10 min., cooled to 0° C., and a solution of trans-4-(Benzyloxycarbonylamino-methyl)-cyclohexanecarboxylic acid ethyl ester (35.8 g, 0.11 mol.) in tetrahydrofuran (200 mL) was added dropwise followed by a solution of 3.0 M methylmagnesium chloride (121 mL, 0.363 mol.) in tetrahydrofuran added dropwise. The mixture was stirred at 0° C. for 1 hr., then quenched with 2N acetic acid added dropwise. The mixture volume was reduced by half, poured into water (800 mL) and acidified with 2N acetic acid to pH 3. then extracted with ethyl acetate (2×800 mL). The organic extracts were combined, washed with sodium bicarbonate (100 mL), water (100 mL), brine (100 mL), dried (MgSO$_4$), and concentrated to give an oil. Flash Chromatography on Silica Gel eluting with ethyl acetate/hexanes (2:3) gave 8.34 g solid. MS (m/e): 323 (M$^+$+NH$_3$, 100).

Preparation 254 trans-4-(Benzyloxycarbonylamino-methyl)-cyclohexanecarboxylic acid ethyl ester

To a stirred solution of trans-4-Aminomethyl-cyclohexanecarboxylic acid ethyl ester (23.8 g, 0.11 mol.) and triethylamine (34 mL, 0.24 mol.) in dioxane (100 mL) at room temperature was added N-(Benzyloxycarbonyloxy) succinimide (26.7 g, 0.11 mol.). The mixture was stirred at room temperature for 18 hr., poured into water (800 mL) and extracted with ethyl acetate (2×800 mL). The organic extracts were combined, washed with 0.5 N sodium hydroxide (100 mL). 0.5 N hydrochloric acid (100 mL), water (100 mL), brine (100 mL), dried (MgSO$_4$), and concentrated to give 36.0 9 solid. MS (m/e): 337 (M$^+$+NH$_3$, 100).

Preparation 255

(R)-(-)-trans-1-(4-Aminomethyl-cyclohexyl)-ethanol

A mixture of (R)-(-)-(trans-4-(1-Hydroxy-ethyl-)cyclohexylmethyl)carbamic acid benzyl ester (870 mg, 2.98 mmol.) and Pearlman's Catalyst (100 mg) in ethyl acetate (100 mL) and methanol (25 mL) was shaken in a Parr Apparatus under 40 psi hydrogen at room temperature for 1 hr. The mixture was filtered through Celite and the filtrate concentrated to give 484 mg oil. α$_D$ (CHCl$_3$) −1.6°.

Preparation 256

(R)-(-)-(trans-4-(1-Hydroxy-ethyl-cyclohexylmethyl)carbamic acid benzyl ester

To a stirred solution of (trans-4-Acetyl-cyclohexylmethyl)-carbamic acid benzyl ester (1.0 g, 3.46 mmol.) and (S)-2-Methyl-CBS-oxazaborolidine monohydrate (102 mg, 0.34 mmol.) in tetrahydrofuran (15 mL) at 0° C. was added dropwise a 2.0 M solution of Borane-Dimethylsulfide complex (1.4 mL, 2.77 mmol.) in tetrahydrofuran over 20 min. The mixture was stirred at 0° C. for 30 min., then quenched with methanol (10 mL). the mixture volume was reduced by half, poured into water (200 mL) and extracted with ethyl acetate (2×200 mL). The organic extracts were combined, washed with pH 4 buffer (40 mL), water (40 mL), brine (40 mL), dried (MgSO$_4$) and concentrated to give an oil. Flash Chromatography on Silica ,Gel eluting with ethyl acetate/hexanes (1:1) gave 870 mg solid α$_D$ (CHCl$_3$) −0.8°.

Preparation 257

(trans-4-Acetyl-cyclohexylmethyl)-carbamic acid benzyl ester

To a stirred solution of (trans-4-(Methoxy-methyl-carbamoyl)-cyclohexylmethyl)-carbamic acid benzyl ester (5.8 g, 0.017 mol.) in tetrahydrofuran (100 mL) at 0° C., was added dropwise a solution of 3.0M Methylmagnesium chloride in tetrahydrofuran (13 mL, 0.038 mol.). The mixture was stirred at 0° C. for 1 hr., then quenched with 2 N acetic acid added dropwise. The mixture was poured into water (300 mL) and extracted with ethyl acetate (2×300 mL). The organic extracts were combined, washed with 0.5 N hydrochloric acid (80 mL), water (80 mL), brine (80 mL), dried (MgSO$_4$) and concentrated to give an oil. Flash Chromatography on Silica Gel eluting with ethyl acetate/hexanes (2:3) gave 2.0 g solid. MS (m/e): 307 (M$^+$+NH$_3$, 100).

Preparation 258

(trans-4-(Methoxy-methyl-carbamoyl)-cyclohexylmethyl)-carbamic acid benzyl ester To a stirred solution of trans-4-(Benzyloxycarbonylamino-methyl)-cyclohexane carboxylic acid (16.7 g, 0.057 mol.), N,O-dimethylhydroxylamine hydrochloride (6.2 g, 0.063 mol.), triethylamine (9 mL, 0.063 mol.) and 1-hydroxy-benzotriazole hydrate (8.5 g, 0.063 mol.) in dimethylformamide (200 mL) at room temperature was added 1-(3-(dimethylamino)-propyl)-3-ethylcarbodiimide hydrochloride (13.1 g, 0.068 mol.). The mixture was stirred at room temperature for 72 hrs., poured into water (800 mL) and extracted with ethyl acetate (2×800 mL). The organic extracts were combined, washed with 1N sodium hydroxide (80 mL), 1N hydrochloric acid (80 mL), water (80 mL), brine (80 mL), dried (MgSO$_4$) and concentrated to give an oil. Flash Chromatography on Silica Gel eluting with ethyl acetate/hexanes (3:2) gave 5.8 g oil. MS (m/e): 352 (M$^+$+NH$_3$, 100).

Preparation 259 trans-4-(Benzyloxycarbonylamino-methyl)-cyclohexane carboxylic acid

To a stirred solution of trans-4-(Aminomethyl)-cyclohexane carboxylic acid (10.0 g, 0.063 mol.) and potassium carbonate (30.5 g, 0.22 mol.) in dioxane (200 mL) and water (200 mL) at room temperature was added benzyl chloroformate (11 mL, 0.08 mol.). The mixture was stirred at room temperature for 18 hrs., poured into water (800 mL) and washed with diethyl ether (800 mL). The aqueous extract was acidified and the resulting precipitate filtered and dried to give 16.7 g white solid. MS (m/e): 309 (M$^+$+NH$_3$, 100).

Mass spectra were determined by the GC-MS, AMPI, APCI or thermospray method.

All $^1$H NMR were taken on 400 MHz instruments.

EXAMPLE 1

2-(4-Fluoro-phenoxy)-N-thiophen-2-ylmethyl-nicotinamide

To a stirred solution of 2-(4-Fluoro-phenoxy)-nicotinic acid (0.300 grams, 1.29 mmole) and NMM (0.137 grams, 1.35 mmole) in dry methylene chloride (15 ml) at −10° C. was added isobutyl chloroformate (0.164 grams, 1.35 mmole). After 30 minutes at −10° C. 2-aminomethylthiophene (0.152 grams, 1.35 mmole) was added and the mixture was allowed to warm to room temperature over night. The mixture was poured into water and extracted with ethyl acetate. The combined organics were washed with 1 N sodium hydroxide and water, dried over MgSO$_4$, filtered, and concentrated to give a clear oil that was purified by chromatography on silica gel eluting with 30% ethyl acetate/hexane to give a solid. Recrystalization from ethyl acetate/hexane gave white crystals (0.326 g). M.P. 89–91° C.; MS (m/e) 329 (M$^+$+1).

The compounds of Examples 2–9 were prepared according to the procedure of Example 1 substituting the corresponding amine for 2-aminomethylthiophene. The duration of reaction was between 1 and 24 hours.

EXAMPLE 2

2-(4-Fluoro-phenoxy)-N-furan-2-ylmethyl-nicotinamide

M.P. 71–73° C.; Anal. calcd. for $C_{17}H_{13}N_2O_3F$: C, 65.38; H, 4.20; N, 6.97. Found: C, 65.53; H, 4.34; N, 9.31.

EXAMPLE 3

(R)(−)2-(4-Fluoro-phenoxy)-N-[1-(4-methoxy-phenyl)-ethyl]-nicotinamide

M.P. 101–103° C.; Anal. calcd. for $C_{12}H_{19}N_2O_3F$: C, 68.84; H, 5.23; N, 7.65. Found: C, 68.46; H, 5.20; N, 7.62.

EXAMPLE 4

(S)-(+) 2-(4-Fluoro-phenoxy)-N-[1-(4-methoxy-phenyl)-ethyl]-nicotinamide

M.P. 97–99° C.; Anal. calcd. for $C_{21}H_{19}N_2O_3F$: C, 68.84; H, 5.23; N, 7.65. Found: C, 68.84; H, 5.17; N, 7.71. $\alpha_D$=+54.2° (C=0.2, chloroform).

EXAMPLE 5

N-(2-Chloro-6-fluoro-benzyl)-2-(4-fluoro-phenoxy)-nicotinamide

M.P. 115–118° C.; Anal. calcd. for $C_{19}H_{13}N_2O_2F_2Cl$: C, 60.89; H, 3.50; N, 7.47. Found: C, 60.63; H, 3.45; N, 7.38.

EXAMPLE 6

(S)(−)2-(4-Fluoro-phenoxy)-N-(1-thiophen-2-yl-ethyl)-nicotinamide

M.P. 59–61° C.; Anal. calcd. for $C_{18}H_{15}N_2SO_2F$: C, 63.14; H, 4.42; N, 8.18. Found: C, 63.21; H, 4.34; N, 8.16. $\alpha_D$=−26.5° (C=0.3, chloroform).

EXAMPLE 7

(R)(+)2-(4-Fluoro-phenoxy)-N-(1-thiophen-2-yl-ethyl)-nicotinamide

M.P. 60–62° C.; Anal. calcd. for $C_{18}H_{15}N_2SO_2F$: C, 63.14; H, 4.42; N, 8.18. Found: C, 35 62.75; H, 4.27; N, 8.06. $\alpha_D$=+26.2° (C=0.4, chloroform).

EXAMPLE 8

N-[1-(5-Chloro-thiophen-2-yl)-ethyl]-2-(4-fluoro-phenoxy)-nicotinamide

M.P. 87–89° C.; Anal. calcd. for $C_{18}H_{14}N_2SO_2ClF$: C, 57.37; H, 3.74; N, 7.43. Found: C, 57.51; H, 3.68; N, 7.48.

EXAMPLE 9

N-(2-Chloro-benzyl)-2-(4-fluoro-phenoxy)-nicotinamide

M.P. 118–120+ C.; Anal. calcd. for $C_{19}H_{14}N_2O_2ClF$: C, 63.96; H, 3.95; N, 7.85. Found: C, 63.54; H, 3.96; N, 7.72.

EXAMPLE 10

N-(2-Chloro-benzyl)-2-(2,4-difluoro-phenoxy)-nicotinamide

To a stirred solution of 2-(2,4-difluoro-phenoxy)-nicotinic acid (0.300 grams, 1.19 mmole) and NMM (0.133 grams, 1.31 mmole) in dry methylene chloride (15 ml) at −10° C. was added isobutyl chloroformate (0.202 grams, 1.31 mmole). After 20 minutes at −10° C. 2-chlorobenzylamine (0.202 grams, 1.43 mmole) was added and the mixture was allowed to warm to room temperature over night. The mixture was poured into water and extracted with ethyl acetate. The combined organics were washed with 1 $\underline{N}$ NaOH, water and brine, dried over $MgSO_4$, filtered and concentrated to give a clear oil that was purified by chromatography on silica gel eluting with 30% ethyl acetate/hexane to give a solid. Recrystalization from ethyl acetate/hexane gave a solid (0.295 g). M.P. 122–124° C.; Anal. calcd. for $C_{19}H_{13}N_2O_2F_2Cl$: C, 60.89; H, 3.50; N, 7.47. Found: C, 60.77; H, 3.44; N, 7.38.

EXAMPLE 11

N-(2-Chloro-benzyl)-2-(3-fluoro-phenoxy)-nicotinamide

To a stirred solution of 2-(3-Fluoro-phenoxy)-nicotinic acid (0.300 grams, 1.29 mmole) and NMM (0.144 grams, 1.41 mmole) in dry methylene chloride (15 ml) at −10° C. was added isobutyl chloroformate (0.193 grams, 1.41 mmole). After 20 minutes at −10° C. 2-chlorobenzylamine (0.219 grams, 1.55 mmole) was added and the mixture was allowed to warm to room temperature over night. The mixture was poured into water and extracted with ethyl acetate. The combined organics were washed with 1 $\underline{N}$ NaOH, water and brine, dried over $MgSO_4$, filtered and concentrated to give a solid that was purified by chromatography on silica gel eluting with 30% ethyl acetate/hexane to give a white solid. Recrystalization from ethyl acetate/hexane gave a solid (0.328 g). M.P. 115–117° C.; Anal. calcd. for $C_{19}H_{14}N_2O_2ClF$: C, 63.96; H, 3.95; N, 7.85. Found: C, 64.04; H, 3.92; N, 7.85.

EXAMPLE 12

N-(2-Chloro-benzyl)-2-(pyridin-3-yloxy)-nicotinamide

To a stirred solution of 2-(pyridin-3-yloxy)-nicotinic acid (0.300 grams, 1.39 mmole), o-chlorobenzylamine (0.216 grams, 1.53 mmole), and 1-hydroxybenzotriazole hydrate (0.207 grams, 1.53 mmole) in dry dimethylformamide (15 ml) was added (3-(dimethylamino)-propyl)-3-ethylcarbodimide hydrochloride (0.319 grams, 1.67 mmole) and stirred over night. The mixture was diluted with 200 ml ethyl acetate washed with 1 $\underline{N}$ NaOH, water and brine, dried over $MgSO_4$, filtered and concentrated to give an oil that was purified by chromatography on silica gel eluting with 5% methanol/methylene chloride. Recrystalization from ethyl acetate/hexane gave a white solid (0.275 g). M.P. 123–125° C.; Anal. calcd. for $C_{18}H_{14}N_3O_2Cl$: C, 63.63; H, 4.15; N, 12.37. Found: C, 63.19; H, 3.85; N, 11.67.

The compounds of Examples 13–44 were prepared according to the procedure of Example 12 substituting the corresponding amine for o-chlorobenzylamine. The duration of reaction was between 1 and 24 hours.

EXAMPLE 13

N-(4-Methyl-benzyl)-2-(pyridin-3-yloxy)-nicotinamide

M.P. 91–93° C.; Anal. calcd. for $C_{19}H_{17}N_3O_2$: C, 71.46; H, 5.37; N, 13.16. Found: C, 71.51; H, 5.40; N, 13.26.

EXAMPLE 14

N-[1-(5-Chloro-thiophen-2-yl)-ethyl]-2-(pyridin-3-yloxy)-nicotinamide

M.P. 74–76° C.; Anal. calcd. for $C_{17}H_{14}N_3SO_2Cl$: C, 56.75; H, 3.92; N, 11.68. Found: C, 56.54; H, 4.06; N, 11.80.

EXAMPLE 15

N-Furan-2-ylmethyl-2-(pyridin-3-yloxy)-nicotinamide

M.P. 84–86° C.; Anal. calcd. for $C_{16}H_{13}N_3O_3$: C, 65.08; H, 4.44; N, 14.23. Found: C, 65.04; H, 4.50; N, 14.55.

EXAMPLE 16

N-(5-Chloro-thiophen-2-ylmethyl)-2-(pyridin-3-yloxy)-nicotinamide

M.P. 110–112° C.; Anal. calcd. for $C_{16}H_{12}N_3SO_2Cl$: C, 55.57; H, 3.50; N, 12.15. Found: C, 55.23; H, 3.57; N, 12.45.

EXAMPLE 17

N-[1-(5-Methyl-thiophen-2-yl)-ethyl]-2-(pyridin-3-yloxy)-nicotinamide

M.P. 162–164° C.; MS (m/e) 340 (M$^+$+1).

EXAMPLE 18

N-(5-Methyl-thiophen-2-ylmethyl)-2-(pyridin-3-yloxy)-nicotinamide

M.P. 111–113° C.; Anal. calcd. for $C_{17}H_{15}N_3SO_2$: C, 62.75; H, 4.65; N, 12.91. Found: C, 62.77; H, 4.67; N, 12.50.

EXAMPLE 19

N-(5-Methyl-furan-2-ylmethyl)-2-(pyridin-3-yloxy)-nicotinamide

M.P. 65–67° C.; Anal. calcd. for $C_{17}H_{15}N_3O_3$: C, 66.01; H, 4.89; N, 13.58. Found: C, 5.77; H, 4.90; N, 13.28.

EXAMPLE 20

N-(3-Methyl-thiophen-2-ylmethyl)-2-(pyridin-3-yloxy)-nicotinamide

M.P. 89–91° C.; Anal. calcd. for $C_{17}H_{15}N_3SO_2$: C, 62.75; H, 4.65; N, 12.91. Found: C, 2.71; H, 4.64; N, 12.80.

EXAMPLE 21

N-(4-Chloro-thiophen-2-ylmethyl)-2-(pyridin-3-yloxy)-nicotinamide

M.P. 118–120° C.; Anal. calcd. for $C_{16}H_{12}N_3SO_2Cl$: C, 55.57; H, 3.50; N, 12.15. Found: C, 55.50; H, 3.89; N, 11.37.

EXAMPLE 22

N-Benzo[b]thiophen-2-ylmethyl-2-(pyridin-3-yloxy)-nicotinamide

M.P. 93–95° C.; Anal. calcd. for $C_{20}H_{15}N_3SO_2$: C, 66.47; H, 4.18; N, 11.63. Found: C, 66.00; H, 4.19; N, 11.66.

EXAMPLE 23

N-(5-Chloro-furan-2-ylmethyl)-2-(pyridin-3-yloxy)-nicotinamide

M.P. 80–82° C.; Anal. calcd. for $C_{16}H_{12}N_3O_3Cl$: C, 58.28; H, 3.67; N, 12.74. Found: C, 58.52; H, 3.73; N, 12.80.

EXAMPLE 24

2-(Pyridin-3-yloxy)-N-thiazol-2-ylmethyl-nicotinamide

M.P. 94–96° C.; MS (m/e) 313 (M$^+$+1).

EXAMPLE 25

2-(Pyridin-3-yloxy)-N-[4-(2,2,2-trifluoro-ethoxy)-benzyl]-nicotinamide

M.P. 98–100° C.; Anal. calcd. for $C_{20}H_{16}N_3O_3F_3$: C, 59.55; H, 4.00; N, 10.42. Found: C, 59.74; H, 3.92; N, 10.53.

EXAMPLE 26

N-(2-Fluoro-benzyl)-2-(pyridin-3-yloxy)-nicotinamide

M.P. 90–92° C.; Anal. calcd. for $C_{18}H_{14}N_3O_2F$: C, 66.87; H, 4.36; N, 13.00. Found: C, 67.08; H, 4.23; N, 13.07.

EXAMPLE 27

N-(4-Difluoromethoxy-benzyl)-2-(pyridin-3-yloxy)-nicotinamide

M.P. 91–93° C.; Anal. calcd. for $C_{19}H_{15}N_3O_3F_2$: C, 61.46; H, 4.07; N, 11.32. Found: C, 61.47; H, 3.84; N, 11.24.

EXAMPLE 28

N-(4-Fluoro-benzyl]-2-(pyridin-3-yloxy)-nicotinamide

M.P. 129–131° C.; Anal. calcd. for $C_{18}H_{14}N_3O_2F$: C, 66.87; H, 4.36; N, 13.00. Found: C, 66.63; H, 4.42; N, 13.04.

EXAMPLE 29

N-(4-Methoxy-benzyl)-2-(pyridin-3-yloxy)-nicotinamide

M.P. 62–64° C.; Anal. calcd. for $C_{19}H_{17}N_3O_3$: C, 68.05; H, 5.11; N, 12.53. Found: C, 68.20; H, 4.96; N, 12.58.

EXAMPLE 30

2-(Pyridin-3-yloxy)-N-(5-trifluoromethyl-thiophen-2-ylmethyl)-nicotinamide

M.P. 122–124° C.; Anal. calcd. for $C_{17}H_{12}N_3O_2SF_3$: C, 53.82; H, 3.19; N, 11.08. Found: C, 54.44; H, 3.22; N, 11.10.

EXAMPLE 31

N-(2-Chloro-benzyl)-2-(pyridin-3-yloxy)-nicotinamide

M.P. 174–176° C.; Anal. calcd. for $C_{18}H_{14}N_3O_2Cl.HCl$; C, 57.46; H, 4.02; N, 11.17. Found: C, 57.16; H, 4.11; N, 11.09.

EXAMPLE 32

N-(5-Fluoro-thiophen-2-ylmethyl)-2-(pyridin-3-yloxy)-nicotinamide

M.P. 99–101° C.; Anal. calcd. for $C_{16}H_{12}N_3O_2SF$: C, 58.35; H, 3.67; N, 12.76. Found: C, 58.35; H, 3.55; N, 12.71.

EXAMPLE 33

N-(2-Oxo-2,3-dihydro-1H-indol-5-ylmethyl)-2-(pyridin-3-yloxy)-nicotinamide

M.P. 109–111° C.; Anal. calcd. for $C_{20}H_{16}N_4O_3$: C, 66.66; H, 4.47; N, 15.55. Found: C, 65.92; H, 4.56; N, 14.84.

EXAMPLE 34

N-(3,5-Di-tert-butyl-4-hydroxy-benzyl)-2-(pyridin-3-yloxy)-nicotinamide

M.P. 42–44° C.; Anal. calcd. for $C_{26}H_{31}N_3O_3$: C, 72.03; H, 7.21; N, 9.69. Found: C, 71.19; H, 7.22; N, 9.79.

EXAMPLE 35

N-[5-(1-Hydroxy-1-methyl-ethyl)-thiophen-2-ylmethyl]-2-(pyridin-3-yloxy)-nicotinamide M.P. 110–1120° C.; Anal. calcd. for $C_{19}H_{19}N_3SO_3$: C, 61.77; H, 5.18, N, 11.37. Found: C, 61.63; H, 5.40; N, 10.60.

EXAMPLE 36

N-[4-(1-Hydroxy-1-methyl-ethyl)-benzyl]-2-(pyridin-3-yloxy)-nicotinamide

M.P. 79–81° C.; Anal. calcd. for $C_{21}H_{21}N_3O_3$: C, 69.41; H, 5.82; N, 11.56. Found: C, 69.19; H, 5.85; N, 11.58.

EXAMPLE 37

4-({[2-(Pyridin-3-yloxy)-pyridine-3-carbonyl]-amino}-methyl)-benzoicacid methyl ester M.P. 125–127° C.; Anal. calcd. for $C_{20}H_{17}N_3O_4$: C, 66.11; H, 4.72; N, 11.56. Found: C, 65.83; H, 4.52; N, 11.39.

EXAMPLE 38

N-[3-Chloro-4-(1-hydroxy-1-methyl-ethyl)-benzyl]-2-(pyridin-3-yloxy)-nicotinamide M.P. 139–141° C.; Anal. calcd. for $C_{21}H_{20}N_3O_3Cl$: C, 63.40; H, 5.07; N, 10.56. Found: C, 63.24; H, 4.85; N, 10.21.

EXAMPLE 39

N-[2-Chloro-4-(1-hydroxy-1-methyl-ethyl)-benzyl]-2-(pyridin-3-yloxy)-nicotinamide MS (m/e) 400/398 (M$^+$+1); $^1$H NMR (400 mhz, CDCl$_3$) d 1.54 (s, 6H), 4.73 (d, 2H), 7.16–7.56 (m, 6H), 8.16 (d, 1H), 8.34 (m, 1H), 8.49 (dd, 2H), 8.61 (d, 1H).

EXAMPLE 40

2-(Pyridin-3-yloxy)-N-[4-(2,2,2-trifluoro-1-hydroxy-ethyl)-benzyl]-nicotinamide

MS (m/e) 404 (M$^+$+1); $^1$H NMR (400 mhz, CDCl$_3$) d 4.70 (dd, 2H), 4.98 (dd, 1H), 7.16–7.56 (m, 7H), 8.00 (m, 1H), 8.18 (dd, 1H), 8.28 (d, 1H), 8.43 (m, 1H), 8.60 (dd, 1H).

EXAMPLE 41

N-(4-Hydroxy-chroman-7-ylmethyl)-2-(pyridin-3-yloxy)-nicotinamide

M.P. 134–136° C.; Anal. calcd. for $C_{21}H_{19}N_3O_4$: C, 66.83; H, 5.07; N, 11.13. Found: C, 66.50; H, 4.90; N, 11.60.

EXAMPLE 42

N-[4-(1-Hydroxy-cyclobutyl)-benzyl]-2-(pyridin-3-yloxy)-nicotinamide

M.P. 116–118° C.; Anal. calcd. for $C_{22}H_{21}N_3O_3$: C, 70.83; H, 5.64; N, 11.19. Found: C, 70.41; H, 5.67; N, 10.97.

EXAMPLE 43

N-[4-(1-Hydroxy-prop-2-ynyl)-benzyl]-2-(pyridin-3-yloxy)-nicotinamide

MS (m/e) 360/344 (M$^+$+1); $^1$H NMR (400 mhz, CDCl$_3$) d 4.69 (d, 2H), 5.19 (m, 1H), 7.15–7.53 (m, 8H), 7.99 (m, 1H), 8.18 (dd, 1H), 8.35 (dd, 1H), 8.49 (d, 1H), 8.63 (dd, 1H).

EXAMPLE 44

N-[3-Chloro-5-(1-hydroxy-1-methyl-ethyl)-thiophen-2-ylmethyl]-2-(pyridin-3-yloxy)-nicotinamide M.P. 74–76° C.; Anal. calcd. for $C_{19}H_{18}N_3O_3SCl$: C, 56.50; H, 4.49; N, 10.40. Found: C, 56.79; H, 4.68; N, 9.64.

EXAMPLE 45

2-(Pyridin-3-yloxy)-N-(1-thiophen-2yl-ethyl)-nicotinamide

To a stirred suspension of 2-(pyridin-3-yloxy)-nicotinic acid (0.300 grams, 1.39 mmole) and NMM (0.155 grams, 1.53 mmole) in dry methylene chloride (15 ml) at −10° C. was added isobutyl chloroformate (0.208 grams, 1.53 mmole). After 20 minutes at −10° C. 1-Thiophen-2-yl-ethylamine (0.195 grams, 1.53 mmole) was added and the mixture was allowed to warm to room temperature over night. The mixture was diluted with 200 ml ethyl acetate, washed with 1 N sodium hydroxide and water, dried over MgSO$_4$, filtered and concentrated to give an oil that was purified by chromatography on silica gel eluting with 5% methanol/methylene chloride to give a solid. Recrystalization from ethyl acetate/hexane gave a white solid (0.191 ). M.P. 90–92° C.; Anal. calcd. for $C_{17}H_{15}N_3O_2S$ C, 62.75; H, 4.65; N, 12.91. Found: C, 62.51; H, 4.69; N, 13.10.

The compounds of Examples 46–47 were prepared according to the procedure of Example 45 substituting the corresponding amine for 1-Thiophen-2-yl-ethylamine. The duration of reaction was between 1 and 24 hours.

EXAMPLE 46

(S)(+)-2-(Pyridin-3-yloxy)-N-(1-thiophen-2-yl-ethyl)-nicotinamide

M.P. 196–198° C.; Anal. calcd. for $C_{17}H_{15}N_3O_2S.HCl$: C, 56.43; H, 4.46; N, 11.61. Found: C, 59.48; H, 5.49; N, 10.04. $\alpha_D$=+28.3° (C=0.2, methanol).

EXAMPLE 47

(R)(−)-2-(Pyridin-3-yloxy)-N-(1-thiophen-2-yl-ethyl)-nicotinamide

M.P. 197–199° C.; Anal. calcd. for $C_{17}H_{15}N_3O_2S.HCl$: C, 56.43; H, 4.46; N, 11.61. Found: C, 57.55; H, 5.12; N, 10.62. $\alpha_D$=+17.9° (C=0.1, methanol).

EXAMPLE 48

2-(5-Chloro-pyridin-3-yloxy)-N-(4-methyl-benzyl)-nicotinamide

To a stirred solution of 2-(5-chloro-pyridin-3-yloxy)-nicotinic acid (0.180 grams, 0.78 mmole), 4-methylbenzylamine (0.104 grams, 0.86 mmole), and 1-hydroxybenzotriazole hydrate (0.116 grams, 0.86 mmole)

in dry dimethylformamide (5 ml) was added 1-(3-(dimethylamino)-propyl)-3-ethylcarbodiimide chloride hydrochloride (0.165 grams, 0.86 mmole) and stirred for 18 hours. The mixture was poured into 100 ml water and extracted with ethyl acetate. The combined organics were washed with water and brine, dried over $MgSO_4$, filtered and concentrated to give an oil that was purified by chromatography on silica gel eluting with 5% methanol/methylene chloride. Recrystalization from ethyl acetate/hexane gave light pink crystals (0.211 g ). M.P. 119–121° C.; Anal. calcd. for $C_{19}H_{16}N_3O_2Cl$: C, 64.50; H, 4.56; N, 11.88. Found: C, 64.44; H, 4.47; N, 11.94.

The compounds of Examples 49–60 were prepared according to the procedure of Example 48 substituting the corresponding amine for 4-methylbenzylamine. The duration of reaction was between 1 and 24 hours.

EXAMPLE 49

2-(5-Chloro-pyridin-3-yloxy)-N-[1-(5-chloro-thiophen-2-yl)-ethyl]-nicotinamide

M.P. 110–112° C., Anal. calcd. for $C_{17}H_{14}N_3O_2SCl_2$: C, 51.66; H, 3.57; N, 10.63. Found: C, 51.49; H, 3.51; N, 10.41.

EXAMPLE 50

2-(5-Chloro-pyridin-3-yloxy)-N-[1-(5-methyl-thiophen-2-yl)-ethyl]-nicotinamide

M.P. 75–77° C.; Anal. calcd. for $C_{18}H_{16}N_3O_2SCl$: C, 57.83; H, 4.31; N, 11.24. Found: C, 57.88; H, 4.42; N, 11.42.

EXAMPLE 51

2-(5-Chloro-pyridin-3-yloxy)-N-(5-chloro-thiophen-2-ylmethyl)-nicotinamide

M.P. 125–127° C.; Anal. calcd. for $C_{16}H_{11}N_3O_2SCl_2$: C, 50.54; H, 2.92; N, 11.05. Found: C, 50.42; H, 2.99; N, 11.07.

EXAMPLE 52

2-(5-Chloro-pyridin-3-yloxy)-N-(5-methyl-thiophen-2-ylmethyl)-nicotinamide

M.P. 81–83° C.; Anal. calcd. for $C_{17}H_{14}N_3O_2SCl$: C, 56.75; H, 3.92; N, 11.68. Found: C, 56.94; H, 4.07; N, 11.19.

EXAMPLE 53

2-(5-Chloro-pyridin-3-yloxy)-N-(5-methyl-furan-2-ylmethyl)-nicotinamide

M.P. 103–105° C.; Anal. calcd. for $C_{17}H_{14}N_3O_3Cl$: C, 59.40; H, 4.10; N, 12.22. Found: C, 59.50; H, 4.15; N, 12.08.

EXAMPLE 54

2-(5-Chloro-pyridin-3-yloxy)-N-(3-methyl-thiophen-2-ylmethyl)-nicotinamide

M.P. 115–117° C.; Anal. calcd. for $C_{17}H_{14}N_3SO_2Cl$: C, 56.75; H, 3.92; N, 11.68. Found: C, 56.75; H, 4.02; N, 11.37.

EXAMPLE 55

2-(5-Chloro-pyridin-3-yloxy)-N-(4-chloro-thiophen-2-ylmethyl)-nicotinamide

M.P. 94–96° C.; MS (m/e) 380/382 (M$^+$+1).

EXAMPLE 56

N-Benzo[b]thiophen-2-ylmethyl-2-(5-chloro-pyridin-3-yloxy)-nicotinamide

M.P. 160–162° C.; Anal. calcd. for $C_{20}H_{14}N_3SO_2Cl$: C, 60.68; H, 3.56; N, 10.61. Found: C, 60.90; H, 3.67; N, 10.49.

EXAMPLE 57

N-(5-Chloro-furan-2-ylmethyl)-2-(5-chloro-pyridin-3-yloxy)-nicotinamide

M.P. 111–113° C.; Anal. calcd. for $C_{16}H_{11}N_3O_3Cl_2$: C, 52.77; H, 3.04; N, 11.54. Found: C, 53.04; H, 3.16; N, 11.21.

EXAMPLE 58

2-(5-Chloro-pyridin-3-yloxy)-N-cyclohexylmethyl-nicotinamide

M.P. 95–97° C.; Anal. calcd. for $C_{18}H_{20}N_3O_2Cl$: C, 62.52; H, 5.83; N, 12.15. Found: C, 62.51; H, 5.80; N, 12.10.

EXAMPLE 59

2-(5-Chloro-pyridin-3-yloxy)-N-[4-(1-hydroxy-1-methyl-ethyl)-benzyl]-nicotinamide M.P. 78–80° C.; Anal. calcd. for $C_{21}H_{20}N_3O_3Cl$: C, 63.40; H, 5.07; N, 10.56. Found: C, 63.24; H, 5.00; N, 10.33.

EXAMPLE 60

N-[3-Chloro-5-(1-hydroxy-1-methyl-ethyl)-thiophen-2-ylmethyl]-2-(5-chloro-pyridin-3-yloxy)-nicotinamide M.P. 72–74° C.; Anal. calcd. for $C_{19}H_{17}N_3O_3SCl_2$: C, 52.66; H, 3.91; N, 9.59. Found: C, 50.27; H, 4.10; N, 9.01.

EXAMPLE 61

N-(5-Chloro-thiophen-2-ylmethyl)-2-(4-fluoro-phenoxy)-nicotinamide

To a stirred solution of 2-(4-Fluoro-phenoxy)-nicotinic acid (0.200 grams, 1.02 mmole), C-(5-Chloro-thiophen-2-yl)-methylamine (0.151 grams, 1.02 mmole), and 1-hydroxybenzotriazole hydrate (0.138 grams, 1.02 mmole) in dry dimethylformamide (3 ml) was added 1-(3-dimethylamino)-propyl)-3-ethylcarbodiimide hydrochloride (0.212 grams, 1.11 mmole) and stirred over night. The mixture was poured into 100 ml water and extracted with ethyl acetate. The combined organics were washed with 1N NaOH, water and brine, dried over $MgSO_4$, filtered and concentrated to give an oil that was purified by chromatography on silica gel eluting with 30% ethyl acetate/hexane. Recrystalization from ethyl acetate/hexane gave a white solid (0.216 g). M.P. 91–93° C.; Anal. calcd. for $C_{17}H_{12}N_2O_2SFCl$: C, 56.28; H, 3.33; N, 7.72. Found: C, 56.34; H, 3.36; N, 7.41.

The compounds of Examples 62–91 were prepared according to the procedure of Example 61 substituting the corresponding amine for C-(5-Chloro-thiophen-2-yl)-methylamine. The duration of reaction was between 1 and 24 hours.

EXAMPLE 62

N-(4-Chloro-thiophen-2-ylmethyl)-2-(4-fluoro-phenoxy)-nicotinamide

M.P. 99–101° C.; Anal. calcd. for $C_{17}H_{12}N_2SO_2FCl$: C, 56.28; H, 3.33; N, 7.72. Found: C, 56.40; H, 3.38; N, 7.60.

EXAMPLE 63

N-(5-Chloro-furan-2-ylmethyl)-2-(4-fluoro-phenoxy)-nicotinamide

M.P. 116–118° C.; Anal. calcd. for $C_{17}H_{12}N_2O_3FCl$: C, 58.89; H, 3.49; N, 8.08. Found: C, 59.07; H, 3.53; N, 7.97.

EXAMPLE 64

N-(2,3-Difluoro-benzyl)-2-(4-fluoro-phenoxy)-nicotinamide

M.P. 71–73° C.; Anal. calcd. for $C_{15}H_{13}N_2O_2F_3$: C, 63.69; H, 3.66; N, 7.82. Found: C, 63.60; H, 3.64; N, 7.70.

EXAMPLE 65

N-Benzo[b]thiophen-2-ylmethyl-2-(4-fluoro-phenoxy)-nicotinamide

M.P. 109–111° C.; Anal. calcd. for $C_{21}H_{15}N_2O_2SF$: C, 66.65; H, 4.00; N, 7.40. Found: C, 66.52; H, 4.02; N, 7.24.

EXAMPLE 66

N-(3,5-Difluoro-benzyl)-2-(4-fluoro-phenoxy)-nicotinamide

M.P.116–118° C.; Anal. calcd. for $C_{15}H_{13}N_2O_2F_3$: C, 63.69; H, 3.66; N, 7.82. Found: C, 65.57; H, 4.24; N, 7.73.

EXAMPLE 67

2-(4-Fluoro-phenoxy)-N-(2,4,6-trifluoro-benzyl)-nicotinamide

M.P. 128–130° C.; Anal. calcd. for $C_{19}H_{12}N_2O_2F_4$: C, 60.64; H, 3.21; N, 7.44. Found: C, 60.83; H, 3.15; N, 7.25.

EXAMPLE 68

N-(3,4-Dichloro-thiophen-2-ylmethyl)-2-(4-fluoro-phenoxy)-nicotinamide

M.P. 132–134° C.; Anal. calcd. for $C_{17}H_{11}N_2SO_2Cl_2F$: C, 51.40; H, 2.79; N, 7.05. Found: C, 51.36; H, 2.86; N, 7.05.

EXAMPLE 69

N-(3-Chloro-thiophen-2-ylmethyl)-2-(4-fluoro-phenoxy)-nicotinamide

M.P. 134–136° C.; Anal. calcd. for $C_{17}H_{12}N_2SO_2ClF$: C, 56.28; H, 3.33; N, 7.72. Found: C, 56.17; H, 3.30; N, 7.70.

EXAMPLE 70

N-(2-Chloro-benzyl)-2-(4-fluoro-benzyloxy)-nicotinamide

M.P. 64–66° C.; Anal. calcd. for $C_{20}H_{16}N_2O_2ClF$: C, 64.78; H, 4.35; N, 7.55. Found: C, 64.88; H, 4.36; N, 7.48.

EXAMPLE 71

2-(4-Fluoro-phenoxyl-N-(1H-indol-5-ylmethyl)-nicotinamide

M.P. 128–130° C.; Anal. calcd. for $C_{21}H_{16}N_3O_2F$: C, 69.80; H, 4.46; N, 11.63. Found: C, 69.46; H, 4.29; N, 11.55.

EXAMPLE 72

2-(4-Fluoro-phenoxy)-N-(4-nitro-benzyl)-nicotinamide

M.P. 155–157° C.; Anal. calcd. for $C_{19}H_{14}N_3O_4F$: $^1H$ NMR (400 mhz, $CDCl_3$) d 4.80 (d, J=6.02 Hz, 2H), 7.21 (m, 5H), 7.51 (m, 2H), 8.20 (m, 3H), 8.35 (s,broad, 1H), 8.65 (m,1H).

EXAMPLE 73

2-(4-Fluoro-phenoxy)-N-(2-oxo-2,3-dihydro-1H-indol-5-ylmethyl)-nicotinamide

M.P. 180–182° C.; Anal. calcd. for $C_{21}H_{16}N_3O_3F$: C, 66.84; H, 4.27, N, 11.13. Found: C, 66.31; H, 4.31; N, 10.76.

EXAMPLE 74

2-(4-Fluoro-phenoxy)-N-(2-oxo-2,3-dihydro-benzooxazol-6-yl)-nicotinamide

M.P. 289–291° C.; Anal. calcd. for $C_{19}H_{12}N_3O_4F$: C, 62.47; H, 3.31, N, 11.50. Found: C, 61.83; H, 3.08; N, 11.56.

EXAMPLE 75

5-({[2-(4-Fluoro-phenoxy)-pyridine-3-carbonyl]-amino}-methyl)-1H-indole-2-carboxylic acid ethyl ester M.P. 185–187° C.; Anal. calcd. for $C_{24}H_{20}N_3O_4F$: C, 66.51; H, 4.65, N, 9.98. Found: C, 66.61; H, 4.66; N, 9.55.

EXAMPLE 76

N-[3,5-Di-tert-butyl-4-hydroxy-benzyl)-2-(4-fluoro-phenoxyl)nicotinamide

M.P. 45–47° C.; Anal. calcd. for $C_{27}H_{31}N_2O_3F$: C, 71.98; H, 6.93, N, 6.22. Found: C, 72.05; H, 7.08; N, 6.28.

EXAMPLE 77

2-(4-Fluoro-phenoxy)-N-[4-(1-hydroxy-1-methyl-ethyl)-benzyl]-nicotinamide

M.P. 106–108° C.; Anal. calcd. for $C_{22}H_{21}N_2O_3F$: C, 69.46; H, 5.56, N, 7.36. Found: C, 69.39; H, 5.48; N, 7.16.

EXAMPLE 78

2-(4-Fluoro-phenoxy)-N-(4-hydroxy-3,5-dimethyl-benzyl)-nicotinamide

M.P. 142–144° C.; Anal. calcd. for $C_{21}H_{19}N_2O_3F$: C, 68.84; H, 5.23, N, 7.65. Found: C, 68.42; H, 5.23; N, 7.61.

EXAMPLE 79

2-(4-Fluoro-phenoxy)-N-[5-(1-hydroxy-1-methyl-ethyl)-furan-2-ylmethyl]-nicotinamide M.P. 88–90° C.; Anal. calcd. for $C_{20}H_{19}N_2O_4F$: C, 64.86; H, 5.17, N, 7.56. Found: C, 64.50; H, 4.99; N, 7.69.

EXAMPLE 80

N-[5-(1-Ethyl-1-hydroxy-propyl)-thiophen-2-ylmethyl]-2-(4-fluoro-phenoxy)-nicotinamide M.P. 95–97° C.; Anal. calcd. for $C_{22}H_{23}N_2O_3SF$: C, 63.75; H, 5.59, N, 6.76. Found: C, 63.42; H, 5.27; N, 7.07.

EXAMPLE 81

N-[4-Chloro-5-(1-hydroxy-1-methyl-ethyl]-thiophen-2-ylmethyl]-2-(4-fluoro-phenoxy)-nicotinamide M.P. 115–117° C.; Anal. calcd. for $C_{20}H_{18}N_2O_3SClF$: C, 57.08; H, 4.31, N, 6.66. Found: C, 57.03; H, 4.10; N, 6.75.

EXAMPLE 82

N-[1-(4-Bromo-phenyl)-ethyl]-2-(4-fluoro-phenoxy)-nicotinamide

M.P. 120–122° C.; $^1$H NMR (CDCl$_3$) d 1.60 (3H, d, J=6.85 Hz), 5.25 (1H, m), 7.1–7.5 (9H, m), 8.10 (1H, bs), 8.20 (1H, m), 8.60 (1H, m).

EXAMPLE 83

2-(4-Fluoro-phenoxy)-N-[4-(1-methoxy-1-methyl-ethyl)-benzyl]-nicotinamide

Anal. calcd. for $C_{23}H_{23}N_2O_3F$: MS (m/e) 395 (M$^+$+1); $^1$H NMR (CDCl$_3$) d 1.50 (6H, s), 3.05 (3H, s), 4.72 (2H, d, J=5.81 Hz), 7.1–7.4 (9H, m), 8.2 (9H, m), 8.65 (1H, m).

EXAMPLE 84

N-[3-Chloro-5-(1-hydroxy-1-methyl-ethyl)-thiophen-2-ylmethyl]-2-(4-fluoro-phenoxy)-nicotinamide M.P. 85–87° C.; Anal. calcd. for $C_{20}H_{18}N_2O_3SClF$: C, 57.08; H, 4.31, N, 6.66. Found: C, 57.30; H, 4.36; N, 6.46.

EXAMPLE 85

2-(4-Fluoro-phenoxy)-N-[4-(1-hydroxy-cyclobutyl)-benzyl]-nicotinamide

M.P. 95–97° C.; Anal. calcd. for $C_{23}H_{21}N_2O_3F$: C, 70.40; H, 5.39, N, 7.14. Found: C, 70.28; H, 5.45; N, 7.03.

EXAMPLE 86

N-[2-Chloro-4-(1-hydroxy-1-methyl-ethyl)-benzyl]-2-(4-fluoro-phenoxy)-nicotinamide M.P. 102–104° C.; Anal. calcd. for $C_{22}H_{20}N_2O_3FCl$: C, 63.69; H, 4.86, N, 6.75. Found: C, 63.69; H, 4.99; N, 6.72.

EXAMPLE 87

N-(4-Azetidin-1-yl-benzyl)-2-(4-fluoro-phenoxy)-nicotinamide

M.P. 128–129° C.; Anal. Calcd for $C_{22}H_{20}N_3O_2F$: C, 70.01; H, 5.34; N, 11.13. Found: C, 69.64; H, 5.27; N, 11.13.

EXAMPLE 88

2-(4-Fluoro-phenoxy)-N-[4-(3-hydroxy-azetidin-1-yl)-benzyl]-nicotinamide

M.P. 157–159° C.; $^1$H NMR (CDCl$_3$) d 2.08 (1H, d, J=7 Hz), 3.62–3.65 (2H, m), 4.09–4.16 (2H, m), 4.59 (2H, d, J=5 Hz), 4.70–4.75 (1H, m), 6.42 (2H, d, J=8 Hz), 7.07–7.24 (7H, m), 8.03 (1H, br s), 8.16–8.18 (1H, m), 8.61–8.64 (1H, m); MS (m/e) 394 (M$^+$+1).

EXAMPLE 89

2-(4-Fluoro-phenoxy)-N-(4-pyrrolidin-1-yl-benzyl)-nicotinamide

M.P. 127–128° C.; $^1$H NMR (CDCl$_3$) d 1.93–2.03 (4H, m), 3.21–3.30 (4H, m), 4.59 (2H, d, J=5 Hz), 6.43–6.60 (2H, m), 7.06–7.24 (7H, m), 8.00 (1H, br s), 8.16–8.18 (1H, m), 8.62–8.64 (1H, m); MS (m/e) 392 (M$^+$+1).

EXAMPLE 90

2-(4-Fluoro-phenoxy)-N-(4-piperidin-1-yl-benzyl)-nicotinamide

M.P. 118–119° C.; $^1$H NMR (CDCl$_3$) d 1.51–1.74 (6H, m), 3.09–3.15 (4H, m), 4.61 (2H, d, J=5 Hz), 6.82–6.90 (2H, m), 7.05–7.24 (7H, m), 8.04 (1H, br s), 8.17–8.18 (1H, m), 8.62–8.64 (1H, m); MS (m/e) 406 (M$^+$+1).

EXAMPLE 91

2-(4-Fluoro-phenoxy)-N-(4-morpholin-4-yl-benzyl)-nicotinamide

M.P. 163–165° C.; Anal. Calcd for $C_{23}H_{22}N_3O_3F$: C, 67.80, H, 5.44; N, 10.31. Found: C, 67.42; H, 5.38; N, 10.37.

EXAMPLE 92

2-(4-Fluoro-phenoxy)-N-[4-(4-oxo-piperidin-1-yl)-benzyl]-nicotinamide

The crude product was further treated in a refluxing mixture of 2:5 aqueous 1 N hydrochloric acid solution: tetrahydrofuran for 2 days to effect hydrolysis of the ketal; work-up was accomplished by partitioning the mixture between EtOAc and saturated aqueous sodium hydrogen-carbonate solution, drying the organic layer (MgSO$_4$), and evaporation. M.P. 138–139° C.; Anal. Calcd for $C_{24}H_{22}N_3O_3F$: C, 68.72; H, 5.29; N, 10.02. Found: C, 68.60; H, 5.22; N, 10.01.

EXAMPLE 93

2-(4-Fluoro-phenoxy)-N-{4-[(2-hydroxy-2-methyl-propyl)-methyl-amino]-benzyl}-nicotinamide $^1$H NMR (DMSO-d$^6$) d 1.04 (6H, s), 2.98 (3H, s), 3.32 (2H, s), 4.01 (2H, d, J=6 Hz), 7.01–7.11 (2H, m), 7.06–7.25 (7H, m), 8.07–8.16 (2H, m), 8.85 (1H, t J=6 Hz); MS (m/e) 424 (M$^+$+1).

EXAMPLE 94

2-(4-Fluoro-phenoxy)-N-[4-(2-methyl-[1,3]dioxolan-2-yl)-benzyl]-nicotinamide

M.P. 78–80° C.; MS (m/e) 408 (M$^+$).

EXAMPLE 95

N(4-Dioxa-spiro[4,5]dec-8-ylmethyl)-2-(4-fluoro-phenoxy)-nicotinamide

M.P. 88–90° C.; MS (m/e) 487 (M$^+$+1).

EXAMPLE 96

N-[4,6-Dichloro-thiophen-2-ylmethyl]-2-(4-fluoro-phenoxy)-nicotinamide

M.P. 127–129° C.; Anal. Calcd for $C_{17}H_{11}N_2O_2FSCl_2$: C, 51.40;H, 2.79; N, 7.05. Found: C, 51.65; H, 3.01; N, 6.93.

EXAMPLE 97

N-(3,5-Dichloro-thiophen-2ylmethyl)-2-(4-fluoro-phenoxy)-nicotinamide

M.P. 132–134° C.; MS (m/e) 397 (M$^+$).

EXAMPLE 98

2-(5-Chloro-pyridin-3-yloxy)-N-cyclopropylmethyl-nicotinamide

To a stirred solution of 2-(5-chloro-pyridin-3-yloxy)-nicotinic acid (0.200 grams, 0.88 mmole), aminomethylcy-clopropane hydrochloride (0.094 grams, 0.88 mmole), triethylamine (0.089 grams, 0.88 mmole) and 1-hydroxybenzotriazole hydrate (0.119 grams, 0.88 mmole) in dry dimethylformamide (3 ml) was added 1-(3-dimethylamino)-propyl)-3-ethylcarbodiimide hydrochloride (0.164 grams, 0.96 mmole) and stirred over night. The mixture was poured into 100 ml water and extracted with ethyl acetate. The combined organics were washed with 1 $\underline{N}$ NaOH, water and brine, dried over MgSO$_4$, filtered and concentrated to give an oil that was purified by chromatography on silica gel eluting with 2.5% methanol/methylene chloride. Recrystalization from ethyl acetate/hexane gave a white solid (0.163 g). M.P. 105–107° C.; Anal. calcd. for $C_{15}H_{14}N_3O_2Cl$: C, 59.31;H, 4.65; N, 13.83. Found: C, 59.41;H, 4.68; N, 13.44.

EXAMPLE 99

2-(3-Cyano-4-fluoro-phenoxy)-N-[2-fluoro4-(1-hydroxy-1-methyl-ethyl)-benzyl]-nicotinamide Prepared from 2-(3-Cyano-4-fluoro-phenoxy)-nicotinic acid and 2-(4-Aminomethyl-3-fluoro-phenyl)-propan-2-ol according to methods analogous to those used in Example 318.

MP:157–159° C., MS: m/e 422 (M$^+$+1)

EXAMPLE 100

2-(5-Chloro-pyridin-3-yloxy)-nicotinic acid benzyl ester

A 15 ml flask was charged with 2-(5-chloro-pyridin-3-yloxy)-nicotinic acid (0.056 grams, 0.22 mmole), benzyl alcohol (0.052 grams, 0.44 mmole), 4-DMAP (~3 mg), 1-(3-dimethylaminopropyl)-3-ethyl carbodiimide hydrochloride (0.048 grams, 0.25 mmole), diethyl ether (4 ml) and pyridine (1 ml) and stirred at room temperature. After 1 hour the mixture was concentrated under reduced pressure and purified by column chromatography on silica gel eluting with 9/1 ethyl acetate/hexane to give 0.060 g of the title compound as a colorless oil. Anal. calcd. for $C_{18}H_{13}ClN_2O_3$: M.S. m/z [M+] 341; $^1$H NMR (CD$_3$OD) d 4.58 (s, 2H), 7.45(m, 7H), 7.71 (s, 1H), 8.28 (m, 2H), 8.38 (m, 2H).

The compounds of Examples 101–102 were prepared according to the procedure of Example 100 substituting the corresponding alcohol for benzyl alcohol. The duration of reaction was between 1 and 6 hours.

EXAMPLE 101

2-(5-Chloro-pyridin-3-yloxy)-nicotinic acid 4-fluoro-benzyl ester

Anal. calcd. for $C_{18}H_{12}N_2O_3ClF$; M.S. m/z [M+] 359; $^1$H NMR (CD$_3$OD) d 4.56 (s, 2H), 7.88 (m, 2H), 7.29 (m, 2H), 7.47 (m, 2H), 7.72 (s, 1H), 8.37 (m, 3H).

EXAMPLE 102

2-(5-Chloro-pyridin-3-yloxy)-nicotinic acid 3,5-difluoro-benzyl ester

Anal. calcd. for $C_{18}H_{11}N_2O_2ClF_2$; M.S. m/z [M+] 377; $^1$H NMR (CD$_3$OD) d 4.59 (s, 2H), 6.77 (m, 2H), 6.85 (m, 3H), 7.07 (m, I H), 7.30 (m, 1H), 8.35 (m, 2H).

EXAMPLE 103

2-(4-Fluoro-phenoxy)-N-(4-hydroxy-benzyl)-nicotinamide

A solution of 1 $\underline{M}$ boron tribromide (1.7 ml, 1.7 mmole) in methylene chloride was added over 2 minutes to a solution of 2-(4-Fluoro-phenoxy)-N-(4-methoxy-benzyl)-nicotinamide (0.200 grams, 0.568 mmole) in dry methylene chloride at −78° C. The resulting slurry was allowed to warm to room temperature over night. The reaction was quenched with water (5 ml) and diluted with ethyl acetate. The organics were filtered, washed with water and brine, dried over Na$_2$SO$_4$, filtered and concentrated to an oil which was purified by chromatography on silica gel eluting with 60% ethyl acetate/hexane. Recrystalization from ethyl acetate/hexane gave white crystals (0.0.058 g). M.P. 185–187° C.; Anal. calcd. for $C_{19}H_{15}N_2O_3F$: C, 67.45; H, 4.47; N, 8.28. Found: C, 67.24; H, 4.45; N, 8.28.

The compound of Example 104 was prepared according to the procedure of Example 103 substituting the corresponding ether for 2-(4-Fluoro-phenoxy)-N-(4-methoxy-benzyl)-nicotinamide. The duration of reaction was between 1 and 24 hours.

EXAMPLE 104

N-(4-Hydroxy-benzyl)-2-(pyridin-3yloxy)-nicotinamide

M.P. 156–158° C.; Anal. calcd. for $C_{18}H_{15}N_3O_3$ : C, 67.28; H, 4.70; N, 13.08. Found: C, 66.86; H, 4.57; N, 12.89.

EXAMPLE 105

2-(3-Nitro-phenoxy)-N-[4-(2,2,2-trifluoro-ethoxy)-benzyl-nicotinamide

To a stirred solution 2-(3-Nitro-phenoxy)-nicotinic acid (0.200 grams, 0.77 mmole), 4-(2,2,2-Trifluoro-ethoxy)-benzylamine (0.173 grams, 0.85 mmole), and 1-hydroxybenzotriazole hydrate (0.125 grams, 0.92 mmole) in dry dimethylformamide (4 ml) was 1-(3-dimethylamino)-propyl)-3-ethylcarbodiimide chloride hydrochloride (0.192 grams, 1.00 mmole) and stirred over night. The mixture was diluted with 50 ml water and extracted with ethyl acetate. The combined organics were washed with 1$\underline{N}$ NaOH, water and brine, and concentrated to give a yellow solid that was purified by chromatography on silica gel eluting with 35% methanol/methylene chloride. Recrystalization from ethyl acetate/hexane gave a white solid (0.340 g). M.P. 90–92° C.; Anal. calcd. for $C_{21}H_{16}N_3O_5F_3$: C, 56.38; H, 3.60; N, 9.39. Found: C, 56.35; H, 3.60; N, 9.47.

The compounds of Examples 106–109 were prepared according to the procedure of Example 105 substituting the corresponding amine for 4-(2,2,2-Trifluoro-ethoxy)-benzylamine. The duration of reaction was between 1 and 24 hours.

EXAMPLE 106

2-(3-Nitro-phenoxy)-N-(2-oxo-2,3-dihydro-1H-indol-5-ylmethyl)-nicotinamide

M.P. 190–192° C.; Anal. calcd. for $C_{21}H_{16}N_4O_5$: C, 62.17; H, 3.99, N, 13.85. Found: C, 62.24; H, 4.12; N, 13.73.

EXAMPLE 107

N-[4-(1-Hydroxy-1-methyl-ethyl)-benzyl]-2-(3-nitro-phenoxy)-nicotinamide

M.P. 43–45° C.; Anal. calcd. for $C_{22}H_{21}N_3O_5$: C, 64.86H, 5.20, N, 10.31. Found: C, 64.14; H, 5.19; N, 10.23.

EXAMPLE 108

N-(4-Hydroxy-3,5-dimethyl-benzyl)-2-(3-nitro-phenoxy)-nicotinamide

M.P. 128–130° C.; Anal. calcd. for $C_{21}H_{19}N_3O_5$: C, 64.12H, 4.87, N, 10.68. Found: C, 63.86; H, 4.71; N, 10.90.

EXAMPLE 109

N-(5-Chloro-thiophen-2-ylmethyl)-2-(3-nitro-phenoxy)-nicotinamide

M.P. 115–117° C.; Anal. calcd. for $C_{17}H_{12}N_3O_4SCl$: C, 52.44H, 3.11, N, 10.80. Found: C, 52.35; H, 3.06; N, 10.78.

EXAMPLE 110

N-(2-Chloro-benzyl)-2-(3-cyano-phenoxy)-nicotinamide

To a stirred solution 2-(3-Cyano-phenoxy)-nicotinic acid (0.085 grams, 0.35 mmole), 2-Chloro-benzylamine (0.055 grams, 0.38 mmole), and 1-hydroxybenzotriazole hydrate (0.057 grams, 0.42 mmole) in dry dimethylformamide (5 ml) was 1-(3-dimethylamino)-propyl)-3-ethylcarbodiimide hydrochloride (0.046 grams, 0.87 mmole) and stirred over night. The mixture was diluted with 50 ml water and extracted with ethyl acetate. The combined organics were washed with 1N NaOH, water and brine, dried over $Na_2SO_4$, filtered and concentrated to give a white solid that was purified by chromatography on silica gel. Recrystalization from ethyl acetate/hexane gave a white solid (0.067 g). M.P. 135–137° C.; Anal. calcd. for $C_{20}H_{14}N_3O_2Cl$: C, 66.03; H, 3.88; N, 11.55. Found. C, 65.40; H, 3.89; N, 11.50.

The compounds of Examples 111–117 were prepared according to the procedure of Example 110 substituting the corresponding amine for 2-Chloro-benzylamine. The duration of reaction was between 1 and 24 hours.

EXAMPLE 111

N-(5-Chloro-thiophen-2-ylmethyl)-2-(3-cyano-phenoxy)-nicotinamide

M.P. 145–147° C.; Anal. calcd. for $C_{18}H_{12}N_3O_2ClS$: C, 58.46; H, 3.27; N, 11.36. Found: C, 58.43; H, 3.06; N, 11.30.

EXAMPLE 112

2-(3-Cyano-phenoxy)-N-(2-oxo-2,3-dihydro-1H-indol-5-ylmethyl)-nicotinamide

M.P. 197–199° C.; Anal. calcd. for $C_{22}H_{16}N_4O_3$: C, 68.74; H, 4.20; N, 14.58. Found: C, 67.71; H, 4.09; N, 14.50.

EXAMPLE 113

2-(3-Cyano-phenoxy)-N-[4-(1-hydroxy-1-methyl-ethyl)-benzyl]-nicotinamide

M.P. 97–99° C.; Anal. calcd. for $C_{23}H_{21}N_3O_3$: C, 70.30;H, 5.46; N, 10.85. Found: C, 70.43; H, 5.39; N, 10.75.

EXAMPLE 114

N-3-Chloro-5-(1-hydroxy-1-methyl-ethyl)-thiophen n-2-ylmethyl]-2-(3-cyano-phenoxy)-nicotinamide M.P. 71–73° C.; Anal. calcd. for $C_{21}H_{18}N_3O_3SCl$: C, 58.95; H, 4.24; N, 9.82. Found: C, 58.97; H, 4.19; N, 9.67.

EXAMPLE 115

2-(3-Cyano-phenoxy-N-[4-(1-hydroxy-cyclobutyl)-benzyl]-nicotinamide

M.P. 161–163° C.; Anal. calcd. for $C_{26}H_{21}N_3O_3$: C, 72.17; H, 5.30; N, 10.52. Found: C, 72.23; H, 5.13; N, 10.46.

EXAMPLE 116

N-[2-Chloro-4-(1-hydroxy-1-methyl-ethyl)-benzyl]-2-(3-cyano-phenoxy)-nicotinamide M.P.121–123° C.; Anal. calcd. for $C_{23}H_{20}N_3O_3Cl$: C, 65.48;H, 4.78; N, 9.96. Found: C, 65.35; H, 4.89; N, 9.83.

EXAMPLE 117

2-(3-Cyano-phenoxy)-N-(-cyclohexyl-3-ethyl-1H-indazol-5-ylmethyl)-nicotinamide

M.P.56–58° C.; $^1$H NMR (400 mhz, $CDCl_3$) d 1.20–2.10 (m, 13H), 2.95 (q, J=7.68 Hz, 2H), 4.30 (m, 1H), 4.80 (d J=5.81 Hz, 2H), 6.05 (m, 1H), 7.10–7.70 (m, 8H), 8.0 (bs, 1H), 8.20 (m, 1H), 8.70 (m, 1H).

EXAMPLE 118

N-(2-Chloro-benzyl)-2-(3-dimethylamino-phenoxy)-nicotinamide

To a stirred solution 2-(3-Dimethylamino-phenoxy)-nicotinic acid (0.200 grams, 0.775 mmole), 2-Chloro-benzylamine (0.120 grams, 0.85 mmole), and 1-hydroxybenzotriazole hydrate (0.126 grams, 0.93 mmole) in dry dimethylformamide (4 ml) was added 1-(3-dimethylamino)-propyl)-3-ethylcarbodiimide chloride hydrochloride (0.193 grams, 1.00 mmole) and stirred over night. The mixture was diluted with 50 ml water and extracted with ethyl acetate. The combined organics were washed with 1N NaOH, water and brine, dried over $Na_2SO_4$, filtered and concentrated to give an oil that was purified by chromatography on silica gel. Recrystalization from ethyl acetate/hexane gave an oil. The product was dissolved in diethyl ether and hydrochloric acid (g) was used to precipitate the salt, which was filtered, dissolved in methylene chloride and concentrated to a solid (0.075 g). M.P. 85–87° C.; Anal. calcd. for $C_{21}H_{20}N_3O_2Cl.HCl$: C, 60.30; H, 5.06; N, 10.04. Found: C, 60.58; H, 5.60; N, 9.28.

EXAMPLE 119

N-(2-Chloro-benzyl)-2-(4-cyano-phenoxy)-nicotinamide

To a stirred solution 2-(4-Cyano-phenoxy)-nicotinic acid (0.130 grams, 0.54 mmole), 2-Chloro-benzylamine (0.083 grams, 0.59 mmole), and 1-hydroxybenzotriazole hydrate (0.088 grams, 0.65 mmole) in dry dimethylformamide (4 ml) was added 1-(3-dimethylamino)-propyl)-3-ethylcarbodiimide hydrochloride (0.134 grams, 0.70 mmole) and stirred over night. The mixture was diluted with 50 ml water and extracted with ethyl acetate. The combined organics were washed with 1N NaOH, water and brine, dried over $Na_2SO_4$, filtered and concentrated to give an oil that was purified by chromatography on silica gel eluting with 50/50 ethyl acetate/hexane. Recrystalization from ethyl acetate/hexane gave a white solid. (0.139 g). M.P. 112–114° C.; Anal. calcd. for $C_{20}H_{14}N_3O_2Cl$: C, 66.03; H, 3.88; N, 11.55. Found: C, 65.09; H, 3.92; N, 11.67.

The compound of Example 120 was prepared according to the procedure of Example 119 substituting the corresponding amine for 2-Chloro-benzylamine. The duration of reaction was between 1 and 24 hours.

EXAMPLE 120

2-(4-Cyano-phenoxy)-N-[4-1-hydroxy-1-methyl-ethyl)-benzyl)-nicotinamide

M.P. 137–139° C.; Anal. calcd. for $C_{23}H_{21}N_3O_3$: C, 71.30; H, 5.46; N, 10.85. Found. C, 70.95; H, 5.69; N, 10.96.

EXAMPLE 121

N-(4-Amino-benzyl)-2-(4fluoro-phenoxy)-nicotinamide

To a degassed solution of 2-(4-Fluoro-phenoxy)-N-(4-nitro-benzyl)-nicotinamide (0.800 g 2.17 mmole) in ethyl acetate was added 10% palladium on carbon (0.160 g). This was shaken under 40 psi hydrogen for 30 minutes. The catalyst was removed by filtration, and the solution was concentrated to give an oil that was purified by chromatography on silica gel eluting with 4% methanol/methylene chloride. Recrystalization from ethyl acetate/hexane gave a solid. (0.562 g). $^1$H NMR (400 mhz, CDCl$_3$) d 3.64 (s, 2H), 4.58 (d, J=5.60 Hz, 2H), 6.64 (d, J=8.30 Hz, 2H), 7.05 (m, 7H), 8.02 (s, broad, 1H), 8.20 (m, 1H), 8.62 (d, 1H).

EXAMPLE 123

N-Allyl-2-(3-chloro-phenoxy)-nicotinamide

To a stirred solution of 2(3-chloro-phenoxy)-nicotinamide (0.084 g, 0.34 mmole) in methylsulfoxide (2 ml) was added potassium hydroxide powder (0.074 grams, 1.32 mmole) followed by allyl bromide ((0.082 grams, 0.68 mmole). After 1 hour the mixture was poured into water and extracted with methylene chloride. The combined organics were washed with brine, dried over MgSO$_4$, filtered and concentrated to give a clear film (0.011 g). $^1$H NMR (400 mhz, CD$_3$OD) d 4.37 (q, J=7.26 Hz, 1H), 4.82 (d, J=5.60 Hz, 1H), 5.26 (d, J=10.58 Hz, 1H), 5.40 (d J=17.0 Hz, 1H), 6.05 (m, 1H), 7.03 (m, 1H), 7.13 (m, 1H), 7.21 (m, 2H), 7.38 (t J=8.1 Hz, 1H), 8.30 (m, 2H).

EXAMPLE 124

N-(4-Acetylamino-benzyl)-2-(4-fluoro-phenoxy)-nicotinamide

A solution of N-(4-Amino-benzyl)-2-(4-fluoro-phenoxy)-nicotinamide (0.105 grams, 0.31 mmole) and triethyl amine (0.047 grams, 0.46 mmole) in methylene chloride was cooled to 0° C., and Acetyl chloride (0.029 grams, 0.37 mmole) was added. The mixture was stirred for 10 minutes and then allowed to warm to room temperature for 30 minutes. The mixture was diluted with water and extracted with methylene chloride. The combined organics were washed with brine, dried over Na$_2$SO$_4$, filtered and concentrated to give a solid. Recrystalization from ethyl acetate/hexane gave a white solid. (0.082 g). M.P. 128–130° C.; Anal. calcd. for C$_{21}$H$_{18}$N$_3$O$_3$F: C, 66.48; H, 4.78; N, 11.08. Found: C, 66.14; H, 4.47; N, 11.08.

EXAMPLE 125

2(3-Acetylamino-phenoxyl-N-(2-chloro-benzyl)-nicotinamide

To a stirred solution 2-(3-Acetylamino-phenoxy)-nicotinic acid (0.400 grams, 1.47 mmole), 2-Chloro-benzylamine (0.228 grams, 1.62 mmole), and 1-hydroxybenzotriazole hydrate (0.238 grams, 1.76 mmole) in dry dimethylformamide (10 ml) was added 1-(3-dimethylamino)-propyl)-3-ethylcarbodiimide chloride hydrochloride (0.367 grams, 1.91 mmole) and stirred over night. The mixture was diluted with water, extracted with ethyl acetate and concentrated to give a product that was purified by chromatography on silica gel eluting with 3% methanol methylene chloride. Recrystalization gave a solid. (0.351 g). M.P. 177–179° C.; Anal. calcd. for C$_{21}$H$_{18}$N$_3$O$_3$Cl: C, 63.72; H, 4.58; N, 10.62. Found: C, 63.47; H, 4.55; N, 10.56.

The compound of Example 126 was prepared according to the procedure of Example 125 substituting the corresponding amine for 2-Chloro-benzylamine. The duration of reaction was between 1 and 24 hours.

EXAMPLE 126

2(3-Acetylamino-phenoxy)-N-[4-(1-hydroxy-1-methyl-ethyl)-benzyl]-nicotinamide M.P. 155–157° C.; Anal. calcd. for C$_{24}$H$_{25}$N$_3$O$_4$: C, 68.72, H, 6.01; N, 10.02. Found: C, 67.98; H, 6.04; N, 9.92.

EXAMPLE 127

(R)-2-(3-Chloro-phenoxy)-N-(2-hydroxy-1-phenyl-ethyl)-nicotinamide

A solution of 2-(3-chloro-phenoxy)-nicotinic acid (0.25 grams, 1.0 mmole) in thionyl chloride (10 ml) was heated to reflux. After 1 hour the reaction mixture was cooled to room temperature and concentrated under reduced pressure. The resulting residue was dissolved in tetrahydrofuran (5 ml) and added dropwise to a solution of (S)-2-hydroxy-1-phenyl ethylamine (0.14 grams, 1.0 mmole) in pyridine (5 ml) at 0° C. After 30 minutes the mixture was warmed to room temperature. After 1 hour the mixture was poured into 1 N hydrochloric acid and extracted with ethyl acetate. The combined organics were washed with 1 N hydrochloric acid followed by brine and dried over Na$_2$SO$_4$. Concentration under reduced pressure resulted in a yellow oil that was purified by chromatography on silica gel eluting with 1:1 ethyl acetate/hexane to give a colorless oil. Anal. calcd. for C$_{20}$H$_{17}$N$_2$O$_3$Cl: C, 65.13; H, 4.65; N, 7.60. Found: C, 65.20; H, 4.78; N, 7.38; M.S. m/z [M+] 369; $^1$H NMR (400 MHz, CDCl$_3$) d 2.54 (s, broad, 1H), 3.95 (m, 2H), 5.32 (m, 1H), 7.23 (m, 10H), 8.22 (m, 1H), 8.58 (m, 2H).

EXAMPLE 128

(R)-2-(3-Chloro-phenoxy)-3-(4-phenyl4,5-dihydro-oxazol-2-yl)-pyridine

A solution of (R)-2-(3-Chloro-phenoxy)-N-(2-hydroxy-1-phenyl-ethyl)-nicotinamide (0.30 grams, 0.813 mmole) and phosprorus oxychloride (10 ml) in toluene (10 ml) was stirred for 10 hours. The mixture was concentrated to dryness and dissolved in methanol (15 ml) and 1 N sodium hydroxide (5 ml) and refluxed for 2 hours. The methanol was evaporated, and the residue was dissolved in water and extracted with ethyl acetate. The combined organics were washed with water and brine, dried over Na$_2$SO$_4$, and concentrated to give a product that was purified by chromatography on silica gel eluting with 1:3 ethyl acetate/hexane to give a colorless oil.; Anal. calcd. for C$_{20}$H$_{17}$N$_2$O$_2$Cl: C, 68.48; H, 4.31; N, 7.99. Found: C, 68.58; H, 4.50; N, 7.63; M.S. m/z [M+] 351; α=+24.1° c=5.6 mg/ml in methylene chloride; $^1$H NMR (400 MHz, CDCl$_3$) d 4.29 (dd, J=8.4, 9.5 Hz, 1H), 5.43 (dd, J=8.1, 10.1 Hz, 1H), 7.22 (m, 10H), 8.30 (m, 2H).

The compound of Example 129 was prepared according to the procedure of Example 128 substituting the corresponding hydroxy nicotinamide for (R)-2-(3-Chloro-phenoxy)-N-(2-hydroxy-1-phenyl-ethyl)-nicotinamide. The duration of reaction was between 1 and 24 hours.

EXAMPLE 129

(S)-2-Phenoxy-3-[4-phenyl-4,5-dihydro-oxazol-2-yl)-pyridine

Anal. calcd. for C$_{29}$H$_{16}$N$_2$O$_2$: C, 75.93; H, 5.10; N, 8.85. Found: C, 76.12; H, 5.44; N, 8.17; M.S. m/z [M+] 317;

α=+21.3° c=8.3 mg/ml in methylene chloride, $^1$H NMR (400 MHz, CDCl$_3$) d 4.30 (t, J=8.3 Hz, 1H), 4.82 (dd, J=8.5, 10.2 Hz, 1H), 5.43 (dd, J=8.2, 10.3 Hz, 1H), 7.06 (m, 1H), 7.29 (m, 10H), 8.28 (m, 2H).

EXAMPLE 130

2,2-Dimethyl-propionic acid 4-({[2-(4-fluoro-phenoxy)-pyridine-3-carbonyl]-amino}-methyl)-phenyl ester A solution 2-(4-Fluoro-phenoxy)-N-(4-hydroxy-benzyl)-nicotinamide (0.050 grams, 0.148 mmole), trimethylacetyl chloride (0.019 grams, 0.163 mmole) and triethyl amine (0.022 grams, 0.222 mmole) in methylene chloride (5 ml) was stirred for 30 minutes. The mixture was diluted with 50 ml 1N sodium hydroxide and extracted with ethyl acetate. The combined organics were washed with water and brine, dried over Na$_2$SO$_4$, filtered and concentrated to give an oil that was purified by chromatography on silica gel eluting with 40% ethyl acetate/hexane. Recrystalization from ethyl acetate/hexane gave a solid (0.043 g). M.P. 91–93° C.; Anal. calcd. for C$_{24}$H$_{23}$N$_2$O$_4$F: C, 68.24; H, 5.49; N, 6.63. Found: C, 66.07; H, 5.24; N, 6.42.

EXAMPLE 131

2-(4-Fluoro-phenoxy)-N-(4-methanesulfonylamino-benzyl)-nicotinamide

To a solution of N-(4-Amino-benzyl)-2-(4-fluoro-phenoxy)-nicotinamide (0.150 grams, 0.445 mmole) and triethyl amine (0.089 g, 0.89 mmole) in methylene chloride (5 ml) was added methanesulfonic anhydride (0.100 grams, 0.578 mmole) and stirred over night. The mixture was concentrated to dryness, dissolved in methanol (10 ml) and 1 N sodium hydroxide (15 ml) and extracted with ethyl acetate. The product was purified by chromatography on silica gel eluting with 5% methanol methylene chloride. Recrystalization gave white crystals. (0.043 g). M.P. 107–109° C.; Anal. calcd. for C$_{20}$H$_{18}$N$_3$O$_4$SF: C, 57.82; H, 4.37; N, 10.11. Found: C, 57.88; H, 4.39; N, 9.78.

EXAMPLE 132

(S)-2-(3-Chloro-phenoxy)-N-(2-hydroxy-1-phenyl-ethyl)-nicotinamide

A solution 2-(3-chloro-phenoxy)-nicotinic acid (0.500 g) in thionyl chloride (10 ml) was refluxed for 1 hour. The mixture was concentrated to dryness, dissolved in 10 ml tetrahydrofuran and used immediately. To a solution of (S)-2-phenylglycinol (0.140 grams, 1.0 mmole) in dry pyridine (5 ml) at 0° C. was added a solution of 2-(3-Chloro-phenoxy)-nicotinoyl chloride (0.270 grams, 1.0 mmole) in tetrahydrofuran (5 ml) dropwise, stirred at 0° C. for 30 minutes and allowed to warm to room temperature over night. The mixture was concentrated under reduced pressure. The resulting residue was taken up in ethyl acetate; washed with 1N HCl, water, and brine; dried over Na$_2$SO$_4$; and concentrated to an oil that was purified by chromatography on silica gel eluting with 1/3 ethyl acetate/hexane to give a colorless oil. Anal. calcd. for C$_{20}$H$_{17}$N$_2$O$_3$Cl: C, 65.13;H, 4.65; N, 7.60. Found: C, 65.16; H, 4.63; N, 6.95; α=−63.20° c=11.0 mg/ml in methylene chloride; $^1$H NMR (400 MHz, CDCl$_3$) d 2.47 (t, J=5.9 Hz, 1H), 3.96 (m, 2H), 5.33 (m, 1H), 7.23 (m, 9H), 8.23 (m, 1H), 8.58 (m, 2H).

The compound of Example 133 was prepared according to the procedure of Example 132 substituting the corresponding amine for (S)-2-phenylglycinol. The duration of reaction was between 30 minutes and 3 hours.

EXAMPLE 133

2-(3-Chloro-phenoxy)-N-(2-hydroxy-2-phenyl-ethyl)-nicotinamide

M.P. 118–119° C.; Anal. calcd. for C$_{20}$H$_{17}$N$_2$O$_3$Cl: C, 65.13; H, 4.65; N, 7.59. Found: C, 65.37; H, 4.46; N, 7.35.

EXAMPLE 134

(S)-2-(3-Chloro-phenoxy)-3-(4-phenyl4,5-dihydro-oxazol-2-y)-pyridine

A solution of (S)-2-(3-Chloro-phenoxy)-N-(2-hydroxy-1-phenyl-ethyl)-nicotinamide (0.340 grams, 0.922 mmole) and phosprorus oxychloride (0.7 ml) in toluene (10 ml) was stirred over night. The mixture was concentrated to dryness and dissolved in methanol (10 ml) and potassium carbonate was added. The mixture was stirred for 2 hours at room temperature and refluxed for 30 minutes. The methanol was evaporated, and the residue taken up in ethyl acetate. It was washed with water and brine, dried over Na$_2$SO$_4$, and concentrated to give a product that was purified by chromatography on silica gel eluting with 1/3 ethyl acetate/hexane to give a pale yellow oil (0.013 g); HRMS 351.0917; M.P. 78–80° C.; Anal. calcd. for C$_{20}$H$_{15}$N$_2$O$_2$Cl: C, 57.37;H, 3.74; N, 7.42. Found: C, 57.31; H, 3.80; N, 7.39.

EXAMPLE 135

2-(3-Chloro-phenoxy)-3-(5-phenyl 4,5-dihydro-oxazol-2-yl)-pyridine

A solution of 2-(3-Chloro-phenoxy)-N-(2-hydroxy-2-phenyl-ethyl)-nicotinamide (0.320 grams, 0.868 mmole) and phosprorus oxychloride (0.7 ml) in toluene (10 ml) was stirred over night. The mixture was concentrated to dryness and dissolved in methanol (10 ml) and potassium carbonate was added. The mixture was stirred for 2 hours at room temperature and refluxed for 30 minutes. The methanol was evaporated, and the residue taken up in ethyl acetate. It was washed with water and brine, dried over Na$_2$SO$_4$, and concentrated to give a product that was purified by chromatography on silica gel eluting with 1/3 ethyl acetate/hexane to give a pale yellow oil (0.102 g). HRMS 351.0897; $^1$H NMR (400 MHz, CDCl$_3$) d 4.06 (dd, J=8.1, 15.0 Hz, 1H), 4.56 (dd, J=10.3, 15.0 Hz, 1H), 5.66 (dd, J=8.0, 10.3 Hz, 1H), 7.24 (m, 10H), 8.8.27 (m, 2H).

EXAMPLE 136

2-(2-Chloro-phenyl)-N-[2-(4-fluoro-phenoxy)-pyridin-3-yl]-acetamide

To a stirred solution 2-Chloro-benzoic acid (0.228g, 1.34 mmole), 2-(4-Fluoro-phenoxy)-pyridin-3-ylamine (0.300 grams, 1.47 mmole), and 1-hydroxybenzotriazole hydrate (0.217 grams, 1.61 mmole) in dry dimethylformamide (10 ml) was added 1-(3-dimethylamino)-propyl)-3-ethylcarbodiimide hydrochloride (0.335 grams, 1.74 mmole) and stirred over night. The mixture was diluted with 50 ml water and extracted with ethyl acetate. The combined organics were washed with 1N NaOH, water and brine, dried over Na$_2$SO$_4$, filtered and concentrated to give an oil that was purified by chromatography on silica. Recrystalization from ethyl acetate/hexane gave a solid. (0.230 g). M.P. 73–75° C.; Anal. calcd. for C$_{19}$H$_{14}$N$_2$O$_2$ClF: C, 63.96, H, 3.95; N, 7.85. Found: C, 63.64; H, 3.85; N, 8.41.

The compound of Example 137 was prepared according to the procedure of Example 136 substituting the corresponding carboxylic acid for 2-Chloro-benzoic acid. The duration of reaction was between 1 and 24 hours.

EXAMPLE 137

2-(4-Acetyl-phenyl)-N-[2-(4-fluoro-phenoxy)-pyridin-3-yl]-acetamide

M.P. 118–120° C.; Anal. calcd. for $C_{21}H_{17}N_2O_3F$: C, 69.22; H, 4.70; N, 7.69. Found: C, 68.90; H, 5.75; N, 8.54.

EXAMPLE 138

N-(2-Chloro-benzyl)-2-(3-[3-(2-methoxy-phenyl)-ureido]-phenoxy}-nicotinamide

A solution of 2-(3-Amino-phenoxy)-N-(2-chloro-benzyl)-nicotinamide (0.100 grams, 0.28 mmole) and 1-Isocyanato-2-methoxy-benzene (0.063 grams, 0.42 mmole) in dioxane (10 ml) was refluxed over night. The mixture was cooled to room temperature and concentrated to an oil which was purified by chromatography on silica gel eluting with 2% methanol/methylene chloride to give a solid. Recrystalization from ethyl acetate/hexane gave a solid (0.083 g). M.P. 180–182° C.; Anal. calcd. for $C_{27}H_{23}N_4O_4Cl$: C, 64.48; H, 4.61; N, 11.14. Found: C, 64.55; H, 4.60; N, 10.74.

The compound of Example 139 was prepared according to the procedure of Example 138 substituting the corresponding isocyanate for 1-Isocyanato-2-methoxy-benzene. The duration of reaction was between 1 and 24 hours.

EXAMPLE 139

N-(2-Chloro-benzyl)-2-[3-(3-naphthalen-1-yl-ureido)-phenoxy]-nicotinamide

M.P.121–123° C.; Anal. calcd. for $C_{30}H_{23}N_4O_3Cl$: C, 68.90; H, 4.43, N, 10.71. Found: C, 69.24; H, 4.52; N, 10.28.

EXAMPLE 140

(−)-N-[1-(5-Chloro-thiophen-2-yl-ethyl]-2-(4-fluoro-phenoxy)-nicotinamide

N-[1-(5-Chloro-thiophen-2-yl)-ethyl]-2-(4-fluoro-phenoxy)-nicotinamide (0.750 g) was separated on a Chiral Cel AS Column eluting with 95% hexane/isopropanol.

M.P. 78–80° C.; Anal. calcd. for $C_{18}H_{14}N_2O_2ClSF$: C, 57.37; H, 3.74; N, 7.42. Found: C, 57.32; H, 3.68; N, 7.42. $\alpha_D$=−53.9° (C=0.2, chloroform).

The compound of Example 141 was prepared according to the procedure of Example 140.

EXAMPLE 141

(+)-N-[1-(5-Chloro-thiophen-2-yl)-ethyl]-2-(4-fluoro-phenoxy)-nicotinamide

M.P. 78–80° C.; Anal. calcd. for $C_{18}H_{14}N_2O_2ClSF$: C, 57.37; H, 3.74; N, 7.42. Found: C, 57.31; H, 3.80; N, 7.39. $\alpha_D$=+52.8° (C=0.3, chloroform).

EXAMPLE 142 cis-2-(3-Chloro-phenoxy)-3-(4-phenyl-[1,31dioxolan-2-yl)-pyridine

A solution of 2-(3-Chloro-phenoxy)-pyridine-3-carbaldehyde (0.182 grams, 0.8 mmole), (S)-1-Phenyl-ethane-1,2-diol (0.110 grams, 0.8 mmole) and pTSA (0.005 g) in toluene (10 ml) was refluxed for 48 hours. The mixture was concentrated and purified by chromatography on silica gel eluting with 4/1 hexane/diethyl ether to give a colorless oil. Anal. calcd. for $C_{20}H_{16}NO_3Cl$: C, 67.90; H, 4.56; N, 3.96. Found: C, 68.57; H, 5.16; N, 3.52; $\alpha$=+49.5°; $^1$H NMR (400 MHz, CDCl$_3$) d 3.97 (dd, J=7.0, 7.8 Hz, 1H), 4.41 (dd, J=7.1, 7.7 Hz, 1H), 5.24 (t, J=7.0 Hz, 1H), 6.36 (s, 1H), 7.25 (m, 10H), 8.09 (m, 1H), 8.19 (m, 1H).

The compound of Example 143 was prepared according to the procedure of Example 142 substituting the corresponding diol for (S)-1-Phenyl-ethane-1,2-diol. The duration of reaction was between 1 and 48 hours.

EXAMPLE 143 trans-2-(3-Chloro-phenoxy)-3-(4-phenyl-[1,3]dioxolan-2-yl)-pyridine

Anal. calcd. for $C_{20}H_{16}NO_3Cl$: HRMS 354.0894; $\alpha$=+40.5°; $^1$H NMR (400 MHz, CDCl$_3$) d 3.91 (t, J=8.1 Hz, 1H), 4.57 (dd, J=6.2, 8.3 Hz, 1H), 5.27 (t, J=7.0 Hz, 1H), 6.52 (s, 1H), 7.25 (m, 10H), 8.05 (m, 1H) 8.17 (m, 1H).

EXAMPLE 144

2-(3-Amino-phenoxy)-N-(2-chloro-benzyl)-nicotinamide

To a solution of 2-(3-Nitro-phenoxy)-N-(2-chloro-benzyl)-nicotinamide (0.530 g 1.38 mmole) in methanol (15 ml) and tetrahydrofuran (20 ml) was added 10% PtO$_2$ (0.0.50 g). This was shaken under 35 psi hydrogen for 1 hour 40 minutes. The catalyst was removed by filtration, and the solution was concentrated to give an oil that was purified by chromatography on silica gel eluting with 2.5% methanol/methylene chloride. Recrystalization from ethyl acetate/hexane gave crystals. (0.327 g). M.P. 101–103° C.; Anal. calcd. for $C_{19}H_{16}N_3O_2Cl$: C, 64.5; H, 4.56; N, 11.88. Found: C, 64.15; H,4.07; N, 11.80.

EXAMPLE 145

(−)-N-[1-(5-Chloro-thiophen-2-yl)-ethyl]-2-(pyridin-3-yloxy)-nicotinamide

N-[1-(5-Chloro-thiophen-2-yl)-ethyl]-2-(pyridin-3-yloxy)-nicotinamide (0.776 g) was separated on a Chiral Cel AD Column eluting with 9/1 heptane/isoPropanol to give the product as an oil. Recrystalization from ethyl acetate/hexane gave a white solid (0.217 g). M.P. 82–84° C.; $\alpha$=−51.50 (c=0.2, CHCl$_3$).

The compound of Example 146 was prepared according to the procedure of Example 145.

EXAMPLE 146

(+)-N-[1-(5-Chloro-thiophen-2-yl)-ethyl]-2-(pyridin-3-yloxy)-nicotinamide

M.P. 83–85° C.; $\alpha$=+49.80° (c=0.3, CHCl$_3$).

EXAMPLE 147

(−)-2-(5-Chloro-pyridin-3-yloxy)-N-[1-(5-chloro-thiophen-2-yl)-ethyl]-nicotinamide 2-(5-Chloro-pyridin-3-yloxy)-N-[1-(5-chloro-thiophen-2-yl)-ethyl]-nicotinamide (0.800 g) was separated on a Chiral Cel AS Column eluting with 90/9.9/0.1 heptane/ isopropanol/diethyl ether to give a solid. Recrystalization from ethyl acetate/hexane gave a solid (0.393 g). M.P. 133–135° C.; α=−48.80° (c=0.2).

The compound of Example 148 was prepared according to the procedure of Example 147.

EXAMPLE 148

(+)-2-(5-Chloro-pyridin-3-yloxy)-N-[1-(5-chloro-thiophen-2-yl)-ethyl]-nicotinamide M.P. 133–135° C.; α=+40.61° (c=0.2).

EXAMPLE 149

(R)-N-(2-Hydroxy-1-phenyl-ethyl)-2-(pyridin-3-yloxy)-nicotinamide

A solution of 2-(Pyridin-3-yloxy)-nicotinic acid (0.250 grams, 1.2 mmole) in thionyl chloride (10 ml) was heated to reflux. After 1 hour the reaction mixture was cooled to room temperature and concentrated under reduced pressure. The resulting residue was suspended in tetrahydrofuran (10 ml) and added dropwise to a solution of (R)-2-hydroxy-1-phenyl ethylamine (0.160 grams, 1.2 mmole) in pyridine (5 ml) at 0° C. After 30 minutes the mixture was warmed to room temperature, stirred at room temperature for 1 hour and concentrated to remove pyridine. The crude product was purified by chromatography on silica gel eluting with ethyl acetate to give a yellow oil. HRMS 336.1324; α=+63.9° 12.3 mg/ml in methylene chloride. $^1$H NMR (400 mhz, CDCl$_3$) d 2.76 (bs, 1H), 3.95–4.02 (m, 2H), 5.31–5.36 (m, 1H), 7.16–7.40 (m, 1H), 8.19 (dd, J=2.1 Hz, 4.8 Hz, 1H), 8.48–8.61 (m, 4H).

EXAMPLE 150

(R)-3-(4-Phenyl-4,5-dihydro-oxazol-2-yl)-2-(Pyridin-3-yloxy)-pyridine

A solution of (R)-N-(2-Hydroxy-2-phenyl-ethyl)-2-(pyridin-3-yloxy)-nicotinamide (0.050 grams, 0.16 mmole) and phosphorus oxychloride (150 μl, 1.6 mmole) in toluene (10 ml) was stirred over night. The mixture was concentrated to dryness and dissolved in methanol (10 ml) and potassium carbonate (250 ml) was added. The mixture was stirred for 24 hours at room temperature. The methanol was evaporated, and the residue taken up in ethyl acetate. It was washed with water and brine, dried over Na$_2$SO$_4$, and concentrated to give a product that was purified by chromatography on silica gel eluting with 1/1 ethyl acetate/hexane to give a colorless oil (0.020 g). HRMS 318.1227; α=+21.20° 9.5 mg/ml in methylene chloride. $^1$H NMR (400 mhz, CDCl$_3$) d 4.31 (t, J=8.3 Hz, 1H), 4.83 (dd, J=8.3 Hz, 10.2 Hz, 1H), 5.46 (dd, J=8.1 Hz, 10.2 Hz, 1H), 7.07–7.20 (m, 1H), 7.27–7.43 (m, 6H), 7.53–7.57 (m, 1H), 8.22–8.53 (m, 4H).

The compound of Example 151 was prepared according to the procedure of Example 150 substituting the corresponding hydroxy nicatinimide for (R)-N-(2-Hydroxy-2-phenyl-ethyl)-2-(pyridin-3-yloxy)-nicotinamide. The duration of reaction was between 1 and 24 hours.

EXAMPLE 151

(S)-3-(4-Phenyl-4,5-dihydro-oxazol-2-yl)-2-(Pyridin-3-yloxy)-pyridine

HRMS 318.1267; α=−19.2°, 11.2 mg/ml in methylene chloride; $^1$H NMR (400 mhz, CDCl$_3$) d 4.31 (t, J=8.3 Hz, 1H), 4.83 (dd, J=10.2 Hz, 8.3 Hz, 1H), 5.46 (dd, J=10.2 Hz, 8.1 Hz, 1H), 7.09–7.57 (m, 7H), 7.54–7.57 (m, 1H), 8.23 (dd, J=4.8 Hz, 1.9 Hz, 8.32–8.53 (m, 3H).

EXAMPLE 152

(S)- N-(2-Hydroxy-1-phenyl-ethyl)-2-(pyridin-3-yloxy)-nicotinamide

A solution 2-(Pyridin-3-yloxy)-nicotinic acid (0.500 g)in thionyl chloride (10 ml) was refluxed for 1 hour. The mixture was concentrated to dryness, dissolved in 10 ml tetrahydrofuran and used immediately. To a solution of (S)-2-phenylglycinol (0.190 grams, 1.4 mmole) in dry pyridine (5 ml) at 0° C. was added a solution of 2-(3-pyridin-3-yloxy)-nicotinoyl chloride (0.325 grams, 1.4 mmole) in tetrahydrofuran (5 ml) and pyridine (5 ml), stirred at 0° C. for 30 minutes and allowed to warm to room temperature over night The mixture was concentrated under reduced pressure and concentrated to a crude product that was purified by chromatography on silica gel eluting with 1:1 ethyl acetate/hexane to give a colorless oil. HRMS 336.1358; α=−69.2° c=6.2 mg/ml in methylene chloride; $^1$H NMR (400 mhz, CDCl$_3$) d 2.77 (bs, 1H), 3.98–4.08 (m, 2H), 5.31–5.36 (m, 1H), 7.14–7.40 (m, 7H), 7.57–7.60 (m, 1H), 8.19 (dd, J=1.9 Hz, 4.8 Hz, 1H), 8.44–8.61 (m, 4H).

The compounds of Examples 153–156 were prepared according to the procedure of Example 152 substituting the corresponding amine for (S)-2-phenylglycinol. The duration of reaction was between 1 and 24 hours.

EXAMPLE 153

(R)-N-(1-Hydroxymethyl-2-methyl-propyl)-2-(pyridin-3-yloxy)-nicotinamide

HRMS 302.15050; α=+6.1° 8.7 mg/ml in methylene chloride. $^1$H NMR (400 mhz, CDCl$_3$) d 1.00 (dd, J=14.9 Hz, 6.8 Hz, 6H), 1.98–2.07 (m, 1H), 2.99 (bs, 1H), 3.73–3.83 (m, 2H), 4.01–4.11 (m, 1H), 7.18–7.24 (m, 1H), 7.38.7.42 (m, 1H), 7.55–7.58 (m, 1H), 7.98 (d, J=6.6 Hz, 1H), 8.18 (dd, J=4.8 Hz, 2.1 Hz, 1H), 8.52–8.62 (m, 3H).

EXAMPLE 154

(S)-N-(1-Hydroxymethyl-2-methyl-propyl)-2-(pyridin-3-yloxy)-nicotinamide

HRMS 302.1475; α=−6.3°, 10.4 mg/ml in methylene chloride. $^1$H NMR (400 mhz, CDCl$_3$) d 1.00 (dd, J=14.9 Hz, 6.8 Hz, 6H), 2.00–2.07 (m, 1H), 3.09 (bs, 1H), 3.785–3.78 (m, 2H), 4.01–4.07 (m, 1H), 7.18–7.25 (m, 1H), 7.38.7.41 (m, 1H), 7.54–7.57 (m, 1H), 7.98 (d, J=6.8 Hz, 1H), 8.17–8.19 (m, 1H), 8.48–8.53 (m, 2H), 8.59–8.61 (m, 1H).

EXAMPLE 155

(S)-N-(1-Hydroxymethyl-2-methyl-butyl)-2-(pyridin-3-yloxy)-nicotinamide

HRMS 316.1661; α=−10.8°, 10.0 mg/ml in methylene chloride. $^1$H NMR (400 mhz, CDCl$_3$) d 0.91 (t, J=7.3 Hz, 3H), 0.99 (d, J=8.8 Hz, 3H), 1.15–1.27 (m, 1H), 1.53–1.60 (m, 1H), 1.74–1.84 (m, 1H), 2.78 (bs, 1H), 3.74–3.87 (m, 2H), 4.08–4.14 (m, 1H), 7.19–7.24 (m, 2H), 7.41 (dd, J=8.1 Hz, 4.57 Hz, 1H), 7.55–7.58 (m, 1H),8.00 (d, J=7.3 Hz, 1H), 8.19 (d, J=4.8 Hz, 1.9 Hz, 1H), 8.53 (s, 1H), 8.60–8.63 (m, 1H).

EXAMPLE 156

N-(2-Hydroxy-1,1-dimethyl-ethyl)-2-(pyridin-3-yloxy)-nicotinamide

HRMS 288.1376; $^1$H NMR (400 mhz, CDCl$_3$) d 1.41 (s, 6H), 3.70 (d, J=5.6 Hz, 2H), 4.54 (bs, 1H), 7.19 (dd, J=6.6

Hz, 4.8 Hz, 1H), 7.39–7.42 (m, 1H), 7.55–7.58 (m, 1H), 7.94 (bs, 1H), 8.18 (dd, J=4.8 Hz, 2.1 Hz, 1H), 8.53–8.59 (m, 3H).

EXAMPLE 157

N-(2-Chloro-benzyl)-2-(1H-indol-4yloxy)-nicotinamide

To a stirred solution 2-(1H-indol-4-yloxy)-nicotinic acid (0.0559, 0.216 mmole) 2-chlorobenzylamine (0.034 grams, 0.238 mmole), and 1-hydroxybenzotriazole hydrate (0.035 grams, 0.259 mmole) in dry dimethylformamide (5 ml) was added 1-(3-dimethylamino)-propyl)-3-ethylcarbodiimide hydrochloride (0.054 grams, 0.281 mmole) and stirred over night. The mixture was diluted with 100 ml water and extracted with ethyl acetate. The combined organics were washed with 1N NaOH, water and brine, dried over $Na_2SO_4$, filtered and concentrated to give an oil that was purified by chromatography on silica. Recrystalization from ethyl acetate/hexane gave a pink/white solid. (0.053 g). M.P. 185–187° C.; Anal. calcd. for $C_{12}H_{16}N_3O_2Cl$: C, 66.76; H, 4.27; N, 11.12. Found: C, 66.42; H, 4.14; N, 10.95.

The compound of Example 158 was prepared according to the procedure of Example 157 substituting the corresponding amine for 2-chlorobenzylamine. The duration of reaction was between 1 and 24 hours.

EXAMPLE 158

N-(5-Chloro-thiophen-2-ylmethyl)-2-(1H-indol-4-yloxy)-nicotinamide

M.P. 157–159° C.; Anal. calcd. for $C_{19}H_{14}N_3O_2ClS$: C, 59.45, H, 3.68; N, 10.9. Found : C, 59.38; H, 3.94; N, 10.95.

EXAMPLE 159

N-(5-Acetyl-thiophen-2-ylmethyl)-2-(pyridin-3-yloxy)-nicotinamide

A solution of N-[5-(2-Methyl-[1,3]dioxolan-2-yl)-thiophen-2-ylmethyl]-2-(pyridin-3-yloxy)-nicotinamide (0.680 g) in 2 N hydrochloric acid (20 ml) and methylene chloride (20 ml) was stirred at room temperature over night. The mixture was extracted with chloroform, washed with water, dried over $MgSO_4$, filtered and concentrated to give a solid which was triturated in diethyl ether to give a white solid. (0.480 g). M.P. 201–203° C.; Anal. calcd. for $C_{18}H_{15}N_3O_3S$: C, 61.18; H, 4.28; N, 11.89. Found: C, 60.09; H, 4.25; N, 11.61.

EXAMPLE 160

N-[5-(1-Hydroxy-ethyl)-thiophen-2-ylmethyl]-2-(pyridin-3yloxy)-nicotinamide

To a stirred suspension of N-(5-Acetyl-thiophen-2-ylmethyl)-2-(pyridin-3-yloxy)-nicotinamide (0.300 grams, 0.85 mmole) in methylene chloride (25 ml) and tetrahydrofuran (25 ml) at room temperature was added sodium borohydride (0.035 grams, 0.93 mmole) and stirred for 2 hours. The mixture was quenched with saturated $NH_4Cl$ (~1 ml) and concentrated under reduced pressure to about 15 ml. This mixture was poured into water and extracted with ethyl acetate. The combined organics were washed with water and brine, dried over $MgSO_4$, filtered and concentrated to give an oil that was purified by chromatography on silica eluting with 5% methanol/methylene chloride. Recrystalization from ethyl acetate/hexane gave a white solid. (0.207 g). M.P. 92–94° C.; Anal. calcd. for $C_{18}H_{17}N_3O_3S$: C, 60.83;H, 4.82; N, 11.82. Found: C, 60.68; H, 4.77; N, 11.89.

EXAMPLE 161

3-(5-Phenyl-4,5-dihydro-oxazol-2-yl)-2-(Pyridin-3-yloxy)-pyridine

A solution of N-(2-Hydroxy-2-phenyl-ethyl)-2-(pyridin-3-yloxy)-nicotinamide (0.450 grams, 1.3 mmole) and phosphorus oxychloride (1.25 ml, 13 mmole) in toluene (5 ml) was stirred over night. The mixture was concentrated to dryness and dissolved in methanol (5 ml) and potassium carbonate (0.500 g) was added. The mixture was stirred at room temperature over night. The mixture was poured into water and extracted with ethyl acetate. The combined organics were washed with water and brine, dried over $Na_2SO_4$, and concentrated to give an oil that was purified by chromatography on silica gel eluting with ethyl acetate to give a colorless oil (0.042 g). HRMS 318.1269; $^1H$ NMR (400 mHz, $CDCl_3$) d 4.09 (dd, J=15.1 Hz, 8.1 Hz, 6H), 4.57 (dd, J=15.1 Hz, 10.3 Hz, 1H), 5.67 (dd, J=10.2 Hz, 7.9 Hz, 1H), 7.09–7.13 (m, 1H), 7.32–7.39 (m, 6H), 7.54–7.57 (m, 1H), 8.20–8.22 (m, 1H), 8.29–8.31 (m, 1H), 8.46 (dd, J=4.6 Hz, 1.0 Hz, 1H), 8.61–8.64 (m, 1H).

EXAMPLE 162

(S) 3-(4-Isopropyl-4,5-dihydro-oxazol-2-yl)-2-(Pyridin-3-yloxy)-pyridine

A solution of N-(1-Hydroxy-2-methyl-propyl)-2-(pyridin-3-yloxy)-nicotinamide (0.090 grams, 0.299 mmole) and phosphorus oxychloride (1.0 ml,) in toluene (5 ml) was stirred over night. The mixture was concentrated to dryness and dissolved in methanol (5 ml) and potassium carbonate (0.250 g) was added. The mixture was stirred at room temperature over night. The mixture was poured into water and extracted with ethyl acetate. The combined organics were washed with brine and concentrated to give a product that was purified by chromatography on silica gel eluting with ethyl acetate to give a colorless oil (0.053 g). MS m/z [M+] 284; α=+47.1°, 5.5 mg/ml in methylene chloride $^1H$ NMR (400 mhz, $CDCl_3$) d 0.98 (dd, J=32.8 Hz, 6.6 Hz, 6H), 1.78–1.89 (m, 1H), 4.12–4.19 (m, 2H), 4.39–4.46 (m, 1H), 7.07–7.10 (m, 1H), 7.31–7.34 (m, 1H), 7.51–7.54 (m, 1H), 8.18–8.22 (m, 2H), 8.44–8.50 (m, 2H).

The compound of Example 163 was prepared according to the procedure of Example 162 substituting the corresponding hydroxy nicatinamide for N-(1-Hydroxy-2-methyl-propyl)-2-(pyridin-3-yloxy)-nicotinamide. The duration of reaction was between 1 and 24 hours.

EXAMPLE 163

(R) 3-(4-Isopropyl-4,5-dihydro-oxazol-2-yl)-2-(Pyridin-3-yloxy)-pyridine

HRMS 284.13915; α=–52.7°, 10.0 mg/ml in methylene chloride. $^1H$ NMR (400 mhz, $CDCl_3$) d 0.98 (dd, J=32.8 Hz, 6.6 Hz, 6H), 1.86–1.92 (m, 1H), 4.12–4.19 (m, 2H), 4.39–4.45 (m, 1H), 7.08 (dd, J=7.5 Hz, 4.8 Hz, 1H), 7.31–7.34 (m, 1H), 7.51–7.5 (m, 1H), 8.18–8.22(m, 2H), 8.44 (dd, J=4.6 Hz, 1.2 Hz, 1H), 8.50 (d, J=2.7 Hz, 1H).

EXAMPLE 164

(R)-3-(4-see-Butyl-4,5-dihydro-oxazol-2-yl)-2-(Pyridin-3-yloxy)-pyridine

A solution of N-(1-Hydroxymethyl-2-methyl-butyl)-2-(pyridin-3-yloxy)-nicotinamide (0.120 grams, 0.400 mmole)

and phosphorus oxychloride (400 μl, 4.0 mmole) in toluene (5 ml) was stirred over night. The mixture was concentrated to dryness and dissolved in methanol (5 ml) and potassium carbonate (0.250 g) was added. The mixture was concentrated to give a crude product that was purified by chromatography on silica gel eluting with ethyl acetate to give a colorless oil (0.060 g); Anal. calcd. for $C_{17}H_{19}N_3O_2$: C, 68.67; H,6.44; N, 14.13. Found: C, 68.28; H, 6.82; N, 13.33; HRMS 298.1530; α=–42.9°, 11.2 mg/ml in methylene chloride, $^1$H NMR (400 mHz, $CDCl_3$) d 0.95 (t, J=7.3 Hz, 3H), 1.19–1.30 (m, 1H), 1.54–1.62 (m, 1H), 1.71–1.77 (m, 1H), 4.14–4.18 (m, 1H), 4.25–4.31 (m, 1H), 4.40 (dd, J=9.8 Hz, 7.1 Hz, 1H), 7.08 (dd, J=7.5 Hz, 5.0 Hz, 1H), 7.31–7.35 (m, 1H), 7.51–7.54 (m, 1H), 8.18–8.22 (m, 2H), 8.44–8.50 (m, 2H).

EXAMPLE 165

5-({[2-(4-Fluoro-phenoxy)-pyridine-3-carbonyl]-amino}-methyl)-1H-indole-2-carboxylic acid A solution of 5-({[2-(4-Fluoro-phenoxy)-pyridine-3-carbonyl]-amino}-methyl)-1H-indole-2-carboxylic acid ethyl ester (0.043 grams, 0.099 mmole) in 1N sodium hydroxide (0.25 ml, 0.25 mmole) and ethanol (5 ml) was refluxed for 9 hours. The mixture was concentrated under reduced pressure to dryness and dissolved in water (2 ml). The mixture was acidified with 2 N hydrochloric acid giving a white solid which was isolated by filtration (0.032 g). M.P. 236–238; Anal. Calcd. for $C_{22}H_{16}N_3O_4F$: C, 65.18; H, 3.98; N, 10.37. Found: C, 65.12; H, 4.08; N, 10.20.

EXAMPLE 166

(R)-3-(4-Phenyl-[1,3]dioxolan-2-yl)-2-(Pyridin-3-yloxy)-pyridine

A solution of 2-(Pyridin-3-yloxy)-pyridine-3-carbaldehyde (0.150 grams, 0.75 mmole), (R)-1-Phenyl-ethane-1,2-diol (0.105 grams, 0.75 mmole) and pTSA (0.005 g) in toluene (10 ml) was refluxed over night. The mixture was concentrated under reduced pressure and dissolved in ethyl acetate. The organics were washed with sat'd bicarb and brine, dried over $Na_2SO_4$ and purified by chromatography on silica gel eluting with diethyl ether to give a yellow oil. (mixture of cis and trans) HRMS 321.1260; α=–46.3° 9.2 mg/ml in methylene chloride; $^1$H NMR (400 mhz, $CDCl_3$) d 3.93–4.00 (m, 1H), 4.42 (dd, J=7.9 Hz, 7.0 Hz,, 1/2H), 4.56–4.60 (m, 1/2H), 5.25–5.30 (m, 1H), 6.39 (s, 12H), 6.56 (s, 1/2H), 7.10–7.12 (m, 1H), 7.30–7.40 (m, 6H), 7.49–7.55 (m, 1H), 8.02–8.16 (m, 2H), 8.43–8.52 (m, 2H).

The compounds of Examples 167–169 were prepared according to the procedure of Example 166 substituting the corresponding diol for (R)-1-Phenyl-ethane-1,2-diol. The duration of reaction was between 1 and 24 hours.

EXAMPLE 167

(S)-3-(4-Phenyl-[1,3]dioxolan-2-yl)-2-(Pyridin-3-yloxy)-pyridine

Anal. calcd. for $C_{19}H_{16}N_2O_3$: C, 71.24; H, 5.03; N, 8.74. Found: C, 71.02; H, 5.32; N, 8.03; α=–48.8° 12.8 mg/ml in methylene chloride; $^1$H NMR (400 mhz, $CDCl_3$) d 3.90–4.00 (m, 1H), 4.42 (dd, J=7.9 Hz, 7.1 Hz, 1/2H), 4.56–4.58 (m, 1/2H), 5.20–5.28 (m, 1H), 6.40 (s, 1/2H), 6.57 (s, 1/2H), 7.08–7.12 (m, 1H), 7.32–7.41 (m, 6H), 7.53–7.55 (m, 1H), 8.10–8.15 (m, 2H). 8.44–8.54 (m, 2H).

EXAMPLE 168

(S)-3-[4-(2-Chloro-phenyl)-[1,3]dioxolan-2-yl]-2-(Pyridin-3-yloxy)-pyridine

Anal. calcd. for $C_{19}H_{15}N_2O_3Cl$; HRMS 355.0864; α=+55.5° 12.1 mg/ml in methylene chloride; $^1$H H NMR (400 mhz, $CDCl_3$) d 3.80–3.96 (m, 1H), 4.56–4.60 (m, 1/2H), 4.78–4.82 (m, 1/2H), 5.58–5.62 (m, 1H), 6.39 (s, 1/2H), 6.53 (s, 1/2H), 7.11–7.15 (m, 1H), 7.20–7.38 (m, 5H), 7.53–7.60 (m, 1H), 8.06–8.18 (m, 2H). 8.44–8.54 (m, 2H).

EXAMPLE 169

(R)-3-[4-(2-Chloro-phenyl)-[1,3]dioxolan-2-yl]-2-(Pyridin-3-yloxy)-pyridine

Mixture of cis and trans isomers; Anal. calcd. for $C_{19}H_{15}N_2O_3Cl$; C, 64.32; H, 4.26; N, 7.90. Found. C, 64.31; H, 4.42; N, 7.72; α=–61.1° 10.2 mg/ml in methylene chloride; $^1$H H NMR (400 mhz, $CDCl_3$) d 3,82 (dd, J=8.2 Hz, 7.3 Hz,, 1/2H), 3.95 (dd, J=7.2 Hz, 6.2 Hz,, 1/2H), 4.58 (dd, J=8.0 Hz, 7.3 Hz, 1/2H), 4.80 (dd, J=8.5 Hz, 6.4 Hz, 1/2H), 5.58–5.62 (m, 1H), 6.39 (s, 1/2H), 6.53 (s, 1/2H), 7.10–7.15 (m, 1H), 7.24–7.38 (m, 4H), 7.55–7.68 (m, 2H), 8.06–8.18 (m, 2H), 8.45–8.55 (m, 2H).

EXAMPLE 170

2-[2-(Pyridin-3-yloxy)-pyridin-3-yl]-3-oxa-1-aza-spiro[4,4]non-1-ene

A solution of N-(1-Hydroxymethyl-cyclopentyl)-2-(pyridin-3-yloxy)-nicotinamide (0.045 grams, 0.144 mmole) and phosphorus oxychloride in toluene (5 ml) was stirred over night. The mixture was concentrated to dryness and dissolved in methanol (5 ml) and potassium carbonate was added. The mixture was concentrated to give a crude product that was purified by chromatography on silica gel eluting with ethyl acetate to give a yellow oil (0.021 g). HRMS 296.1417; $^1$H NMR (400 mhz, $CDCl_3$) d 1.65–1.74 (m, 4H), 1.86–1.91 (m, 2H), 1.96–2.03 (m, 2H), 4.25 (s, 2H), 7.08 (dd, J=7.5 Hz, 5.0 Hz, 1H), 7.32 (dd, J=8.3 Hz, 4.8 Hz, 1H), 7.51–7.54 (m, 1H), 8.15–8.22 (m, 2H), 8.43–8.50 (m, 2H).

EXAMPLE 171

N-Propyl-2-(pyridin-3-yloxy)-nicotinamide

To a solution of 2-(pyridin-3-yloxy)-nicotinic acid (0.100 g 0.462 mmole), BOP (0.205 grams, 0.463 mmole) and DIEA (0.242 μl) in dimethylformamide (5 ml) was added n-propyl amine (40 μl, 0.486 mmole) and stirred for 4 hours at room temperature. The reaction was quenched with 10 μl water and extracted with ethyl acetate. The combined organics were washed with alternating portions of 5% citric acid and sat'd bicarb, dried over $Na_2SO_4$, filtered and concentrated to a product which was purified by chromatography on silica gel eluting with diethyl ether to give a white crystalline solid (0.068 g). M.P. 55–56° C.; $^1$H H NMR (400 mhz, $CDCl_3$) d 0.98 (t, J=7.3 Hz, 3H), 1.61–1.70 (m, 2H), 3.45–3.50 (m, 2H), 7.19 (dd, J=7.5 Hz, 4.8 Hz, 1H), 7.38–7.41 (m, 1H), 7.52–7.55 (m, 1H), 7.72 (bs, 1H), 8.16 (dd, J=4.8 hz, 2.1 Hz, 1H), 8.52–8.63 (m, 3H).

The compounds of Examples 177–182 were prepared according to the procedure of Example 171 substituting the corresponding amine for n-propyl amine. The duration of reaction was between 1 and 24 hours.

EXAMPLE 172

N-Isopropyl-2-(pyridin-3-yloxy)-nicotinamide $^1$H NMR (400 mhz, $CDCl_3$) d 1.27 (d, J=6.4 Hz, 6H), 4.29–4.34 (m, 1H), 7.18 (dd, J=7.7 Hz, 4.8 Hz, 1H), 7.39–7.42 (m, 1H), 7.51 (bs, 1H), 7.53–7.57 (m, 1H), 8.16 (dd, J=4.8 Hz, 2.1 Hz, 1H), 8.53–8.62 (m, 3H).

EXAMPLE 173

N-Isobutyl-2-(pyridin-3-yloxy)-nicotinamide

Anal. calcd. for $C_{15}H_{17}N_3O_2$; $^1H$ NMR (400 mhz, CDCl$_3$) d 0.97 (d, J=6.6 Hz, 6H), 1.71–1.95 (m, 1H), 3.35 (dd, J=6.6 Hz, 5.8 Hz, 2H), 7.19 (dd, J=7.8 Hz, 4.8 Hz, 1H), 7.39–7.42 (m, 1H), 7.53–7.56 (m, 1H), 7.76 (bs, 1H), 8.16 (dd, J=4.8 Hz, 1.9 Hz, 1H), 8.52–8.63 (m, 3H).

EXAMPLE 174

N-Butyl-2-(pyridin-3-yloxy)-nicotinamide

M.P. 55–56° C.; Anal. calcd. for $C_{15}H_{17}N_3O_2$; $^1H$ NMR (400 mhz, CDCl$_3$) d 0.93 (t, J=7.5 Hz, 3H), 1.37–1.44 (m, 2H), 1.57–1.65 (m, 2H), 3.48–3.53 (m, 2H), 7.16–7.19 (m, 1H), 7.38–7.42 (m, 1H), 7.52–7.55 (m, 1H), 7.70 (bs, 1H), 8.15 (dd, J=4.8 Hz, 1.9 Hz, 1H), 8.51–8.63 (m, 3H).

EXAMPLE 175

N-Pentyl-2-(pyridin-3-yloxy)-nicotinamide

M.P. 61–62° C.; Anal. calcd. for $C_{16}H_{19}N_3O_2$; C, 67.32; H, 6.71; N, 14.72. Found: C, 67.52; H, 6.88; N, 14.23

EXAMPLE 176

(S)-N-sec-Butyl-2-(pyridin-3-yloxy)-nicotinamide

M.P. 64–65° C.; Anal. calcd. for $C_{15}H_{17}N_3O_2$; C, 66.40; H, 6.32; N, 15.49. Found: C, 66.66; H, 6.48; N, 14.89. α=+9.0° 10.9 mg/ml in methylene chloride.

EXAMPLE 177

(R)-N-sec-Butyl-2-(pyridin-3-yloxy)-nicotinamide

M.P. 55–56° C.; Anal. calcd. for $C_{15}H_{17}N_3O_2$; C, 66.40; H, 6.32; N, 15.49. Found: C, 67.14; H, 6.37; N, 14.70. α=−8.48° 12.5 mg/ml in methylene chloride.

EXAMPLE 178

2-(Pyridin-3-yloxy)-N-(4-sulfamoyl-benzyl)-nicotinamide

M.P. 196–197° C.; Anal. calcd. for $C_{18}H_{16}N_4O_4S$: C, 56.24; H, 4.20; N, 14:75. Found: C, 54.95; H, 4.30; N, 14.11.

EXAMPLE 179

2-(Pyridin-3-yloxy)-N-(1-sulfamoyl-piperidin-4-ylmethyl)-nicotinamide

M.P. 165–166° C.; HRMS 392.1382.

EXAMPLE 180

N-(1H-Indol-4-ylmethyl)-2-(pyridin-3yloxy)-nicotinamide

M.P. 134–135° C.; Anal. calcd. for $C_{20}H_{16}N_4O_2$: C, 69.76; H, 4.68; N, 16.27. Found: C, 69.45; H, 4.63; N, 16.15.

EXAMPLE 181

N-Pyridin-2-ylmethyl-2-(pyridin-3-yloxy)-nicotinamide

M.P. 118–119° C.; Anal. calcd. for $C_{17}H_{14}N_4O_2$: C, 66.66; H, 4.61; N, 18.29. Found: C, 66.24; H, 4.58; N, 18.21.

EXAMPLE 182

N-Benzo[1,3]dioxol-5-ylmethyl-2-(pyridin-3-yloxy)-nicotinamide

M.P. 130–131° C.; Anal. calcd. for $C_{19}H_{15}N_3O_4$: C, 65.32; H, 4.33; N, 12.03. Found: C, 64.62; H, 4.14; N, 11.87.

EXAMPLE 183

N-[4-(1-Hydroxy-1-methyl-ethyl)-benzyl]-2-(3-trifluoromethyl-phenoxy)-nicotinamide To a stirred solution 2-(3-Trifluoromethyl-phenoxy)-nicotinic acid (0.311 g, 1.1 mmole) 2-(4-Aminomethyl-phenyl)-propan-2-ol (0.200 grams, 1.21 mmole), and 1-hydroxybenzotriazole hydrate (0.178 grams, 1.32 mmole) in dry dimethylformamide (15 ml) was added 1-(3-dimethylamino)-propyl)-3-ethylcarbodiimide hydrochloride (0.275 grams, 1.43 mmole) and stirred over night The mixture was diluted with 250 ml water and extracted with ethyl acetate. The combined organics were washed with water and brine, dried over Na$_2$SO$_4$, filtered and concentrated to give an oil that was purified by chromatography on silica eluting with 4% methanol/methylene chloride to give a foam. (0.350 g). M.P. 37–39° C.; $^1H$ NMR (CDCl$_3$) d 1.56 (6H, s), 4.69 (2H, d, J=5.81 Hz), 7.2–7.6 (9H, m), 8.02 (1H, s), 8.20 (1H, m), 8.64 (1H, m).

The compound of Example 184 was prepared according to the procedure of Example 183 substituting the corresponding amine for) 2-(4-Aminomethyl-phenyl)-propan-2-ol. The duration of reaction was between 1 and 24 hours.

EXAMPLE 184

N-(2-Chloro-benzyl)-2-(3-trifluoromethyl-phenoxy)-nicotinamide

M.P. 88–90° C.; Anal. calcd. for $C_{20}H_{14}N_2O_2F_3Cl$; C, 59.05; H, 3.47; N, 6.89. Found: C, 58.89; H, 3.39; N, 6.94.

EXAMPLE 185

2-(2-Chloro-phenyl)-N-[2-(pyridin-3-yloxy)-pyridin-3-yl]-acetamide

To a stirred solution 2-chloro-benzoic acid (0.200 g, 1.17 mmole), 2-(Pyridin-3-yloxy)-pyridin-3-ylamine (0.239 grams, 1.28 mmole), and 1-hydroxybenzotriazole hydrate (0.190 grams, 1.40 mmole) in dry dimethylformamide (15 ml) was added 2-diethylaminoethyl chloride hydrochloride (0.292 g, 1.52 mmole) and stirred over the weekend. The mixture was diluted with 200 ml water and extracted with ethyl acetate. The combined organics were washed with 1N NaOH, water and brine, dried over Na$_2$SO$_4$, filtered and concentrated to give an oil that was purified by chromatography on silica. Recrystalization from ethyl acetate/hexane gave a solid. (0.093 g). M.P. 137–139° C.; Anal. calcd. for $C_{18}H_{14}N_3O_2Cl$: C, 63.63; H, 4.15; N, 12.37. Found: C, 63.30; H, 4.30; N, 12.34.

The compound of Example 186 was prepared according to the procedure of Example 187 substituting the corresponding carboxylic acid for 2-chloro-benzoic acid. The duration of reaction was between 1 and 24 hours.

EXAMPLE 186

2-(4-Acetyl-phenyl)-N-[2-(pyridin-3-yloxy)-pyridin-3-yl]-acetamide

M.P. 110–112° C.; $^1H$ NMR (CDCl$_3$) d 2.6 (3H, s), 3.90 (2H, s), 7.0–8.7 (12H, m).

EXAMPLE 187

2-(3-Chloro-phenoxy)-N-[4-(1-hydroxy-1-methyl-ethyl)-benzyl]-nicotinamide

To a stirred solution 2-(3-chloro-phenoxy)-nicotinic acid (0.301 g, 1.21 mmole) 2-(4-Aminomethyl-phenyl)-propan-2-ol (0.200 grams, 1.21 mmole), and 1-hydroxybenzotriazole hydrate (0.178 grams, 1.32 mmole) in dry dimethylformamide (15 ml) was added 1-(3-dimethylamino)-propyl)-3-ethylcarbodiimide hydrochloride (0.275 grams, 1.43 mmole) and stirred over night. The mixture was diluted with 200 ml water and extracted with ethyl acetate. The combined organics were washed with water, 1N sodium hydroxide and brine, dried over $MgSO_4$, filtered and concentrated to give an oil that was purified by chromatography on silica eluting with 6% methanol/methylene chloride to give a solid. (0.258 g). M.P. 57–59° C.; Anal. calcd. for $C_{22}H_{21}N_2O_3Cl$: C, 66.50; H, 5.33; N, 7.06. Found: C, 67.15; H, 5.95; N, 6.68.

The compound of Example 189 was prepared according to the procedure of Example 188 substituting the corresponding amine for 2-(4-Aminomethyl-phenyl)-propan-2-ol. The duration of reaction was between 1 and 3 hours.

EXAMPLE 189

N-(2-Chloro-benzyl)-2-(3-chloro-phenoxy)-nicotinamide

M.P. 126–128° C.; Anal. calcd. for $C_{19}H_{14}N_2O_2Cl_2$: C, 61.14; H, 3.78; N, 7.51. Found C, 61.07; H, 3.73; N,7.51.

EXAMPLE 190

(S)-2-(4-{2-[2-(4-Fluoro-phenoxy)-pyridin-3-yl]-[1,3]dioxolan-4-yl}-phenyl)-propan-2-ol To a solution of (S)-4-{2-[2-(4-Fluoro-phenoxy)-pyridin-3-yl]-[1,3]dioxolan-4-yl}-benzoic acid ethyl ester (0.085 grams, 0.2 mmole) in tetrahydrofuran (5 ml) at −78° C. 1.4 M methyl lithium in diethyl ether (0.45 ml, 0.6 mmole) was added dropwise to keep the temperature below −60° C. and stirred at −78° C. for 90 minutes. The mixture was warmed to 0° C., quenched with sat'd $NH_4Cl$ and extracted with ethyl acetate. The combined organics were washed with water and brine, dried over $MgSO_4$, filtered and concentrated to an oil which was purified by chromatography on silica eluting with 1/4 ethyl acetate/hexane to give a colorless oil. (0.45 g); Anal. calcd. for $C_{23}H_{22}NO_4F$: C, 69.86; H, 5.61; N, 3.54. Found: C,70.85; H, 6.22; N, 3.15; $^1H$ NMR (400 mhz, $CDCl_3$) d 1.58 (s, 6H), 3.90–4.00 (m, 1H), 4.38–4.42 (m, 1/2H), 4.54–4.58 (m, 1/2H), 5.21–5.28 (m, 1H), 6.37 (s, 1/2H), 6.55 (s, 1/2H), 6.98–7.15 (m, 5H), 7.34–7.38 (m, 2H), 7.44–7.52 (m, 2H), 7.99–8.16 (m, 2H).

The compounds of Examples 191–192 were prepared according to the procedure of Example 190 substituting the corresponding ester for of (S)-4-{2-[2-(4-Fluoro-phenoxy)-pyridin-3-yl]-[1,3]dioxolan-4-yl}-benzoic acid ethyl ester. The duration of reaction was between 1 and 3 hours.

EXAMPLE 191 cis-(R)-2-(4-{2-[2-(4-Fluoro-phenoxy)-pyridin-3-yl]-[1,3]dioxolan-4-yl}-phenyl)-propan-2-ol Anal. calcd. for $C_{23}H_{22}NO_4F$: α=−45.3° 15.2 mg/ml in methylene chloride; $^1H$ NMR (400 mhz, $CDCl_3$) d 1.58 (s, 6H), 3.96–4.00 (m, 1H), 4.39–4.42 (m, 1H), 5.21–5.24 (m, 1H), 6.38 (s, 1H), 7.04–7.14 (m, 5H), 7.40 (d, J=8.1 Hz, 2H), 7.50 (d, J=8.5 Hz, 2H), 8.05–8.16)m, 2H).

EXAMPLE 192 trans-(R)-2-(4-{2-[2-(4-Fluoro-phenoxy)-pyridin-3-yl]-[1,3]dioxolan-4-yl}-phenyl)-propan-2-ol Anal. calcd. for $C_{23}H_{22}NO_4F$: $^1H$ NMR (400 mhz, $CDCl_3$) d 1.58 (s, 6H), 3.92 (t, J=7.9 Hz, 1H), 4.55–4.58 (m, 1H), 5.23–5.28 (m, 1H), 6.54 (s, 1H), 7.03–7.19 (m, 5H), 7.40 (d, J=8.3 Hz, 2H), 7.51 (d, J=8.1 Hz, 2H),7.99–8.15 (m, 2H).

EXAMPLE 193

2-(4-Fluoro-phenoxy)-N-(4-sulfamoyl-benzyl)-nicotinamide

To a solution of 2-(4-Fluoro-phenoxy)-nicotinic acid (0.110 g 0.470 mmole), BOP (0.205 grams, 0.470 mmole) and DIEA (0.242 μl, 1.42 mmole) in dimethylformamide (5 ml) was added 4-Aminomethyl-benzenesulfonamide (0.105 grams, 0.470 mmole) and stirred at room temperature over night. The reaction was quenched with water and extracted with ethyl acetate. The combined organics were washed with alternating portions of 5% citric acid and sat'd bicarb, dried over $Na_2SO_4$, filtered and concentrated to a product which recrystalized from ethyl acetate to give white crystals (0.100 9). M.P. 222–223° C.; Anal. calcd. for $C_{19}H_{16}N_3O_4SF$; C, 56.85; H, 4.02; N, 10.47. Found: C, 55.52; H, 4.14; N, 10.16.

The compounds of Examples 194–195 were prepared according to the procedure of Example 193 substituting the corresponding amine for 4-Aminomethyl-benzenesulfonamide. The duration of reaction was between 1 and 3 hours.

EXAMPLE 194

2-(4-Fluoro-phenoxy)-N-(1-sulfamoyl-piperidin-4-ylmethyl)-nicotinamide

M.P. 225–226° C.; Anal. calcd. for $C_{18}H_{21}N_4O_4SF$: C, 52.93; H, 5.18; N, 13.72. Found: C, 52.73; H, 5.16; N, 13.72.

EXAMPLE 195

N-(3,4-Dihydro-2H-pyran-2-ylmethyl)-2-(4-fluoro-phenoxy)-nicotinamide

M.P. 55–57° C.; HRMS 329.1324.

EXAMPLE 196

2-(3-Cyano-phenoxy)-N-(4-sulfamoyl-benzyl)-nicotinamide

To a solution of 2-(3-Cyano-phenoxy)-nicotinic acid (0.140 g 0.600 mmole), BOP (0.260 grams, 0.600 mmole) and DIEA (0.310 μl, 1.8 mmole) in dimethylformamide (5 ml) was added 4-Aminomethyl-benzenesulfonamide (0.135 grams, 0.600 mmole) and stirred at room temperature over night. The reaction was quenched with water and extracted with ethyl acetate. The combined organics were washed with alternating portions of 5% citric acid and sat'd bicarb, dried over $Na_2SO_4$, filtered and concentrated to a product which was recrystalized from ethyl acetate to give a white solid (0.100 g). M.P. 179–180° C.; Anal. calcd. for $C_{20}H_{16}N_4O_4S$; C, 58.81; H, 3.95; N, 13.72. Found: C, 57.47; H, 4.15; N. 13.45.

EXAMPLE 197

N-(4-Sulfamoyl-benzyl)-2-(3-tetrazol-1yl-phenoxy)-nicotinamide

To a stirred solution 2-(3-Tetrazol-1-yl-phenoxy)-nicotinic acid (0.050 g, 0.180 mmole) 4-Aminomethyl-benzenesulfonamide (0.060 grams, 0.26 mmole), and 1-hydroxybenzotriazole hydrate (0.031 grams,0.23 mmole) in dry dimethylformamide (2 ml) was added 2-diethylaminoethyl chloride hydrochloride (0.044 grams, 0.23 mmole) and stirred over night. The mixture was diluted with 200 ml water and extracted with ethyl acetate. The combined organics were washed with water, 1N sodium hydroxide and brine, dried over $MgSO_4$, filtered and concentrated to give a product that was purified by chromatography on silica eluting with 5% methanol/methylene chloride to give a white solid. (0.013 g). M.P. 72–74° C.; $^1$H NMR (400 mhz, $CDCl_3$) d 4.55 (d, J=6.0 Hz, 2H), 6.74–6.84 (m, 2H), 7.21–7.37 (m, 4H), 7.49 (d, J=8.5 Hz, 2H), 7.72 (d, J=8.3 Hz, 2H), 8.10–8.21 (m, 2H), 9.05 (t, J=6.0 Hz, 1H).

EXAMPLE 198

N-[4-(1-Hydroxy-1-methyl-ethyl)-cyclohexylmethyl]-2-(3-methoxy-phenoxy)-nicotinamide To a solution 4-({[2-(3-Methoxy-phenoxy)-pyridine-3-carbonyl]-amino}-methyl)-cyclohexanecarboxylic acid ethyl ester (0.260 grams, 0.63 mmole) in tetrahydrofuran (5 ml) at −78° C. 1.4 M methyl lithium in diethyl ether (1.4 ml, 1.89 mmole) was added dropwise to keep the temperature below −60° C. and stirred at −78° C. for 2 hours and allowed to warm to room temperature over the weekend. The mixture was quenched with sat'd $NH_4Cl$ and extracted with ethyl acetate. The combined organics were washed with water and brine, dried over $Na_2SO_4$, filtered and concentrated to a product which was purified by chromatography on silica eluting with 1/1 ethyl acetate/hexane to give a pale yellow oil. (0.077 g); $^1$H NMR (400 mhz, $CDCl_3$) d 1.02–1.22 (m, 10H), 1.52–1.56 (m, 2H), 1.82–1.88 (m, 4H), 3.32–3.36 (m, 2H), 3.80 (s, 3H), 6.70–6.74 (m, 2H), 6.80–6.83 (m, 1H), 7.12–7.16 (m, 1H),7.33 (t, J=8.1 Hz, 1H), 7.93 (bs, 1H), 8.20–8.22 (m, 1H), 8.60–8.61 (m, 1H).

EXAMPLE 199

2-(3-Chloro-phenoxy)-N-[4-(1-hydroxy-1-methyl-ethyl)-cyclohexylmethyl]-nicotinamide To a 4-({[2-(3-Chloro-phenoxy)-pyridine-3-carbonyl]-amino}-methyl)-cyclohexanecarboxylic acid ethyl ester (0.220 grams, 0.53 mmole) in tetrahydrofuran (5 ml) at −78° C. 1.4 M methyl lithium in diethyl ether (1.13 ml, 1.58 mmole) was added dropwise to keep the temperature below −60° C. and stirred at −78° C. for 2 hours and allowed to warm to room temperature. The mixture was quenched with sat'd $NH_4Cl$ and extracted with ethyl acetate. The combined organics were washed with water and brine, dried over $Na_2SO_4$, filtered and concentrated to a product which was purified by chromatography on silica eluting with 2/3 ethyl acetate/hexane to give an off-white oil. (0.040 g); $^1$H NMR (400 mhz, $CDCl_3$) d 0.84–1.70 (m, 12H), 1.83–1.87 (m, 4H), 3.30–3.37 (m, 2H), 7.04–7.07 (m, 1H), 7.11–7.19 (m, 2H), 7.24–7.27 (m, 1H), 7.35–7.39 (m, 1H), 7.79 (bs, 1H), 8.19–8.21 (m, 1H), 8.60–8.62 (m, 1H).

EXAMPLE 200

2-(3-Methoxy-phenoxy)-N-(4-sulfamoyl-benzyl)-nicotinamide

To a solution of 2-(3-Methoxy-phenoxy)-nicotinic acid (0.200 g 0.820 mmole), BOP (0.360 grams, 0.820 mmole) and DIEA (425 μl, 2.45 mmole) in dimethylformamide (5 ml) was added 4-Aminomethyl-benzenesulfonamide (0.182 grams, 0.820 mmole) and stirred at room temperature over night. The reaction was quenched with water and extracted with ethyl acetate. The combined organics were washed with alternating portions of 5% citric acid and sat'd bicarb, dried over $Na_2SO_4$, filtered and concentrated to a product which recrystalized from ethyl acetate to give a white solid (0.260 g). M.P. 142–143° C.; Anal. calcd. for $C_{20}H_{19}N_3O_5S$; C, 58.10; H, 4.63; N, 10.16. Found: C, 58.11; H, 4.91; N, 9.83.

The compound of Example 201 was prepared according to the procedure of Example 200 substituting the corresponding amine for 4-Aminomethyl-benzenesulfonamide. The duration of reaction was between 1 and 3 hours.

EXAMPLE 201

N-[4-(1-Hydroxy-1-methyl-ethyl)-benzyl]-2-(3-methoxy-phenoxy)-nicotinamide

M.P. 69–71° C.; Anal. calcd. for $C_{23}H_{24}N_2O_4$: C, 72.39; H, 6.16; N, 7.14. Found: C, 69.42; H, 6.34; N,7.17.

EXAMPLE 202

2-(3-Fluoro-phenoxy)-N-[4-(1-hydroxy-1-methyl-ethyl)-benzyl]-nicotinamide

To a stirred solution 2-(3-Fluoro-phenoxy)-nicotinic acid (0.250 g, 1.07 mmole), 2-(4-Aminomethyl-phenyl)-propan-2-ol (0.195 grams, 1.18 mmole) and 1-hydroxybenzotriazole hydrate (0.173 grams, 1.28 mmole) in dry dimethylformamide (15 ml) was added 1-(3-dimethylamino)-propyl)-3-ethylcarbodiimide hydrochloride (0.173 grams, 1.28 mmole) and stirred over night. The mixture was diluted with 300 ml water and extracted with ethyl acetate. The combined organics were washed with water and brine, dried over $MgSO_4$, filtered and concentrated to give an oil that was purified by chromatography on silica. Recrystalization from ethyl acetate/hexane gave a solid (0.400 g). M.P. 106–108° C.; Anal. calcd. for $C_{22}H_{21}N_2O_3F$: C, 69.46; H, 5.56; N, 7.36. Found: C, 69.05; H, 5.68; N, 7.25.

EXAMPLE 203

N-[2-(4-Fluoro-phenoxy)-pyridin-3-yl]-2-[4-(1-hydroxy-1-methyl-ethyl)-phenyl]-acetamide To a 2-(4-Acetyl-phenyl)-N-[2-(4-fluoro-phenoxy)-pyridin-3-yl]-acetamide (0.270 grams, 0.741 mmole) in tetrahydrofuran (15 ml) at −78° C. 1.0 M methyl lithium in tetrahydrofuran (1.63 ml, 1.63 mmole) was added via syringe and stirred at −78° C. for 75 minutes. Another 0.8 ml methyl lithium was added and the mixture was warmed to 0° C. for 10 minutes and cooled to −78° C. The mixture was quenched with water, allowed to warm to room temperature and extracted with ethyl acetate. The combined organics were washed with water and brine, dried over $MgSO_4$, filtered and concentrated to a white solid which was purified by chromatography on silica eluting with 2% methanol/methylene chloride to give a white solid. Recrystalization from ethyl acetate/hexane gave a solid (0.032 g). M.P. 135–137° C.; Anal. calcd. for $C_{22}H_{21}N_2O_3F$: C, 69.46; H, 5.56; N, 7.36. Found: C, 69.46; H, 5.92; N, 7.73.

EXAMPLE 204

(−)-N-[5-(1-Hydroxy-ethyl)-thiophen-2-ylmethyl]-2-(pyridin-3-yloxy)-nicotinamide N-[5-(1-Hydroxy-ethyl)-thiophen-2-ylmethyl]-2-(pyridin-3-yloxy)-nicotinamide (0.287 g) was separated on a Chiral Cel OJ Column eluting with 70/30 heptane/ isopropanol to give a product. Recrystalization from ethyl acetate/hexane gave a solid (0.070 g). M.P. 85–870° C.; Anal. calcd. for $C_{18}H_{17}N_3O_3S$: C, 60.83; H, 8.82; N, 11.82. Found: C, 55.38; H, 4.68; N, 10.82. α=−7.02°.

The compound of Example 205 was prepared according to the procedure of Example 204.

EXAMPLE 205

(+)-N-[5-(1-Hydroxy-ethyl)-thiophen-2-ylmethyl]-2-(pyridin-3-yloxy)-nicotinamide M.P. 88–90° C.; Anal. calcd. for $C_{18}H_{17}N_3O_3S$: C, 60.83; H, 8.82; N, 11.82. Found: C, 57.80; H, 5.06; N, 11.21. α=+7.73°.

EXAMPLE 206

N-[4-(1-Hydroxy-1-methyl-ethyl)-benzyl]-2-(3-methylsulfanyl-phenoxy)-nicotinamide To a stirred solution 2-(3-Methylsulfanyl-phenoxy)-nicotinic acid (2.5 grams, 9.58 mmole), 2-(4-Aminomethyl-phenyl)-propan-2-ol (1.896 grams, 11.50 mmole) and 1-hydroxybenzotriazole hydrate (1.55 grams, 11.50 mmole) in dry dimethylformamide (60 ml) was added 1-(3-dimethylamino)-propyl)-3-ethylcarbodiimide hydrochloride (2.39 grams, 12.45 mmole) and stirred over night. The mixture was diluted with 300 ml water and extracted with ethyl acetate. The combined organics were washed with water and brine, dried over $MgSO_4$, filtered and concentrated to give a yellow oil that was purified by chromatography on silica eluting with 3.5% methanol/methylene chloride to give a white solid. Recrystalization from ethyl acetate/hexane gave a solid (0.550 g). M.P. 107–109° C.; Anal. calcd. for $C_{23}H_{24}N_2O_3S$: C, 67.62; H, 5.92; N, 6.86. Found: C, 67.53, H, 5.76; N, 6.91.

EXAMPLE 207

N-[4-(1-Hydroxy-1-methyl-ethyl)-benzyl]-2-(3-methanesulfonyl-phenoxy)-nicotinamide A solution of N-[4-(1-Hydroxy-1-methyl-ethyl)-benzyl]-2-(3-methylsulfanyl-phenoxy)-nicotinamide (3.5 grams, 8.5 mmole) and MCPBA (3.945 grams, 18.8 mmole) in methylene chloride (40 ml) was stirred at room temperature for 1 hour. The mixture was diluted with ethyl acetate, washed with water, 1 $\underline{N}$ sodium hydroxide and brine, dried over $MgSO_4$, filtered and concentrated to give a white solid that was purified by chromatography on silica eluting with 2% methanol/methylene chloride to give a white solid. (1.64 g). M.P. 51–53° C.; Anal. calcd. for $C_{23}H_{24}N_2O_5S$: C, 62.71; H, 5.49; N,6.38. Found: C, 61.87; H, 5.48; N, 6.29.

EXAMPLE 208

N-Pyridin4-ylmethyl-2-(pyridin-3-yloxy)-nicotinamide

A solution of 2-(Pyridin-3-yloxy)-nicotinic acid (0.0664 grams, 0.31 mmole) in thionyl chloride (1.12 ml, 15.4 mmole) was heated to 50° C. After 1.5 hours the reaction mixture was cooled to room temperature and concentrated under reduced pressure. Pyridine (2.5 ml) was added followed by C-Pyridin-4-yl-methylamine (47 µl, 0.47 mmole) at room temperature. After 2 hours the mixture was concentrated to remove pyridine. The crude product was purified by chromatography on silica gel eluting with 9/1 ethyl acetate/methanol to give a solid. (0.0331 g). M.P. 142–144° C.; Anal. calcd. for $C_{17}H_{14}N_4O_2$: C, 66.66; H, 4.61; N, 18.29. Found: C, 66.40; H, 4.56; N, 17.94.

EXAMPLE 209

2-(4-Fluoro-phenoxy)-N-(5-methyl-pyrazin-2-ylmethyl)-nicotinamide

A solution of 2-(4-Fluoro-phenoxy)-nicotinic acid (0.0766 grams, 0.33 mmole) in thionyl chloride (2 ml) was heated to 50° C. After 1.5 hours the reaction mixture was cooled to room temperature and concentrated under reduced pressure. The resulting residue was dissolved in pyridine (2 ml) and C-(5-Methyl-pyrazin-2-yl)-methylamine (0.14 grams, 1.0 mmole) was added. After 1.5 hours the mixture was concentrated under reduced pressure and purified by chromatography on silica gel eluting with 1:1 ethyl acetate/hexane to give a white solid. M.P. 159° C.; Anal. calcd. for $C_{18}H_{15}N_4O_2F$: C, 63.90; H, 4.47; N, 16.56. Found: C, 63.78; H, 4.39; N, 16.26.

The compound of Example 63a was prepared according to the procedure of Example 63 substituting the corresponding amine for Methyl-pyrazin-2-yl)-methylamine. The duration of reaction was between 1 and 24 hours.

EXAMPLE 210

5-{[2-(4-Fluoro-phenoxy)-pyridine-3-carbonyl]-amino}-pentanoic acid ethyl ester

Anal. calcd. for $C_{19}H_{21}N_2O_4F$: C, 63.32; H, 5.87; N, 7.77. Found: C, 62.42; H, 5.62; N, 7.52; $^1H$ NMR ($CDCl_3$) d 1.21 (3H, t, J=7.1 Hz), 1.69 (4H, m), 2.33 (2H, t, J=6.2 Hz), 349 (2H, m), 4.08 (2H, q, J=7.06, 14.11), 7.13 (4H, m), 7.86 (1H, s), 8.17 (1H, s), 8.17 (1H, dd, J=2.08, 4.77), 8.59 (1H, dd, J=2.07, 7.67).

EXAMPLE 211

2-[4-(1-Hydroxy-1-methyl-ethyl)-phenyl]-N-[2-(pyridin-3-yloxy)-pyridin-3-yl]-acetamide To a solution of 2-(4-Acetyl-phenyl)-N-[2-(pyridin-3-yloxy)-pyridin-3-yl]-acetamide (0.130 grams, 0.374 mmole) in tetrahydrofuran (10 ml) at −78° C. 1.0 M methyl lithium in tetrahydrofuran (1.123 ml, 1.123 mmole) was added and stirred at −78° C. for 30 minutes, allowed to warm to room temperature for 30 minutes and cooled to −78° C. The mixture was quenched with water and extracted with ethyl acetate. The combined organics were washed with water and brine, dried over $MgSO_4$, filtered and concentrated to a product which was purified by chromatography on silica eluting with 3% methanol/methylene chloride. Recrystalization from ethyl acetate/hexane gave a solid (0.045 g). M.P. 122–124° C.; Anal. calcd. for $C_{21}H_{21}N_3O_3$: C, 69.41; H, 5.82; N, 11.50. Found: C, 69.02; H, 6.12; N, 11.30.

EXAMPLE 212

2-(4-Fluoro-phenoxy)-N-(5-hydroxy-5-methyl-hexyl)-nicotinamide

To a solution of 5-{[2-(4-Fluoro-phenoxy)-pyridine-3-carbonyl]-amino}-pentanoic acid ethyl ester (0.0231 grams, 0.06 mmole) in tetrahydrofuran (1 ml) at −78° C. 1.4 M methyl lithium in diethyl ether (186 µl, 0.26 mmole) was added via syringe and stirred at −78° C. for 2 hours, 200 µl water was added and the mixture warmed to room temperature. The reaction was diluted with ethyl acetate, dried over MgSO$_4$, filtered and concentrated to give a clear oil. Anal. calcd. for C$_{19}$H$_{23}$N$_2$O$_3$F: C, 65.88; H, 6.69; N, 8.09. Found: C, 63.17; H, 5.73; N, 7.46; $^1$H NMR (CDCl$_3$) d 1.21 (6H, m), 1.51 (3H, m), 1.67 (2H, m), 3.52 (2H, m), 4.10 (1H, q, 7.17, 14.30), 7.17 (4H, m), 7.86 (1H, s), 8.20 (1H, dd, J=2.11, 4.89), 8.58 (1H, dd, J=2.16, 7.67).

EXAMPLE 213

N-[2-(3-Acetyl-phenoxy)-pyridin-3-yl]-2-[4-(1-hydroxy-1-methyl-ethyl)-phenyl]-acetamide To a solution of 2-(4-Acetyl-phenyl)-N-[2-(3-cyano-phenoxy)-pyridin-3-yl]-acetamide (0.250 grams, 1.484 mmole) in tetrahydrofuran (15 ml) at −78° C. 1.0 M methyl lithium in tetrahydrofuran (5.2 ml, 5.2 mmole) was added and stirred at −78° C. for 1 hour. Another 2.0 ml methyl lithium was added and stirred for 5 minutes allowing to warm to room temperature. The reaction was quenched with water and extracted with ethyl acetate. The combined extracts were washed with water and brine, dried over MgSO$_4$, filtered and concentrated to give an oil which was purified by chromatography on silica eluting with 30% ethyl acetate/hexane. Recrystalization from ethyl acetate/ hexane gave white crystals (0.082 g). M.P. 85–87° C.; Anal. calcd. for C$_{24}$H$_{24}$N$_2$O$_4$: C, 71.27; H, 5.98; N, 6.93. Found: C, 68.61; H, 6.30; N, 6.19.

EXAMPLE 214

2-(3-Cyano-phenoxy)-N-[4-(1-hydroxy-1-methyl-ethyl)-cyclohexylmethyl]-nicotinamide To a solution of 4-{[2-(3-Cyano-phenoxy)-pyridin-3-ylcarbamoyl]-methyl}-cyclohexanecarboxylic acid ethyl ester (0.180 grams, 0.46 mmole) in tetrahydrofuran (6 ml) at −78° C. 1.4 M methyl lithium in diethyl ether (980 μl, 1.37 mmole) was added via syringe and stirred at −78° C. for 2 hours. The reaction was quenched with 200 μl sat'd NH$_4$Cl and warmed to room temperature. The reaction was diluted with ethyl acetate, dried over MgSO$_4$, filtered and concentrated to give a light yellow oil which crystalized on standing. M.P. 129–130° C.; Anal. calcd. for C$_{23}$H$_{27}$N$_3$O$_3$: C, 70.21; H, 6.92; N, 10.68. Found: C, 69.23; H, 6.88; N, 10.37.

EXAMPLE 215

3-{3-[4-(1-Hydroxy-1-methyl-ethyl)-benzylcarbamoyl]-pyridin-2-yloxy}-benzoicacid methyl ester To a stirred solution of 2-(3-Methoxycarbonyl-phenoxy)-nicotinic acid (0.400 grams, 1.463 mmole), 2-(4-Aminomethyl-phenyl)-propan-2-ol (0.266 grams, 1.61 mmole), and 1-hydroxybenzotriazole hydrate (0.237 grams, 1.755 mmole) in dry dimethylformamide (20 ml) was added 2-diethylaminoethyl chloride hydrochloride (0.365 grams, 1.90 mmole) and stirred over night. The mixture was diluted with water and extracted with ethyl acetate. The combined extracts were washed with water and brine, dried over MgSO$_4$, filtered and concentrated to give a white foam. (0.360 g); MS (m/e) 420 (M$^+$+1); $^1$H NMR (CDCl$_3$) d 1.50 (6H, s), 3.90 (3H, s), 4.70 (2H, d, J=5.60 Hz), 7.20–8.65 (12H, m).

EXAMPLE 216

2-(4-Fluoro-phenoxy)-N-(5-oxo-morpholin-2-ylmethyl)-nicotinamide

A solution of 6-Aminomethyl-morpholin-3-one hydrochloride (0.200 grams, 1.2 mmole) and triethyl amine (0.150 grams, 1.5 mmole) in dimethylformamide was stirred at room temperature for 30 minutes. To the stirring solution 2-(4-Fluoro-phenoxy)-nicotinic acid (0.280 grams, 1.2 mmole), 1-hydroxybenzotriazole hydrate (0.237 grams, 1.755 mmole) and 2-diethylaminoethyl chloride hydrochloride (0.30 grams, 1.56 mmole) was added and stirred over night. The mixture was diluted with water and extracted with ethyl acetate. The combined extracts were washed with 1 N NaOH, water and brine, dried over MgSO$_4$, filtered and concentrated to give a white solid which was purified by chromatography on silica eluting with 5% methanol/methylene chloride. Recrystalization from ethyl acetate/ hexane gave white crystals. (0.175 g); M.P. 157–159° C.; Anal. calcd. for C$_{17}$H$_{16}$N$_3$O$_4$F: C, 59.14; H, 4.67; N, 12.17. Found: C, 59.00; H, 4.69; N, 12.19.

EXAMPLE 217

2-(3-Cyano-phenoxy)-N-(5-methyl-pyrazin-2-ylmethyl)-nicotinamide

A solution of 2-(3-Cyano-phenoxy)-nicotinic acid (0.0067 grams, 0.03 mmole) in thionyl chloride (500 μl, 6.9 mmole) was stirred at room temperature for 3 hours and concentrated under reduced pressure to give a white solid. To the residue was added pyridine (300 μl) and C-(5-Methyl-pyrazin-2-yl)-methylamine (0.0038 grams, 0.03 mmole). The mixture stood at room temperature for 3 hours and then was concentrated under reduced pressure to white solid. (0.0093 g); Anal. calcd. for C$_{19}$H$_{15}$N$_5$O$_2$: C, 66.08; H, 4.38; N, 20.26. Found: C, 56.89; H, 5.02; N, 18.31.

EXAMPLE 218

N-[2-(3-Cyano-phenoxy)-pyridin-3-yl]-2-[4-(1-hydroxy-1methyl-ethyl)-phenyl]-acetamide To a solution of 2-(4-Acetyl-phenyl)-N-[2-(3-cyano-phenoxy)-pyridin-3-yl]-acetamide (0.360 grams, 0.96 mmole) in tetrahydrofuran (15 ml) at −78° C. 1.0 M methyl lithium (2.03 ml, 2.03 mmole) in tetrahydrofuran (20 ml) was added and stirred at −78° C. for 1 hour. The reaction was quenched with water and extracted with ethyl acetate. The combined extracts were washed with water and brine, dried over MgSO$_4$, filtered and concentrated to give a white solid which was purified by chromatography on silica eluting with 40% ethyl acetate/hexane. Recrystalization from ethyl acetate/hexane gave white crystals (0.115 g). M.P. 97–99° C.; Anal. calcd. for C$_{23}$H$_{21}$N$_3$O$_3$: C, 71.30; H, 5.46; N, 10.85. Found: C, 70.96; H, 5.30; N, 10.69.

EXAMPLE 219

2-(Pyridin-3-yloxy)-N-(4-trifluoroacetyl-benzyl)-nicotinamide

To a stirred solution of 2-(Pyridin-3-yloxy)-N-[4-(2,2,2-trifluoro-1-hydroxy-ethyl)-benzyl]-nicotinamide (0.350 grams, 0.87 mmole), NMO (0.153 grams, 1.3 mmole) and 4 Å molecular sieves (0.5 g) in methylene chloride was added TPAP (0.015 grams, 0.04 mmole) and stirred at room temperature for 4 hours. The mixture was filtered through celite, washed with water, dried over MgSO$_4$, filtered and concentrated under reduced pressure to give an oil which was purified by chromatography on silica eluting with 5% methanol/methylene chloride to give a solid (0.151 g). M.P. 134–136°C.; Anal. calcd. for C$_{20}$H$_{14}$N$_3$O$_3$F$_3$: C, 59.85; H, 3.52; N, 10.47. Found: C, 59.56; H, 3.63; N, 10.20.

EXAMPLE 220

2-(3-Acetyl-phenoxy)-N-pyridin-4-ylmethyl-nicotinamide

A solution of 2-(3-Acetyl-phenoxy)-nicotinic acid (0.356 grams, 1.39 mmole C-Pyridin-4-yl-methylamine (0.150 grams, 1.39 mmole), and 1-hydroxybenzotriazole hydrate (0.224 grams, 1.66 mmole) in dry dimethylformamide was added 1-(3-dimethylamino)-propyl)-3-ethylcarbodiimide hydrochloride (0.319 grams, 1.66 mmole) and stirred over night. The mixture was diluted with 100 ml water and extracted with ethyl acetate. The combined organics were washed with water and brine, dried over $MgSO_4$, filtered and concentrated to give a white solid that was purified by chromatography on silica eluting ethyl acetate to give a white solid. Recrystalization from ethyl acetate/hexane gave a white solid (0.220 g). M.P. 148–150° C.; Anal. calcd. for $C_{20}H_{17}N_3O_3$: C, 67.15; H, 4.93; N, 12.10. Found: C, 66.57; H, 4.55; N, 11.43.

The compound of Examples 221–224 was prepared according to the procedure of Example 220 substituting the corresponding amine for C-Pyridin-4-yl-methylamine. The duration of reaction was between 1 and 24 hours.

EXAMPLE 221

2-(3-Acetyl-phenoxy)-N-[4-(1-hydroxy-1-methyl-ethyl)-benzyl]-nicotinamide

M.P. 52–54° C.; Anal. calcd. for $C_{24}H_{24}N_2O_4$: C, 71.27; H, 5.98; N, 6.93. Found: C, 69.78; H, 5.54; N, 6.83.

EXAMPLE 222

2-(3-Acetyl-phenoxy)-N-(2-chloro-benzyl)-nicotinamide

M.P. 140–142° C.; Anal. calcd. for $C_{21}H_{17}N_2O_3Cl$: C, 66.23; H, 4.50; N, 7.36. Found: C, 65.84; H, 4.22; N, 6.88.

EXAMPLE 223

2-(3-Acetyl-phenoxy)-N-[4-(1-hydroxy-ethyl)-benzyl]-nicotinamide

M.P. 105–107° C.; MS (m/e) 391 ($M^+$+1).

EXAMPLE 224

2-(3-Acetyl-phenoxy)-N-(4-sulfamoyl-benzyl)-nicotinamide

M.P, 162–164° C.; MS (m/e) 425 ($M^+$); $^1$H NMR (DMSO-$d^6$) d 2.55 (3H, s), 4.56 (2H, d, J=6.0 Hz), 7.2–9.2 (12H, m).

EXAMPLE 225

2-[3-(1-Hydroxy-1-methyl-ethyl)-phenoxy]-N-pyridin-4-ylmethyl-nicotinamide

To a solution of 2-(3-Acetyl-phenoxy)-N-pyridin-4-ylmethyl-nicotinamide (0.180 grams, 0.51 mmole) in tetrahydrofuran (20 ml) at −78° C. 1.0 M methyl lithium in THF/cumene (1.14 ml, 1.14 mmole) was added and stirred at −78° C. for 1 hour. The reaction was quenched with water and diluted with ethyl acetate. The organics were washed with water and brine, dried over $MgSO_4$, filtered and concentrated to give a product which was purified by chromatography on silica eluting with ethyl acetate to give a white foam. MS (m/e) 364 ($M^+$+1); $^1$H NMR (CDCl$_3$) d 1.58 (6H, s), 4.70 (2H, d, J=5.81 Hz), 7.0–8.7 (12H, m).

EXAMPLE 226

N-(2-Chloro-benzyl)-2-[3-(1-hydroxy-1-methyl-ethyl)-phenoxy]-nicotinamide

To a solution of 2-(3-Acetyl-phenoxy)-N-(2-chloro-benzyl)-nicotinamide (0.410 grams, 1.307 mmole) in tetrahydrofuran (20 ml) at −78° C. 1.0 M methyl lithium (2.7 ml, 2.697 mmole) was added, stirred at −78° C. for 1 hour and allowed to warm to room temperature for 1 hour. The reaction was quenched with water and diluted with ethyl acetate. The organics were washed with water and brine, dried over $MgSO_4$, filtered and concentrated to give an oil which was purified by chromatography on silica eluting with 2% methanol/methylene chloride to give an oil. MS (m/e) 397 ($M^+$+1); $^1$H NMR (CDCl$_3$) d 1.60 (6H, s), 4.78 (2H, d, J=6.01 Hz), 7.0–7.5 (9H, m), 8.20 (1H, m), 8.55 (1H, bs), 8.62 (1H, m).

The compound of Examples 227 was prepared according to the procedure of Example 226 substituting the corresponding ketone for 2-(3-Acetyl-phenoxy)-N-[4-(1-hydroxy-1-methyl-ethyl)-benzyl]-nicotinamide. The duration of reaction was between 1 and 24 hours.

EXAMPLE 227

N-[4-(1-Hydroxy-1-methyl-ethyl)-benzyl]-2-[3-(1-hydroxy-1-methyl-ethyl)-phenoxy]nicotinamide MS (m/e) 421 ($M^+$+1); $^1$H NMR (CDCl$_3$) d 1.54 (6H, s), 1.57 (6H, s), 4.67 (2H, d), 7.0–7.5 (9H, m), 8.10–8.70 (3H, m).

EXAMPLE 228

N-[4-(1-Hydroxy-1-methyl-ethyl)-benzyl]-2-(3-trifluoromethoxy-phenoxy)-nicotinamide A solution of 2-(3-Trifluoromethoxy-phenoxy)-nicotinic acid (0.409 grams, 1.366 mmole) 2-(4-Aminomethyl-phenyl)-propan-2-ol (0.200 grams, 1.24 mmole), and 1-hydroxybenzotriazole hydrate (0.185 grams, 1.366 mmole) in dry dimethylformamide was added 1-(3-dimethylamino)-propyl)-3-ethylcarbodiimide hydrochloride (0.286 grams, 1.50 mmole) and stirred over night. The mixture was diluted ethyl acetate which was washed with water and brine, dried over $MgSO_4$, filtered and concentrated to give an oil that was purified by chromatography on silica eluting with 3.5% methanol/methylene chloride to give an oil. (0.430 g). MS (m/e) 447 ($M^+$+1); $^1$H NMR (CDCl$_3$) d 1.50 (6H, s), 4.70 (2H, d, J=5.81 Hz), 7.0–7.5 (9H, m), 8.00 (1H, bs), 8.20 (1H, m), 8.65 (1H, m).

EXAMPLE 229

N-(4-Acetyl-cyclohexylmethyl)-2-(4-fluoro-phenoxy)-nicotinamide

To 4-{[2-(4-Fluoro-phenoxy)-pyridin-3-ylcarbamoyl]-methyl}-cyclohexanecarboxylic acid ethyl ester (3.01 grams, 7.5 mmole) in tetrahydrofuran (40 ml) at −78° C. 1.4 M methyl lithium in diethyl ether (16.1 ml, 22.5 mmole) was added slowly, stirred at −78° C. for 1 hour and slowly warmed to −30° C. The reaction was quenched with 600 µl sat'd $NH_4Cl$ and warmed to room temperature. The reaction was diluted with ethyl acetate, dried over $MgSO_4$, filtered and concentrated to give a light yellow oil which was purified by chromatography on silica eluting with 3/2 hexane/ethyl acetate to 1/3 hexane/ethyl acetate to give a clear oil that solidified on standing. (0.3500 g). M.P. 110–111° C.; Anal. calcd. for $C_{21}H_{23}N_2O_3F$: C, 68.09; H, 6.26; N, 7.56. Found: C, 67.32; H, 6.26; N, 7.40.

EXAMPLE 230

2-(2,4-Difluoro-phenoxy)-N-[4-(1-hydroxy-1-methyl-ethyl)-benzyl]-nicotinamide

A solution of 2-(2,4-difluoro-phenoxy)-nicotinic acid (0.300 grams, 1.19 mmole) 2-(4-Aminomethyl-phenyl)- propan-2-ol (0.217 grams, 1.31 mmole), and 1-hydroxybenzotriazole hydrate (0.177 grams, 1.31 mmole) in dry dimethylformamide was added 1-(3-dimethylamino)-propyl)-3-ethylcarbodiimide hydrochloride (0.273 grams, 1.43 mmole) and stirred over night. The mixture was poured into 100 ml water and extracted with ethyl acetate. The combined extracts were washed with 1 N NaOH, water and brine, dried over $MgSO_4$, filtered and concentrated to give an oil that was purified by chromatography on silica eluting with 40% ethyl acetate/hexane to give a white solid. Recrystalization from ethyl acetate/hexane gave a white solid (0.336 g). M.P. 92–94° C.; Anal. calcd. for $C_{22}H_{20}N_2O_3F_2$: C, 66.32; H, 5.06; N, 7.03. Found: C, 66.28; H, 4.92; N, 6.89.

EXAMPLE 231

2-(3,4-Difluoro-phenoxy)-N-[4-(1-hydroxy-1-methyl-ethyl)-benzyl]-nicotinamide

A solution of 2-(2,3-difluoro-phenoxy)-nicotinic acid (0.300 grams, 1.19 mmole), 2-(4-Aminomethyl-phenyl)-propan-2-ol (0.217 grams, 1.31 mmole), and 1-hydroxybenzotriazole hydrate (0.177 grams, 1.31 mmole) in dry dimethylformamide was added 1-(3-dimethylamino)-propyl)-3-ethylcarbodiimide hydrochloride (0.273 grams, 1.43 mmole) and stirred over night. The mixture was poured into 100 ml water and extracted with ethyl acetate. The combined extracts were washed with 1 N NaOH, water and brine, dried over $MgSO_4$, filtered and concentrated to give an oil that was purified by chromatography on silica eluting with 40% ethyl acetate/hexane to give an oil. Recrystalization from ethyl acetate/hexane gave a white solid (0.337 g). M.P. 98–100° C.; Anal. calcd. for $C_{22}H_{20}N_2O_3F_2$: C, 66.32; H, 5.06; N, 7.03. Found: C, 66.40; H, 4.94; N, 6.89.

The compounds of Example 232–233 were prepared according to the procedure of Example 231 substituting the corresponding amine for 2-(4-Aminomethyl-phenyl)-propan-2-ol. The duration of reaction was between 1 and 24 hours.

EXAMPLE 232

2-(3,4-Difluoro-phenoxy)-N-[4-(1-hydroxy-cyclobutyl)-benzyl]-nicotinamide

M.P. 74–76° C.; Anal. calcd. for $C_{23}H_{20}N_2O_3F_2$: C, 67.31; H, 4.91; N, 6.83. Found: C, 67.14; H, 4.93; N, 6.67.

EXAMPLE 233

N-[2-Chloro-4-(1-hydroxy-1-methyl-ethyl)-benzyl]-2-(3,4-difluoro-phenoxy)-nicotinamide M.P. 119–211° C.; Anal. calcd. for $C_{22}H_{19}N_2O_3F_2Cl$: C, 61.65; H, 4.42; N, 6.47. Found: C, 61.31; H, 4.56; N, 6.65.

EXAMPLE 234

4-({[2-(3-Acetyl-phenoxy)-pyridine-3-carbonyl]-amino}-methyl)-cyclohexanecarboxylic acid ethyl ester A solution of 4-Aminomethyl-cyclohexanecarboxylic acid ethyl ester hydrochloride (0.410 grams, 1.853 mmole), 2-(3-Acetyl-phenoxy)-nicotinic acid (0.500 grams, 1.946 mmole), 1-hydroxybenzotriazole hydrate (0.275 grams, 2.04 mmole) and 1-(3-dimethylamino)-propyl)-3-ethylcarbodiimide hydrochloride (0.330 grams, 2.22 mmole) in dimethylformamide (30 ml) was stirred for 10 minutes. To the stirring solution was added triethyl amine (0.280 grams, 2.78 mmole) and stirred over night at room temperature. The mixture was diluted with water (200 ml) and extracted with ethyl acetate. The combined extracts were washed with water and brine, dried over $MgSO_4$, filtered and concentrated to give a yellow solid which was purified by chromatography on silica eluting with 40% ethyl acetate/hexane. Recrystalization from ethyl acetate/hexane gave white crystals. (0.680 g); M.P. 118–120° C.; $^1$H NMR ($CDCl_3$) d 1.02 (2H, q, J=12.866 Hz),1.2 (3H, t), 1.4 (2H, q), 1.6 (1H, m), 1.85 (2H, d, J=12.5 Hz), 2.0 (2H, d, J=12.5 Hz), 2.2 (1H, m), 2.6 (3H, s), 3.4 (2H, m), 4.10 (2H, t), 7.2–8.7 (7H, m).

The compounds of Examples 235–237 were prepared according to the procedure of Example 234 substituting the corresponding amine for 4-Aminomethyl-cyclohexanecarboxylic acid ethyl ester hydrochloride. The duration of reaction was between 1 and 24 hours.

EXAMPLE 235

2-(3-Acetyl-phenoxy)-N-[2-chloro-4-(1-hydroxy-1-methyl-ethyl)-benzyl]-nicotinamide M.P. 102–104° C.; Anal. calcd. for $C_{24}H_{23}N_2O_4Cl$: C, 65.68; H, 5.28; N, 6.38. Found: C, 65.39; H, 5.08; N, 6.15.

EXAMPLE 236

2-(4-Acetyl-phenoxy)-N-[4-(1-hydroxy-1-methyl-ethyl)-benzyl]-nicotinamide

M.P. 95–97° C.; Anal. calcd. for $C_{24}H_{24}N_2O_4$: C, 71.27; H, 5.98; N, 6.93. Found: C, 70.19; H, 5.93; N, 7.02.

EXAMPLE 237

2-(3-Acetyl-phenoxy)-N-[2-fluoro-4-(1-hydroxy-1-methyl-ethyl)-benzyl]nicotinamide M.P.68–70° C.; MS (m/e) 423 ($M^+$+1).

EXAMPLE 238

2-(3,5-Difluoro-phenoxy)-N-[4-(1-hydroxy-1-methyl-ethyl)-benzyl]-nicotinamide

A solution of 2-(3,5-difluoro-phenoxy)-nicotinic acid (0.300 grams, 1.19 mmole), 2-(4-Aminomethyl-phenyl)-propan-2-ol (0.197 grams, 1.19 mmole) and 1-hydroxybenzotriazole hydrate (0.177 grams, 1.31 mmole) in dry dimethylformamide was added 1-(3-dimethylamino)-propyl)-3-ethylcarbodiimide hydrochloride (0.273 grams, 1.43 mmole) and stirred over night. The mixture was poured into 100 ml water and extracted with ethyl acetate. The combined extracts were washed with 1 N NaOH, water and brine, dried over $MgSO_4$, filtered and concentrated to give an oil that was purified by chromatography on silica eluting with 40% ethyl acetate/hexane to give an oil. Recrystalization from ethyl acetate/hexane gave a white solid (0.328 g). M.P. 68–70° C.; Anal. calcd. for $C_{22}H_{20}N_2O_3F_2$: C, 66.32; H, 5.06; N, 7,03; N, 703. Found: C, 67.30; H, 5.39; N, 6.56.

EXAMPLE 239 trans-2-(2,4-Difluoro-phenoxy)-N-[4-(1-hydroxy-1-methyl-ethyl)-cyclohexylmethyl]-nicotinamide To trans-4-({[2-(2,4-Difluoro-phenoxy)-pyridine-3-carbonyl]-amino}-methyl)-cyclohexanecarboxylic acid ethyl ester (0.516 grams, 1.23 mmole) in tetrahydrofuran (20 ml) at 0° C. 3.0 M methyl magnesium chloride (1.2 ml, 3.7 mmole) was added dropwise and stirred 1 hour. The reaction was poured into 150 ml water, acidified with oxalic acid to pH=3 and extracted with ethyl acetate. The combined extracts were washed with 1N HCl, 1N NaOH, water and brine, dried over $MgSO_4$, filtered and concentrated to give an oil which was purified by chromatography on silica eluting with 50% hexane/ethyl acetate to give an oil. Recrystalization from ethyl acetate/hexane gave a white solid. (0.207 g). M.P. 92–94° C.; Anal. calcd. for $C_{22}H_{26}N_2O_3F_2$: C, 65.33; H, 6.48; N, 6.93. Found: C, 65.27; H, 6.26; N, 6.73.

The compound of Example 240 was prepared according to the procedure of Example 239 substituting the corresponding ester for trans-4-({[2-(2,4-Difluoro-phenoxy)-pyridine-3-carbonyl]-amino}-methyl)-cyclohexanecarboxylic acid ethyl ester. The duration of reaction was between 1 and 24 hours.

EXAMPLE 240 trans-2-(3,4-Difluoro-phenoxy)-N-[4-(1-hydroxy-1-methyl-ethyl)-cyclohexylmethyl]-nicotinamide M.P. 80–82° C.; MS (m/e) 405 ($M^+$+1).

EXAMPLE 241

4-({[2-(3-Nitro-phenoxy)-pyridine-3-carbonyl]-amino}-methyl)-cyclohexanecarboxylic acid ethyl ester To a stirred solution of 4-Aminomethyl-cyclohexanecarboxylic acid ethyl ester hydrochloride (0.500 grams, 2.26 mmole), 2-(3-Nitro-phenoxy)-nicotinic acid (0.588 grams, 2.26 mmole), 1-hydroxybenzotriazole hydrate (0.366 grams, 2.71 mmole) and 1-(3-dimethylamino)-propyl)-3-ethylcarbodiimide hydrochloride (0.564 grams, 2.93 mmole) in dimethylformamide (50 ml) was was added triethyl amine (0.456 grams, 4.52 mmole) and stirred over the weekend at room temperature. The mixture was diluted with water (150 ml) and extracted with ethyl acetate. The combined extracts were washed with water and brine, dried over $MgSO_4$, filtered and concentrated to give an oil which was purified by chromatography on silica eluting with 40% ethyl acetate/hexane to give an oil. (1.05 g). MS (m/e) 428 ($M^+$+1); $^1$H NMR ($CDCl_3$) d 1.01 (2H, m), 1.2 (3H, t), 1.4 (2H, q), 1.6 (1H, m), 1.90 (2H, d, J=12.5 Hz), 2.0 (1H, d, J=12.5 Hz), 2.2 (1H, m), 3.4 (2H, m), 4.10 (2H, q), 7.20–8.7 (7H, m).

EXAMPLE 242

2-(3-Acetyl-phenoxy)-N-[4-(1-hydroxy-1-methyl-ethyl)-cyclohexylmethyl]-nicotinamide A solution of N-[4-(1-Hydroxy-1-methyl-ethyl)-cyclohexylmethyl]-2-[3-(2-methyl-[1,3]dioxolan-2-yl)-phenoxy]-nicotinamide (0.400 grams, 0.88 mmole) in acetic acid (10 ml) was stirred for 3 hours at room temperature. The mixture was diluted with 250 ml ethyl acetate, washed with 1 N NaOH, water and brine, dried over $MgSO_4$, filtered and concentrated to an oil which was purified by chromatography on silica eluting with 40% ethyl acetate/hexane. Recrystalization gave a solid. (0.055 g). M.P. 105–107° C.; Anal. calcd. for $C_{24}H_{30}N_2O_4$: C, 70.22; H, 7.37; N, 6.82. Found: C, 68.43; H, 7.32; N, 6.71.

EXAMPLE 243

2-(3-Cyano-4-fluoro-phenoxy)-N-[4-(1-hydroxy-1-methyl-ethyl)-benzyl]-nicotinamide A solution of 2-(3-Cyano-4-fluoro-phenoxy)-nicotinic acid (0.300 grams, 1.16 mmole) 2-(4-Aminomethyl-phenyl)-propan-2-ol (0.192 grams, 1.16 mmole), and 1-hydroxybenzotriazole hydrate (0.172 grams, 1.28 mmole) in dry dimethylformamide was added 1-(3-dimethylamino)-propyl)-3-ethylcarbodiimide hydrochloride (0.267 g, 1.39 mmole) and stirred over night. The mixture was poured into 100 ml water and extracted with ethyl acetate. The combined extracts were washed with 1 N NaOH, water and brine, dried over $MgSO_4$, filtered and concentrated to give an oil that was purified by chromatography on silica eluting with 50% ethyl acetate/hexane to give an oil. Recrystalization from ethyl acetate/hexane gave a white solid (0.276 g). M.P. 147–149° C.; Anal. calcd. for $C_{23}H_{20}N_3O_3F$: C, 68.14; H, 4.97; N, 10.36. Found: C, 67.77; H, 5.00; N, 10.15.

The compound of Example 244 was prepared according to the procedure of Example 243 substituting the corresponding amine for 2-(4-Aminomethyl-phenyl)-propan-2-ol. The duration of reaction was between 1 and 24 hours.

EXAMPLE 244

N-[2-Chloro-4-(1-hydroxy-1-methyl-ethyl)-benzyl]-2-(3-cyano-4-fluoro-phenoxy)-nicotinamide M.P. 151–153° C.; Anal. calcd. for $C_{23}H_{19}N_3O_3FCl$: C, 62.80; H, 4.35; N, 9.55. Found: C, 63.16; H, 4.44; N, 9.49.

EXAMPLE 245

2-(4-Fluoro-phenoxy)-N-[4-(1-hydroxy-1-methyl-ethyl)-cyclohexylmethyl]-nicotinamide To 4-({[2-(4-Fluoro-phenoxy)-pyridine-3-carbonyl]-amino}-methyl)-cyclohexanecarboxylic acid methyl ester (0.0221 grams, 0.06 mmole) in tetrahydrofuran (1 ml) at −78° C. 1.4 M methyl lithium in diethyl ether (171 $\mu$l, 0.24 mmole) was added and stirred at −78° C. for 2 hours. The reaction was quenched with 200 $\mu$l sat'd $NH_4Cl$ and warmed to room temperature. The reaction was filtered through a pad of magnesium sulfate and concentrated to give a light brown foam which was purified by chromatography on silica eluting with 1/1 hexane/ethyl acetate to 95/5 methylene chloride/methanol to give a clear film. (0.0111 g). M.P. 78–80° C.; Anal, calcd. for $C_{22}H_{27}N_2O_3F$: C, 68.37; H, 7.04; N, 7.25. Found: C, 68.32; H, 7.04; N, 7.27.

EXAMPLE 246

N-(2-Chloro-benzyl)-2-(pyridin-3-ylmethoxy)-nicotinamide

A solution of 2-(Pyridin-3-ylmethoxy)-nicotinic acid (0.300 grams, 1.3 mmole) 2-Chloro-benzylamine (0.202 grams, 1.43 mmole), and 1-hydroxybenzotriazole hydrate (0.210 grams, 1.56 mmole) in dry dimethylformamide (10 ml) was added 1-(3-dimethylamino)-propyl)-3-ethylcarbodiimide hydrochloride (0.324 grams, 1.69 mmole) and stirred over night. The mixture was diluted with 50 ml water and 50 ml 1N sodium hydroxide and extracted with ethyl acetate. The combined extracts were washed with 1 N NaOH, water and brine, dried over $Na_2SO_4$, filtered and concentrated to give an oil that was purified by chromatography on silica eluting with 5% methanol/methylene chloride. Recrystalization from ethyl acetate/hexane gave white crystals (0.116 g). M.P. 91–93° C.; Anal. calcd. for $C_{19}H_{16}N_3O_2Cl$: C, 64.50; H, 4.56; N, 11.88. Found: C, 64.38; H, 4.58; N, 11.97.

EXAMPLE 247

N-[[4-(Dimethylamino)phenyl]methyl]-2-(4-fluorophenoxy)-3-pyridinecarboxamide

To a solution of 1.00 g (2.96 mmol) N-(4-Amino-benzyl)-2-(4-fluoro-phenoxy)-nicotinamide in 20 mL of acetonitrile was added 1.44 mL (17.8 mmol) of aqueous 37% formaldehyde solution followed by 0.558 g (4.45 mmol) of NaCNBH$_3$. After stirring for 16 h at rt, the mixture was acidified to destroy excess NaCNBH$_3$ and was partially evaporated to remove acetonitrile. The residue was adjusted to pH 6–7 and then extracted with EtOAc (2×200 mL). The combined extracts were washed with saturated aqueous sodium hydrogencarbonate solution (1×100 mL), brine (1×100 mL), dried (Na$_2$SO$_4$), and evaporated to 1.55 g of an oil. Purification by flash chromatography using a 40% EtOAc-hexane eluant gave 992 mg of an oil which slowly solidified. Trituration in hexane afforded 872 mg (81% yield) of the title compound as a white solid, mp 99.5–101.5° C. Anal. Calcd for C$_{21}$H$_{20}$N$_3$O$_2$F: C, 69.03; H, 5.51; N, 11.50. Found: C, 69.32; H, 5.52; N, 11.58.

EXAMPLE 248

2-(4-Fluorophenoxy)-a-[2-(4-methoxyphenyl)ethyl]-3-pyridinemethanol

A solution of 0.250 g (1.15 mmol) 2-(4-Fluorophenoxy)-3-pyridinecarboxaldehyde in 5 mL of tetrahydrofuran was cooled to −78° C. and treated dropwise with 1.0 mL of a solution of the Grignard reagent prepared from 2.62 g (15.3 mmol) of 1-(2-chloroethyl)-4-methoxybenzene and 0.559 g (23.0 mmol) of magnesium turinings in 13 mL of THF. After 2 h of stirring, an additional 0.5 mL of Grignard reagent was added, and the mixture was quenched by the addition of 2 mL of saturated aqueous NH$_4$Cl solution. After warming to rt, the mixture was partitioned between 50 mL of water and 200 mL of EtOAc, and the separated organic layer was washed with saturated aqueous sodium hydrogencarbonate solution, brine, dried (Na$_2$SO$_4$), and evaporated to give 0.53 g of a colorless oil. Two purifications by flash chromatography using 25% EtOAc-hexane and 25% ether-toluene, respectively, as eluants afforded 339 mg (64% yield) of the the title compound as an oil. Thermospray MS: m/e 354 (M$^+$+1).

EXAMPLE 249

1-[2-(4-Fluorophenoxy)-3-pyridinyl]-3-(4-methoxyphenyl)-1-propanone

A solution of 353 mg (1.00 mmol) 2-(4-Fluorophenoxy)-a-[2-(4-methoxyphenyl)ethyl]-3-pyridinemethanol in 5 mL of acetone was cooled to 0° C. and treated with 1.6 mL (2.00 mmol) of 1.25 M Jones Reagent solution. The mixture was allowed to warm to rt and then quenched by the addition of 5 mL of isopropanol. The precipitate was removed by filtration, and the filtrate was evaporated and partitioned between 50 mL of saturated aqueous sodium hydrogencarbonate solution and 100 mL of EtOAc. The separated organic layer was combined with a 100 mL EtOAc backwash of the aqueous layer, washed with brine (50 mL), dried (Na$_2$SO$_4$), and evaporated. Trituration of the residue in hexane gave 271 mg (77% yield) of the title compound, mp 73–74° C. $^1$H NMR (CDCl$_3$) d 3.03 (2H, t, J=7 Hz), 3.43 (2H, t, J=7 Hz), 3.78 (3H, s), 6.75–7.18 (9H, m), 8.17 (1H, dd, J=2.8 Hz), ), 8.25 (1H, dd, J=2.4 Hz); Anal. Calcd for C$_{21}$H$_{18}$NO$_3$F.0.25 H$_2$O; C, 70.87; H, 5.10; N, 3.94. Found: C, 70.88; H, 4.79; N, 3.79.

EXAMPLE 250

3-(2-Chlorophenyl)-1-[2-(4-fluorophenoxy)-3-pyridinyl]-1-propanone

A solution of 226 mg (0.496 mmol) a-[(2-Chlorophenyl)methyl]-2-(4-fluorophenoxy)-β-oxo-3-pyridinepropanoic Acid t-Butyl Ester in 5 mL of trifluoroacetic acid was stirred at rt for 4 h. The mixture was evaporated, and the residue was diluted with 5 mL of toluene, heated to reflux for 2 h, and evaporated. The residue was dissolved in 100 mL of EtOAc, washed successively with saturated aqueous sodium hydrogencarbonate solution (1×50 mL) and brine (1×50 mL), dried (Na$_2$SO$_4$), and and evaporated to 125 mg of an oil. Purification by flash chromatography using 40% etherhexane as eluant yield 120 mg (68% yield) of the title compound as a colorless oil. $^1$H NMR (CDCl$_3$) d 3.20 (2H, t, J=8 Hz), 3.49 (2H, t, J =8 Hz), 7.06–7.32 (9H, m), 8.19 (1H, dd, J=2.7 Hz), 8.25 (1H, dd, J=2.5 Hz); Thermospray MS (m/e) 356,358 (M$^+$+1).

The compounds of Examples 251–255 were prepared according to the procedure of Example 250 substituting the indicated substrate for the compound of Preparation 60. Mass spectra were determined by the thermospray method.

EXAMPLE 251

1-[2-(4-Fluoro-phenoxy)-pyridin-3-yl]-3-(4-fluoro-phenyl)-propan-1-one $^1$H NMR (CDCl$_3$) d 3.07 (2H, t, J=7 Hz), 3.45 (2H, t, J=7 Hz), 6.92–7.20 (9H, m), 8.18 (1H, dd, J=2.8 Hz), 8.25 (1H, dd, J=2.5 Hz); MS (m/e) 340 (M$^+$+1).

EXAMPLE 252

1-[2-(4-Fluoro-phenoxy)-pyridin-3-yl]-3-(4-trifluoromethyl-phenyl)-propan-1-one

M.P. 94–95° C.; Anal. Calcd for C$_{21}$H$_{15}$F$_4$NO$_2$: C, 64.78; H, 3.88; N, 3.60. Found: C, 64.44; H, 3.93; N, 3.45.

EXAMPLE 253

1-[2-(4-Fluoro-phenoxy)-pyridin-3-yl]-3-(4-trifluoromethoxy-phenyl)-propan-1-one M.P. 79–81° C.; Anal. Calcd for C$_{21}$H$_{15}$F$_4$NO$_3$: C, 62.23; H, 3.73; N, 3.46. Found: C, 62.11; H, 3.77; N, 3.57.

EXAMPLE 254

3-(3,5-Difluoro-phenyl)-1-[2-(4-fluoro-phenoxy)-pyridin-3-yl]-propan-1-one

M.P. 69–70° C.; Anal. Calcd for C$_{20}$H$_{14}$F$_3$NO$_2$: C, 67.22; H, 3.95; N, 3.92. Found: C, 67.19; H, 3.74; N, 3.92.

EXAMPLE 255

1-[2-(4-Fluoro-phenoxy)-pyridin-3-yl]-3-(2,4,6-trifluoro-phenyl)-propan-1-one

M.P. 84–85° C.; Anal. Calcd for C$_{20}$H$_{13}$F$_4$NO$_2$: C, 64.00; H, 3.49, N, 3.73. Found: C, 64.07; H, 3.31; N, 3.66.

EXAMPLE 256

1-[2-(4-Fluorophenoxy)-3-pyridinyl]-3-phenyl-1-propanone

To the sodium hydride obtained by washing 351 mg (7.73 mmol) of 50% sodium hydride dispersion in mineral oil with pentane was added 10 mL of dimethylformamide followed by 867 mg (7.73 mmol) of p-fluorophenol. After the hydrogen evolution ceased, 886 mg (3.87 mmol) 1-(2-Fluoropyridin-3-yl)-3-phenyl-propan-1-one was added dissolved in a minimum amount of DMF. The mixture was heated to 80° C. for 3 h, and the solvent was evaporated under high vacuum. The residue was partitioned between 200 mL of ether and 50 mL of aqueous 1 N sodium hydroxide solution, and the separated organic layer was washed with aqueous 1 N sodium hydroxide solution (1×50 mL), brine (1×100 mL), dried ($Na_2SO_4$), and evaporated to 1.16 g of a white solid. Recrystallization from hexane gave 1.06 g (85% yield) of the title compound as a white solid, mp 82–83° C. Anal. Calcd for $C_{20}H_{16}FNO_2$: C, 74.75; H, 5.02; N, 4.36. Found: C, 74.63; H, 4.97; N, 4.31.

The compounds of examples 257–270 were prepared according to the procedure of Example 256 substituting the indicated substrate for the compound of Preparation 63a and, when indicated, 3-hydroxypyridine for p-fluorophenol. Products were purified by direct trituration and/or flash chromatography. Mass spectra were determined by the APCI method.

EXAMPLE 257

3-Phenyl-1-[2-(pyridin-3-yloxy)-pyridin-3-yl]-propan-1-one

M.P. 45–46° C.; Anal. Calcd for $C_{19}H_{16}N_2O_2$: C, 74.98 H, 5.36; N, 9.20. Found: C, 74.80; H, 5.35; N, 9.11.

EXAMPLE 258

3-(4-Fluoro-phenyl)-1-[2-(pyridin-3-yloxy)-pyridin-3-yl]-propan-1-one

M.P. 62–64° C.; Anal. Calcd for $C_{19}H_{15}FN_2O_2$: C, 70.80; H, 4.69; N, 8.69. Found: C, 70.55; H, 4.80; N, 8.69.

EXAMPLE 259

1-[2-(4-Fluoro-phenoxy)-pyridin-3-yl]-2-methyl-3-phenyl-propan-1-one $^1$H NMR ($CDCl_3$) d 1.19 (3H, d, J=7 Hz), 2.92 (2H, ABX pattern, $J_{AB}$=13 Hz, $J_{AX}$=6 Hz, $J_{BX}$=8 Hz), 3.87–3.94 (1H, m), 7.02–7.24 (10H, m), 7.95 (1H, dd, J=2.7 Hz), 8.19 (1H, dd, J=2. 5 Hz); MS (m/e) 336 ($M^+$+1).

EXAMPLE 260

2-Methyl-3-phenyl-1-[2-(pyridin-3-yloxy)-pyridin-3-yl]-propan-1-one $^1$H NMR ($CDCl_3$) d 1.20 (3H, d, J=7 Hz), 2.93 (2H, ABX pattern, $J_{AB}$=14 Hz, $J_{AX}$=6 Hz, $J_{BX}$=8 Hz), 3.86–3.95 (1H, m), 7.06–7.49 (8H, m), 7.94–7.97 (1H, m), 8.16–8.18 (1H, m), 8.47–8.50 (2H, m); MS (m/e) 319 ($M^+$+1).

EXAMPLE 261

1-[2-(4-Fluoro-phenoxy)-pyridin-3-yl]-3-phenyl-butan-1-one $^1$H NMR ($CDCl_3$) d 1.31 (3H, d, J=7 Hz), 3.30–3.52 (3H, m), 7.02–7.27 (10H, m), 8.01 (1H, dd, J=2.8 Hz), 8.20 (1H, dd, J=2.5 Hz); MS (m/e) 336 ($M^+$+1).

EXAMPLE 262

3-Phenyl-1-[2-(pyridin-3-yloxy)-pyridin-3-yl]-butan-1-one $^1$H NMR ($CDCl_3$) d 1.31 (3H, d, J=7 Hz), 3.32–3.52 (3H, m), 7.06–7.53 (8H, m), 8.05 (1H, dd, J=2.8 Hz), 8.19 (1H, dd, J=2.5 Hz); 8.49–8.51 (2H, m); MS (m/e) 319 ($M^+$+1).

EXAMPLE 263

3-[4-(1-Hydroxy-1-methyl-ethyl)-phenyl]-1-[2-(pyridin-3-yloxy)-pyridin-3-yl]-propan-1-one $^1$H NMR ($CDCl_3$) d 1.54 (6H, s), 1.88 (1H, br s), 3.07 (2H, t, J=8 Hz), 3.44 (2H, t, J=8 Hz), 7.11–7.55 (7H, m), 8.17–8.21(2H, m), 8.21–8.49 (2H, m); MS (m/e) 345 ($M^+$+ 1–18 ($H_2O$)).

EXAMPLE 264

1-[2-(4-Fluoro-phenoxy)-pyridin-3-yl]-2-phenyl-ethanone

M.P. 81–82° C.; Anal. Calcd for $C_{19}H_{14}FNO_2$: C, 74.26; H, 4.59; N, 4.56. Found: C, 74.13; H, 4.61; N, 4.56.

EXAMPLE 265

1-[2-(4-Fluoro-phenoxy)-pyridin-3-yl]-2-phenoxy-ethanone

M.P. 105.5–106.5° C.; $^1$H NMR ($CDCl_3$) d 5.34 (2H, s), 6.73–7.28 (10H, m), 8.28–8.33 (2H, m); MS (m/e) 324 ($M^+$+1).

EXAMPLE 266

2-(2-Chloro-phenoxy)-1-[2-(4-fluoro-phenoxy)-pyridin-3-yl]-ethanone

M.P. 92–93° C.; Anal. Calcd for $C_{19}H_{13}NO_3ClF$: C, 63.79; H, 3.66; N, 3.91. Found: C, 63.43; H, 3.52; N, 3.94.

EXAMPLE 267

1-[2-(4-Fluoro-phenoxy)-pyridin-3-yl]-3-phenyl-propenone

M.P. 110–111° C.; $^1$H NMR ($CDCl_3$) d 7.07–7.58 (11H, m), 7.75 (1H, d, J=16 Hz), 8.13 (1H, dd, J=2,7 Hz), 8.27 (1H, dd, J=2,5 Hz); MS (m/e) 320 ($M^+$+1).

EXAMPLE 268

Benzofuran-2-yl-[2-(4-fluoro-phenoxyl-pyridin-3-yl]-methanone

M.P. 102–103° C.; Anal. Calcd for $C_{20}H_{12}NO_3F$: C, 72.07; H, 3.63; N, 4.20. Found: C, 71.84; H, 3.43; N, 4.15.

EXAMPLE 269

[2-(4-Fluoro-phenoxy)-pyridin-3-yl]-(1H-indol-2-yl)-methanone

M.P. 169–170° C.; $^1$H NMR ($CDCl_3$) d 7.04–7.17 (7H, m), 7.36 (1H, dd, J=1.8 Hz), 7.46 (1H, d, J=8 Hz), 7.67 (1H, d, J=8 Hz), 7.95 (1H, dd, J=2, 8 Hz), 8.28 (1H, dd, J=2.5 Hz), 9.20 (1H, s); MS (m/e) 333 ($M^+$+1).

EXAMPLE 270

1-[2-(4-Fluoro-phenoxy)-pyridin-3-yl]-2-(methyl-phenyl-amino)-ethanone

M.P. 126–128° C.; $^1$H NMR ($CDCl_3$) d 3.10 (3H, s), 4.85 (2H, s), 6.61–6.73 (3H, m), 7.09–7.21 (7H, m), 8.22 (1H, dd, J=2.8 Hz), 8.27 (1H, dd, J=2.5 Hz); MS (m/e) 337 ($M^+$+1).

EXAMPLE 271

1-[2-(4-Fluorophenoxy)-3-pyridinyl]-3-hydroxy-3-phenyl-1-propanone

A solution of 0.114 mL (111 mg, 1.10 mmol) of diisopropylamine in 8 mL of tetrahydrofuran was cooled to −78°

C. and treated dropwise with 0.440 mL (1.10 mmol) of a solution of 2.5 M n-butyllithium in hexane. After stirring for 30 min, a solution of 231 mg (1.00 mmol) 1-[2-(4-Fluorophenoxy)-3-pyridinyl]-ethanone in 2 mL of tetrahydrofuran was added dropwise. After stirring for 30 min, 0.112 mL (1.07 mmol) of benzaldehyde was added dropwise, and stirring was continued for 1 h. The mixture was quenched by the addition of 2 mL of saturated aqueous NH$_4$Cl solution and was allowed to warm to rt. The mixture was partitioned between 50 mL of saturated aqueous NH$_4$Cl solution and 300 mL of EtOAc. The separated organic layer was washed with 50 mL of saturated aqueous sodium hydrogencarbonate solution, 50 mL of brine, dried (Na$_2$SO$_4$), and evaporated to 259 mg of an oil. Purification by flash chromatography using a 40% EtOAc-hexane eluant afforded 211 mg (63% yield) of the title compound as an oil; $^1$H NMR (CDCl$_3$) d 3.23 (1H, br s), 3.54–3.56 (2H, m), 5.34–5.37 (1H, m), 7.07–7.41 (10H, m), 8.21–8.26 (2H, m); APCI MS (m/e) 338 (M$^+$+1).

EXAMPLE 272

1-[2-(3-Pyridyloxy)-3-pyridinyl]-3-hydroxy-3-phenyl-1-propanone $^1$H NMR (CDCl$_3$) d 3.29 (1H, br s), 3.52–3.57 (2H, m), 5.35–5.38 (1H, m), 7.13–7.51 (8H, m), 8.23–8.26 (2H, m), 8.46–8.49 (2H, m); APCI MS (m/e) 321 (M$^+$+1).

EXAMPLE 273 a-[2-(2-Chlorophenyl)ethyl]-2-(4-fluorophenoxy)-3-pyridinemethanol

A solution of 76.0 mg (0.214 mmol) 3-(2-Chlorophenyl)-1-[2-(4-fluorophenoxy)-3-pyridinyl]-1-propanone in 5 mL of methanol was cooled to 0° C. and treated with 8.0 mg (0.21 mmol) of NaBH$_4$. The mixture was stirred for 30 min at 0° C. and quenched by the addition of 1 mL of aqueous 1 N hydrochloric acid solution. The mixture was evaporated, and the residue was partitioned between 100 mL of EtOAc and 50 mL of saturated aqueous sodium hydrogencarbonate solution. The organic layer was washed with brine, dried (Na$_2$SO$_4$), and evaporated to give 79 mg (100%) of the title compound as an oil. $^1$H NMR (CDCl$_3$) d 2.10–2.32 (2H, m), 2.35 (1H, d, J=6 Hz), 2.83–3.08 (2H, m), 5.06–5.15 (1H, m), 7.01–7.33 (9H, m), 7.85 (1H, dd, J=2, 7 Hz), 8.05 (1H, dd, J=2, 5 Hz); thermospray MS (m/e) 358 and 360 (M$^+$+1).

The compounds of Examples 274–276 were prepared according to the procedure of Example 273 substituting the indicated substrate for the compound 3-(2-Chlorophenyl)-1-[2-(4-fluorophenoxy)-3-pyridinyl]-1-propanone.

EXAMPLE 274

1-[2-(4-Fluoro-phenoxy)-pyridin-3-yl]-3-(2,4,6-trifluoro-phenyl)-propan-1-ol

M.P. 90–91° C.; $^1$H NMR (CDCl$_3$) d 2.00–2.20 (2H, m), 2.31 (1H, d, J=5 Hz), 2.71–2.90 (2H, m), 4.98–5.08 (1H, m), 6.56–6.61 (2H, m), 6.99–7.10 (5H, m), 7.81 (1H, dd, J=1, 8 Hz), 8.02 (1H, dd, J=2, 5 Hz); thermospray MS (m/e) 378 (M$^+$+1).

EXAMPLE 275

1-[2-(4-Fluoro-phenoxy)-pyridin-3-yl]-3-phenyl-propan-1-ol $^1$H NMR (CDCl$_3$) d 2.10–2.25 (2H, m), 2.20 (1H, br s), 2.72–2.92 (2H, m), 5.01–5.09 (1H, m), 6.99–7.30 (10H, m), 7.79 (1H, dd, J=1, 7 Hz), 8.03 (1H, dd, J=2, 5 Hz); AMPI MS (m/e) 324 (M$^+$+1).

EXAMPLE 276

3-Phenyl-1-[2-(pyridin-3-yloxy)-pyridin-3-yl]-propan-1-ol $^1$H NMR (CDCl$_3$) d 2.08–2.23 (2H, m), 2.60 (1H, br s), 2.73–2.89 (2H, m), 5.07–5.12 (1H, m), 7.04–7.48 (8H, m), 7.86–7.89 (1H, m), 8.01 (1H, dd, J=2, 5 Hz), 8.40–8.43 (2H, m); AMPI MS (m/e) 307 (M$^+$+1).

EXAMPLE 277

(E)-2-(4-Fluorophenoxy)-3-[3-(4-methoxyphenyl)-1-propenyl]-pyridine

A mixture of 0.97 g (2.7 mmol) 2-(4-Fluorophenoxy)-a-[2-(4-methoxyphenyl)ethyl]-3-pyridinemethanol, 0.93 g (3.9 mmol) of Burgess Reagent, and 20 mL of benzene was heated to reflux for 4 h. The cooled mixture was partitioned between 300 mL of EtOAc and 100 mL of saturated aqueous sodium hydrogencarbonate solution, and the separated organic layer was washed with 100 mL of brine, dried (Na$_2$SO$_4$), and evaporated to 1.10 g of an oil. Purification by flash chromatography using 15% EtOAc-hexane as eluant gave 0.39 g (42% yield) of the title compound as an oil. $^1$H NMR (CDCl$_3$) d 3.60 (2H, d, J=7 Hz), 3.82 (3H, s), 6.48 (1H, dt, J=7, 16 Hz), 6.78 (1H, d, J=16 Hz), 6.86–7.18(9H, m), 7.79 (1H, dd, J=2, 8 Hz), 7.99 (1H, dd, J=2, 5 Hz).

Example 278 was prepared according to the procedure of Example 277 substituting the corrsponding alcohol for 2-(4-Fluorophenoxy)-a-[2-(4-methoxyphenyl)ethyl]-3-pyridinemethanol.

EXAMPLE 278

(E)-2-(4-Fluorophenoxy)-3-[3-phenyl-1-propenyl]-pyridine $^1$H NMR (CDCl$_3$) d 3.62 (2H, d, J=7 Hz), 6.51 (1H, dt, J=7, 16 Hz), 6.81 (1H, d, J=16 Hz), 6.83–7.35 (10H, m), 7.78 (1H, dd, J=2, 8 Hz), 8.00 (1H, dd, J=2, 5 Hz), AMPI MS (m/e) 306 (M$^+$+1).

EXAMPLE 279 syn-3-[1,2-Dihydroxy-3-(4-methoxyphenyl)propyl]-2-(4-fluorophenoxy)-pyridine

To a mixture of 161 mg (1.19 mmol) of N-methylmorpholine-N-oxide hydrate, 0.175 g (0.0175 mmol) of a 2.5% solution of OsO$_4$ in t-butanol, 0.6 mL of acetone, and 0.4 mL of water was added 200 mg (0.596 mg) (E)-2-(4-Fluorophenoxy)-3-[3-phenyl-1-propenyl]-pyridine dissolved in 2 mL of acetone and 0.5 mL of water. The mixture was stirred for 16 h at rt, at which time 5 g of solid sodium sulfite was added. The suspension was stirred for 5 min, and the solids were removed by filtration rinsing with 100 mL of acetone. The filtrate was concentrated, and the residue was partitioned between 100 mL of EtOAc and 50 mL of brine, The organic layer was separated, combined with a 100 mL EtOAc backwash of the aqueous layer, dried (Na$_2$SO$_4$), and evaporated to 195 mg of a solid. Recrystallization from toluene gave 140 mg (64% yield) of the title compound as a white solid, mp 125–126° C. $^1$H NMR (CDCl$_3$) d 2.13 (1H, d, J=4 Hz), 2.87 (2H, d, J=6 Hz), 2.94 (1H, d, J=6 Hz), 3.78 (3H, s), 4.05–4.14 (1H, m), 5.02 (1H, t, J=5 Hz), 6.80–7.16 (9H, m), 7.89 (1H, dd, J=2,7 Hz), 8.08 (1H,dd, J=2, 4 Hz).

Example 280 was prepared according to the procedure of Example 279 substituting the corresponding starting material.

EXAMPLE 280 syn-3-(1,2-Dihydroxy-3-phenylpropyl)-2-(4-fluorophenoxy)-pyridine

M.P. 125–126° C.; Anal. Calcd for $C_{20}H_{18}NO_3F$: C, 70.78 H, 5.35; N, 4.13. Found: C, 70.68; H, 5.19; N, 4.24.

EXAMPLE 281

3-[(Benzyloxy)methyl]-2-(4-fluorophenoxy)-pyridine

To a suspension of 122 mg (2.53 mmol) of 50% sodium hydride dispersion in mineral oil in 10 mL of dimethylformamide was added 500 mg (2.30 mmol) 2-(4-Fluorophenoxy)-3-pyridinemethanol followed by 0.343 mL (396 mg, 2.53 mmol) of 4-methoxybenzyl chloride and 420 mg (2.53 mmol) of KI. After stirring 1 h at rt, the mixture was partitioned between 100 mL of water and 100 mL of EtOAc. The separated organic layer was washed with brine, dried ($Na_2SO_4$), and evaporated to 949 mg of a yellow oil. Purification by flash chromatography using a 20% EtOAc-hexane eluant gave 552 mg of a colorless oil which solidified on standing. Trituration in hexane afforded 464 mg (59% yield) of the title compound as a white solid, mp 49–50° C. Anal. Calcd for $C_{20}H_{18}NO_3F$: C, 70.78 H, 5.35; N, 4.13. Found: C, 70.79; H, 5.09; N, 4.03.

EXAMPLE 282

1-[2-(4-Fluorophenoxy)-3-pyridinyl]-3-(4-methoxyphenyl)propane

To a solution of 60 mg (0.18 mmol) (E)-2-(4-Fluorophenoxy)-3-[3-(4-methoxyphenyl)-1-propenyl]-pyridine in 50 mL of ethanol was added 50 mg of 10%Pd/C, and the mixture was hydrogenated at 45 psi on a Parr Shaker Apparatus for 2 h. The catalyst was removed by filtration, and the filtrate was concentrated to afford 50 mg (83% yield) of the title compound as a colorless oil. $^1H$ NMR ($CDCl_3$) d 1.92–2.06 (2H, m), 2.67 (2H, t, J=8 Hz), 2.75 (2H, t, J=8 Hz), 3.80 (3H, s), 6.82–7.14 (9H, m), 7.52 (1H, dd, J=2, 7 Hz), 7.99 (1H, dd, J=2, 5 Hz); thermospray MS: m/e 338 ($M^++1$).

EXAMPLE 283

N-(2-Chloro-benzyl)-2-(3-methoxy-phenoxy)-nicotinamide

To a solution of 2-(3-methoxy-phenoxy)-nicotinic acid (0,300 grams, 1.224 mmole) 2-Chloro-benzylamine (0.166 grams, 1.160 mmole), and 1-hydroxybenzotriazole hydrate (0.173 grams, 1.283 mmole) in dry dimethylformamide (30 ml) was added 1-(3-dimethylamino)-propyl)-3-ethylcarbodiimide hydrochloride (0.269 grams, 1.399 mmole) and stirred over night. The mixture was diluted with 200 ml water and extracted with ethyl acetate. The combined extracts were washed with water and brine, dried over $MgSO_4$, filtered and concentrated to give an oil that was purified by chromatography on silica eluting with 30% ethyl acetate/hexane to give an oil which solidified on standing. (0.300 g). M.P. 71–74° C.; Anal. calcd. for $C_{20}H_{17}N_2O_3Cl$: C, 65.13; H, 4.65; N, 7.60. Found: C, 64.94; H, 4.69; N, 7.63.

EXAMPLE 284

N-[4-(1-Hydroxy-1-methyl-ethyl)-benzyl]-2-(1-oxo-indan-4-yloxy)-nicotinamide

To a solution of 2-(1-Oxo-indan-4-ylmethoxy)-nicotinic acid (0.220 grams, 0.818 mmole), 2-(4-Aminomethyl-phenyl)-propan-2-ol (0.128 grams, 0.779 mmole), and 1-hydroxybenzotriazole hydrate (0.116 grams, 0.857 mmole) in dry dimethylformamide (30 ml) was added 1-(3-dimethylamino)-propyl)-3-ethylcarbodiimide hydrochloride (0.1795 grams, 0.935 mmole) and stirred over night. The mixture was diluted with water and extracted with ethyl acetate. The combined extracts were washed with water and brine, dried over $MgSO_4$, filtered and concentrated to give an oil that was purified by chromatography on silica eluting with 60% ethyl acetate/hexane to give a yellow solid. (0.078 g). M.P. 145–147° C.; Anal. calcd. for $C_{25}H_{24}N_2O_4$: C, 72.10; H, 5.81; N, 6.73. Found: C, 71.79; H, 5.67; N, 6.61.

EXAMPLE 285

N-[4-Acetyl-benzyl)-2-(4-fluoro-phenoxy)-nicotinamide

A solution of 2-(4-Fluoro-phenoxy)-N-[4-(2-methyl-[1,3]dioxolan-2-yl)-benzyl]-nicotinamide (1.2 grams, 2.9 mmole) in 2 $\underline{N}$ hydrochloric acid (3.7 ml, 7.35 mmole) and tetrahydrofuran (30 ml) was stirred at room temperature for 3 hours. The mixture was diluted with 100 ml water and extracted with ethyl acetate. The combined extracts were washed with 1N NaOH, water and brine, dried over $MgSO_4$, filtered and concentrated to give a solid which was recrystalized from ethyl acetate/hexane to give a white solid. (0.78 0 g). M.P. 106–108° C.; Anal. calcd. for $C_{21}H_{17}N_2O_3F$: C, 69.22; H, 4.70; N, 7.69. Found: C, 68.87; H, 4.70; N, 7.55.

The compound of Example 286 was prepared according to the procedure of Example 285 substituting the corresponding ketal for 2-(4-Fluoro-phenoxy)-N-[4-(2-methyl-[1,3]dioxolan-2-yl)-benzyl]-nicotinamide. The duration of reaction was between 1 and 24 hours.

EXAMPLE 286

2-(4-Fluoro-phenoxy)-N-(4-oxo-cyclohexylmethyl)-nicotinamide

M.P. 157–159° C.; MS: m/e 343 ($M^++1$).

EXAMPLE 287

2-(4-Fluoro-phenoxy)-N-[4-(1-hydroxy-ethyl)-benzyl]-nicotinamide

To a stirred solution of N-(4-Acetyl-benzyl)-2-(4-fluoro-phenoxy)-nicotinamide (0.300 grams, 0.823 mmole) in methanol (10 ml) and tetrahydrofuran (10 ml) at room temperature was added sodium borohydride (0.121 grams, 3.993 mmole) and stirred for 1 hour. This mixture was poured into ice water and extracted with ethyl acetate. The combined organics were washed with water and brine, dried over $MgSO_4$, filtered and concentrated to give a solid. Recrystalization from ethyl acetate/hexane gave a solid. (0.180 g). M.P. 112–114° C.; Anal. calcd. for $C_{21}H_{17}N_2O_3F$: C, 68.84; H, 5.23, N, 7.65. Found: C, 68.58; H, 5.15; N, 7.44.

The compound of Example 288 was prepared according to the procedure of Example 289 substituting the corresponding ketone for N-(4-Acetyl-benzyl)-2-(4-fluoro-phenoxy)-nicotinamide. The duration of reaction was between 1 and 24 hours.

EXAMPLE 288

2-(4-Fluoro-phenoxy)-N-(4-hydroxy-cyclohexylmethyl)-nicotinamide

M.P. 110–112° C.; MS: m/e 345 (M$^+$+1).

EXAMPLE 289

2-(3-Carbamoyl-phenoxy)-N-(2-chloro-benzyl)-nicotinamide

To a stirred solution of 2-(3-Carbamoyl-phenoxy)-N-(2-chloro-benzyl)-nicotinic acid (0.300 grams, 1.25 mmole), o-chlorobenzylamine (0.195 grams, 1.375 mmole), and 1-hydroxybenzotriazole hydrate (0.203 grams, 1.50 mmole) in dry dimethylformamide (3 ml) was added 1-(3-dimethylamino)-propyl)-3-ethylcarbodiimide hydrochloride (0.311 grams, 1.63 mmole) and stirred over night. The mixture poured into 100 ml water and extracted with ethyl acetate. The combined extracts were washed with 1 $\underline{N}$ NaOH, water and brine, dried over $Na_2SO_4$, filtered and concentrated to give a white solid that was purified by chromatography on silica gel eluting with 7% methanol/methylene chloride. Recrystalization from ethyl acetate/hexane gave a white solid (0.239 g). M.P. 153–155° C.; Anal. calcd. for $C_{20}H_{16}N_3O_3Cl$: C, 62.91; H, 4.22; N, 11.01. Found: C, 62.92; H, 4.30; N, 11.09.

EXAMPLE 290

2-(3-Dimethylcarbamoyl-phenoxy)-N-[4-(1-hydroxy-1-methyl-ethyl)-benzyl]-nicotinamide To a stirred solution of 2-(3-Dimethylcarbamoyl-phenoxy)-N-[4-(1-hydroxy-1-methyl-ethyl)-benzyl]-nicotinic acid (0.300 grams, 1.05 mmole), 2-(4-Aminomethyl-phenyl)-propan-2-ol (0.190 grams, 1.15 mmole), and 1-hydroxybenzotriazole hydrate (0.155 grams, 1.15 mmole) in dry dimethylformamide (5 ml) was added 1-(3-dimethylamino)-propyl)-3-ethylcarbodiimide hydrochloride (0.242 grams, 1.26 mmole) and stirred over night. The mixture poured into 100 ml water and extracted with ethyl acetate. The combined extracts were washed with 1 $\underline{N}$ NaOH, water and brine, dried over $MgSO_4$, filtered and concentrated to give an oil that was purified by chromatography on silica gel eluting with 2.5% methanol/methylene chloride (0.360 g). $^1$H NMR (CDCl$_3$) d 1.54 (6H, s), 3.00 (3H, s), 3.08 (3H, s), 4.66 (2H, d), 7.20 (3H, m), 7.29 (4H, m), 7.43 (2H, m) 8.08 (1H, m), 8.18 (1H, dd), 8.63 (1H, dd); MS: m/e 433 (M$^+$).

EXAMPLE 291

N-[4-(1-Hydroxy-1-methyl-ethyl)-benzyl]-2-(3-trifluoroacetyl-phenoxy)-nicotinamide To a stirred solution of N-[4-(1-Hydroxy-1-methyl-ethyl)-benzyl]-2-[3-(2,2,2-trifluoro-1-hydroxy-ethyl)-phenoxy]-nicotinamide (0.520 grams, 1.13 mmole), NMO (0.192 grams, 1.7 mmole) and 4 Å molecular sieves (0.5 g) in methylene chloride (15 ml) was added TPAP (0.020 grams, 0.06 mmole) and stirred at room temperature for 1 hour. The mixture was filtered through celite, washed with methylene chloride. The filtrate was diluted with 150 ml methylene chloride, washed with water, dried over $MgSO_4$, filtered and concentrated under reduced pressure to give an oil which was purified by chromatography on silica eluting with 2.5% methanol methylene chloride to give a foam (0.506 g). $^1$H NMR (CDCl$_3$) d 1.54 (6H, s), 4.69 (2H, d), 7.50–7.15 (9H, m), 8.16 (1H, m), 8.64 (1H, m); MS: m/e 458 (M$^+$).

EXAMPLE 292

N-[4-(1-Hydroxy-1-methyl-ethyl)-benzyl]-2-[3-(2,2,2-trifluoro-1-hydroxy-ethyl)-phenoxy]nicotinamide To a stirred solution of N-[4-(1-Hydroxy-1-methyl-ethyl)-benzyl]-2-[3-(2,2,2-trifluoro-1-hydroxy-ethyl)-phenoxy]-nicotinic acid (0.400 grams, 1.28 mmole), 2-(4-Aminomethyl-phenyl)-propan-2-ol (0.232 grams, 1.40 mmole), and 1-hydroxybenzotriazole hydrate (0.189 grams, 1.40 mmole) in dry dimethylformamide (5 ml) was added 1-(3-dimethylamino)-propyl)-3-ethylcarbodiimide hydrochloride (0.294 grams, 1.54 mmole) and stirred over night. The mixture poured into 100 ml water and extracted with ethyl acetate. The combined extracts were washed with water and brine, dried over $MgSO_4$, filtered and concentrated to give an oil that was purified by chromatography on silica gel eluting with 2.5% methanol/methylene chloride (0.550 g). $^1$H NMR (CDCl$_3$) d 1.54 (6H, s), 3.53 (1H, d), 4.66 (2H, d), 4.92 (1H, m), 7.46–7.15 (9H, m), 8.12 (1H, m), 8.16 (1H, dd) 8.62 (1H, dd). MW 313.25 MS (m/e) 313 (M$^+$).

EXAMPLE 293

2-(Benzo[1,3]dioxol-5-yloxy)-N-[4-(1-hydroxy-1-methyl-ethyl)-benzyl]-nicotinamide To a stirred solution 2-(Benzo[1,3]dioxol-5-yloxy)-nicotinic acid (0.300 grams, 1.158 mmole 2-(4-Aminomethyl-phenyl)-propan-2-ol (0.182 grams, 1.103 mmole), and 1-hydroxybenzotriazole hydrate (0.163 grams, 1.20 mmole) in dry dimethylformamide (15 ml) was added 1-(3-dimethylamino)-propyl)-3-ethylcarbodiimide hydrochloride (0.254 grams, 1.32 mmole) and stirred over night. The mixture was diluted with 200 ml water and extracted with ethyl acetate. The combined organics were washed with water, 1$\underline{N}$ sodium hydroxide and brine, dried over $MgSO_4$, filtered and concentrated to give an oil that was purified by chromatography on silica eluting with 30% ethyl acetate/hexane to give an oil. Recrystalization from ethyl acetate/hexane gave a white solid (0.323 g). M.P. 118–120° C.; MS 407 (M$^+$+1).

EXAMPLE 294

2-(3-Carbamoyl-phenoxy)-N-[4(1-hydroxy-1-methyl-ethyl)-benzyl]-nicotinamide

To a stirred solution of 2-(3-Carbamoyl-phenoxy)-N-[4-(1-hydroxy-1-methyl-ethyl)-benzyl]-nicotinic acid (0.400 grams, 1.549 mmole), 2-(4-Aminomethyl-phenyl)-propan-2-ol (0.243 grams, 1.475 mmole), and 1-hydroxybenzotriazole hydrate (0.219 grams, 1.623 mmole) in dry dimethylformamide (15 ml) was added 1-(3-dimethylamino)-propyl)-3-ethylcarbodiimide hydrochloride (0.3401 grams, 1.77 mmole) and stirred over night. The mixture poured into water and extracted with ethyl acetate. The combined extracts were washed with 1 $\underline{N}$ NaOH, water and brine, dried over $Na_2SO_4$, filtered and concentrated to give an oil that was purified by chromatography on silica gel eluting with 7% methanol/methylene chloride (0.250 g). M.P. 145–147° C.; MS (m/e) 387 (M$^+$–18).

The compound of Example 295 was prepared according to the procedure of Example 294 substituting the corresponding amine for 2-(4-Aminomethyl-phenyl)-propan-2-ol. The duration of reaction was between 1 and 24 hours.

EXAMPLE 295

4-({[2-(3-Carbamoyl-phenoxy)-pyridine-3-carbonyl]-amino}-methyl)-cyclohexanecarboxylic acid ethyl ester M.P.160–162° C.; MS (m/e) 426 (M$^+$+1).

EXAMPLE 296

2-(3-Acetyl-phenoxy)-N-(4-sulfamoyl-benzyl)-nicotinamide

A solution of 4-Aminomethyl-benzenesulfonamide (0.248 grams, 1.11 mmole), 2-(3-Acetyl-phenoxy)-nicotinic acid (0.300 grams, 1.167 mmole), 1-hydroxybenzotriazole hydrate (0.165 grams, 1.22 mmole) and 1-(3-dimethylamino)-propyl)-3-ethylcarbodiimide hydrochloride (0.256 grams, 1.33 mmole) in dimethylformamide (15 ml) was stirred for 10 minutes. To the stirring solution was added triethyl amine (0.280 grams, 2.78 mmole) and stirred over night at room temperature. The mixture was diluted with ethyl acetate and washed with water and brine, dried over MgSO$_4$, filtered and concentrated to give a solid. Recrystalization from ethyl acetate/hexane gave a solid. (0.280 g); M.P.162–164° C.; MS (m/e) 425 (M$^+$).

EXAMPLE 297

2-(4-Fluoro-phenoxy)-N-[4-(1-hydroxy-1-methyl-ethyl)-cyclohex-1-enylmethyl]-nicotinamide A solution of 2-(4-Aminomethyl-cyclohex-3-enyl)-propan-2-ol (0.360 grams, 2.127 mmole), 2-diethylaminoethyl chloride hydrochloride (0.530 grams, 2.765 mmole), 2-(4-Fluoro-phenoxy)-nicotinic acid (0.645 grams, 2.765 mmole), 1-hydroxybenzotriazole hydrate (0.374 grams, 2.765 mmole) and triethyl amine (0.430 grams, 4.254 mmole) in methylene chloride (40 ml) was added and stirred over night. The mixture was concentrated and partitioned between ethyl acetate and 1 N HCl. The organic extracts were washed with saturated sodium hydrogencarbonate and brine, dried over MgSO$_4$, filtered and concentrated to give an oil which was purified by chromatography on silica eluting with 50% ethyl acetate/hexane to 100% ethyl acetate to give a yellow oil (0.080 g); M.W. 384.455; MS 385 (M$^+$+1).

Compounds in Examples 298–317 were synthesized in a manner analogous to that in Example 183 using the indicated carboxylic acid and amine.

EXAMPLE 298

N-(4-( -Hydroxy-1-methyl-ethyl-)-benzyl)-2-(3-oxo-indan-5-yloxy)-nicotinamide

Prepared from 2-(3-Oxo-indan-5-yloxy)-nicotinic acid and 2-(4-aminomethyl-phenyl)-propan-2-ol. MS (m/e): 435 (M$^+$+NH$_3$), 417 (M$^+$+1), 400 (100). NMR (CDCl$_3$): 8.62 (dd, J=2,8 Hz, 1H), 8.15 (dd, J=2,5 Hz, 1H), 8.07 (m, 1H), 7.32 (m, 8H), 4.67 (d, J=6 Hz, 2H), 313 (t, J=6 Hz, 2H), 2.72 (dt, J=2,4 Hz, 2H), 1.53 (s, 6H).

EXAMPLE 299

N-(4-(1-Hydroxy-1-methyl-ethyl-)-benzyl)-2-(2-methyl-benzothiazol-5-yloxy)-nicotinamide Prepared from 2-(2-Methyl-benzothiazol-5-yloxy)-nicotinic acid and 2-(4-amino-methyl-phenyl)-propan-2-ol. mp 124–6° C.

Anal. Calcd. for C$_{24}$H$_{23}$N$_3$SO$_3$: C, 66.49; H, 5.35; N, 9.69. Found: C, 66.34; H, 5.38; N, 9.57.

EXAMPLE 300

N-(4-(1-Hydroxy-1-methylethyl-)-benzyl)-2-(2-methyl-benzothiazol-6-yloxy)-nicotinamide Prepared from 2-(2-Methyl-benzothiazol-6-yloxy)-nicotinic acid and 2-(4-amino-ethyl-phenyl)-propan-2-ol. mp 131–3° C.

Anal. Calcd. for C$_{24}$H$_{23}$N$_3$SO$_3$: C, 66.49; H, 5.35; N, 9.69. Found: C, 66.43; H, 5.42; N, 9.72.

EXAMPLE 301

2-(Benzothiazol-6-yloxy)-N-(4-(1-hydroxy-1-methyl-ethyl)-benzyl)-nicotinamide

Prepared from 2-(Benzothiazol-6-yloxy)-nicotinic acid and 2-(4-aminomethyl-phenyl)-propan-2-ol. mp195–7° C.

Anal. Calcd. for C$_{23}$H$_{21}$N$_3$SO$_3$: C, 65.85; H, 5.05; N, 10.02. Found: C, 68.74; H, 5.49; N, 9.96.

EXAMPLE 302

2-(Benzooxazol-6-yloxy)-N-(4-(1-hydroxy-1-methyl-ethyl)-benzyl)-nicotinamide

Prepared from 2-(Benzooxazol-6-yloxy)-nicotinic acid and 2-(4-aminomethyl-phenyl)-propan-2-ol. mp 92–4° C.

Anal. Calcd. for C$_{23}$H$_{21}$N$_3$O$_4$: C, 68.47; H, 5.25; N, 10.42. Found: C, 68.47; H, 5.32; N, 10.42.

EXAMPLE 303

2-(3-Acetyl-4-chloro-phenoxy)-N-(4-(1-hydroxy-1-methyl-ethyl)-benzyl)-nicotinamide Prepared from 2-(3-Acetyl-4-chloro-phenoxy)-nicotinic acid and 2-(4-aminomethyl-phenyl)-propan-2-ol. MS (m/e): 456/458 (M$^+$+NH$_3$, 100). NMR (CDCl$_3$): 8.64 (dd, J=2,8 Hz, 1H), 8.18 (dd, J=2,5 Hz, 1H), 7.95 (m, 1H), 7.46 (m, 3H), 7.31 (m, 3H), 7.19 (m, 2H), 4.68 (d, J=6 Hz, 2H), 2.66 (s, 3H), 1.56 (s, 6H).

EXAMPLE 304

N-(4-(1-Hydroxy-1-methyl-ethyl)-benzyl)-2-(3-methyl-benzo(d)isoazol-7-yloxy)-nicotinamide Prepared from 2-(3-Methyl-benzo-(d)isoxazol-7-yloxy)-nicotinic acid and 2-(4-aminomethyl-phenyl)-propan-2-ol. mp 194–6° C.

Anal. Calcd. for C$_{24}$H$_{23}$N$_3$O$_4$: C, 69.05; H, 5.55; N, 10.07. Found: C, 68.70; H, 5.64; N, 9.81.

EXAMPLE 305

2-(3-Acetyl-5-chloro-phenoxy)-N-(4-(1-Hydroxy-1-methyl-ethyl)-benzyl)-nicotinamide Prepared from 2-(3-Acetyl-5-chloro-phenoxy)-nicotinic acid and 2-(4-amino-methyl-phenyl)-propan-2-ol. mp 110–2° C.

Anal. Calcd. for C$_{24}$H$_{23}$N$_2$O$_4$Cl: C, 65.68; H, 5.28; N, 6.38. Found: C, 65.69; H, 5.35; N, 6.35.

EXAMPLE 306

(S)-(-)-2-(3-Acetyl-phenoxy)-N-(4-(1-hydroxy-ethyl)-benzyl)-nicotinamide

Prepared from 2-(3-Acetyl-phenoxy)-nicotinic acid and (S)-(-)-1-(4-Aminomethyl-cyclohexyl)-ethanol. mp 102–4° C. α$_D$ (CHCl$_3$) –13.8°.

Anal. Calcd. for $C_{23}H_{22}N_2O_4$: C, 70.75; H, 5.68; N, 7.17. Found: C, 70.48; H, 5.70; N, 7.12.

EXAMPLE 307

(R)-(+)-2-(3-Acetyl-phenoxy)-N-(4-(1-hydroxy-ethyl)-benzyl)-nicotinamide

Prepared from 2-(3-Acetyl-phenoxy)-nicotinic acid and (R)-(+)-1-(4-Aminomethyl-cyclohexyl)-ethanol. mp 104–6° C. $\alpha_D$ (CHCl$_3$) +14.0°.

Anal. Calcd. for $C_{23}H_{22}N_2O_4$: C, 70.75; H, 5.68; N, 7.17. Found: C, 70.30; H, 5.71; N, 7.10.

EXAMPLE 308

2-(3-Acetyl-5-chloro-phenoxy)-N-(trans-4-(1-hydroxy-1-methyl-ethyl)-cyclohexylmethyl)-nicotinamide Prepared from 2-(3-Acetyl-5-chloro-phenoxy)-nicotinic acid and trans-2-(Amino-methyl-cyclohexyl)-propan-2-ol. mp 133–5° C.

Anal Calcd. for $C_{24}H_{29}N_2O_4Cl$: C, 64.78; H, 6.57; N, 6.30. Found: C, 64.75; H, 6.57; N, 6.17.

EXAMPLE 309

2-(3-Acetyl-4-chloro-phenoxy)-N-(trans-4-(1-hydroxy-1-methyl-ethyl)-cyclohexylmethyl)-nicotinamide Prepared from 2-(3-Acetyl-4-chloro-phenoxy)-nicotinic acid and trans-2-(Amino-methyl-cyclohexyl)-propan-2-ol. mp 106–8° C.

Anal Calcd. for $C_{24}H_{29}N_2O_4Cl$: C, 64.78; H, 6.57; N, 6.30. Found: C, 64.66; H, 6.58; N, 6.11.

EXAMPLE 310

(R)-(−)-2-(3-Acetyl-phenoxy)-N-(trans-4-(1-hydroxy-ethyl)-cyclohexylmethyl)-nicotinamide Prepared from 2-(3-Acetyl-phenoxy)-nicotinic acid and (R)-(−)-trans-1-(4-Amino-ethyl-cyclohexyl)-ethanol. mp 101–3° C. $\alpha_D$ (CHCl$_3$) −1.5°.

EXAMPLE 311

(S)-(+)-2-(3-Acetyl-phenoxy)-N-(trans-4-(1-hydroxy-ethyl)-cyclohexylmethyl-nicotinamide Prepared from 2-(3-Acetyl-phenoxy)-nicotinic acid and (S)-(+)-trans-1-(4-Aminomethyl-cyclohexyl)-ethanol. mp 103–5° C. $\alpha_D$ (CHCl$_3$) +1.5°.

EXAMPLE 312

2-(3-Acetyl-phenoxy)-N-(2-fluoro-4-(1-hydroxy-1-methyl-ethyl)-benzyl)-nicotinamide Prepared from 2-(3-Acetyl-phenoxy)-nicotinic acid and 2-(4-Aminomethyl-3-fluoro-phenyl)-propan-2-ol. mp 68–70° C.

Anal. Calcd. for $C_{24}H_{23}N_2O_4F$: C, 68.24; H, 5.49; N, 6.63. Found: C, 67.17, H, 5.93; N, 5.97.

EXAMPLE 313

2-(3-Acetyl-5-chloro-phenoxy)-N-(2-chloro-4-(1-hydroxy-1-methyl-ethyl-)-benzyl)-nicotinamide Prepared from 2-(3-Acetyl-5-chloro-phenoxy)-nicotinic acid and 2-(4-Amino-methyl-3-chloro-phenyl)-propan-2-ol. mp 58–60° C.

Anal. Calcd. for $C_{24}H_{22}N_2O_4Cl_2$: C, 60.90; H, 4.68; N, 5.92. Found: C, 60.73; H, 4.79; N, 5.78.

EXAMPLE 314

2-(3-Acetyl-4-chloro-phenoxy)-N-(2-chloro-4-(1-hydroxy-4-methyl-ethyl-)-benzyl)-nicotinamide Prepared from 2-(3-Acetyl-4-chloro-phenoxy)-nicotinic acid and 2-(4-Aminomethyl-3-chloro-phenyl)-propan-2-ol. MS (m/e): 490/492 (M$^+$+NH$_3$, 100). NMR (CDCl$_3$): 8.60 (dd, J=2,8 Hz, 1H), 8.31 (m, 1H), 8.17 (dd, J=2,5 Hz, 1H), 7.46 (m, 3H), 7.33 (m, 2H), 7.20 (m, 2H), 4.73 (d, J=6 Hz, 2H), 2.67 (s, 3H), 1.54 (s, 6H).

EXAMPLE 315

N-(4-(1-Hydroxy-1-methyl-ethyl)-cyclohexylmethyl)-2-(3-methyl-benzo(d)-isoxazol-5-yloxy)-nicotinamide Prepared from 2-(3-Methyl-benzo-(d)isoxazol-5-yloxy)-nicotinic acid and trans-2-Aminomethyl-cyclohexyl)-propan-2-ol. mp 135–7° C.

Anal. Calcd. for $C_{24}H_{29}N_3O_4$: C, 68.07; H, 6.90; N, 9.92. Found: C, 68.07; H, 7.04; N, 9.64.

EXAMPLE 316

N-(4-(1-Hydroxy-1-methyl-ethyl)-benzyl)-2-(3-methyl-benzo(d)-isoxazol-5-yloxy)-nicotinamide Prepared from 2-(3-Methyl-benzo-(d)isoxazol-5-yloxy)-nicotinic acid and 2-(4-aminomethyl-phenyl)-propan-2-ol. mp 128–30° C. MS (m/e): 418 (M$^+$+1).

EXAMPLE 317

N-(4-(1-Hydroxy-1-methyl-ethyl)-cyclohexylmethyl)-2-(3-methyl-benzo(d)-isoxazol-7-yloxy)-nicotinamide Prepared from 2-(3-Methyl-benzo-(d)isoxazol-7-yloxy)-nicotinic acid and trans-2-(Aminomethyl-cyclohexyl)-propan-2-ol. mp 170–2° C.

Anal. Calcd. for $C_{24}H_{29}N_3O_4$: C, 68.07; H, 6.90; N, 9.92. Found: C, 68.04; H, 6.89; N, 9.80.

EXAMPLE 318

N-[4-(1-Hydroxy-1-methyl-ethyl)-cyclohexylmethyl]-2-(3-nitro-phenoxy)-nicotinamide A solution of 2-(3-nitro-phenoxy)-nicotinic acid (86.9 mg, 0.33 mmol), trans-2-(4-Aminomethyl-cyclohexyl)-propan-2-ol (57.2 mg, 0.33 mmol), benzotriazol-1-yloxy-tris(dimethylamino)phosphonium hexafluorophosphate (148 mg, 0.33 mmol), and diisopropylethyl amine (0.29 mL, 1.67 mmol) in 10 mL of dry DMF was stirred overnight. The solution was then diluted with ethyl acetate and washed with water, 5% citric acid, saturated sodium bicarbonate, and brine, dried over magnesium sulfate and concentrated to an oil. Purified through a pad of silica eluted with ethyl acetate to give a clear oil (120 mg.) $^1$HNMR (CDCl$_3$) δ1.04 (4H, dd), 1.14 (6H, s), 1.55 (2 s), 1.88 (4. m), 3.37 (2H, t) 7.23 (1H, m), 7.51 (1H, d), 7.64 (1H, t), 8.07 (1H, t), 8.16 (2H, m), 8.63 (1H, dd); MS: m/e 414 (M$^+$+1).

The compounds for examples 319–328 were synthesized in a manner analagous to that in Example 318 using the indicated carboxylic acid and amine.

EXAMPLE 319

(+)-2-(Benzo[1,3]dioxol-5-yloxy)-N-[4-(1-hydroxy-ethyl)-cyclohexylmethyl]-nicotinamide Prepared from 2-(Benzo[1,3]dioxol-5-yloxy)-nicotinic acid and (+)-trans-1-(4-Aminomethyl-cyclohexyl)-ethanol. $^1$HNMR (CDCl$_3$) δ0.97 (1,m), 1.10 (3, m), 1.17 (4, m), 1.19 (4,m), 3.23 (1,t), 3.44(2,q), 6.00(2,s), 6.58 (1, dd), 6.64 (1,s), 6.8 (1, d), 7.10 (1,m), 7.9 (1,m), 8.18 (1,m), 8.53 (1, d); MS: m/e 399 (M$^+$+1).

EXAMPLE 320

(−)-2-(3-Cyano-4-fluoro-phenoxy)-N-[4-(1-hydroxy-ethyl)-cyclohexylmethyl]-nicotinamide Prepared from 2-(3-cyano-4-fluoro-phenoxy)-nicotinic acid and (−)-trans-1-(4-Aminomethyl-cyclohexyl)-ethanol.
MP: 134–135° C.; MS: m/e 398 (M$^+$+1).

EXAMPLE 321

(+)-2-(3-Cyano-4-fluoro-phenoxy)-N-[4-(1-hydroxy-ethyl)-cyclohexylmethyl]-nicotinamide Prepared from 2-(3-Cyano-4-fluoro-phenoxy)-nicotinic acid and (+)-trans-1-(4-Aminomethyl-cyclohexyl)-ethanol.
MP: 134–135° C.; MS: m/e 398 (M$^+$+1).

EXAMPLE 322

2-(3-Cyano-4-fluoro-phenoxy)-N-[4-(1-hydroxy-1-methyl-ethyl)-cyclohexylmethyl]-nicotinamide Prepared from 2-(3-Cyano-4-fluoro-phenoxy)-nicotinic acid and 2-trans-(4-Aminomethyl-cyclohexyl)-propan-2-ol.
MP: 85–88° C.; MS: m/e 410 (M$^+$+1).

EXAMPLE 323

2-(2,3-Dihydro-benzo[1,4]dioxin-6-yloxy)-N-[4-(1-hydroxy-1-methyl-ethyl)-benzyl]-nicotinamide Prepared from 2-(2,3-Dihydro-benzo[1,4]dioxin-6-yloxy)-nicotinic acid and 2-(4-Aminomethyl-phenyl)-propan-2-ol. MS: m/e 421 (M$^+$+1), $^1$HNMR (CDCl$_3$) δ1.51 (6H, s), 4.24 (4H, s), 4.66(2H, d), 6.57 (1H, dd), 6.85 (1h, d), 7.11(1H, dd), 7.28(2H, d), 7.41(2H, d), 8.19(2H, m), 8.61(1H, d).

EXAMPLE 324

(+)-2-(2,3-Dihydro-benzo[1,4]dioxin-6-yloxy)-N-[4-(1-hydroxy-ethyl)-cyclohexylmethyl]-nicotinamide Prepared from 2-(2,3-Dihydro-benzo[1,4]dioxin-6-yloxy)-nicotinic acid and (+)-trans-1-4-Aminomethyl-cyclohexyl)-ethanol.

MS: m/e 413 (M$^+$+1), $^1$HNMR (CDCl$_3$) δ0.98(4H, m),1.11(3H, m), 1.22(2H, m), 1.70(2H, m), 1.84(2H, m), 3.33(2H, m), 3.51(1H, m), 4.25(4H, s), 6.65(1H, m), 6.87 (1H, d), 7.11(1H, m), 7.90(1H, m), 8.20(1H, m), 8.60(1H, d).

EXAMPLE 325

2-(2,3-Dihydro-benzo[1,4]dioxin-6-yloxy)-N-[4-(1-hydroxy-1-methyl-ethyl)-cyclohexylmethyl]-nicotinamide Prepared from 2-(2,3-Dihydro-benzo[1,4]dioxin-6-yloxy)-nicotinic acid and 2-trans-(4-Aminomethyl-cyclohexyl)-propan-2-ol.

MS: m/e 427 (M$^+$+1), $^1$HNMR (CDCl$_3$) δ1.03(4H, m), 1.13(6H, s), 1.85(4H, m), 3.33(2H, t), 4.26(4H, s), 6.61(1H, d), 6.70(1H, s), 6.88(1H, d), 7.11(1H, dd), 7.90(1H, m), 8.20(1H, dd), 8.58(1H, dd).

EXAMPLE 326

(−)-2-(2,3-Dihydro-benzo[1,4]dioxin-6-yloxy)-N-[4-(1-hydroxy-ethyl)-cyclohexylmethyl]-nicotinamide Prepared from 2-(2,3-Dihydro-benzo1,4]dioxin-6-yloxy)-nicotinic acid and (−)-trans-1-(4-Aminomethyl-cyclohexyl)-ethanol.
MP:57–59° C., MS: m/e 422 (M$^+$+1).

EXAMPLE 327

2-(Benzo[1,3]dioxol-5-yloxy)-N-[2-fluoro-4-(1-hydroxy-1-methyl-ethyl)-benzyl]-nicotinamide Prepared from 2-(Benzo[1,3]dioxol-5-yloxy)-nicotinic acid and and 2-(4-Aminomethyl-3-fluoro-phenyl)-propan-2-ol.
MP: 94–95° C. MS: m/e: 425 (M$^+$+1).

EXAMPLE 328

N-[2-Fluoro-4-(1-hydroxy-1-methyl-ethyl)-benzyl]-2-(4-fluoro-phenoxy)-nicotinamide Prepared from 2-(4-Fluoro-phenoxy)-nicotinic acid and 2-(4-Aminomethyl-3-fluoro-phenyl)-propan-2-ol.
MP: 93–94° C. MS: m/e 399 (m$^+$+1)

What is claimed is:

1. A compound of the formula

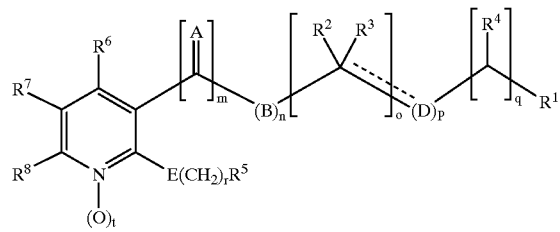

or the pharmaceutically acceptable salt thereof;

m is 1;

n is 1;

o is 0;

p is 0 or 1;

q is 0, 1, 2or 3;

r is 0;

t is 0;

A is oxygen;

B is NH,

D is NR$^9$, wherein R$^9$ is hydrogen or (C$_1$–C$_6$)alkyl;

E is O;

R$^1$ is thiophene;

wherein said thiophene is optionally substituted by one to three substituents independently, selected from the substituents consisting of halo, cyano, carboxy, amino, nitro, hydroxy, (C$_1$–C$_6$)alkyl, (C$_1$–C$_6$)alkoxy, (C$_3$–C$_7$) cycloalkyl, hydroxy(C$_1$–C$_6$)alkyl, hydroxy(C$_1$–C$_6$) alkylamino, (C$_1$–C$_6$)alkoxy, difluoromethyl, trifluoromethyl, difluoromethoxy, trifluoromethoxy, ($C_1$–$C_6$)acyl, ($C_1$–$C_6$)acylamino, ($C_1$–$C_6$)acyloxy, ($C_1$–$C_6$)alkylamino, (($C_1$–$C_6$)alkyl)$_2$amino, ($C_1$–$C_6$)alkyl-NH—(C=O)—, (($C_1$–$C_6$)alkyl)$_2$—N—(C=O)—, aminosulfonyl, ($C_1$–$C_6$)alkylaminosulfonyl, or a saturated or unsaturated cyclic or bicyclic ($C_3$–$C_7$) heterocycle;

or said thiophene is additionally optionally independently substituted with from one to three substituents of the formula

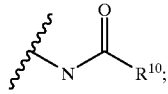

wherein $R^{10}$ is hydrogen, ($C_1$–$C_6$)alkyl, ($C_1$–$C_6$)alkoxy, ($C_3$–$C_7$)cycloalkyl, ($C_3$–$C_7$)cycloalkenyl, ($C_6$–$C_{10}$)arylamino, or ($C_6$–$C_{10}$)aryl, wherein $R^4$ is independently hydrogen, hydroxy, halo, cyano, carboxy, nitro, amino, ($C_1$–$C_6$)alkylamino, (($C_1$–$C_6$)alkyl)$_2$amino, hydroxyamino, ($C_1$–$C_6$)alkyl, hydroxy($C_1$–$C_6$)alkyl, or a group of the formula

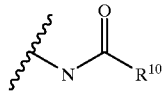

wherein $R^{10}$ is as defined above;
$R^5$ is a group of the formula

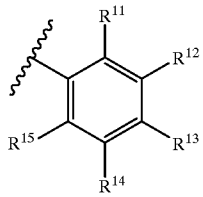

wherein $R^{11}$, $R^{12}$, $R^{13}$, $R^{14}$ and $R^{15}$ are each substituents independently selected from the group consisting of hydrogen, halo, cyano, carboxy, amino, nitro, hydroxy, ($C_1$–$C_6$)alkyl ($C_1$–$C_6$)alkoxy, ($C_3$–$C_7$)cycloalkyl, hydroxy ($C_1$–$C_6$)alkyl, ($C_1$–$C_5$)alkoxy, difluoromethyl, trifluoromethyl, difluoromethoxy, trifluoromethoxy, ($C_1$–$C_6$)acyl, ($C_1$–$C_6$)acylamino, ($C_1$–$C_6$)alkyl-NH—(C=O)—, ($C_1$–$C_6$)alkyl-(C=O)—NH—(C=O)—, ($C_6$–$C_{10}$)aryl-(C=O)—NH—(C=O)—; ($C_1$–$C_6$)acyloxy, ($C_1$–$C_6$)alkylamino, (($C_1$–$C_6$)alkyl)$_2$amino, ($C_1$–$C_6$)alkyl-NH—(C=O)—, ($C_1$–$C_6$)alkyl)$_2$—N—(C=O)—, aminosulfonyl, ($C_1$–$C_6$)alkylaminosulfonyl, or a saturated or unsaturated cyclic or bicyclic ($C_3$–$C_7$)heterocycle containing one to four heteroatoms independently selected from oxygen, sulfur, nitrogen and $NR^9$, wherein $R^9$ is as defined above, and wherein said heterocycle is optionally substituted by one to three substituents independently selected from the group consisting of halo, cyano, carboxy, amino, nitro, hydroxy, ($C_1$–$C_6$)alkyl, hydroxy ($C_1$–$C_6$)alkyl, ($C_1$–$C_6$)alkoxy, ($C_1$–$C_6$)alkylthio, difluoromethyl, trifluoromethyl, difluoromethoxy, trifluoromethoxy, ($C_1$–$C_6$)acyl, ($C_6$–$C_{10}$)aryl, ($C_1$–$C_6$)acylamino, ($C_1$–$C_6$)acyloxy, ($C_1$–$C_6$)alkylamino, (($C_1$–$C_6$)alkyl)$_2$amino, ($C_1$–$C_6$)alkylsulfonyl, aminosulfonyl, ($C_1$–$C_6$)alkylaminosulfonyl, (($C_1$–$C_6$)alkyl)$_2$aminosulfonyl or ($C_2$–$C_9$)heteroaryl;

or $R^{11}$, $R^{12}$, $R^{13}$, $R^{14}$ and $R^{15}$ are optionally independently a group of the formula

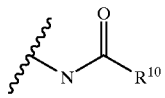

wherein $R^{10}$ is as defined above;
$R^6$, $R^7$, and $R^8$ are each hydrogen;

with the proviso that when m is 1; n is 1; o is 0; p is 0; q is 0; r is 0; A is oxygen, B is NH; $R^1$ is phenyl substituted by methyl, methoxy, chloro or fluoro; E is oxygen and $R^5$ is phenyl optionally substituted by one or two fluoro or chloro; then $R^1$ must be at least di-substituted by substituents other than methyl, methoxy or halo.

2. A compound according to claim 1, wherein m is 1; n is 1; o is 0; p is 0; q is 0; r is 0; A is oxygen; $R^1$ is thiophene optionally substituted by halo, ($C_1$–$C_6$)alkyl, ($C_1$–$C_6$)alkoxy, hydroxy($C_1$–$C_6$)alkyl, amino, ($C_1$–$C_6$)alkylamino, (($C_1$–$C_6$)$_2$amino or hydroxy($C_1$–$C_6$)alkylamino; E is oxygen and $R^5$ is a group of the formula

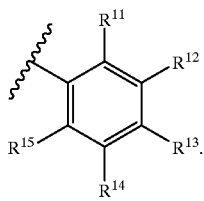

3. A compound according to claim 1, wherein m is 1; n is 1; o is 0; p is 1; q is 1; r is 0; $R^4$ is hydrogen; $R^1$ is thiophene optionally substituted by halo, ($C_1$–$C_6$)alkyl, $C_1$–$C_6$)alkoxy, hydroxy($C_1$–$C_8$)alkyl, amino, ($C_1$–$C_6$)alkylamino, (($C_1$–$C_6$)alkyl)$_2$amino or hydroxy($C_1$–$C_6$)alkylamino; E is oxygen and $R^5$ is a group of the formula

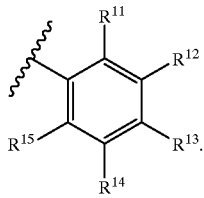

4. A compound according to claim 1, wherein m is 1; n is 1; o is 0; p is 0; q is 2; r is 0; $R^4$ is independently hydrogen or hydroxy; $R^1$ is thiophene optionally substituted by halo, ($C_1$–$C_6$)alkyl, ($C_1$–$C_6$)alkoxy, hydroxy($C_1$–$C_6$)alkyl, amino, ($C_1$–$C_6$)alkylamino, (($C_1$–$C_6$)alkyl)$_2$amino or hydroxy ($C_1$–$C_6$)alkylamino; E is oxygen and $R^5$ is a group of the formula

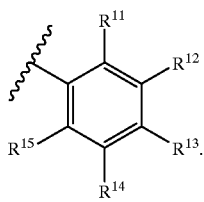

5. A compound according to claim 1, wherein m is 1; n is 1; o is 0; p is 0; q is 1; r is 0; $R^4$ is hydroxy ($C_1$–$C_6$)alkyl; $R^1$ is thiophene optionally substituted by halo, ($C_1$–$C_6$)alkyl, ($C_1$–$C_6$)alkoxy, hydroxy($C_1$–$C_6$)alkyl, amino, ($C_1$–$C_6$)

alkylamino, (($C_1$–$C_6$)alkyl)$_2$amino or hydroxy($C_1$–$C_6$) alkylamino; E is oxygen and $R^5$ is a group of the formula

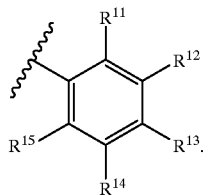

6. A compound according to claim 1, 2-(4-Fluoro-phenoxy)-N-(1-thiophen-2-yl-ethyl)-nicotinamide.

7. A pharmaceutical composition for the treatment of respiratory, allergic and inflammatory disorders comprising asthma, chronic obstructive pulmonary disease, acute respiratory disease syndrome, pulmonary hypersensitivity, and allergic rhinitis in a mammal, including a human, comprising an amount of a compound of claim 1 or a pharmaceutically acceptable salt thereof, effective in such treatment, and a pharmaceutically acceptable carrier.

8. A method for the treatment of respiratory, allergic, and inflammatory disorders comprising asthma, chronic obstructive pulmonary disease, acute respiratory disease syndrome, pulmonary hypersensitivity, and allergic rhinitis in a mammal, including a human comprising administering to said mammal an amount of a compound of claim 1 or a pharmaceutically salt thereof, effective in such treatment.

* * * * *